US008536174B2

(12) United States Patent
Maryanoff et al.

(10) Patent No.: US 8,536,174 B2
(45) Date of Patent: *Sep. 17, 2013

(54) UROTENSIN II RECEPTOR ANTAGONISTS

(75) Inventors: Bruce E. Maryanoff, Forest Grove, PA (US); William A. Kinney, Newtown, PA (US); Edward C. Lawson, Pipersville, PA (US); Diane K. Luci, Horsham, PA (US); Shyamali Ghosh, Norristown, PA (US)

(73) Assignee: Janssen Pharmaceutica NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/459,708

(22) Filed: Apr. 30, 2012

(65) Prior Publication Data
US 2012/0214817 A1 Aug. 23, 2012

Related U.S. Application Data

(62) Division of application No. 13/026,549, filed on Feb. 14, 2011, now Pat. No. 8,193,191, which is a division of application No. 11/651,848, filed on Jan. 10, 2007, now Pat. No. 7,915,260.

(60) Provisional application No. 60/757,692, filed on Jan. 10, 2006.

(51) Int. Cl.
*A61K 31/4995* (2006.01)
*C07D 487/08* (2006.01)

(52) U.S. Cl.
USPC .......................................... 514/249; 544/349

(58) Field of Classification Search
None
See application file for complete search history.

(56) References Cited

U.S. PATENT DOCUMENTS

| 6,011,050 | A | 1/2000 | Muller et al. |
| 6,884,887 | B1 | 4/2005 | Riermeier et al. |
| 6,911,464 | B2 | 6/2005 | Man et al. |
| 7,043,052 | B2 | 5/2006 | Rhoads et al. |
| 8,193,191 | B2 * | 6/2012 | Maryanoff et al. ........... 514/249 |
| 2004/0229871 | A1 | 11/2004 | Cesure et al. |
| 2004/0259873 | A1 | 12/2004 | Man et al. |
| 2004/0267051 | A1 | 12/2004 | Boerner et al. |
| 2005/0143393 | A1 | 6/2005 | Dean et al. |
| 2005/0203090 | A1 | 9/2005 | Man et al. |
| 2005/0239867 | A1 | 10/2005 | Zeldis |
| 2005/0282819 | A1 | 12/2005 | Graham |

FOREIGN PATENT DOCUMENTS

| WO | WO 98/52919 | | 11/1998 |
| WO | WO 01/05741 | A1 | 1/2001 |
| WO | WO 02/47687 | | 6/2002 |
| WO | WO 03/014061 | A1 | 2/2003 |
| WO | WO 03/104216 | | 12/2003 |
| WO | WO 2004/024702 | | 3/2004 |
| WO | WO 2004/080422 | A2 | 9/2004 |
| WO | WO 2004/080423 | A2 | 9/2004 |
| WO | WO 2004/259873 | A2 | 9/2004 |
| WO | WO 2004/259873 | A3 | 9/2004 |
| WO | WO 2005/034873 | A2 | 4/2005 |
| WO | WO 2005/034873 | A3 | 4/2005 |
| WO | WO 2005/072226 | A2 | 8/2005 |
| WO | WO 2005/72226 | A3 | 8/2005 |
| WO | WO 2006/020879 | | 2/2006 |
| WO | WO 2007/008541 | | 1/2007 |

OTHER PUBLICATIONS

Matsumoto et al, "Intracerebroventricular administration of urotensin II promotes anxiogenic-like behaviors in rodents," Neuroscience Letters, 2004, pp. 99-102, vol. 358, Elsevier Ireland Ltd.
Pearson et al, "Urotensin II: A somatostatin-like peptide in the caudal neurosecretory system of fishes," Proc. Natl Acad. Sci., 1980, pp. 5021-5024, vol. 77, No. 8, Physiological Sciences, USA.
Tal et al, "A Novel Putative Neuropeptide Receptor Expressed in Neural tissue, including Sensory Epiethelia," Biochemical and Biophysical Research Communications, 1995, pp. 752-759, vol. 209, No. 2, Academic Press, Inc.
Marchese et al "Cloning and Chromosomal Mapping of Three Novel Genes, GPR9, GPR10, and GPR14, Encoding Receptors Related to Interleukin 8, Neuropeptide Y, and Somatostatin Receptors," Genomics, 1995, pp. 335-344, vol. 29, Academic Press, Inc.
Douglas et al, "Human Urotensin-II, the Most Potent Mammalian Vasoconstrictor Identified to Date, as a Therapeutic Target for the Management of Cardiovascular Disease," TCM, 2000, pp. 229-237, vol. 10, No. 6, Elsevier.
Zou et al, "Urotensin II induces hypertrophic responses in cultured cardiomyocytes from neonatal rats," Febs Letters, 2001, pp. 57-60, vol. 508, Elsevier Science B.V.
Bousette et al, "Increased expression of urotensin II and its cognate receptor GPR14 in atherosclerotic lesions of the human aorta," Atherosclerosis, 2004, pp. 117-123, vol. 176, Elsevier Ireland Ltd.
Totsune et al, "Role of Urotensin II in patients on dialysis," The Lancet, 2001, pp. 810-811, vol. 358, Research Letters.
Conlon et al, "Distribution and Molecular Forms of Urotensin II and Its Role in Cardiovascular Regulation in Vertebrates," The Journal of Experimental Zoology, 1996, pp. 226-238, vol. 275, Wiley-Liss, Inc.
Totsune et al, "Increased plasma Urotensin II levels in patients with diabetes mellitus," Clinical Science, The Biochemical Society and the Medical Research Society, 2003, pp. 1-5, vol. 104, Great Britain.
Gartlon et al, "Central effects of urotensin-II following Icv administration in rats," Psychophaarmacology, 2001, pp. 426-433, vol. 155, Springer-Verlag.
Gartlon et al, "Urotensin-II, a neuropeptide ligand for GPR14, induces c-*fos* in the rat brain," European Journal of Pharmacology, 2004, pp. 95-98, vol. 493, Elsevier.

(Continued)

*Primary Examiner* — Emily Bernhardt
(74) *Attorney, Agent, or Firm* — Yuriy P. Stercho

(57) ABSTRACT

The invention is directed to Urotensin II antagonists. More specifically, the present invention relates to certain novel compounds, methods for preparing compounds, compositions, intermediates and derivatives thereof and methods for treating Urotensin-II mediated disorders. Pharmaceutical and veterinary compositions and methods of treating cardiovascular disorders and various other disease states or conditions using compounds of the invention are also described.

23 Claims, No Drawings

(56) References Cited

OTHER PUBLICATIONS

Silvestre et al, "Inhibition of Insulin Release by Urotensin II—A Study on the Perfused Rat Pancreas," Horm Metab Res., 2001, pp. 379-381, vol. 33, Georg Thieme Verlag Stuttgart, New York.

Ames et al, "Human urotensin-II is a potent vasoconstrictor and agonist for the Orphan Receptor GPR14," Letters to Nature, 1999, pp. 282-286, vol. 401, Macmillan Magazine Ltd.

Vippagunta, et al, "Crystalline Solids", Advanced Drug Delivery Reviews, 2001, pp. 3-26, vol. 48.

Lim, et al., "Differential Effect of Urotensin II on Vascular Tone in Normal Subjects and Patients with Chronic Heart Failure," Circulation, 2004, pp. 1212-1214, vol. 109, America Heart Association.

Watamabe. et, al., "Synergistic Effect of Urotensin II with Midly Oxidized LDL on DNA Synthesis in Vascular Smooth Muscle Cells", Circulation, 2001, pp. 16-18, vol. 104, American Heart Association.

International Search Report, PCT/US07/00644, Apr. 2007.

European Search Report, 07717845.Jul. 2101/1993554, PCT/US2007000644, Jul. 2010.

\* cited by examiner

UROTENSIN II RECEPTOR ANTAGONISTS

CROSS REFERENCE TO RELATED APPLICATIONS

The present application is a divisional of U.S. application Ser. No. 13/026,549, filed on Feb. 14, 2011, now U.S. Pat. No. 8,193,191, issued on Jun. 5, 2012, which is a divisional of U.S. application Ser. No. 11/651,848, filed on Jan. 10, 2007, now U.S. Pat. No. 7,915,260, issued on Mar. 29, 2011, that claims benefit of U.S. Provisional Application Ser. No. 60/757,692, filed Jan. 10, 2006, which are all incorporated herein by reference in their entirety and for all purposes.

FIELD OF THE INVENTION

The present invention relates to certain novel compounds, methods for preparing compounds, compositions, intermediates and derivatives thereof and methods for treating Urotensin-II mediated disorders. More particularly, the compounds of the present invention are Urotensin-II receptor antagonists useful for treating Urotensin-II mediated disorders.

BACKGROUND OF THE INVENTION

Urotensin-II (U-II) is a cysteine-linked cyclic peptide, which exerts potent effects on the cardiovascular, renal, pancreatic, and central nervous systems. Originally, this substance was isolated from the urophysis (a caudal neurosecretory organ) of the goby fish (*Gillichthys mirabilis*) as a 12-mer, AGTAD-cyclo(CFWKYC)-V (D. Pearson. J. E. Shively, B. R. Clark, I. I. Geschwind, M. Barkley, R. S, Nishioka, H. A. Bern, *Proc. Natl. Acad. Sci. USA* 1980, 77, 5021-5024), but it has now been identified in all classes of vertebrates. The composition of U-II ranges from 11 amino acids in humans to 14 amino acids in mice, always with a conserved cysteine-linked macrocycle, CFWKYC. Recently, the U-II receptor was identified (R. S. Ames, H. M. Sarau, J. K. Chambers, R. N. Willette, N. V. Aiyar, A. M. Romanic, C. S. Louden, J. J. Foley, C. F. Sauermelch, R. W. Coatney, Z. Ao, J. Disa, S. D. Holmes, J. M. Stadel, J. D. Martin, W.-S. Liu, G. I. Glover, S. Wilson, D. E. McNulty, C. E. Ellis, N. A. Elshourbagy, U. Shabon, J. J. Trill, D. W. P. Hay, E. H. Ohlstein, D. J. Bergsma, S. A. Douglas, *Nature* (London) 1999, 401, 282-286) as a G-protein-coupled receptor (GPCR) previously known as the GPR14 orphan receptor, (M. Tal, D. A. Ammar, M. Karpuj, V. Krizhanovsky, M. Naim, D. A. Thompson, *Biochem. Biophys. Res. Commun.* 1995, 209, 752-759; and A. Marchese, M. Heiber, T. Nguyen, H. H. Q. Heng, V. R. Saldivia, R. Cheng, P. M. Murphy, L.-C. Tsui, X. Shi, P. Gregor, S. R. George, B. F. O'Dowd, J. M. Docherty, *Genomics* 1995, 29, 335-344) which is expressed predominantly in cardiovascular tissues.

Goby U-II possesses powerful vasoconstrictor activity in fish, mammals, and humans (J. M. Conlon, K. Yano, D. Waugh, N. Hazon, *J. Exp. Zool.* 1996, 275, 226-238; F. Böhm, J. Pernow, *Br. J. Pharmacol.* 2002, 135, 25-27). Moreover, it appears to be the most potent vasoconstrictor known, (S. A. Douglas, E. H. Ohlstein, *Trends Cardiovasc. Med.* 2000, 10, 229-237), causing concentration-dependent contraction of isolated arterial rings of rats and humans with an $EC_{50}$ value of less than 1 nM, which is ca. ten times more potent than endothelin-1. Recently, Kikkawa, H. and Kushida, H. in International Publication WO 2005/072226 disclosed the use of Urotensin-II antagonists for the prevention and/or treatment of inflammatory bowel diseases including, but not limited to, Crohn's disease, ulcerative colitis, and inflammatory colitis caused by bacteria, ischemia, radiation, drugs, or chemical substances.

Relative to the role of U-II in chronic vascular disease, this peptide was reported to induce hypertrophy in cardiomyocytes (Y. Zou, R. Nagai, T. Yamazaki, *FEBS Letters* 2001, 508, 57-60) and the proliferation of smooth muscle cells (T. Watanabe, R. Pakala, T. Katagiri, C. R. Benedict, *Circulation* 2001, 104, 16-18), which suggests an involvement in heart failure and atherosclerosis. In addition, U-II has been shown to increase peripheral vascular tone, a characteristic of chronic heart failure (M. Lim, S. Honisett, C. D. Sparkes, P. Komesaroff, A. Kompa, H. Krum, *Circulation* 2004, 109, 1212-1214). Recent results have shown increased U-II receptor levels observed in the atherosclerotic lesions of the human aorta (N. Bousette, L. Patel, S. A. Douglas, E. H. Ohlstein, A. Giaid, *Atherosclerosis* 2004, 176, 117-123).

Relative to healthy individuals, the expression of U-II-like immunoreactivity was 2-fold higher in the plasma of patients with renal dysfunction who were not on dialysis, and 3-fold higher in those on haemodialysis (K. Totsune, K. Takahashi, Z. Arihara, M. Sone, F. Satoh, S. Ito, Y. Kimura, H. Sasano, O. Murakami, *Lancet* 2001, 358, 810-811). Recently, Kinoshita, M. and Kushida, H. in International Publication WO 2005/034873 disclosed the use of Urotensin-II antagonists for reducing nephrotoxicity and diarrhea caused by anti-neoplastic agents.

U-II has been described as a potential mediator in diabetes. For instance, U-II was shown to inhibit the release of insulin in the perfused rat pancreas in response to increasing glucose levels (R. A. Silvestre, J. Rodríguez-Gallardo, E. M. Egido, J. Marco, *Horm. Metab. Res.* 2001, 33, 379-381). Elevated U-II levels were seen in patients with diabetis mellitus (K. Totsune, K. Takahashi, Z. Arihara, M. Sone, S. Ito, O. Murakami, *Clin. Sci.* 2003, 104, 1-5) even without renal failure.

A U-II antagonist may be useful for the treatment of pain, neurological and psychiatric conditions, migraine, neuromuscular deficit, and cardiovascular disorders. ICV (intracerebroventricular) administration of U-II increases rearing, grooming, and motor activity suggesting a CNS stimulatory activity (J. Gartlon, F. Parker, D. C. Harrison, S. A. Douglas, T. E. Ashmeade, G. J. Riley, Z. A. Hughes, S. G. Taylor, R. P. Munton, J. J. Hagan, J. A. Hunter, D. N. C. Jones, *Psychopharmacology* 2001, 155, 426-433). U-II increases Fos expression in the cingulate cortex and periaqueductal grey brain regions important in cognitive, emotional, and motor responses; the perceptions of pain; and panic responses (J. E. Gartlon, T. Ashmeade, M. Duxon, J. J. Hagan, D. N. C. Jones, *Eur. J. of Pharmacol.* 2004, 493, 95-98). U-II induces anxiogenic-like responses in rodents in the elevated plus maze and hole-board tests (Y. Matsumoto, M. Abe, T. Watanabe, Y. Adachi, T. Yano, H. Takahashi, T. Sugo, M. Mori, C. Kitada, T. Kurokawa, M. Fujino, *Neuroscience Letters* 2004, 358, 99-102).

U.S. Pat. No. 6,911,464 and Application Publications US2004/0259873 and US2005/0203090 (equivalent to Man, H-W. and Muller, G. W. International Publication WO/2004080422) disclose N-alkyl-hydroxamic acid-isoindolyl compounds for treatment or prevention of various diseases and disorders mediated by PDE4 inhibition, associated with abnormal TNA-alpha levels, and/or mediated by MMP inhibition.

U.S. Pat. No. 7,043,052 and Application Publications US2004/0259873 and US2005/0203090 (equivalent to Man, H-W., Muller, G. W., and Zhang, W. International Publication WO2004/080423) disclose 7-amido-isoindolyl compounds for the treatment, prevention or management of various diseases and disorders, including but not limited to cancer, inflammatory bowel disease and myelodysplastic syndrome.

Kawasaki, H., Shinagawa, Y., and Mimura, T. in International Publication WO98/52919 disclose phthalamide derivatives and an antiallergic agent containing the same, having selective IgE and IL-5 production inhibitory activities.

United States Patent Application Publication US2004/0267051 (from International Publication WO2003/014061) describes a method for the production of amines by reductive amination of carbonyl compounds under transfer-hydrogenation conditions.

U.S. Pat. No. 6,884,887 (from PCT Publication WO2001/005741) describes a method for producing amines by homogeneously catalyzed reductive amination of carbonyl compounds.

Accordingly, it is an object of the present invention to provide compounds that are Urotensin-II antagonists useful for treating Urotensin-II mediated disorders. It is another object of the invention to provide a process for preparing compounds, compositions, intermediates and derivatives thereof. It is a further object of the invention to provide methods for treating Urotensin-II mediated disorders including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke.

SUMMARY OF THE INVENTION

The present invention is directed to a compound of Formula (I):

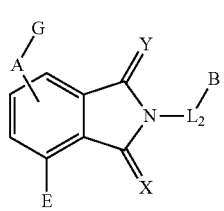

Formula (I)

wherein:
when A is present, then G is selected from hydrogen, $C_{1-8}$alkyl, $C_{2-8}$alkenyl, $C_{3-14}$cycloalkyl or a —C[($R_1$)($R_{11}$)]-L-D moiety:

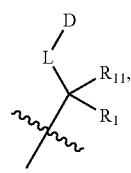

wherein $C_{1-8}$alkyl is optionally substituted with one, two or three fluoro substituents, and
wherein $C_{3-14}$cycloalkyl is optionally substituted with one, two or three $C_{1-3}$alkyl substituents; or,
when A is absent and $R_2$ is other than benzyloxymethyl, then G is $C_{1-8}$alkoxy or heterocyclyloxy, wherein $C_{1-8}$alkoxy is substituted with one of amino, ($C_{1-8}$alkyl)amino, di($C_{1-8}$alkyl)amino, (benzyl)amino or [(benzyl)($C_{1-4}$alkyl)]amino, and
wherein heterocyclyloxy is optionally substituted on heterocyclyl with one, two or three $C_{1-3}$alkyl substituents;
$R_1$ is selected from the group consisting of hydrogen, $C_{1-8}$alkyl, $C_{2-8}$alkenyl, and $C_{2-8}$alkynyl;
$R_{11}$ is selected from the group consisting of hydrogen, $C_{1-8}$alkyl and cyclopropyl;
L is absent or $C_{1-4}$alkylene;
D is aryl (other than naphthalen-2-yl), $C_{3-14}$cycloalkyl, $C_{5-14}$cycloalkenyl, heterocyclyl, or heteroaryl,
wherein aryl and heteroaryl are optionally substituted with one, two, three or four substitutents independently selected from the group consisting of $C_{1-3}$alkyl, $C_{1-3}$alkoxy, $C_{2-3}$alkenyl, $C_{2-3}$alkenyloxy, hydroxy, $C_{1-3}$alkylthio, fluoro, chloro, cyano, $C_{1-3}$alkylcarbonyl, ($C_{1-3}$alkylcarbonyl)amino, ($C_{1-3}$alkyl)amino, di($C_{1-3}$alkyl)amino and $C_{3-14}$cycloalkyl, wherein $C_{3-14}$cycloalkyl is optionally substituted with one, two, three or four $C_{1-3}$alkyl substituents,
provided that D is other than 2-hydroxy-5-chloro-phenyl, 3-methoxy-phenyl, 4-ethyl-phenyl, 6,6-dimethyl-bicyclo [3.1.1]hept-2-en-2-yl-methyl, cyclohex-3-enyl, 2,6-dichloro-phenyl and 2-chloro-4-fluoro-phenyl;
A is an optionally present biradical selected from the group consisting of a-1, optionally unsaturated a-2, a-3, a-4, optionally unsaturated a-5 and a-6,
wherein, the lower portion of A is attached, relative to the nitrogen atom of Formula (I), to the 3 or 4 position on the benzene ring portion of Formula (I);

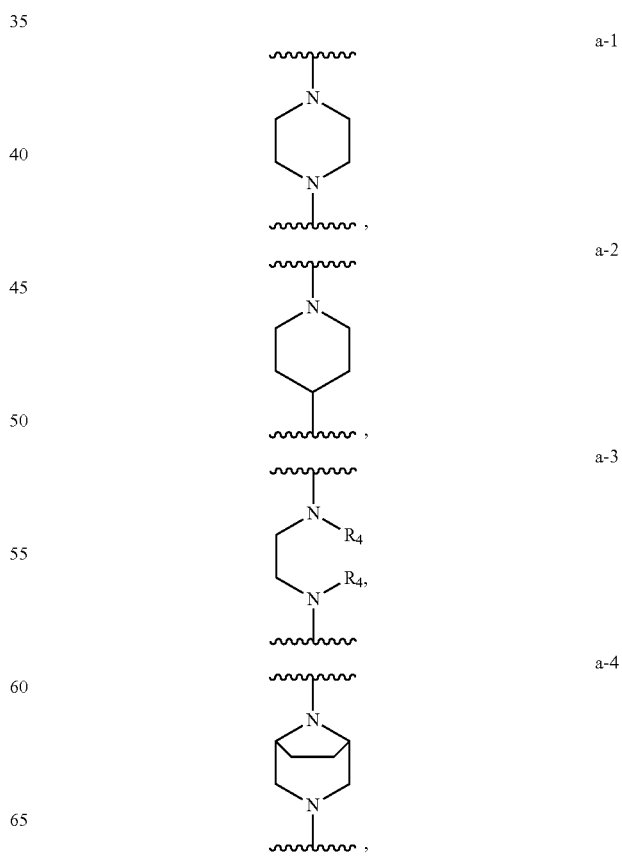

-continued a-5 and a-6 wherein a-1, a-2, a-3, a-4 and a-5 are optionally substituted with one to two $C_{1-4}$alkyl substituents;

provided that A is other than cis-(1,2)-cyclohexyldiamino;

$R_4$ is hydrogen or $C_{1-8}$alkyl;

$L_2$ is absent or —C($R_2$)($R_5$)—(C$R_6R_7$)$_r$—, wherein r is 0, 1 or 2; and wherein $R_5$, $R_6$, and $R_7$ are independently hydrogen or $C_{1-3}$alkyl;

provided that $L_2$ is other than —CH(R-carboxymethyl)-;

$R_2$ is selected from the group consisting of hydrogen, a heteroaryl that is not fused to another ring, phenyl, and $C_{1-6}$alkyl, wherein phenyl is optionally substituted with ($R_{200}$—$C_{1-6}$alkyl)amino, or [(hydroxysulfonyl)($R_a$)]amino, and wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, $R_{200}$-oxy, aminocarbonyl, carboxy-$C_{1-6}$alkoxy, aminocarbonyl-$C_{1-6}$alkoxy, ($C_{1-6}$alkyl)aminocarbonyl, di($C_{1-6}$alkyl)aminocarbonyl, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, (amino-$C_{1-6}$alkylcarbonyl)amino, [($C_{1-6}$alkyl)amino-$C_{1-6}$alkylcarbonyl]amino, [di($C_{1-6}$alkyl)amino-$C_{1-6}$alkylcarbonyl]amino, ($C_{1-6}$alkylcarbonyl-acetonitrile-carbonyl)amino, ureido, thioureido, acetamidino, guanidino, {[($R_{200}$)($R_a$)]aminocarbonyl-($R_c$)}amino, [($R_{200}$-oxycarbonyl)($R_a$)]amino, [($R_{200}$)($R_a$)]aminocarbonyloxy, aminosulfonyl, $C_{1-6}$alkylsulfonyl, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, aminosulfonyloxy, ($C_{1-6}$alkyl)aminosulfonyloxy, di($C_{1-6}$alkyl)aminosulfonyloxy, aminosulfonylamino, ($C_{1-6}$alkyl)aminosulfonylamino, [di($C_{1-6}$alkyl)aminosulfonyl]amino, [(hydroxysulfonyl)($R_a$)]amino, [($R_{200}$-oxysulfonyl)($R_a$)]amino, [($R_{200}$-sulfonyl)($R_a$)]amino, [($R_{200}$)($R_a$)]aminosulfonyloxy, or ({[($R_{200}$)($R_a$)]aminosulfonyl}($R_c$))amino;

$R_a$ and $R_c$ are independently selected from the group consisting of hydrogen and $C_{1-6}$alkyl; and $R_b$ is hydrogen, $C_{1-6}$alkyl, $C_{6-10}$aryl, heteroaryl, $C_{3-8}$cycloalkyl, or heterocyclyl;

$R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, aryl, heteroaryl, aryl-$C_{1-6}$alkyl, aryl-sulfonyl and heteroaryl-sulfonyl, wherein heterocyclyl is optionally substituted with one, two or three oxo substituents;

B is $C_{6-10}$aryl, tetralinyl, indanyl, or a heteroaryl selected from the group consisting of pyridin-2-yl, pyridin-4-yl, pyrazol-4-yl, pyrimidin-4-yl, pyrimidin-5-yl, pyrazin-2-yl, imidazol-1-yl, thien-2-yl, isoquinolinyl, indolyl, quinolinyl, and thiazol-5-yl, wherein B is optionally substituted with one, two or three substituents independently selected from the group consisting of $C_{1-4}$alkyl, $C_{1-4}$alkoxy, fluorinated ($C_{1-4}$)alkoxy, halogen, cyano, hydroxy, aminocarbonyl, ($C_{1-4}$alkylaminocarbonyl, di($C_{1-4}$alkylaminocarbonyl, aminosulfonyl, ($C_{1-4}$alkylaminosulfonyl, di($C_{1-4}$alkylaminosulfonyl, hydroxysulfonyl, aminosulfonylamino, ($C_{1-4}$alkylaminosulfonylamino, di($C_{1-4}$alkylaminosulfonylamino, aminosulfonyloxy, ($C_{1-4}$alkylaminosulfonyloxy, and di($C_{1-4}$alkylaminosulfonyloxy, provided that when B is selected from the group consisting of $C_{6-10}$aryl, tetralinyl, indanyl, thien-2-yl, and indolyl, then B is independently substituted with two to three substitutents selected from the group consisting of $C_{1-3}$alkoxy and hydroxy, provided that, when B is phenyl substituted at the 3,4-, 3,5- or 4,5-positions with an unbranched $C_{1-3}$alkoxy substituent at each position, then phenyl may be further optionally substituted at a remaining open 3-, 4-, or 5-position with an additional $C_{1-3}$alkoxy or hydroxy substituent, and provided that B is other than 3-hydroxy-4-methoxy-phenyl and 3-(n-propyloxy)-4-methoxy-phenyl;

E is hydrogen, halogen, $C_{1-3}$alkoxy, $C_{2-5}$alkyl-$R_E$, or —CH=CH—$C_{0-3}$alkyl-$R_E$;

wherein $R_E$ is selected from the group consisting of carboxy, amino, ($C_{1-6}$alkyl)amino, di($C_{1-6}$alkyl)amino, aminocarbonyl, ($C_{1-6}$alkyl)aminocarbonyl, di($C_{1-6}$alkyl)aminocarbonyl, ($C_{1-6}$alkyl)carbonylamino, $C_{1-6}$alkoxycarbonylamino, aminocarbonyl($C_{1-6}$)alkoxy, ureido, thioureido, aminosulfonyl, $C_{1-6}$alkylsulfonyl, $C_{1-6}$alkylsulfonylamino, aminosulfonyloxy, ($C_{1-6}$alkyl)aminosulfonyloxy, di($C_{1-6}$alkyl)aminosulfonyloxy, aminosulfonylamino, ($C_{1-6}$alkyl)aminosulfonylamino, di($C_{1-6}$alkyl)aminosulfonylamino, ($R_{200}$)($R_a$)aminocarbonyl-($R_c$)amino, $R_{200}$-carbonylamino, $R_{200}$oxycarbonyl-($R_a$)amino, ($R_{200}$)($R_a$)aminocarbonyloxy, $R_{200}$oxysulfonyl-($R_a$)amino, $R_{200}$sulfonyl-($R_a$)amino, ($R_{200}$)($R_a$)aminosulfonyloxy, and ($R_{200}$)($R_a$)aminosulfonyl-($R_c$)amino;

X and Y are independently O or S;

and enantiomers, diastereomers, tautomers, solvates, and pharmaceutically acceptable salts thereof.

Example 1 of the present invention is directed to an embodiment wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein below, are excluded from the genus of Formula (I) described herein above.

Example 1a of the present invention is directed to an embodiment wherein compounds where $R_2$ is H are excluded from the genus of Formula (I) described hereinabove.

The present invention is also directed to a compound of Formula (II):

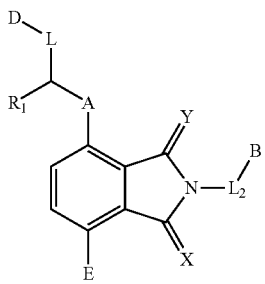

Formula (II)

wherein:

$R_1$ is one to two substituents independently selected from the group consisting of hydrogen, $C_{1-8}$alkyl, $C_{2-8}$alkenyl, $C_{2-8}$alkynyl, and cyclopropyl; or, when $R_1$ and D are each other than hydrogen, $R_1$ and D are optionally taken together with the atoms to which they are attached to form a 5-8 membered ring optionally substituted with one to three $C_{1-3}$alkyl substituents;

L is absent or $C_{1-4}$alkylene;

D is hydrogen; aryl (other than naphthalen-2-yl); $C_{1-8}$alkyl; $C_{1-8}$alkenyl; $C_{3-14}$cycloalkyl optionally substituted with one to four $C_{1-3}$alkyl substituents; $C_{5-14}$cycloalkenyl (other than cyclohex-3-enyl) optionally substituted with one to four $C_{1-3}$alkyl substituents; heterocyclyl; or heteroaryl;

wherein aryl and heteroaryl are optionally substituted with one to three substitutents independently selected from the group consisting of $C_{1-3}$alkyl, $C_{1-3}$alkoxy, $C_{2-3}$alkenyloxy, hydroxy, $C_{1-3}$alkylthio, fluoro, chloro, cyano, $C_{1-3}$alkylcarbonyl, $C_{1-3}$alkylcarbonylamino, $C_{1-3}$alkylamino, and di($C_{1-3}$alkyl)amino;

or, D is —O(CH$_2$)$_{1-3}$O— attached at two adjacent carbon atoms;

A is a biradical selected from the group consisting of a-1, optionally unsaturated a-2, and a-3 such that the lower portion of A is attached to the phenyl ring of Formula (II);

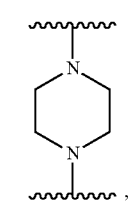

a-1

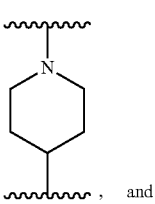

a-2

, and

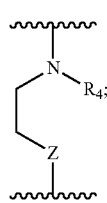

a-3 wherein a-1, a-2, and a-3 are optionally substituted with one to two $C_{1-4}$alkyl substituents which, when attached at adjacent carbon atoms, are optionally taken together with the atoms to which they are attached to form a 5 to 8 membered cycloalkyl;

Z is O, CH$_2$, or NH;

$R_4$ is hydrogen or $C_{1-8}$alkyl;

$L_2$ is absent or —C(R$_2$)(R$_5$)(CR$_6$R$_7$)$_r$—, wherein r is 0 to 2; and wherein $R_5$, $R_6$, and $R_7$ are independently hydrogen or $C_{1-3}$alkyl;

$R_2$ is selected from the group consisting of hydrogen, a heteroaryl that is not fused to another ring, phenyl, and $C_{1-6}$alkyl; wherein $C_{1-6}$alkyl is optionally substituted with carboxy, hydroxy, NR$_a$R$_b$, R$_{200}$oxy, aminocarbonyl, ($C_{1-6}$alkyl)aminocarbonyl, di($C_{1-6}$alkyl)aminocarbonyl, ($C_{1-6}$alkyl)carbonylamino, $C_{1-6}$alkoxycarbonylamino, aminocarbonyl($C_{1-6}$)alkoxy, ureido, thioureido, (R$_{200}$)(R$_a$)aminocarbonyl-(R$_c$)amino, R$_{200}$-carbonylamino, R$_{200}$oxycarbonyl-(R$_a$)amino, (R$_{200}$)(R$_a$)aminocarbonyloxy, aminosulfonyl, $C_{1-6}$alkylsulfonyl, $C_{1-6}$alkylsulfonylamino, aminosulfonyloxy, ($C_{1-6}$alkyl)aminosulfonyloxy, di($C_{1-6}$alkyl)aminosulfonyloxy, aminosulfonylamino, ($C_{1-6}$alkyl)aminosulfonylamino, di($C_{1-6}$alkyl)aminosulfonylamino, R$_{200}$oxysulfonyl-(R$_a$)amino, R$_{200}$sulfonyl-(R$_a$)amino, (R$_{200}$)(R$_a$)aminosulfonyloxy, or (R$_{200}$)(R$_a$)aminosulfonyl-(R$_c$)amino;

wherein R$_a$ and R$_c$ are independently selected from the group consisting of hydrogen and $C_{1-6}$alkyl; and R$_b$ is hydrogen, $C_{1-6}$alkyl, $C_{6-10}$aryl, heteroaryl, $C_{3-8}$cycloalkyl, or heterocyclyl;

and, wherein R$_{200}$ is $C_{6-10}$aryl, heteroaryl, $C_{3-8}$cycloalkyl, or heterocyclyl; and R$_{200}$ is optionally substituted with one to three substituents independently selected from the group consisting of $C_{1-4}$alkyl, $C_{1-4}$alkoxy, chloro, and fluoro;

B is $C_{6-10}$aryl, tetralinyl, indanyl, or a heteroaryl selected from the group consisting of pyridin-2-yl, pyridin-4-yl, pyrazol-4-yl, pyrimidin-4-yl, pyrimidin-5-yl, pyrazin-2-yl, imidazol-1-yl, thien-2-yl, isoquinolinyl, indolyl, quinolinyl, and thiazol-5-yl;

wherein B is optionally substituted with one to three substituents independently selected from the group consisting of $C_{1-4}$alkyl, $C_{1-4}$alkoxy, fluorinated ($C_{1-4}$)alkoxy, halogen, cyano, hydroxy, aminocarbonyl, ($C_{1-4}$alkylaminocarbonyl, di($C_{1-4}$alkylaminocarbonyl, aminosulfonyl, ($C_{1-4}$alkylaminosulfonyl, di($C_{1-4}$alkylaminosulfonyl, hydroxysulfonyl, aminosulfonylamino, ($C_{1-4}$alkylaminosulfonylamino, di($C_{1-4}$alkylaminosulfonylamino, aminosulfonyloxy, ($C_{1-4}$alkylaminosulfonyloxy, and di($C_{1-4}$alkylaminosulfonyloxy;

provided that when B is selected from the group consisting of $C_{6-10}$aryl, tetralinyl, indanyl, thien-2-yl, and indolyl, B is independently substituted with two to three unbranched $C_{1-3}$alkoxy or hydroxy substitutents;

and further provided that, when B is phenyl, the phenyl is substituted at the 3,4- 3,5- or 4,5-positions with two unbranched $C_{1-3}$alkoxy substituents, and the phenyl is optionally substituted at a 3-, 4-, or 5-position with an additional $C_{1-3}$alkoxy or hydroxy substituent;

E is hydrogen, halogen, $C_{1-3}$alkoxy, $C_{2-5}$alkyl-$R_E$, or —CH=CH—$C_{0-3}$alkyl-$R_E$; wherein $R_E$ is selected from the group consisting of carboxy, amino, ($C_{1-6}$alkyl)amino, di($C_{1-6}$alkyl)amino, aminocarbonyl, ($C_{1-6}$alkyl)aminocarbonyl, di($C_{1-6}$alkyl)aminocarbonyl, ($C_{1-6}$alkyl)carbonylamino, $C_{1-6}$alkoxycarbonylamino, aminocarbonyl($C_{1-6}$)alkoxy, ureido, thioureido, aminosulfonyl, $C_{1-6}$alkylsulfonyl, $C_{1-6}$alkylsulfonylamino, aminosulfonyloxy, ($C_{1-6}$alkyl)aminosulfonyloxy, di($C_{1-6}$alkyl)aminosulfonyloxy, aminosulfonylamino, ($C_{1-6}$alkyl)aminosulfonylamino, di($C_{1-6}$alkyl)aminosulfonylamino, ($R_{200}$)($R_a$)aminocarbonyl-($R_c$)amino, $R_{200}$-carbonylamino, $R_{200}$oxycarbonyl-($R_a$)amino, ($R_{200}$)($R_a$)aminocarbonyloxy, $R_{200}$oxysulfonyl-($R_a$)amino, $R_{200}$sulfonyl-($R_a$)amino, ($R_{200}$)($R_a$)aminosulfonyloxy, and ($R_{200}$)($R_a$)aminosulfonyl-($R_c$)amino;

X and Y are independently O or S;

and enantiomers, diastereomers, tautomers, solvates, and pharmaceutically acceptable salts thereof;

provided that the compound of Formula (II) is other than a compound wherein D is phenyl, L is absent, $R_1$ is (R)-methyl, A is piperazinyl, E is H, X is O, Y is O, $L_2$ is —CH$_2$—, and B is 3-hydroxy-4-methoxy-phenyl;

a compound wherein D is 2-hydroxy-5-chloro-phenyl, L is absent, $R_1$ is H, A is piperazinyl, E is H, X is O, Y is O, $L_2$ is —CH$_2$—, and B is 3,4-dimethoxy-phenyl;

a compound of wherein D is 3-methoxy-phenyl, L is absent, $R_1$ is H, A is piperazinyl, E is H, X is O, Y is O, $L_2$ is —CH$_2$—, and B is 3,4-dimethoxy-phenyl;

a compound wherein D is 4-ethyl-phenyl, L is absent, $R_1$ is H, A is piperazinyl, E is H, X is O, Y is O, $L_2$ is —CH$_2$—, and B is 3,4-dimethoxy-phenyl;

a compound wherein D is 6,6-dimethyl-bicyclo[3.1.1]hept-2-ene-2-methyl, L is absent, $R_1$ is H, A is piperazinyl, E is H, X is O, Y is O, $L_2$ is —CH$_2$—, and B is 3,4-dimethoxy-phenyl;

a compound wherein D is 2,6-dichloro-phenyl, L is absent, $R_1$ is H, A is piperazinyl, E is H, X is O, Y is O, $L_2$ is —CH$_2$—, and B is 3,4-dimethoxy-phenyl;

a compound wherein D is 2-chloro-4-fluoro-phenyl, L is absent, $R_1$ is H, A is piperazinyl, E is H, X is O, Y is O, $L_2$ is —CH$_2$—, and B is 3,4-dimethoxy-phenyl;

a compound wherein D is phenyl, L is absent, $R_1$ is H, A is cis-(1,4)-2,5-diazabicyclo[2.2.1]heptan-2-yl, E is H, X is O, Y is O, $L_2$ is —CH$_2$—, and B is 3,4-dimethoxy-phenyl;

a compound wherein D is phenyl, L is absent, $R_1$ is H, A is cis-(1,2)-cyclohexyldiamino, E is H, X is O, Y is O, $L_2$ is —CH$_2$—, and B is 3,4-dimethoxy-phenyl;

a compound wherein D is phenyl, L is absent, $R_1$ is (R)-methyl, A is piperazinyl, E is H, X is O, Y is O, $L_2$ is —CH(R-carboxymethyl)-, and B is 3,4-dimethoxy-phenyl; or a compound wherein D is phenyl, L is absent, $R_1$ is (R)-methyl, A is piperazinyl, E is H, X is O, Y is O, $L_2$ is —CH$_2$—, and B is 3-(n-propyloxy)-4-methoxy-phenyl.

Example 2 of the present invention is directed to an embodiment wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, and 86, as described herein, are excluded from the genus of Formula (II) described herein above.

Example 2a of the present invention is directed to an embodiment wherein compounds where $R_2$ is H are excluded from the genus of Formula (II) described herein above.

Illustrative of the invention is a pharmaceutical composition comprising a pharmaceutically acceptable carrier and a compound of Formula (I) or Formula (II). Illustrative of the invention is a process for making a pharmaceutical composition comprising mixing a compound of Formula (I) or Formula (II) and a pharmaceutically acceptable carrier.

The present invention is further directed to methods for treating or ameliorating a Urotensin II-mediated disorder. In particular, the method of the present invention is directed to treating or ameliorating a Urotensin II-mediated disorder including, but not limited to, vascular hypertension, heart failure, atherosclerosis, renal failure, nephrotoxicity and diarrhea caused by anti-neoplastic agents, post-myocardial infarctin, pulmonary hypertension/fibrosis, diabetes, and CNS indications including pain, Alzheimer's, convulsions, depression, migraine, psychosis, anxiety, neuromuscular deficit, and stroke.

The present invention is also directed to methods for producing the instant compounds and pharmaceutical compositions and medicaments thereof.

DETAILED DESCRIPTION OF THE INVENTION

As used herein, with reference to substituents, the term "independently" means that when more than one of such substituent is possible, such substituents may be the same or different from each other.

The term "$C_{1-8}$alkyl" means a straight or branched chain hydrocarbon alkyl radical or alkyldiyl linking group, respectively, comprising from 1 to 8 carbon atoms, wherein the radical is derived by the removal of one hydrogen atom from a single carbon atom and the alkyldiyl linking group is derived by the removal of one hydrogen atom from each of two carbon atoms in the chain. Examples include methyl, ethyl, 1-propyl, 2-propyl, 1-butyl, 2-butyl, tertiary butyl (also referred to as t-butyl or tert-butyl), 1-pentyl, 2-pentyl, 3-pentyl, 1-hexyl, 2-hexyl, 3-hexyl and the like. Other examples include $C_{1-4}$alkyl groups. $C_{1-8}$alkyl is substituted on one or more available carbon chain atoms with one or more substituents where allowed by available valences.

The term "$C_{1-8}$alkylene" means a biradical substituent formed from an alkyl group, as defined herein, in which the biradical is formed by the removal of two hydrogen atoms.

The terms "$C_{2-8}$alkenyl" and "$C_{2-8}$alkynyl" mean straight or branched carbon chains having 2 to 8 carbon atoms or any number within this range, wherein a $C_{2-8}$alkenyl chain has at least one double bond in the chain and a $C_{2-8}$alkynyl chain has at least one triple bond in the chain.

The term "$C_{1-8}$alkoxy" means a straight or branched chain hydrocarbon alkyl radical or alkyldiyl linking group of the formula —O—$C_{1-8}$alkyl, comprising from 1 to 8 carbon atoms, wherein the alkyldiyl linking group is derived by the removal of one hydrogen atom from a carbon atom in the chain. Examples include methoxy, ethoxy, propoxy and the like. Other examples include $C_{1-4}$alkoxy and $C_{2-3}$alkenyloxy groups. $C_{1-8}$alkoxy is substituted on one or more available carbon chain atoms with one or more substituents where allowed by available valences.

The term "$C_{3-14}$cycloalkyl" means a saturated or partially unsaturated, monocyclic or polycyclic hydrocarbon ring system radical derived by the removal of one hydrogen atom from a single ring carbon atom. The term also includes $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$cycloalkyl, $C_{5-14}$cycloalkenyl or benzofused $C_{3-14}$cycloalkyl ring systems. Examples include cyclopropyl, cyclobutyl, cyclopentyl, cyclohexyl, cyclohexyl, cyclohexenyl, cycloheptyl, cyclooctyl, 1H-indenyl, indanyl, 9H-fluorenyl, tetrahydro-naphthalenyl, acenaphthenyl, adamantanyl, bicyclo[2.2.1]heptenyl and the like. $C_{3-14}$cycloalkyl radicals may be attached to a core molecule and further substituted on any atom where allowed by available valences.

The term "aryl" means monocyclic or bicyclic aromatic ring systems containing from 6 to 12 carbons in the ring. Examples include phenyl, biphenyl, naphthalene (also referred to as naphthalenyl and naphthyl), azulenyl, anthracenyl and the like. Aryl radicals may be attached to a core molecule and further substituted on any atom where allowed by available valences.

The term "hetero," when used as a prefix for a ring system, refers to the replacement of at least one carbon atom member in the ring system with a heteroatom selected from N, O, S, S(O), or $SO_2$. A hetero ring may have 1, 2, 3, or 4 carbon atom members replaced by a nitrogen atom. Alternatively, a ring may have 0, 1, 2, or 3 nitrogen atom members and 1 oxygen or sulfur atom member. Alternatively, up to two adjacent ring members may be heteroatoms, wherein one heteroatom is nitrogen and the other heteroatom is selected from N, S, or O.

The term "heterocyclyl" means a saturated or partially unsaturated monocyclic or polycyclic "hetero" ring system radical having a cycloalkyl ring as the core molecule. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl and the like.

The term "heterocyclyl" also includes a benzofused-heterocyclyl ring system radical and the like, such as indolinyl (also referred to as 2,3-dihydro-indolyl), benzo[1,3]dioxolyl (also referred to as 1,3-benzodioxolyl), 2,3-dihydro-1,4-benzodioxinyl, 2,3-dihydro-benzofuranyl, 1,2-dihydro-phthalazinyl and the like. Heterocyclyl radicals may be attached to a core molecule and further substituted on any atom where allowed by available valences.

The term "heteroaryl" means an aromatic monocyclic or polycyclic heterocyclyl radical. Heteroaryl ring systems include furyl, thienyl, pyrrolyl, oxazolyl, thiazolyl, 1H-imidazolyl, pyrazolyl, isoxazolyl, isothiazolyl, oxadiazolyl, triazolyl, thiadiazolyl, 1H-tetrazolyl, 2H-tetrazolyl, 1H-[1,2,3]triazolyl, 2H-[1,2,3]triazolyl, 4H-[1,2,4]triazolyl, pyridinyl, pyridazinyl, pyrimidinyl, pyrazinyl and the like. Heteroaryl radicals may be attached to a core molecule and further substituted on any atom where allowed by available valences.

The term "heteroaryl" also includes a benzofused-heteroaryl ring system radical and the like, such as indolizinyl, indolyl, indolinyl, azaindolyl, isoindolyl, benzo[b]furanyl, benzo[b]thienyl, indazolyl, azaindazolyl, benzoimidazolyl, benzothiazolyl, benzooxazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. Benzofused-heteroaryl radicals may be attached to a core molecule and further substituted on any atom where allowed by available valences.

The term "benzofused," when used as a prefix for a ring system, refers to a radical formed by any monocyclic radical fused with a benzene ring; the benzofused radical may be attached to a core molecule via either ring of the bicyclic system.

The term "$C_{1-8}$alkoxycarbonyl" means a radical of the formula: —C(O)—O—$C_{1-8}$alkyl. Examples include $C_{1-6}$alkoxycarbonyl.

The term "($C_{1-8}$alkoxycarbonyl)amino" means a radical of the formula: —NH—C(O)—O—$C_{1-8}$alkyl. Examples include ($C_{1-6}$alkoxycarbonyl)amino.

The term "($C_{1-6}$alkoxy-$C_{1-6}$alkylcarbonyl)amino" means a radical of the formula: —NH—C(O)—$C_{1-6}$alkyl-O—$C_{1-6}$alkyl.

The term "($C_{1-8}$alkyl)amino" means a radical of the formula: —NH—$C_{1-8}$alkyl. Examples include ($C_{1-3}$alkyl)amino.

The term "di($C_{1-8}$alkyl)amino" means a radical of the formula: —N($C_{1-8}$alkyl)$_2$. Examples include di($C_{1-3}$alkyl)amino.

The term "$C_{1-8}$alkylcarbonyl" means a radical of the formula: —C(O)—$C_{1-8}$alkyl. Examples include $C_{1-3}$alkylcarbonyl.

The term "$C_{1-8}$alkylthio" means a radical of the formula: —S—$C_{1-8}$alkyl.

The term "($C_{1-8}$alkylcarbonyl)amino" means a radical of the formula: —NH—C(O)—$C_{1-8}$alkyl. Examples include ($C_{1-6}$alkylcarbonyl)amino and ($C_{1-3}$alkylcarbonyl)amino.

The term "(amino-$C_{1-8}$alkylcarbonyl)amino" means a radical of the formula: —NH—C(O)—$C_{1-8}$alkyl-NH$_2$. Examples include ($C_{1-6}$alkylcarbonyl)amino and ($C_{1-3}$alkylcarbonyl)amino.

The term "[($C_{1-6}$alkyl)amino-$C_{1-6}$alkylcarbonyl]amino" means a radical of the formula: —NH—C(O)—$C_{1-6}$alkyl-NH—$C_{1-6}$alkyl.

The term "[di($C_{1-6}$alkyl)amino-$C_{1-6}$alkylcarbonyl]amino" means a radical of the formula: —NH—C(O)—$C_{1-6}$alkyl-N($C_{1-6}$alkyl)$_2$.

The term "$C_{1-6}$alkylcarbonyl-acetonitrile-carbonyl)amino" means a radical of the formula: —NH—C(O)—CH(CN)—C(O)—$C_{1-6}$alkyl.

The term "$C_{1-6}$alkylsulfonyl" means a radical of the formula: —SO$_2$—$C_{1-6}$alkyl.

The term "($C_{1-6}$alkylsulfonyl)amino" means a radical of the formula: —NH—SO$_2$—$C_{1-6}$alkyl.

The term "($C_{1-6}$alkylsulfonyl-$C_{1-6}$alkylsulfonyl)amino" means a radical of the formula: —NH—SO$_2$—$C_{1-6}$alkyl-SO$_2$—$C_{1-6}$alkyl.

The term "($C_{2-6}$alkenyl-sulfonyl)amino" means a radical of the formula: —NH—SO$_2$—$C_{2-6}$alkenyl.

The term "amino" means a radical of the formula: —NH$_2$.

The term "($C_{1-6}$alkyl)amino" means a radical of the formula: —NH—$C_{1-6}$alkyl. Examples include ($C_{1-4}$)alkylamino.

The term "di($C_{1-6}$alkyl)amino" means a radical of the formula: —N($C_{1-6}$alkyl)$_2$. Examples include di($C_{1-4}$)alkylamino.

The term "aminocarbonyl" means a radical of the formula: —C(O)—NH$_2$.

The term "aminocarbonyloxy" means a radical of the formula: —O—C(O)—NH$_2$.

The term "aminocarbonyl-$C_{1-6}$alkoxy" means a radical of the formula: —O—$C_{1-6}$alkyl-C(O)—NH$_2$.

The term "($C_{1-6}$alkyl)aminocarbonyl" means a radical of the formula: —C(O)—NH—$C_{1-6}$alkyl. Examples include ($C_{1-4}$)alkylaminocarbonyl.

The term "di($C_{1-6}$alkyl)aminocarbonyl" means a radical of the formula: —C(O)—N($C_{1-6}$alkyl)$_2$. Examples include di($C_{1-4}$)alkylaminocarbonyl.

The term "aminosulfonyl" means a radical of the formula: —SO$_2$—NH$_2$.

The term "($C_{1-6}$alkyl)aminosulfonyl" means a radical of the formula: —$SO_2$—NH—$C_{1-6}$alkyl. Examples include ($C_{1-4}$alkyl)aminosulfonyl.

The term "di($C_{1-6}$alkyl)aminosulfonyl" means a radical of the formula: —$SO_2$—N($C_{1-6}$alkyl)$_2$. Examples include di($C_{1-4}$alkyl)aminosulfonyl.

The term "aminosulfonylamino" means a radical of the formula: —NH—$SO_2$—$NH_2$.

The term "($C_{1-6}$alkyl)aminosulfonylamino" means a radical of the formula: —NH—$SO_2$—NH—$C_{1-6}$alkyl. Examples include ($C_{1-4}$alkyl)aminosulfonylamino.

The term "di($C_{1-6}$alkyl)aminosulfonylamino" means a radical of the formula: —NH—$SO_2$—N($C_{1-6}$alkyl)$_2$. Examples include di($C_{1-4}$alkyl)aminosulfonylamino.

The term "aminosulfonyloxy" means a radical of the formula: —O—$SO_2$—$NH_2$.

The term "($C_{1-6}$alkyl)aminosulfonyloxy" means a radical of the formula: —O—$SO_2$—NH—$C_{1-6}$alkyl. Examples include ($C_{1-4}$alkyl)aminosulfonyloxy.

The term "di($C_{1-6}$alkyl)aminosulfonyloxy" means a radical of the formula: —O—$SO_2$—N($C_{1-6}$alkyl)$_2$. Examples include di($C_{1-4}$alkyl)aminosulfonyloxy.

The term "(benzyl)amino" means a radical of the formula: —NH—$CH_2$-phenyl.

The term "[(benzyl)($C_{1-4}$alkyl)]amino" means a radical of the formula: —N($C_{1-4}$alkyl)-$CH_2$-phenyl.

The term "carboxy" means a radical of the formula: —C(O)OH.

The term "carboxy-$C_{1-8}$alkoxy" means a radical of the formula: —O—$C_{1-8}$alkyl-C(O)OH. Examples include carboxy-$C_{1-8}$alkoxy.

The term "aryl-$C_{1-6}$alkyl" means a radical of the formula: —$C_{1-6}$alkyl-aryl.

The term "aryl-sulfonyl" means a radical of the formula: —$SO_2$-aryl.

The term "heterocyclyloxy" means a radical of the formula: —O-heterocyclyl.

The term "heteroaryl-sulfonyl" means a radical of the formula: —$SO_2$-heteroaryl.

The term "oxy" means a radical of the formula: —O—.

The term "ureido" mean a radical of the formula: —NH—C(O)—$NH_2$; also referred to as "aminocarbonylamino."

The term "thioureido" means a radical of the formula: —NH—C(S)—$NH_2$.

The term "acetamidino" means a radical of the formula: —C(NH)—$NH_2$.

The term "guanidino" means a radical of the formula: —NH—C(NH)—$NH_2$.

The term "halogen" or "halo" means the group chloro, bromo, fluoro or iodo. Substituents that are substituted with multiple halogens are substituted in a manner that provides compounds, which are stable.

The term "trihalo-$C_{1-4}$alkyl" means a radical of the formula: —$C_{1-4}$alkyl(halo)$_3$, wherein one or more halogen atoms may be substituted on $C_{1-4}$alkyl where allowed by available valences.

The term "trihalo-$C_{1-4}$alkoxy" means a radical of the formula: —O—$C_{1-4}$alkyl(halo)$_3$, wherein one or more halogen atoms may be substituted on $C_{1-4}$alkyl where allowed by available valences.

The term "fluorinated ($C_{1-4}$)alkoxy" means a radical of the formula: —O—$C_{1-4}$alkyl(fluoro)$_n$, where n represents one or more halogen atoms substituted on $C_{1-4}$alkyl where allowed by available valences.

The term "(trihalo-$C_{1-4}$alkylcarbonyl)amino" means a radical of the formula: —NH—C(O)—$C_{1-4}$alkyl(halo)$_3$, wherein one or more halogen atoms may be substituted on $C_{1-4}$alkyl where allowed by available valences.

The term "hydroxysulfonyl" means a radical of the formula: —$SO_2$—OH.

The term "(hydroxysulfonyl)amino" means a radical of the formula: —NH—$SO_2$—OH.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment.

Thus, for example, a "phenyl-$C_{1-6}$alkyl-amino-carbonyl-$C_{1-6}$alkyl" substituent refers to a group of the formula:

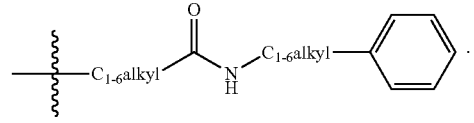

Further, when referring to substitution on the compound of Formula (I), the present invention uses the following numbering system to designate the point of attachment for substituents relative to the nitrogen atom of Formula (I):

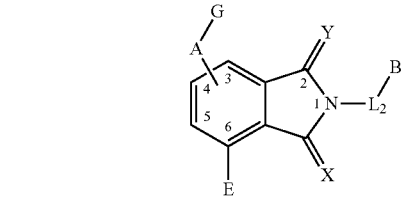

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "neoplasm" refers to an abnormal growth of cells or tissue and is understood to include benign, i.e., non-cancerous growths, and malignant, i.e., cancerous growths. The term "neoplastic" means of or related to neoplasm.

As used herein, the term "agent" is understood to mean a substance that produces a desired effect in a tissue, system, animal, mammal (in particular human), or other subject. Accordingly, the term "anti-neoplastic agent" is understood to mean a substance producing an anti-neoplastic effect in a tissue, system, animal, mammal (in particular human), or other subject. It is understood that an "agent" may be a single compound or a combination or composition of two or more compounds.

Some of the typical anti-neoplastic agents include alkylating agents such as melphalan, chlorambucil, cyclophosphamide, mechlorethamine, hexamethylmelamine, busulfan, carmustine, lomustine, and dacarbazine; antimetabolites such as 5-fluorouracil, methotrexate, cytarabine, mercaptopurine, and thioguanine; antimitotic agents such as paclitaxel, docetaxel, vinblastine, vincristine; topoisomerase I inhibitors such as irinotecan, camptothecin and camptothecin derivatives, for example topotecan; topoisomerase II inhibitors such as doxorubicin; and platinum coordination complexes such as cisplatin and carboplatin.

An example 3 of the present invention is directed to a compound of Formula (I) wherein:
when A is present, then G is selected from hydrogen, $C_{1-8}$alkyl, $C_{2-8}$alkenyl, $C_{3-14}$cycloalkyl or a —C[($R_1$)($R_{11}$)]-L-D moiety:

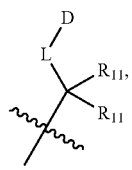

wherein $C_{1-8}$alkyl is optionally substituted with one, two or three fluoro substituents; or,
when A is absent and $R_2$ is other than benzyloxymethyl, then G is $C_{1-8}$alkoxy or heterocyclyloxy,
wherein $C_{1-8}$alkoxy is substituted with one of di($C_{1-8}$alkyl)amino, (benzyl)amino or [(benzyl)($C_{1-4}$alkyl)]amino, and
wherein heterocyclyloxy is optionally substituted on heterocyclyl with $C_{1-3}$alkyl;
$R_1$ is selected from the group consisting of hydrogen, $C_{1-8}$alkyl and $C_{2-8}$alkynyl;
$R_{11}$ is selected from the group consisting of hydrogen, $C_{1-8}$alkyl and cyclopropyl;
L is absent or $C_{1-4}$alkylene;
D is aryl (other than naphthalen-2-yl), $C_{3-14}$cycloalkyl or heteroaryl,
wherein aryl and heteroaryl are optionally substituted with one or two substitutents independently selected from the group consisting of $C_{1-3}$alkyl, $C_{1-3}$alkoxy, hydroxy, fluoro, chloro and cyano,
provided that D is other than 2-hydroxy-5-chloro-phenyl, 3-methoxy-phenyl, 4-ethyl-phenyl, 2,6-dichloro-phenyl and 2-chloro-4-fluoro-phenyl;
A is an optionally present biradical selected from the group consisting of a-1, optionally unsaturated a-2, a-3, a-4, optionally unsaturated a-5 and a-6,
wherein, the lower portion of A is attached, relative to the nitrogen atom of Formula (I), to the 3 or 4 position on the benzene ring portion of Formula (I);

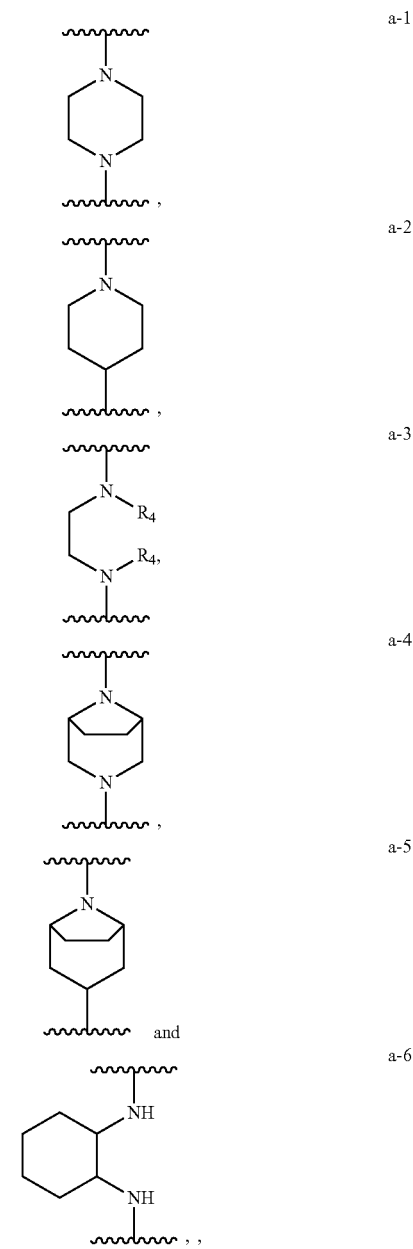

wherein a-1 is optionally substituted with two $C_{1-4}$alkyl substituents;
provided that A is other than cis-(1,2)-cyclohexyldiamino;
$R_4$ is hydrogen;
$L_2$ is absent or —C($R_2$)($R_5$)—($CR_6R_7$)$_r$—, wherein r is 0, 1 or 2; and wherein $R_5$, $R_6$, and $R_7$ are hydrogen,
provided that $L_2$ is other than —CH(R-carboxymethyl)-;

R₂ is selected from the group consisting of hydrogen, phenyl, and C₁₋₆alkyl, wherein phenyl is optionally substituted with (R₂₀₀—C₁₋₆alkyl)amino, or [(hydroxysulfonyl)(Rₐ)]amino, and wherein C₁₋₆alkyl is optionally substituted with carboxy, hydroxy, R₂₀₀, NRₐRᵦ, C₁₋₆alkoxy, R₂₀₀—C₁₋₆alkoxy, carboxy-C₁₋₆alkoxy, [(R₂₀₀—C₁₋₆alkyl)(Rₐ)]amino, (C₁₋₆alkylcarbonyl)amino, (trihalo-C₁₋₄alkylcarbonyl)amino, (R₂₀₀—C₁₋₆alkylcarbonyl)amino, (C₁₋₆alkoxycarbonyl)amino, (R₂₀₀—C₁₋₆alkoxycarbonyl)amino, (C₁₋₆alkoxy-C₁₋₆alkylcarbonyl)amino, (R₂₀₀-carbonyl)amino, [di(C₁₋₆alkyl)amino-C₁₋₆alkylcarbonyl]amino, (C₁₋₆alkylcarbonyl-acetonitrile-carbonyl)amino, acetamidino, guanidino, {[(R₂₀₀)(Rₐ)]aminocarbonyl-(R_c)}amino, (C₁₋₆alkylsulfonyl)amino, (R₂₀₀—C₁₋₆alkylsulfonyl)amino, (R₂₀₀—C₂₋₆alkenylsulfonyl)amino, (C₁₋₆alkylsulfonyl-C₁₋₆alkylsulfonyl)amino, R₂₀₀-sulfonyloxy, di(C₁₋₆alkyl)aminosulfonyloxy, aminosulfonylamino, [di(C₁₋₆alkyl)aminosulfonyl]amino, [(hydroxysulfonyl)(Rₐ)]amino or [(R₂₀₀-sulfonyl)(Rₐ)]amino;

Rₐ and R_c are independently selected from the group consisting of hydrogen and C₁₋₆alkyl; and Rᵦ is hydrogen, C₁₋₆alkyl, heteroaryl or heterocyclyl;

R₂₀₀ is C₆₋₁₀aryl, heteroaryl, C₃₋₈cycloalkyl, or heterocyclyl, each optionally substituted with one, two or three substituents independently selected from the group consisting of C₁₋₄alkyl, trihalo-C₁₋₄alkyl, C₁₋₄alkoxy, C₁₋₆alkylcarbonyl, C₁₋₆alkoxycarbonyl, (C₁₋₆alkylcarbonyl)amino, C₁₋₆alkylsulfonyl, hydroxysulfonyl, aminosulfonyl, chloro, fluoro, bromo, heteroaryl, aryl-C₁₋₆alkyl, aryl-sulfonyl and heteroaryl-sulfonyl, wherein heterocyclyl is optionally substituted with two oxo substituents;

B is C₆₋₁₀aryl, indanyl, or a heteroaryl selected from the group consisting of pyridin-2-yl, pyridin-4-yl, pyrazol-4-yl and imidazol-1-yl, wherein B is optionally substituted with one, two or three substituents independently selected from the group consisting of C₁₋₄alkyl, C₁₋₄alkoxy, halogen, and hydroxy, provided that when B is selected from the group consisting of C₆₋₁₀aryl and indanyl, then B is independently substituted with two substituents selected from the group consisting of C₁₋₃alkoxy and hydroxy, and provided that B is other than 3-hydroxy-4-methoxy-phenyl and 3-(n-propyloxy)-4-methoxy-phenyl;

E is hydrogen, halogen or —CH═CH-sulfonyl-C₁₋₆alkyl;

X and Y are O;

and enantiomers, diastereomers, tautomers, solvates, and pharmaceutically acceptable salts thereof.

Example 3a of the present invention is directed to an embodiment wherein Compounds 5, 12, 16, 17, 22, 23, 24, 29, 31, 33, 36, 38, 40, 44, 46, 47, 55, 56, 57, 77, 78, 79, 80, 81, 82, 83, 84, 85, 86 and 87, as described herein, are excluded from Example 3 described herein above.

Example 3b of the present invention is directed to an embodiment wherein compounds where R₂ is H are excluded from Example 3 described hereinabove.

An example 4 of the present invention is directed to a compound of Formula (I) wherein:

when A is present, then G is selected from hydrogen, C₁₋₈alkyl, C₂₋₈alkenyl, C₃₋₁₄cycloalkyl or a —C[(R₁)(R₁₁)]-L-D moiety:

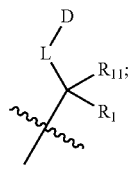

or, when A is absent and R₂ is other than benzyloxymethyl, then G is C₁₋₈alkoxy, wherein C₁₋₈alkoxy is substituted with one of di(C₁₋₈alkyl)amino;

R₁ is selected from the group consisting of hydrogen, C₁₋₈alkyl and C₂₋₈alkynyl;

R₁₁ is hydrogen;

L is absent or C₁₋₄alkylene;

D is aryl (other than naphthalen-2-yl), C₃₋₁₄cycloalkyl or heteroaryl, wherein aryl and heteroaryl are optionally substituted with one or two substituents independently selected from the group consisting of C₁₋₃alkyl or fluoro, provided that D is other than 4-ethyl-phenyl;

A is an optionally present biradical selected from the group consisting of a-1, a-2 and a-4, wherein, the lower portion of A is attached, relative to the nitrogen atom of Formula (I), to the 3 position on the benzene ring portion of Formula (I);

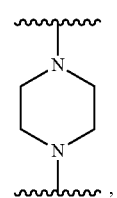

a-1

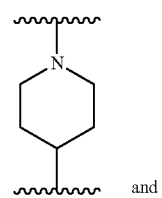

a-2 and

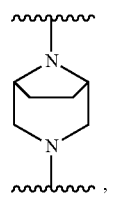

a-4

L₂ is —CH(R₂)—;

R₂ is selected from the group consisting of hydrogen, phenyl, and C₁₋₆alkyl, wherein phenyl is optionally substituted with (R₂₀₀—C₁₋₆alkyl)amino, or [(hydroxysulfonyl)(Rₐ)]amino, and wherein C₁₋₆alkyl is optionally substituted with hydroxy, R₂₀₀, NRₐRᵦ, C₁₋₆alkoxy, R₂₀₀—C₁₋₆alkoxy, carboxy-C₁₋₆alkoxy, [(R₂₀₀—C₁₋₆alkyl)(Rₐ)]amino, (C₁₋₆alkylcarbonyl)amino, (trihalo-C₁₋₄alkylcarbonyl)amino, (R₂₀₀—C₁₋₆alkylcarbonyl)amino, (C₁₋₆alkoxycarbonyl)amino, (R₂₀₀—C₁₋₆alkoxycarbonyl)amino, (C₁₋₆alkoxy-C₁₋₆ alkylcarbonyl)amino, $(R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, $\{[(R_{200})(R_a)]$aminocarbonyl-$(R_c)\}$amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [(hydroxysulfonyl)($R_a$)]amino or [($R_{200}$-sulfonyl)($R_a$)]amino;

$R_a$ and $R_c$ are independently selected from the group consisting of hydrogen and $C_{1-6}$alkyl; and $R_b$ is hydrogen, $C_{1-6}$alkyl, heteroaryl or heterocyclyl;

$R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, heteroaryl, aryl-$C_{1-6}$alkyl, aryl-sulfonyl and heteroaryl-sulfonyl, wherein heterocyclyl is optionally substituted with two oxo substituents;

B is $C_{6-10}$aryl or indanyl each substituted with two substituents independently selected from the group consisting of $C_{1-4}$alkoxy and hydroxy, provided that B is other than 3-hydroxy-4-methoxy-phenyl and 3-(n-propyloxy)-4-methoxy-phenyl;

E is hydrogen, halogen or —CH=CH-sulfonyl-$C_{1-6}$alkyl;

X and Y are O;

and enantiomers, diastereomers, tautomers, solvates, and pharmaceutically acceptable salts thereof.

Example 4a of the present invention is directed to an embodiment wherein Compounds 5, 12, 16, 17, 22, 24, 29, 33, 36, 40, 46, 77, 78, 79, 80, 81, 82, 83, 84, 86 and 87, as described herein, are excluded from Example 4 described herein above.

Example 4b of the present invention is directed to an embodiment wherein compounds where $R_2$ is H are excluded from Example 4 described hereinabove.

An example 5 of the present invention is directed to a compound of Formula (I) wherein:

when A is present, then G is selected from hydrogen, $C_{1-8}$alkyl, $C_{2-8}$alkenyl, indanyl, adamantanyl, cyclobutyl, cyclopentyl, cyclohexyl or a —C[($R_1$)($R_{11}$)]-L-D moiety:

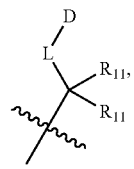

wherein $C_{1-8}$alkyl is optionally substituted with one, two or three fluoro substituents, and wherein indanyl, adamantanyl, cyclobutyl, cyclopentyl and cyclohexyl are optionally substituted with one, two or three $C_{1-3}$alkyl substituents; or, when A is absent and $R_2$ is other than benzyloxymethyl, then G is $C_{1-8}$alkoxy, pyrrolidinyl-oxy, or piperidinyl-oxy, wherein $C_{1-8}$alkoxy is substituted with one of amino, ($C_{1-8}$alkyl)amino, di($C_{1-8}$alkyl)amino, (benzyl)amino or [(benzyl)($C_{1-4}$alkyl)]amino, and wherein pyrrolidinyl-oxy and piperidinyl-oxy are optionally substituted on pyrrolidinyl and piperidinyl with one, two or three $C_{1-3}$alkyl substituents;

$R_1$ is selected from the group consisting of hydrogen, $C_{1-8}$alkyl, $C_{2-8}$alkenyl, and $C_{2-8}$alkynyl;

$R_{11}$ is selected from the group consisting of hydrogen, $C_{1-8}$alkyl and cyclopropyl;

L is absent or $C_{1-4}$alkylene;

D is selected from phenyl, cyclopentyl, $C_{5-14}$cycloalkenyl, heterocyclyl, furanyl, thienyl or pyridinyl, wherein phenyl and furanyl are optionally substituted with one, two, three or four substitutents independently selected from the group consisting of $C_{1-3}$alkyl, $C_{1-3}$alkoxy, $C_{2-8}$alkenyl, $C_{2-3}$alkenyloxy, hydroxy, $C_{1-3}$alkylthio, fluoro, chloro, cyano, $C_{1-3}$alkylcarbonyl, ($C_{1-3}$alkylcarbonyl)amino, ($C_{1-3}$alkyl)amino, di($C_{1-3}$alkyl)amino and $C_{3-14}$cycloalkyl, wherein $C_{3-14}$cycloalkyl is optionally substituted with one, two, three or four $C_{1-3}$alkyl substituents, provided that D is other than 2-hydroxy-5-chloro-phenyl, 3-methoxy-phenyl, 4-ethyl-phenyl, 6,6-dimethyl-bicyclo[3.1.1]hept-2-en-2-yl-methyl, cyclohex-3-enyl, 2,6-dichloro-phenyl and 2-chloro-4-fluoro-phenyl;

A is an optionally present biradical selected from the group consisting of a-1, optionally unsaturated a-2, a-3, a-4, optionally unsaturated a-5 and a-6, wherein, the lower portion of A is attached, relative to the nitrogen atom of Formula (I), to the 3 or 4 position on the benzene ring portion of Formula (I);

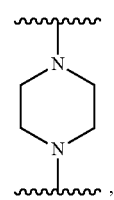

a-1

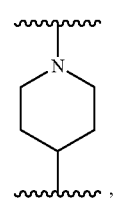

a-2

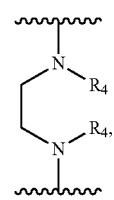

a-3

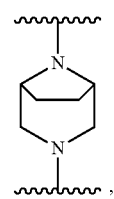

a-4

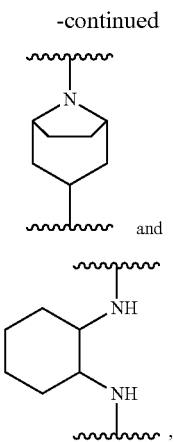

wherein a-1, a-2, a-3, a-4 and a-5 are optionally substituted with one to two $C_{1-4}$alkyl substituents;

provided that A is other than cis-(1,2)-cyclohexyldiamino;

$R_4$ is hydrogen or $C_{1-8}$alkyl;

$L_2$ is absent or —C($R_2$)($R_5$)—(C$R_6$$R_7$)$_r$—, wherein r is 0, 1 or 2; and wherein $R_5$, $R_6$, and $R_7$ are independently hydrogen or $C_{1-3}$alkyl;

provided that $L_2$ is other than —CH(R-carboxymethyl)-;

$R_2$ is selected from the group consisting of hydrogen, a heteroaryl that is not fused to another ring, phenyl, and $C_{1-6}$alkyl, wherein phenyl is optionally substituted with ($R_{200}$—$C_{1-6}$alkyl)amino, or [(hydroxysulfonyl)($R_a$)]amino, and wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, $R_{200}$-oxy, aminocarbonyl, carboxy-$C_{1-6}$alkoxy, aminocarbonyl-$C_{1-6}$alkoxy, ($C_{1-6}$alkyl)aminocarbonyl, di($C_{1-6}$alkyl)aminocarbonyl, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, (amino-$C_{1-6}$alkylcarbonyl)amino, [($C_{1-6}$alkyl)amino-$C_{1-6}$alkylcarbonyl]amino, [di($C_{1-6}$alkyl)amino-$C_{1-6}$alkylcarbonyl]amino, ($C_{1-6}$alkylcarbonyl-acetamidino-carbonyl)amino, ureido, thioureido, acetamidino, guanidino, {[($R_{200}$)($R_a$)]aminocarbonyl-($R_c$)}amino, [($R_{200}$-oxycarbonyl)($R_a$)]amino, [($R_{200}$)($R_a$)]aminocarbonyloxy, aminosulfonyl, $C_{1-6}$alkylsulfonyl, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, aminosulfonyloxy, ($C_{1-6}$alkyl)aminosulfonyloxy, di($C_{1-6}$alkyl)aminosulfonyloxy, aminosulfonylamino, ($C_{1-6}$alkyl)aminosulfonylamino, [di($C_{1-6}$alkyl)aminosulfonyl]amino, [(hydroxysulfonyl)($R_a$)]amino, [($R_{200}$-oxysulfonyl)($R_a$)]amino, [($R_{200}$-sulfonyl)($R_a$)]amino, [($R_{200}$)($R_a$)]aminosulfonyloxy, or ({[($R_{200}$)($R_a$)]aminosulfonyl}($R_c$))amino;

$R_a$ and $R_c$ are independently selected from the group consisting of hydrogen and $C_{1-6}$alkyl; and $R_b$ is hydrogen, $C_{1-6}$alkyl, $C_{6-10}$aryl, pyridinyl, pyrimidinyl, $C_{3-8}$cycloalkyl, piperidinyl or 4,5-dihydro-1H-pyrrolyl;

$R_{200}$ is phenyl, furanyl, thienyl, pyrrolyl, imidazolyl, pyrazolyl, isoxazolyl, thiazolyl, pyridinyl, pyridazinyl, quinolinyl, benzothienyl, benzoimidazolyl, imidazo[2,1-b]thiazolyl, cyclobutyl, cyclopentyl, tetrahydro-furanyl, tetrahydro-thienyl, pyrrolidinyl, or piperidinyl, each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, aryl, isoxazolyl, phenyl-$C_{1-6}$alkyl, phenyl-sulfonyl and thienyl-sulfonyl, wherein tetrahydro-thienyl is optionally substituted with one, two or three oxo substituents;

B is phenyl, tetralinyl, indanyl, or a heteroaryl selected from the group consisting of pyridin-2-yl, pyridin-4-yl, pyrazol-4-yl, pyrimidin-4-yl, pyrimidin-5-yl, pyrazin-2-yl, imidazol-1-yl, thien-2-yl, isoquinolinyl, indolyl, quinolinyl, and thiazol-5-yl, wherein B is optionally substituted with one, two or three substituents independently selected from the group consisting of $C_{1-4}$alkyl, $C_{1-4}$alkoxy, fluorinated ($C_{1-4}$)alkoxy, halogen, cyano, hydroxy, aminocarbonyl, ($C_{1-4}$)alkylaminocarbonyl, di($C_{1-4}$)alkylaminocarbonyl, aminosulfonyl, ($C_{1-4}$)alkylaminosulfonyl, di($C_{1-4}$alkylaminosulfonyl, hydroxysulfonyl, aminosulfonylamino, ($C_{1-4}$)alkylaminosulfonylamino, di($C_{1-4}$)alkylaminosulfonylamino, aminosulfonyloxy, ($C_{1-4}$)alkylaminosulfonyloxy, and di($C_{1-4}$alkylaminosulfonyloxy, provided that when B is selected from the group consisting of phenyl, tetralinyl, indanyl, thien-2-yl, and indolyl, then B is independently substituted with two to three substitutents selected from the group consisting of $C_{1-3}$alkoxy and hydroxy, provided that, when B is phenyl substituted at the 3,4-, 3,5- or 4,5-positions with an unbranched $C_{1-3}$alkoxy substituent at each position, then phenyl may be further optionally substituted at a remaining open 3-, 4-, or 5-position with an additional $C_{1-3}$alkoxy or hydroxy substituent, and provided that B is other than 3-hydroxy-4-methoxy-phenyl and 3-(n-propyloxy)-4-methoxy-phenyl;

E is hydrogen, halogen, $C_{1-3}$alkoxy, $C_{2-5}$alkyl-$R_E$, or —CH═CH—$C_{0-3}$alkyl-$R_E$;

wherein $R_E$ is selected from the group consisting of carboxy, amino, ($C_{1-6}$alkyl)amino, di($C_{1-6}$alkyl)amino, aminocarbonyl, ($C_{1-6}$alkyl)aminocarbonyl, di($C_{1-6}$alkyl)aminocarbonyl, ($C_{1-6}$alkyl)carbonylamino, $C_{1-6}$alkoxycarbonylamino, aminocarbonyl($C_{1-6}$)alkoxy, ureido, thioureido, aminosulfonyl, $C_{1-6}$alkylsulfonyl, $C_{1-6}$alkylsulfonylamino, aminosulfonyloxy, ($C_{1-6}$alkyl)aminosulfonyloxy, di($C_{1-6}$alkyl)aminosulfonyloxy, aminosulfonylamino, ($C_{1-6}$alkyl)aminosulfonylamino, di($C_{1-6}$alkyl)aminosulfonylamino, ($R_{200}$)($R_a$)aminocarbonyl-($R_c$)amino, $R_{200}$-carbonylamino, $R_{200}$oxycarbonyl-($R_a$)amino, ($R_{200}$)($R_a$)aminocarbonyloxy, $R_{200}$oxysulfonyl-($R_a$)amino, $R_{200}$sulfonyl-($R_a$)amino, ($R_{200}$)($R_a$)aminosulfonyloxy, and ($R_{200}$)($R_a$)aminosulfonyl-($R_c$)amino;

X and Y are independently O or S;

and enantiomers, diastereomers, tautomers, solvates, and pharmaceutically acceptable salts thereof.

Example 5a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 5 described herein above.

Example 5b of the present invention is directed to an embodiment wherein compounds where $R_2$ is H are excluded from Example 5 described hereinabove.

An example 6 of the present invention is directed to a compound of Formula (I) wherein when A is present, then G is selected from hydrogen, $C_{1-8}$alkyl, $C_{2-8}$alkenyl, indanyl, adamantanyl, cyclobutyl, cyclopentyl, cyclohexyl, or a —C[($R_1$)($R_{11}$)]-L-D moiety:

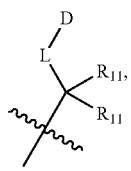

wherein $C_{1-8}$alkyl is optionally substituted with three fluoro substituents; or, when A is absent and $R_2$ is other than benzyloxymethyl, then G is $C_{1-8}$alkoxy, pyrrolidinyl-oxy, or piperidinyl-oxy, wherein $C_{1-8}$alkoxy is substituted with one of di($C_{1-8}$alkyl)amino, (benzyl)amino or [(benzyl)($C_{1-4}$alkyl)]amino, and wherein pyrrolidinyl-oxy and piperidinyl-oxy are optionally substituted on pyrrolidinyl and piperidinyl with one, two or three $C_{1-3}$alkyl substituents;

$R_1$ is selected from the group consisting of hydrogen, $C_{1-8}$alkyl and $C_{2-8}$alkynyl;

$R_{11}$ is selected from the group consisting of hydrogen, $C_{1-8}$alkyl and cyclopropyl;

L is absent or $C_{1-4}$alkylene;

D is selected from phenyl, cyclopentyl, furanyl, thienyl, or pyridinyl, wherein phenyl and furanyl are optionally substituted with one or two substitutents independently selected from the group consisting of $C_{1-3}$alkyl, $C_{1-3}$alkoxy, hydroxy, fluoro, chloro and cyano, provided that D is other than 2-hydroxy-5-chloro-phenyl, 3-methoxy-phenyl, 4-ethyl-phenyl, 2,6-dichloro-phenyl and 2-chloro-4-fluoro-phenyl;

A is an optionally present biradical selected from the group consisting of a-1, optionally unsaturated a-2, a-3, a-4, optionally unsaturated a-5 and a-6, wherein, the lower portion of A is attached, relative to the nitrogen atom of Formula (I), to the 3 or 4 position on the benzene ring portion of Formula (I);

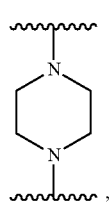
a-1

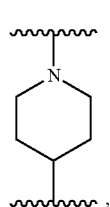
a-2

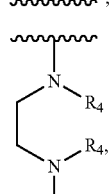
a-3

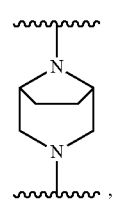
a-4

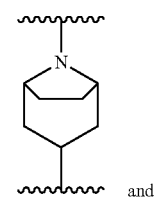
a-5

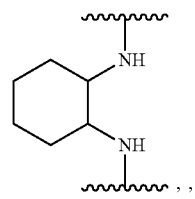
a-6 wherein a-1 is optionally substituted with two $C_{1-4}$alkyl substituents;

provided that A is other than cis-(1,2)-cyclohexyldiamino;

$R_4$ is hydrogen;

$L_2$ is absent or —C($R_2$)($R_5$)—($CR_6R_7$)$_r$—, wherein r is 0, 1 or 2; and wherein $R_5$, $R_6$, and $R_7$ are hydrogen;

provided that $L_2$ is other than —CH(R-carboxymethyl)-;

$R_2$ is selected from the group consisting of hydrogen, phenyl, and $C_{1-6}$alkyl, wherein phenyl is optionally substituted with ($R_{200}$—$C_{1-6}$alkyl)amino, or [(hydroxysulfonyl)($R_a$)]amino, and wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, carboxy-$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, {[($R_{200}$)($R_a$)]aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [(hydroxysulfonyl)($R_a$)]amino or [($R_{200}$-sulfonyl)($R_a$)]amino;

$R_a$ and $R_c$ are independently selected from the group consisting of hydrogen and $C_{1-6}$alkyl; and $R_b$ is hydrogen, $C_{1-6}$alkyl, pyridinyl, pyrimidinyl, piperidinyl or 4,5-dihydro-1H-pyrrolyl;

$R_{200}$ is phenyl, furanyl, thienyl, pyrrolyl, imidazolyl, pyrazolyl, isoxazolyl, thiazolyl, pyridinyl, pyridazinyl, quinolinyl, benzothienyl, benzoimidazolyl, imidazo[2,1-b]thiazolyl, cyclobutyl, cyclopentyl, tetrahydro-furanyl, tetrahydro-thienyl, pyrrolidinyl, or piperidinyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, isoxazolyl, phenyl-$C_{1-6}$alkyl, phenyl-sulfonyl and thienyl-sulfonyl,
wherein tetrahydro-thienyl is optionally substituted with two oxo substituents;
B is phenyl, indanyl, or a heteroaryl selected from the group consisting of pyridin-2-yl, pyridin-4-yl, pyrazol-4-yl and imidazol-1-yl,
wherein B is optionally substituted with two or three substituents independently selected from the group consisting of $C_{1-4}$alkyl, $C_{1-4}$alkoxy, halogen and hydroxy,
provided that when B is selected from the group consisting of phenyl, and indanyl, then B is independently substituted with two substituents selected from the group consisting of $C_{1-3}$alkoxy and hydroxy, and
provided that B is other than 3-hydroxy-4-methoxy-phenyl and 3-(n-propyloxy)-4-methoxy-phenyl;
E is hydrogen, halogen or —CH═CH-sulfonyl-$C_{1-6}$alkyl;
X and Y are O;
and enantiomers, diastereomers, tautomers, solvates, and pharmaceutically acceptable salts thereof.

Example 6a of the present invention is directed to an embodiment wherein wherein Compounds 5, 12, 16, 17, 22, 23, 24, 29, 31, 33, 36, 38, 40, 44, 46, 47, 55, 56, 57, 77, 78, 79, 80, 81, 82, 83, 84, 85, 86 and 87, as described herein, are excluded from Example 6 described herein above.

Example 6b of the present invention is directed to an embodiment wherein compounds where $R_2$ is H are excluded from Example 6 described hereinabove.

An example 7 of the present invention is directed to a compound of Formula (I) wherein
when A is present, then G is selected from hydrogen, $C_{1-8}$alkyl, $C_{2-8}$alkenyl, adamantanyl, cyclobutyl, cyclohexyl, or a —C[($R_1$)($R_{11}$)]-L-D moiety:

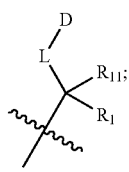

or,
when A is absent and $R_2$ is other than benzyloxymethyl, then G is $C_{1-8}$alkoxy,
wherein $C_{1-8}$alkoxy is substituted with one of di($C_{1-8}$alkyl)amino;
$R_1$ is selected from the group consisting of hydrogen, $C_{1-8}$alkyl and $C_{2-8}$alkynyl;
$R_{11}$ is hydrogen;
L is absent or $C_{1-4}$alkylene;
D is selected from phenyl, cyclopentyl, furanyl, thienyl, or pyridinyl,
wherein phenyl and furanyl are optionally substituted with one or two substituents independently selected from the group consisting of $C_{1-3}$alkyl and fluoro,
provided that D is other than 4-ethyl-phenyl;
A is an optionally present biradical selected from the group consisting of a-1, a-2 and a-4,
wherein, the lower portion of A is attached, relative to the nitrogen atom of Formula (I), to the 3 position on the benzene ring portion of Formula (I);

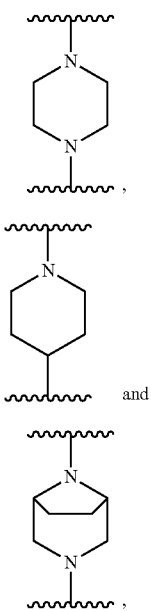

wherein a-1 is optionally substituted with two $C_{1-4}$alkyl substituents;
$L_2$ is —CH($R_2$)—;
$R_2$ is selected from the group consisting of hydrogen, phenyl, and $C_{1-6}$alkyl,
wherein phenyl is optionally substituted with ($R_{200}$—$C_{1-6}$alkyl)amino, or [(hydroxysulfonyl)($R_a$)]amino, and
wherein $C_{1-6}$alkyl is optionally substituted with hydroxy, $R_{200}$, $NR_aR_b$, $C_{1-6}$alkoxy, $R_{200}$—$C_{1-6}$alkoxy, carboxy-$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, {[($R_{200}$)($R_a$)]aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [(hydroxysulfonyl)($R_a$)]amino or [($R_{200}$-sulfonyl)($R_a$)]amino;
$R_a$ and $R_c$ are independently selected from the group consisting of hydrogen and $C_{1-6}$alkyl; and $R_b$ is hydrogen, $C_{1-6}$alkyl, pyridinyl, pyrimidinyl, piperidinyl or 4,5-dihydro-1H-pyrrolyl;
$R_{200}$ is phenyl, furanyl, thienyl, pyrrolyl, imidazolyl, pyrazolyl, isoxazolyl, thiazolyl, pyridinyl, pyridazinyl, quinolinyl, benzoimidazolyl, imidazo[2,1-b]thiazolyl, cyclobutyl, cyclopentyl, tetrahydro-furanyl, tetrahydro-thienyl, pyrrolidinyl, or piperidinyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, isoxazolyl, phenyl-$C_{1-6}$alkyl, phenyl-sulfonyl and thienyl-sulfonyl,
wherein tetrahydro-thienyl is optionally substituted with two oxo substituents;

B is phenyl or indanyl each substituted with two substituents independently selected from the group consisting of $C_{1-4}$alkoxy and hydroxy, provided that B is other than 3-hydroxy-4-methoxy-phenyl and 3-(n-propyloxy)-4-methoxy-phenyl;

E is hydrogen, halogen or —CH═CH-sulfonyl-$C_{1-6}$alkyl;

X and Y are O;

and enantiomers, diastereomers, tautomers, solvates, and pharmaceutically acceptable salts thereof.

Example 7a of the present invention is directed to an embodiment wherein wherein Compounds 5, 12, 16, 17, 22, 24, 29, 33, 36, 40, 46, 77, 78, 79, 80, 81, 82, 83, 84, 86 and 87, as described herein, are excluded from Example 7 described herein above.

Example 7b of the present invention is directed to an embodiment wherein compounds where $R_2$ is H are excluded from Example 7 described hereinabove.

An example 8 of the present invention is directed to a compound of Formula (I) wherein when A is present, then G is selected from hydrogen, $C_{1-8}$alkyl, $C_{2-8}$alkenyl, $C_{3-14}$cycloalkyl or a —C[($R_1$)($R_{11}$)]-L-D moiety:

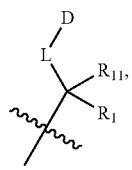

wherein $C_{1-8}$alkyl is optionally substituted with one, two or three fluoro substituents; or, when A is absent and $R_2$ is other than benzyloxymethyl, then G is $C_{1-8}$alkoxy or heterocyclyloxy, wherein $C_{1-8}$alkoxy is substituted with one of di($C_{1-8}$alkyl)amino, (benzyl)amino or [(benzyl)($C_{1-4}$alkyl)]amino, and wherein heterocyclyloxy is optionally substituted on heterocyclyl with $C_{1-3}$alkyl.

Example 8a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 8 described herein above.

Example 8b of the present invention is directed to an embodiment wherein compounds where $R_2$ is H are excluded from Example 8 described hereinabove.

An example 9 of the present invention is directed to a compound of Formula (I) wherein when A is present, then G is selected from hydrogen, $C_{1-8}$alkyl, $C_{2-8}$alkenyl, $C_{3-14}$cycloalkyl or a —C[($R_1$)($R_{11}$)]-L-D moiety:

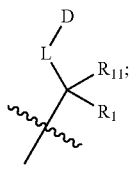

or, when A is absent and $R_2$ is other than benzyloxymethyl, then G is $C_{1-8}$alkoxy, wherein $C_{1-8}$alkoxy is substituted with one of di($C_{1-8}$alkyl)amino.

Example 9a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 9 described herein above.

Example 9b of the present invention is directed to an embodiment wherein compounds where $R_2$ is H are excluded from Example 9 described hereinabove.

An example 10 of the present invention is directed to a compound of Formula (I) wherein when A is present, then G is selected from hydrogen, $C_{1-8}$alkyl, $C_{2-8}$alkenyl, indanyl, adamantanyl, cyclobutyl, cyclopentyl, cyclohexyl or a —C[($R_1$)($R_{11}$)]-L-D moiety:

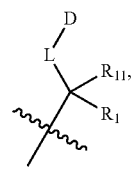

wherein $C_{1-8}$alkyl is optionally substituted with one, two or three fluoro substituents, wherein indanyl, adamantanyl, cyclobutyl, cyclopentyl and cyclohexyl are optionally substituted with one, two or three $C_{1-3}$alkyl substituents; or, when A is absent and $R_2$ is other than benzyloxymethyl, then G is $C_{1-8}$alkoxy, pyrrolidinyl-oxy, or piperidinyl-oxy, wherein $C_{1-8}$alkoxy is substituted with one of amino, ($C_{1-8}$alkyl)amino, di($C_{1-8}$alkyl)amino, (benzyl)amino or [(benzyl)($C_{1-4}$alkyl)]amino, and wherein pyrrolidinyl-oxy and piperidinyl-oxy are optionally substituted on pyrrolidinyl and piperidinyl with one, two or three $C_{1-3}$alkyl substituents.

Example 10a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 10 described herein above.

Example 10b of the present invention is directed to an embodiment wherein compounds where $R_2$ is H are excluded from Example 10 described hereinabove.

An example 11 of the present invention is directed to a compound of Formula (I) wherein when A is present, then G is selected from hydrogen, $C_{1-8}$alkyl, $C_{2-8}$alkenyl, adamantanyl, cyclobutyl, cyclohexyl or a —C[($R_1$)($R_{11}$)]-L-D moiety:

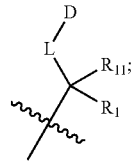

or, when A is absent and $R_2$ is other than benzyloxymethyl, then G is $C_{1-8}$alkoxy, wherein $C_{1-8}$alkoxy is substituted with one of di($C_{1-8}$alkyl)amino.

Example 11a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 11 described herein above.

Example 11b of the present invention is directed to an embodiment wherein compounds where $R_2$ is H are excluded from Example 11 described hereinabove.

An example 12 of the present invention is directed to a compound of Formula (I) wherein D is aryl (other than naphthalen-2-yl), $C_{3-14}$cycloalkyl or heteroaryl, wherein aryl and heteroaryl are optionally substituted with one or two substitutents independently selected from the group consisting of $C_{1-3}$alkyl, $C_{1-3}$alkoxy, hydroxy, fluoro, chloro and cyano, provided that D is other than 2-hydroxy-5-chloro-phenyl, 3-methoxy-phenyl, 4-ethyl-phenyl, 2,6-dichloro-phenyl and 2-chloro-4-fluoro-phenyl.

Example 12a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 12 described herein above.

Example 12b of the present invention is directed to an embodiment wherein compounds where $R_2$ is H are excluded from Example 12 described hereinabove.

An example 13 of the present invention is directed to a compound of Formula (I) wherein D is aryl (other than naphthalen-2-yl), $C_{3-14}$cycloalkyl or heteroaryl, wherein aryl and heteroaryl are optionally substituted with one or two substitutents independently selected from the group consisting of $C_{1-3}$alkyl or fluoro, provided that D is other than 4-ethyl-phenyl.

Example 13a of the present invention is directed to an embodiment wherein wherein Compounds 5, 12, 16, 17, 22, 23, 24, 29, 33, 34, 36, 40, 46, 47, 52, 55, 60, 77, 78, 79, 80, 81, 82, 83, 84, 86 and 87, as described herein, are excluded from Example 13 described herein above.

Example 13b of the present invention is directed to an embodiment wherein compounds where $R_2$ is H are excluded from Example 13 described hereinabove.

An example 14 of the present invention is directed to a compound of Formula (I) wherein D is selected from phenyl, cyclopentyl, $C_{5-14}$cycloalkenyl, heterocyclyl, furanyl, thienyl or pyridinyl, wherein phenyl and furanyl are optionally substituted with one, two, three or four substitutents independently selected from the group consisting of $C_{1-3}$alkyl, $C_{1-3}$alkoxy, $C_{2-8}$alkenyl, $C_{2-3}$alkenyloxy, hydroxy, $C_{1-3}$alkylthio, fluoro, chloro, cyano, $C_{1-3}$alkylcarbonyl, ($C_{1-3}$alkylcarbonyl)amino, ($C_{1-3}$alkyl)amino, di($C_{1-3}$alkyl)amino and $C_{3-14}$cycloalkyl, wherein $C_{3-14}$cycloalkyl is optionally substituted with one, two, three or four $C_{1-3}$alkyl substituents, provided that D is other than 2-hydroxy-5-chloro-phenyl, 3-methoxy-phenyl, 4-ethyl-phenyl, 6,6-dimethyl-bicyclo[3.1.1]hept-2-en-2-yl-methyl, cyclohex-3-enyl, 2,6-dichloro-phenyl and 2-chloro-4-fluoro-phenyl.

Example 14a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 14 described herein above.

Example 14b of the present invention is directed to an embodiment wherein compounds where $R_2$ is H are excluded from Example 14 described hereinabove.

An example 15 of the present invention is directed to a compound of Formula (I) wherein D is selected from phenyl, cyclopentyl, furanyl, thienyl, or pyridinyl, wherein phenyl and furanyl are optionally substituted with one or two substitutents independently selected from the group consisting of $C_{1-3}$alkyl, $C_{1-3}$alkoxy, hydroxy, fluoro, chloro and cyano, provided that D is other than 2-hydroxy-5-chloro-phenyl, 3-methoxy-phenyl, 4-ethyl-phenyl, 2,6-dichloro-phenyl and 2-chloro-4-fluoro-phenyl.

Example 15a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 15 described herein above.

Example 15b of the present invention is directed to an embodiment wherein compounds where $R_2$ is H are excluded from Example 15 described hereinabove.

An example 16 of the present invention is directed to a compound of Formula (I) wherein D is selected from phenyl, cyclopentyl, furanyl, thienyl, or pyridinyl, wherein phenyl and furanyl are optionally substituted with one or two substitutents independently selected from the group consisting of $C_{1-3}$alkyl and fluoro, provided that D is other than 4-ethyl-phenyl.

Example 16a of the present invention is directed to an embodiment wherein wherein Compounds 5, 12, 16, 17, 22, 23, 24, 29, 33, 34, 36, 40, 46, 47, 52, 55, 60, 77, 78, 79, 80, 81, 82, 83, 84, 86 and 87, as described herein, are excluded from Example 16 described herein above.

Example 16b of the present invention is directed to an embodiment wherein compounds where $R_2$ is H are excluded from Example 16 described hereinabove.

An example 17 of the present invention is directed to a compound of Formula (I) wherein A is an optionally present biradical selected from the group consisting of a-1, optionally unsaturated a-2, a-3, a-4, optionally unsaturated a-5 and a-6, wherein, the lower portion of A is attached, relative to the nitrogen atom of Formula (I), to the 3 or 4 position on the benzene ring portion of Formula (I);

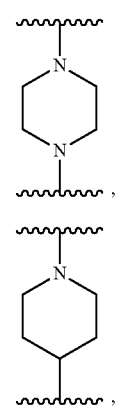

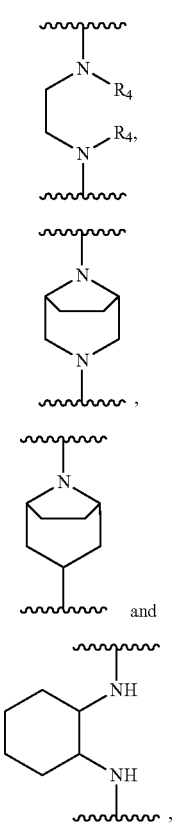

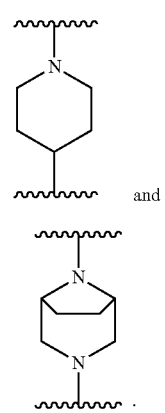

wherein a-1 is optionally substituted with two $C_{1-4}$alkyl substituents, provided that A is other than cis-(1,2)-cyclohexyldiamino; and $R_4$ is hydrogen.

Example 17a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 17 described herein above.

Example 17b of the present invention is directed to an embodiment wherein compounds where $R_2$ is H are excluded from Example 17 described hereinabove.

An example 18 of the present invention is directed to a compound of Formula (I) wherein A is an optionally present biradical selected from the group consisting of a-1, a-2 and a-4, wherein, the lower portion of A is attached, relative to the nitrogen atom of Formula (I), to the 3 position on the benzene ring portion of Formula (I);

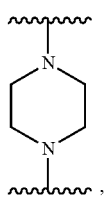

Example 18a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 18 described herein above.

Example 18b of the present invention is directed to an embodiment wherein compounds where $R_2$ is H are excluded from Example 18 described hereinabove.

An example 19 of the present invention is directed to a compound of Formula (I) wherein A is an optionally present biradical selected from the group consisting of piperazine and 3,8-diaza-bicyclo[3.2.1]octane attached, relative to the nitrogen atom of Formula (I), to the 3 position on the benzene ring portion of Formula (I).

Example 19a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 19 described herein above.

Example 19b of the present invention is directed to an embodiment wherein compounds where $R_2$ is H are excluded from Example 19 described hereinabove.

An example 20 of the present invention is directed to a compound of Formula (I) wherein A is a piperazine biradical attached, relative to the nitrogen atom of Formula (I), to the 3 position on the benzene ring portion of Formula (I).

Example 20a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 20 described herein above.

Example 20b of the present invention is directed to an embodiment wherein compounds where $R_2$ is H are excluded from Example 20 described hereinabove.

An example 21 of the present invention is directed to a compound of Formula (I) wherein $L_2$ is absent or —C($R_2$)($R_5$)—(C$R_6R_7$)$_r$—, wherein r is 0, 1 or 2, and wherein $R_5$, $R_6$, and $R_7$ are hydrogen, provided that $L_2$ is other than —CH(R-carboxymethyl)-.

Example 21a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 21 described herein above.

Example 21b of the present invention is directed to an embodiment wherein compounds where $R_2$ is H are excluded from Example 21 described hereinabove.

An example 22 of the present invention is directed to a compound of Formula (I) wherein $L_2$ is —CH($R_2$)—, provided that $L_2$ is other than —CH(R-carboxymethyl)-.

Example 22a of the present invention is directed to an embodiment wherein wherein Compounds 5, 12, 16, 17, 22, 23, 24, 29, 31, 33, 34, 36, 38, 40, 44, 46, 52, 55, 56, 57, 60, 77, 78, 79, 80, 81, 82, 83, 84, 85, 86 and 87, as described herein, are excluded from Example 22 described herein above.

Example 22b of the present invention is directed to an embodiment wherein compounds where $R_2$ is H are excluded from Example 22 described hereinabove.

An example 23 of the present invention is directed to a compound of Formula (I) wherein $R_2$ is selected from the group consisting of hydrogen, phenyl, and $C_{1-6}$alkyl, wherein phenyl is optionally substituted with ($R_{200}$—$C_{1-6}$alkyl)amino, or [(hydroxysulfonyl)($R_a$)]amino, and wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, carboxy-$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, {[($R_{200}$)($R_a$)]aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [(hydroxysulfonyl)($R_a$)]amino or [($R_{200}$-sulfonyl)($R_a$)]amino.

Example 23a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 23 described herein above.

Example 23b of the present invention is directed to an embodiment wherein compounds where $R_2$ is H are excluded from Example 23 described hereinabove.

An example 24 of the present invention is directed to a compound of Formula (I) wherein $R_a$ and $R_c$ are independently selected from the group consisting of hydrogen and $C_{1-6}$alkyl; and $R_b$ is hydrogen, $C_{1-6}$alkyl, heteroaryl or heterocyclyl.

An example 25 of the present invention is directed to a compound of Formula (I) wherein $R_a$ and $R_c$ are independently selected from the group consisting of hydrogen and $C_{1-6}$alkyl; and $R_b$ is hydrogen, $C_{1-6}$alkyl, $C_{6-10}$aryl, pyridinyl, pyrimidinyl, $C_{3-8}$cycloalkyl, piperidinyl or 4,5-dihydro-1H-pyrrolyl.

An example 26 of the present invention is directed to a compound of Formula (I) wherein $R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, heteroaryl, aryl-$C_{1-6}$alkyl, aryl-sulfonyl and heteroaryl-sulfonyl, wherein heterocyclyl is optionally substituted with two oxo substituents.

An example 27 of the present invention is directed to a compound of Formula (I) wherein $R_{200}$ is phenyl, furanyl, thienyl, pyrrolyl, imidazolyl, pyrazolyl, isoxazolyl, thiazolyl, pyridinyl, pyridazinyl, quinolinyl, benzothienyl, benzoimidazolyl, imidazo[2,1-b]thiazolyl, cyclobutyl, cyclopentyl, tetrahydro-furanyl, tetrahydro-thienyl, pyrrolidinyl, or piperidinyl, each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, aryl, isoxazolyl, phenyl-$C_{1-6}$alkyl, phenyl-sulfonyl and thienyl-sulfonyl, wherein tetrahydro-thienyl is optionally substituted with one, two or three oxo substituents.

An example 28 of the present invention is directed to a compound of Formula (I) wherein B is $C_{6-10}$aryl, indanyl, or a heteroaryl selected from the group consisting of pyridin-2-yl, pyridin-4-yl, pyrazol-4-yl and imidazol-1-yl, wherein B is optionally substituted with one, two or three substituents independently selected from the group consisting of $C_{1-4}$alkyl, $C_{1-4}$alkoxy, halogen, and hydroxy, provided that when B is selected from the group consisting of $C_{6-10}$aryl and indanyl, then B is independently substituted with two substitutents selected from the group consisting of $C_{1-3}$alkoxy and hydroxy, and provided that B is other than 3-hydroxy-4-methoxy-phenyl and 3-(n-propyloxy)-4-methoxy-phenyl.

Example 28a of the present invention is directed to an embodiment wherein wherein Compounds 5, 12, 16, 17, 22, 23, 24, 29, 31, 33, 36, 38, 40, 44, 46, 47, 55, 56, 57, 77, 78, 79, 80, 81, 82, 83, 84, 85, 86 and 87, as described herein, are excluded from Example 28 described herein above.

Example 28b of the present invention is directed to an embodiment wherein compounds where $R_2$ is H are excluded from Example 28 described hereinabove.

An example 29 of the present invention is directed to a compound of Formula (I) wherein B is $C_{6-10}$aryl or indanyl each substituted with two substituents independently selected from the group consisting of $C_{1-4}$alkoxy and hydroxy, provided that B is other than 3-hydroxy-4-methoxy-phenyl and 3-(n-propyloxy)-4-methoxy-phenyl.

Example 29a of the present invention is directed to an embodiment wherein wherein Compounds 5, 12, 16, 17, 22, 24, 29, 31, 33, 36, 38, 40, 44, 46, 56, 57, 77, 78, 79, 80, 81, 82, 83, 84, 85, 86 and 87, as described herein, are excluded from Example 29 described herein above.

Example 29b of the present invention is directed to an embodiment wherein compounds where $R_2$ is H are excluded from Example 29 described hereinabove.

An example 30 of the present invention is directed to a compound of Formula (I) wherein E is hydrogen, halogen or —CH=CH-sulfonyl-$C_{1-6}$alkyl.

Example 30a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 30 described herein above.

Example 30b of the present invention is directed to an embodiment wherein compounds where $R_2$ is H are excluded from Example 30 described hereinabove.

An example 31 of the present invention is directed to a compound of Formula (I) wherein
when A is present, then G is selected from hydrogen, $C_{1-8}$alkyl, $C_{2-8}$alkenyl, $C_{3-14}$cycloalkyl or a —C[($R_1$)($R_{11}$)]-L-D moiety:

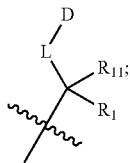

or,
when A is absent and $R_2$ is other than benzyloxymethyl, then G is $C_{1-8}$alkoxy,
wherein $C_{1-8}$alkoxy is substituted with one of di($C_{1-8}$alkyl)amino;
$R_1$ is selected from the group consisting of hydrogen and $C_{1-8}$alkyl;
$R_{11}$ is hydrogen;
L is absent;
D is aryl (other than naphthalen-2-yl) or heteroaryl,
wherein aryl is optionally substituted with one fluoro substitutent;
A is an optionally present biradical selected from the group consisting of piperazine and 3,8-diaza-bicyclo[3.2.1]octane attached, relative to the nitrogen atom of Formula (I), to the 3 position on the benzene ring portion of Formula (I);
$L_2$ is absent or —CH($R_2$)—;
$R_2$ is selected from the group consisting of hydrogen, phenyl, and $C_{1-6}$alkyl,
wherein phenyl is optionally substituted with ($R_{200}$—$C_{1-6}$alkyl)amino, or [(hydroxysulfonyl)($R_a$)]amino, and
wherein $C_{1-6}$alkyl is optionally substituted with hydroxy, $R_{200}$, $NR_aR_b$, $C_{1-6}$alkoxy, $R_{200}$—$C_{1-6}$alkoxy, carboxy-$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, {[($R_{200}$)($R_a$)]aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [(hydroxysulfonyl)($R_a$)]amino or [($R_{200}$-sulfonyl)($R_a$)]amino;
$R_a$ and $R_c$ are independently selected from the group consisting of hydrogen and $C_{1-6}$alkyl; and $R_b$ is hydrogen, $C_{1-6}$alkyl, heteroaryl or heterocyclyl;
$R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, heteroaryl, aryl-$C_{1-6}$alkyl and heteroarylsulfonyl,
wherein heterocyclyl is substituted with one, two or three oxo substituents;

B is $C_{6-10}$aryl or indanyl optionally substituted with two $C_{1-4}$alkoxy substituents, provided that B is other than 3-(n-propyloxy)-4-methoxy-phenyl;
E is hydrogen or halogen;
X and Y are O;
and enantiomers, diastereomers, tautomers, solvates, and pharmaceutically acceptable salts thereof.

Example 31a of the present invention is directed to an embodiment wherein wherein Compounds 5, 12, 17, 78, 79, 81, 82, 83, 84, 86 and 87, as described herein, are excluded from Example 31 described herein above.

Example 31b of the present invention is directed to an embodiment wherein compounds where $R_2$ is H are excluded from Example 31 described hereinabove.

An example 32 of the present invention is directed to a compound of Formula (I) wherein
when A is present, then G is selected from hydrogen, $C_{1-8}$alkyl, $C_{2-8}$alkenyl, adamantanyl, cyclobutyl, cyclopentyl, cyclohexyl or a —C[($R_1$)($R_{11}$)]-L-D moiety:

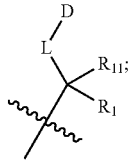

or,
when A is absent and $R_2$ is other than benzyloxymethyl, then G is $C_{1-8}$alkoxy,
wherein $C_{1-8}$alkoxy is substituted with one of di($C_{1-8}$alkyl)amino;
$R_1$ is selected from the group consisting of hydrogen and $C_{1-8}$alkyl;
$R_{11}$ is hydrogen;
L is absent;
D is phenyl, furanyl, thienyl or pyridinyl,
wherein phenyl is optionally substituted with one fluoro substitutent;
A is an optionally present biradical selected from the group consisting of piperazine and 3,8-diaza-bicyclo[3.2.1]octane attached, relative to the nitrogen atom of Formula (I), to the 3 position on the benzene ring portion of Formula (I);
$L_2$ is absent or —CH($R_2$)—;
$R_2$ is selected from the group consisting of hydrogen, phenyl, and $C_{1-6}$alkyl,
wherein phenyl is optionally substituted with ($R_{200}$—$C_{1-6}$alkyl)amino, or [(hydroxysulfonyl)($R_a$)]amino, and
wherein $C_{1-6}$alkyl is optionally substituted with hydroxy, $R_{200}$, $NR_aR_b$, $C_{1-6}$alkoxy, $R_{200}$—$C_{1-6}$alkoxy, carboxy-$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, {[($R_{200}$)($R_a$)]aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [(hydroxysulfonyl)($R_a$)]amino or [($R_{200}$-sulfonyl)($R_a$)]amino;

$R_a$ and $R_c$ are independently selected from the group consisting of hydrogen and $C_{1-6}$alkyl; and $R_b$ is hydrogen, $C_{1-6}$alkyl, heteroaryl or heterocyclyl;

$R_{200}$ is phenyl, furanyl, thienyl, pyrrolyl, imidazolyl, pyrazolyl, isoxazolyl, thiazolyl, pyridinyl, pyridazinyl, quinolinyl, benzoimidazolyl, imidazo[2,1-b]thiazolyl, cyclobutyl, cyclopentyl, tetrahydro-furanyl, tetrahydro-thienyl, pyrrolidinyl or piperidinyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, isoxazolyl, phenyl-$C_{1-6}$alkyl and thienyl-sulfonyl, wherein tetrahydro-thienyl is substituted with two oxo substituents;

B is phenyl or indanyl optionally substituted with two $C_{1-4}$alkoxy substituents, provided that B is other than 3-(n-propyloxy)-4-methoxy-phenyl;

E is hydrogen or halogen;

X and Y are O;

and enantiomers, diastereomers, tautomers, solvates, and pharmaceutically acceptable salts thereof.

Example 32a of the present invention is directed to an embodiment wherein wherein Compounds 5, 12, 17, 78, 79, 81, 82, 83, 84, 86 and 87, as described herein, are excluded from Example 32 described herein above.

Example 32b of the present invention is directed to an embodiment wherein compounds where $R_2$ is H are excluded from Example 32 described hereinabove.

An example 33 of the present invention is directed to a compound of Formula (I) wherein G is hydrogen, $C_{1-8}$alkyl, $C_{2-8}$alkenyl, $C_{3-14}$cycloalkyl or a —C[($R_1$)($R_{11}$)]-L-D moiety:

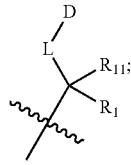

$R_1$ is selected from the group consisting of hydrogen and $C_{1-8}$alkyl;

$R_{11}$ is hydrogen;

L is absent;

D is aryl (other than naphthalen-2-yl) or heteroaryl;

A is a piperazine biradical attached, relative to the nitrogen atom of Formula (I), to the 3 position on the benzene ring portion of Formula (I);

$L_2$ is —CH($R_2$)—;

$R_2$ is selected from the group consisting of hydrogen and $C_{1-6}$alkyl, wherein $C_{1-6}$alkyl is optionally substituted with hydroxy, $R_{200}$, $NR_aR_b$, $R_{200}$—$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, ($R_{200}$—$C_{1-6}$alkylsulfonyl)amino, ($C_{1-6}$alkylsulfonyl-$C_{1-6}$alkylsulfonyl)amino, di($C_{1-6}$alkyl) aminosulfonyloxy, aminosulfonylamino, [di($C_{1-6}$alkyl) aminosulfonyl]amino, [(hydroxysulfonyl)($R_a$)]amino or [($R_{200}$-sulfonyl)($R_a$)]amino;

$R_a$ and $R_c$ are independently selected from the group consisting of hydrogen and $C_{1-6}$alkyl; and $R_b$ is heteroaryl or heterocyclyl;

$R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, trihalo-$C_{1-4}$alkyl, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, heteroaryl and heteroaryl-sulfonyl, wherein heterocyclyl is substituted with two oxo substituents;

B is $C_{6-10}$aryl substituted with two $C_{1-4}$alkoxy substituents, provided that B is other than 3-(n-propyloxy)-4-methoxyphenyl;

E is hydrogen;

X and Y are O;

and enantiomers, diastereomers, tautomers, solvates, and pharmaceutically acceptable salts thereof.

Example 33a of the present invention is directed to an embodiment wherein wherein Compounds 5, 78, 79, 81, 82, 83, 84, 86 and 87, as described herein, are excluded from Example 33 described herein above.

Example 33b of the present invention is directed to an embodiment wherein compounds where $R_2$ is H are excluded from Example 33 described hereinabove.

An example 34 of the present invention is directed to a compound of Formula (I) wherein G is hydrogen, $C_{1-8}$alkyl, $C_{2-8}$alkenyl, cyclobutyl, cyclopentyl, cyclohexyl or a —C[($R_1$)($R_{11}$)]-L-D moiety:

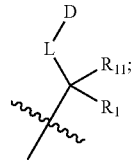

$R_1$ is selected from the group consisting of hydrogen and $C_{1-8}$alkyl;

$R_{11}$ is hydrogen;

L is absent;

D is phenyl, furanyl, thienyl or pyridinyl;

A is a piperazine biradical attached, relative to the nitrogen atom of Formula (I), to the 3 position on the benzene ring portion of Formula (I);

$L_2$ is —CH($R_2$)—;

$R_2$ is selected from the group consisting of hydrogen and $C_{1-6}$alkyl, wherein $C_{1-6}$alkyl is optionally substituted with hydroxy, $R_{200}$, $NR_aR_b$, $R_{200}$—$C_{1-6}$alkoxy, [($R_{200}$—$C_{1-6}$alkyl)($R_a$)] amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl] amino, ($C_{1-6}$alkylcarbonyl-acetonitrile-carbonyl)amino, acetamidino, guanidino, ($R_{200}$—$C_{1-6}$alkylsulfonyl)amino, ($C_{1-6}$alkylsulfonyl-$C_{1-6}$alkylsulfonyl)amino, di($C_{1-6}$alkyl) aminosulfonyloxy, aminosulfonylamino, [di($C_{1-6}$alkyl) aminosulfonyl]amino, [(hydroxysulfonyl)($R_a$)]amino or [($R_{200}$-sulfonyl)($R_a$)]amino;

$R_a$ and $R_c$ are independently selected from the group consisting of hydrogen and $C_{1-6}$alkyl; and $R_b$ is pyridinyl, pyrimidinyl or 4,5-dihydro-1H-pyrrolyl;

$R_{200}$ is phenyl, furanyl, thienyl, pyrrolyl, imidazolyl, pyrazolyl, isoxazolyl, thiazolyl, pyridinyl, pyridazinyl, quinolinyl, benzoimidazolyl, cyclobutyl, cyclopentyl, tetrahydro-furanyl, tetrahydro-thienyl, pyrrolidinyl, or piperidinyl, each optionally substituted with one, two or three substituents independently selected from the group consisting of $C_{1-4}$alkyl, trihalo-$C_{1-4}$alkyl, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, isoxazolyl and thienyl-sulfonyl, wherein tetrahydro-thienyl is substituted with two oxo substituents;

B is phenyl substituted with two $C_{1-4}$alkoxy substituents, provided that B is other than 3-(n-propyloxy)-4-methoxyphenyl;

E is hydrogen;

X and Y are O;

and enantiomers, diastereomers, tautomers, solvates, and pharmaceutically acceptable salts thereof.

Example 34a of the present invention is directed to an embodiment wherein wherein Compounds 5, 78, 79, 81, 82, 83, 84, and 86, as described herein, are excluded from Example 34 described herein above.

Example 34b of the present invention is directed to an embodiment wherein compounds where $R_2$ is H are excluded from Example 34 described hereinabove.

An example 35 of the present invention is directed to a compound of Formula (I) wherein G is hydrogen, $C_{1-8}$alkyl, $C_{2-8}$alkenyl, $C_{3-14}$cycloalkyl or a —C[($R_1$)($R_{11}$)]-L-D moiety:

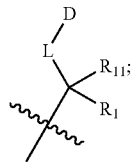

$R_1$ is selected from the group consisting of hydrogen and $C_{1-8}$alkyl;

$R_{11}$ is hydrogen;

L is absent;

D is aryl (other than naphthalen-2-yl) or heteroaryl;

A is a piperazine biradical attached, relative to the nitrogen atom of Formula (I), to the 3 position on the benzene ring portion of Formula (I);

$L_2$ is —CH($R_2$)—;

$R_2$ is selected from the group consisting of hydrogen and $C_{1-6}$alkyl, wherein $C_{1-6}$alkyl is substituted with $NR_aR_b$, $R_{200}$—$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, ($R_{200}$—$C_{1-6}$alkylsulfonyl)amino, ($C_{1-6}$alkylsulfonyl-$C_{1-6}$alkylsulfonyl)amino, aminosulfonylamino, [di($C_{1-6}$alkyl)aminosulfonyl]amino, [(hydroxysulfonyl)($R_a$)]amino or [($R_{200}$-sulfonyl)($R_a$)]amino;

$R_a$ is selected from the group consisting of hydrogen and $C_{1-6}$alkyl; and $R_b$ is heteroaryl or heterocyclyl;

$R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, $C_{1-6}$alkylcarbonyl, $C_{1-6}$alkoxycarbonyl, $C_{1-6}$alkylsulfonyl, aminosulfonyl and chloro, wherein heterocyclyl is substituted with two oxo substituents;

B is $C_{6-10}$aryl substituted with two $C_{1-4}$alkoxy substituents, provided that B is other than 3-(n-propyloxy)-4-methoxyphenyl;

E is hydrogen;

X and Y are O;

and enantiomers, diastereomers, tautomers, solvates, and pharmaceutically acceptable salts thereof.

Example 35a of the present invention is directed to an embodiment wherein wherein Compounds 5, 78, 79, 81, 82, 83, 84, 86 and 87, as described herein, are excluded from Example 35 described herein above.

Example 35b of the present invention is directed to an embodiment wherein compounds where $R_2$ is H are excluded from Example 35 described hereinabove.

An example 36 of the present invention is directed to a compound of Formula (I) wherein G is hydrogen, $C_{1-8}$alkyl, $C_{2-8}$alkenyl, cyclobutyl, cyclopentyl, cyclohexyl or a —C[($R_1$)($R_{11}$)]-L-D moiety:

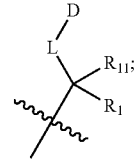

$R_1$ is selected from the group consisting of hydrogen and $C_{1-8}$alkyl;

$R_{11}$ is hydrogen;

L is absent;

D is phenyl, furanyl, thienyl or pyridinyl;

A is a piperazine biradical attached, relative to the nitrogen atom of Formula (I), to the 3 position on the benzene ring portion of Formula (I);

$L_2$ is —CH($R_2$)—;

$R_2$ is selected from the group consisting of hydrogen and $C_{1-6}$alkyl, wherein $C_{1-6}$alkyl is substituted with $NR_aR_b$, $R_{200}$—$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, ($R_{200}$—$C_{1-6}$alkylsulfonyl)amino, ($C_{1-6}$alkylsulfonyl-$C_{1-6}$alkylsulfonyl)amino, aminosulfonylamino, [di($C_{1-6}$alkyl)aminosulfonyl]amino, [(hydroxysulfonyl)($R_a$)]amino or [($R_{200}$-sulfonyl)($R_a$)]amino;

$R_a$ is selected from the group consisting of hydrogen and $C_{1-6}$alkyl; and $R_b$ is pyrimidinyl or 4,5-dihydro-1H-pyrrolyl;

$R_{200}$ is phenyl, furanyl, thienyl, pyrrolyl, imidazolyl, pyrazolyl, isoxazolyl, thiazolyl, pyridinyl, pyridazinyl, quinolinyl, cyclobutyl, cyclopentyl, tetrahydro-furanyl, tetrahydro-thienyl or pyrrolidinyl, each optionally substituted with one, two or three substituents independently selected from the group consisting of $C_{1-4}$alkyl, $C_{1-6}$alkylcarbonyl, $C_{1-6}$alkoxycarbonyl, $C_{1-6}$alkylsulfonyl, aminosulfonyl and chloro, wherein tetrahydro-thienyl is substituted with two oxo substituents;
B is phenyl substituted with two $C_{1-4}$alkoxy substituents, provided that B is other than 3-(n-propyloxy)-4-methoxy-phenyl;
E is hydrogen;
X and Y are O;
and enantiomers, diastereomers, tautomers, solvates, and pharmaceutically acceptable salts thereof.

Example 36a of the present invention is directed to an embodiment wherein wherein Compounds 5, 78, 79, 81, 82, 83, 84, and 86, as described herein, are excluded from Example 36 described herein above.

Example 36b of the present invention is directed to an embodiment wherein compounds where $R_2$ is H are excluded from Example 36 described hereinabove.

An example 37 of the present invention is directed to a compound of Formula (I) wherein
G is $C_{1-8}$alkyl, $C_{3-14}$cycloalkyl or a —C[($R_1$)($R_{11}$)]-L-D moiety:

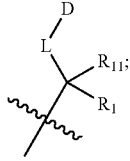

$R_1$ is $C_{1-8}$alkyl;
$R_{11}$ is hydrogen;
L is absent;
D is aryl (other than naphthalen-2-yl) or heteroaryl;
A is a piperazine biradical attached, relative to the nitrogen atom of Formula (I), to the 3 position on the benzene ring portion of Formula (I);
$L_2$ is —CH($R_2$)—;
$R_2$ is $C_{1-6}$alkyl substituted with ($C_{1-6}$alkylcarbonyl)amino, ($C_{1-6}$alkoxy-$C_{1-6}$alkylcarbonyl)amino, ($R_{200}$-carbonyl)amino, ($C_{1-6}$alkylcarbonyl-acetonitrile-carbonyl)amino, [(hydroxysulfonyl)($R_a$)]amino or [($R_{200}$-sulfonyl)($R_a$)]amino;
$R_a$ is hydrogen;
$R_{200}$ is heteroaryl or heterocyclyl, each optionally substituted with one, two or three $C_{1-4}$alkyl substituents;
B is $C_{6-10}$aryl substituted with two $C_{1-4}$alkoxy substituents, provided that B is other than 3-(n-propyloxy)-4-methoxy-phenyl;
E is hydrogen;
X and Y are O;
and enantiomers, diastereomers, tautomers, solvates, and pharmaceutically acceptable salts thereof.

An example 38 of the present invention is directed to a compound of Formula (I) wherein
G is $C_{1-8}$alkyl, cyclobutyl, cyclopentyl or a —C[($R_1$)($R_{11}$)]-L-D moiety:

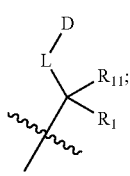

$R_1$ is $C_{1-8}$alkyl;
$R_{11}$ is hydrogen;
L is absent;
D is phenyl or furanyl;
A is a piperazine biradical attached, relative to the nitrogen atom of Formula (I), to the 3 position on the benzene ring portion of Formula (I);
$L_2$ is —CH($R_2$)—;
$R_2$ is $C_{1-6}$alkyl substituted with ($C_{1-6}$alkylcarbonyl)amino, ($C_{1-6}$alkoxy-$C_{1-6}$alkylcarbonyl)amino, ($R_{200}$-carbonyl)amino, ($C_{1-6}$alkylcarbonyl-acetonitrile-carbonyl)amino, [(hydroxysulfonyl)($R_a$)]amino or [($R_{200}$-sulfonyl)($R_a$)]amino;
$R_a$ is hydrogen;
$R_{200}$ is thienyl, imidazolyl, pyrazolyl or tetrahydro-furanyl, each optionally substituted with one, two or three $C_{1-4}$alkyl substituents;
B is phenyl substituted with two $C_{1-4}$alkoxy substituents, provided that B is other than 3-(n-propyloxy)-4-methoxy-phenyl;
E is hydrogen;
X and Y are O;
and enantiomers, diastereomers, tautomers, solvates, and pharmaceutically acceptable salts thereof.

An example 39 of the present invention is directed to a compound of Formula (I) wherein
G is ethyl, isopropyl, cyclobutyl, cyclopentyl or a —C[($R_1$)($R_{11}$)]-L-D moiety:

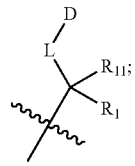

$R_1$ is methyl;
$R_{11}$ is hydrogen;
L is absent;
D is phenyl or furanyl;
A is piperazine attached, relative to the nitrogen atom of Formula (I), to the 3 position on the benzene ring portion of Formula (I);
$L_2$ is —CH($R_2$)—;
$R_2$ is 3-[(1,2-dimethyl-1H-imidazol-5-yl-sulfonyl)-amino]-prop-1-yl, 3-[(1,3-dimethyl-1H-pyrazol-4-yl-sulfonyl)-amino]-prop-1-yl, 3-[(1,3,5-trimethyl-1H-pyrazol-4-yl-sulfonyl)-amino]-prop-1-yl, 3-[(1-methyl-1H-pyrazol-4-yl-sulfonyl)-amino]-prop-1-yl, 3-[(1,5-dimethyl-1H-pyrazol-4-yl-sulfonyl)amino]-prop-1-yl, 3-{[(1H-pyrazol-4-yl)-carbonyl]-amino}-prop-1-yl, 3-(tetrahydro-furan-2-yl-carbonyl-amino)-prop-1-yl, 3-(ethyl-carbonyl-amino)-prop-1-yl, 3-[(methoxy-ethyl-carbonyl)-amino]-prop-1-yl, 3-[(methoxy-methyl-carbonyl)-amino]-prop-1-yl, 3-[(ethoxy-methyl-carbonyl)amino]-prop-1-yl, 3-[(ethoxy-ethyl-carbonyl)amino]-prop-1-yl, 3-(t-butyl-carbonyl-amino)-prop-1-yl, 3-[(methyl-carbonyl-acetonitrile-carbonyl)amino]-prop1-yl, 3-(thien-2-yl-sulfonyl-amino)-prop-1-yl or 3-(hydroxy-sulfonyl-amino)-prop-1-yl;
B is 3,4-dimethoxy-phenyl;
E is hydrogen;
X and Y are O;
and enantiomers, diastereomers, tautomers, solvates, and pharmaceutically acceptable salts thereof.

An example 40 of the present invention is directed to compounds selected from the group consisting of:

Cpd 1
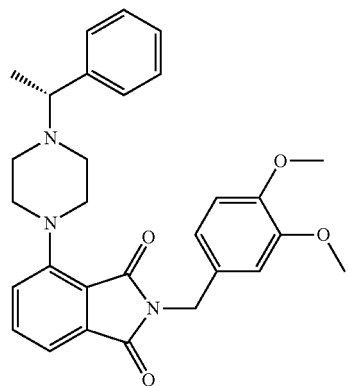
Cpd 2
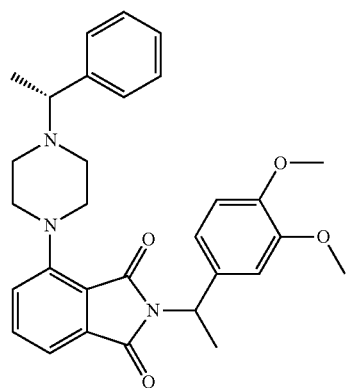
Cpd 3
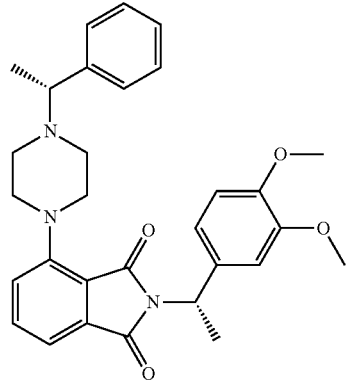
Cpd 4
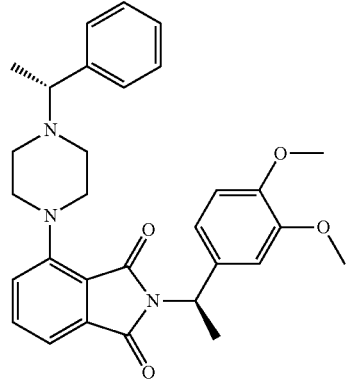
Cpd 5
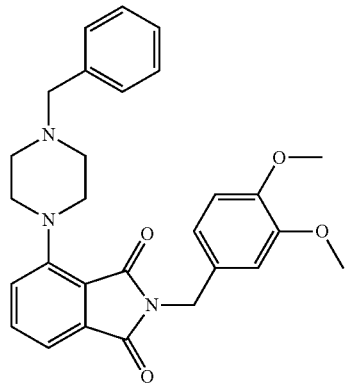
Cpd 6
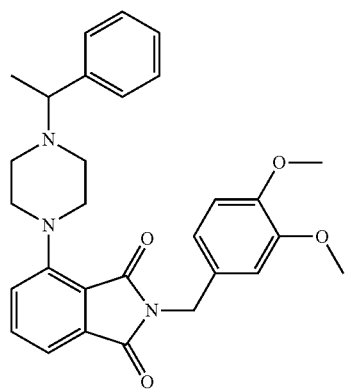
Cpd 7
Cpd 8

Cpd 9
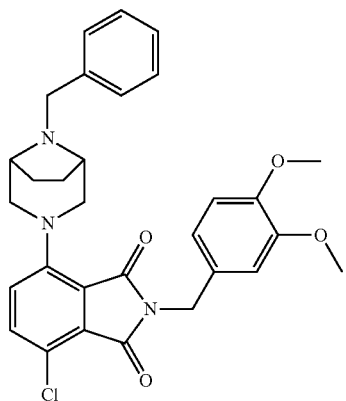
Cpd 10
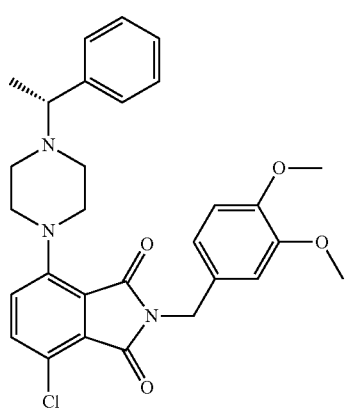
Cpd 11
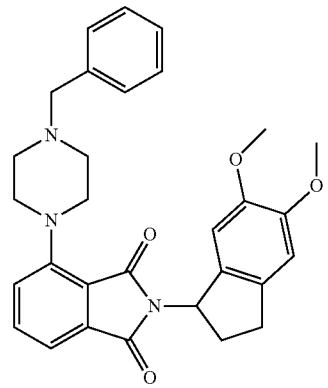
Cpd 12
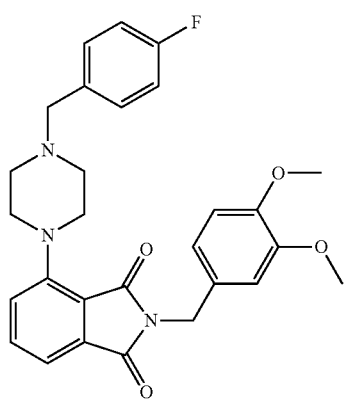
Cpd 13
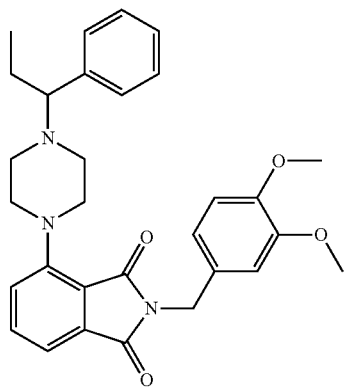
Cpd 14
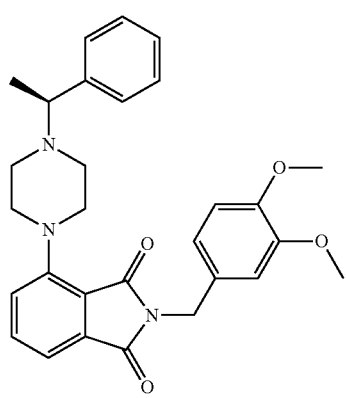
Cpd 15
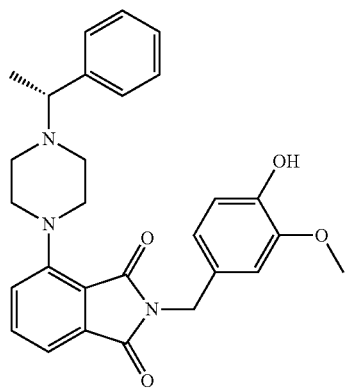
Cpd 16
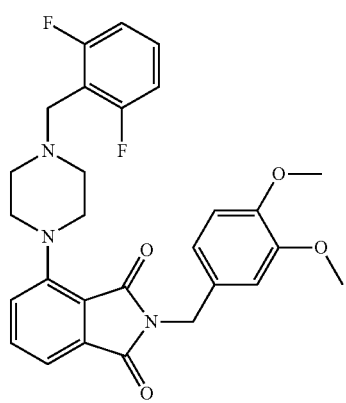

Cpd 17
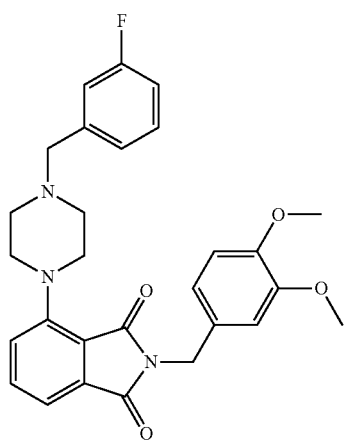
Cpd 18
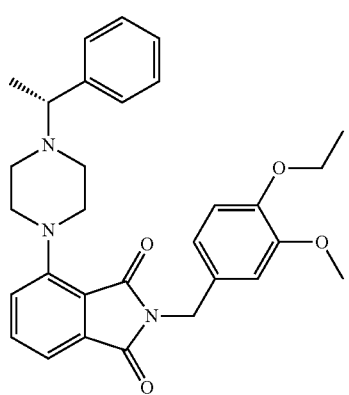
Cpd 19
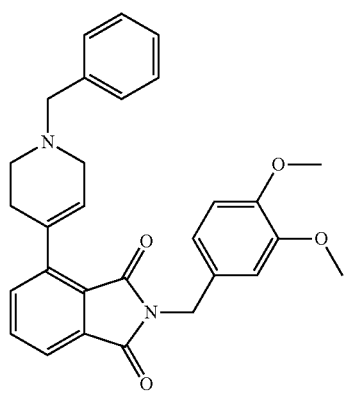
Cpd 20
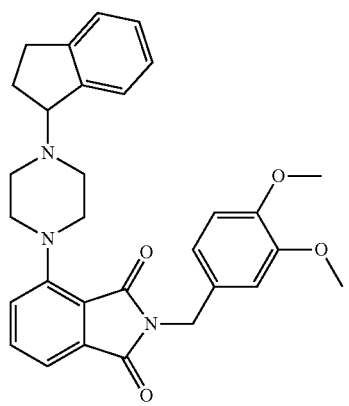
Cpd 21
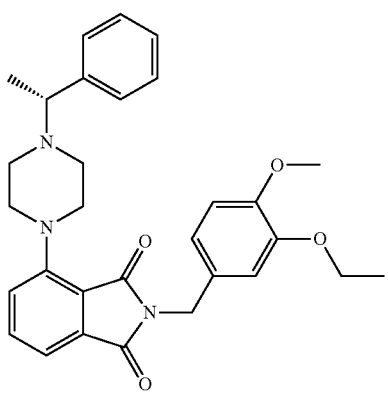
Cpd 22
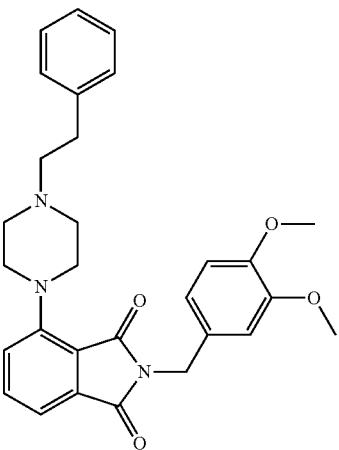
Cpd 23
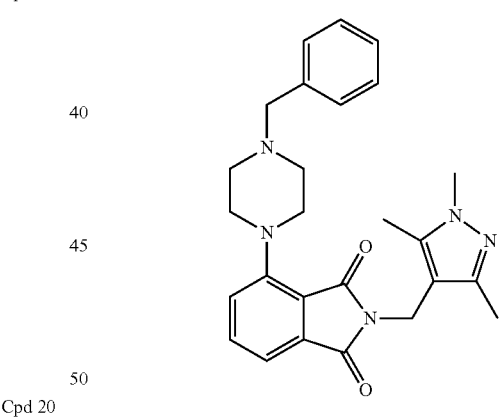
Cpd 24
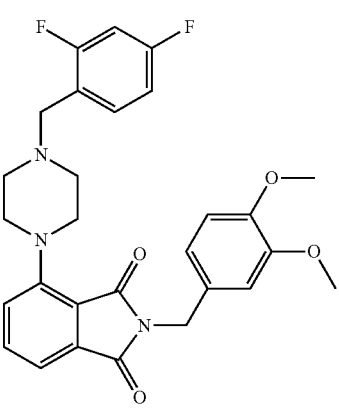

Cpd 25
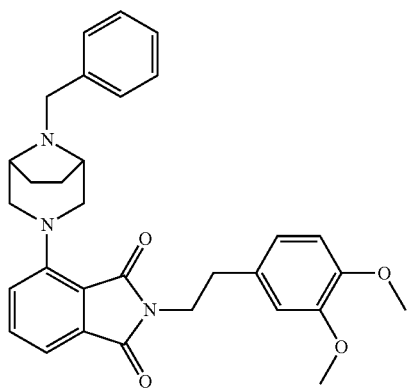
Cpd 26
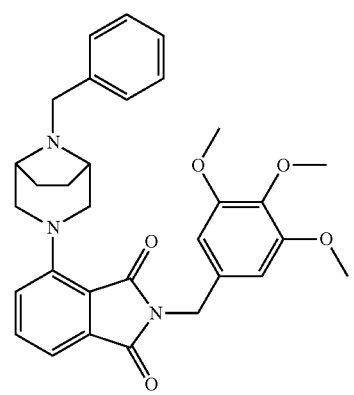
Cpd 27
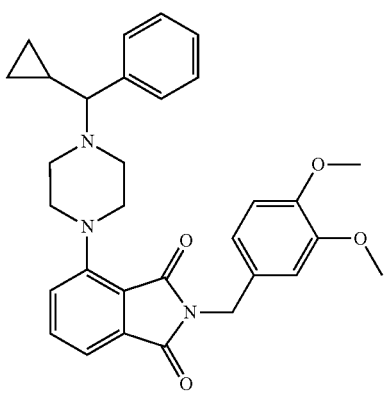
Cpd 28
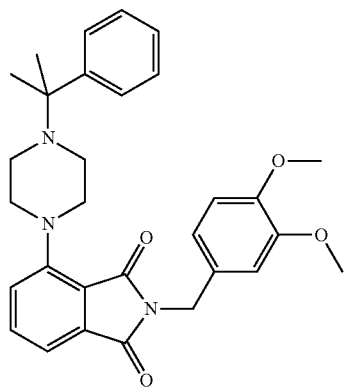
Cpd 29
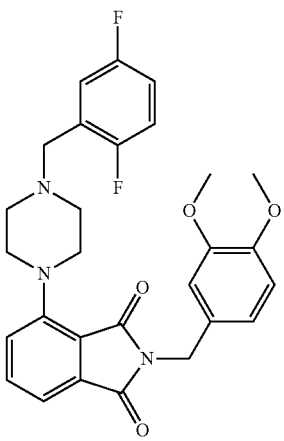
Cpd 30
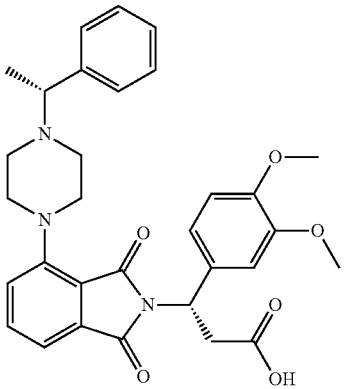
Cpd 31
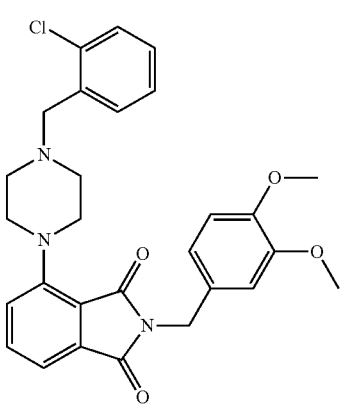
Cpd 32
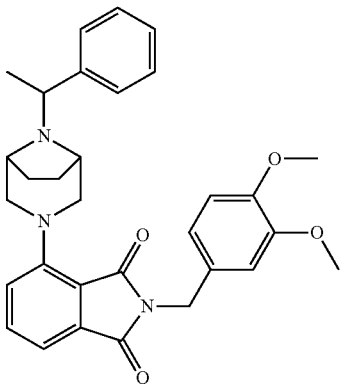

Cpd 33
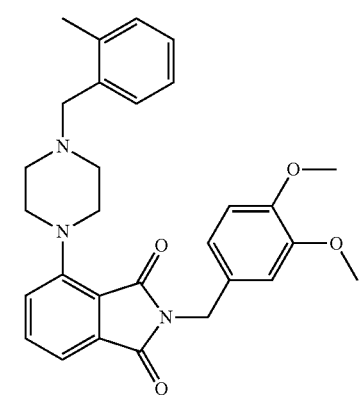
Cpd 34
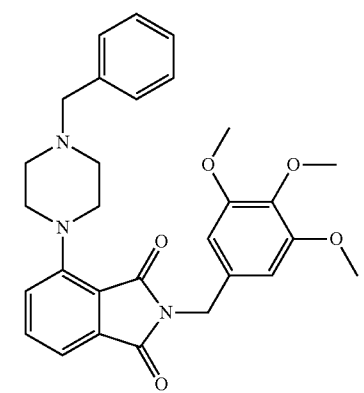
Cpd 35
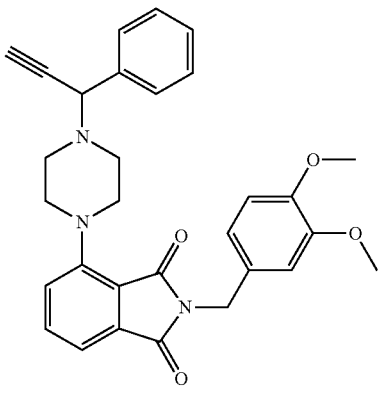
Cpd 36
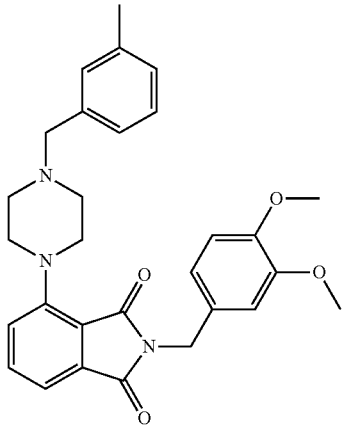
Cpd 37
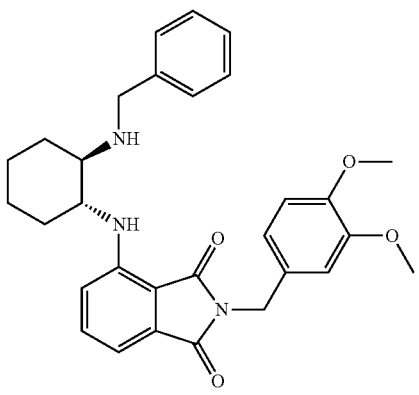
Cpd 38
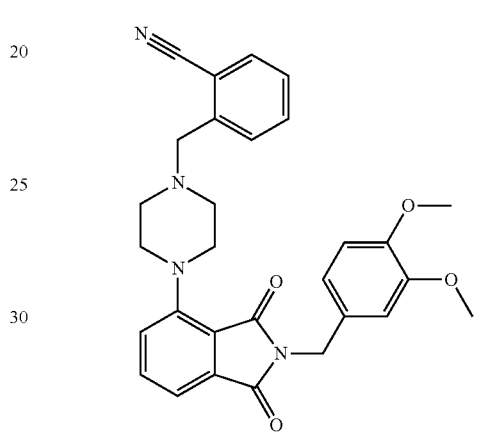
Cpd 39
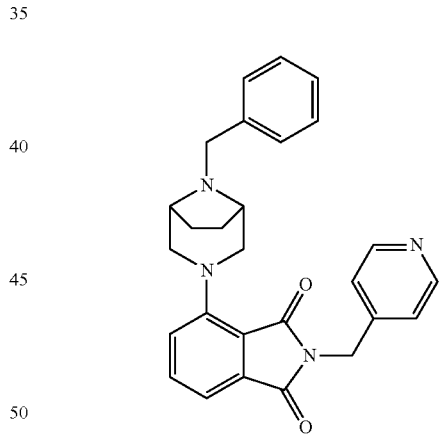
Cpd 40
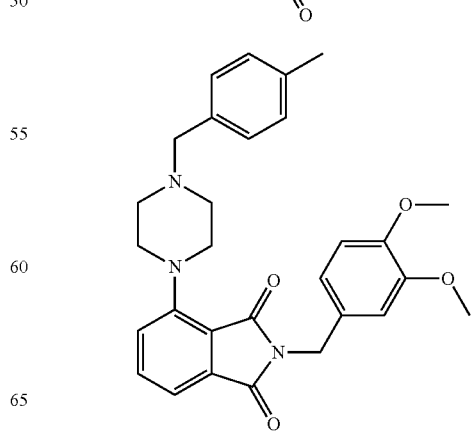

Cpd 41
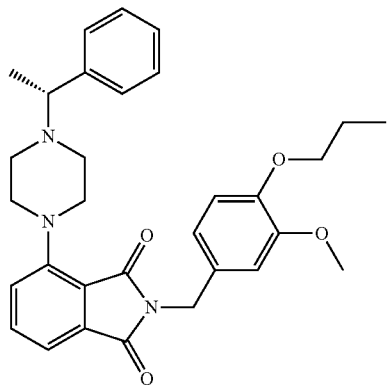
Cpd 42
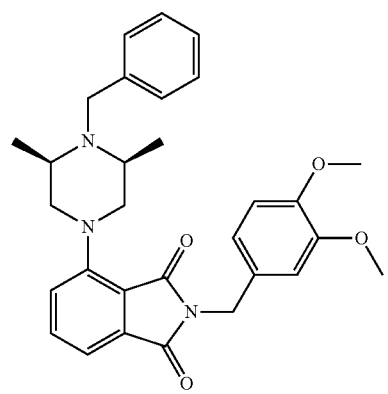
Cpd 43
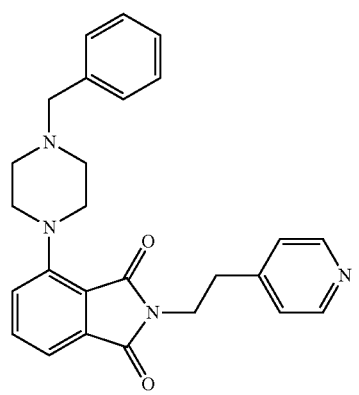
Cpd 44
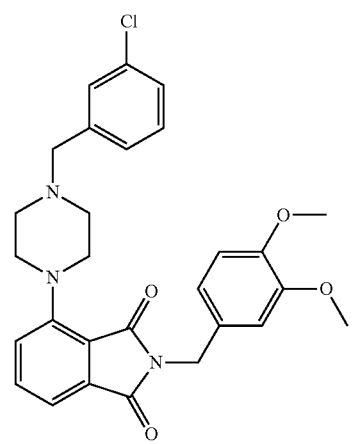
Cpd 45
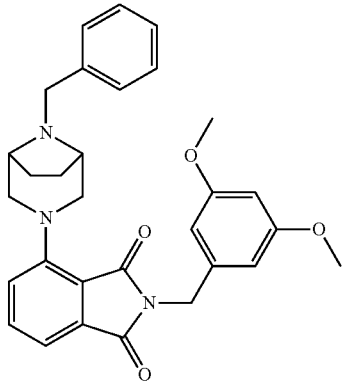
Cpd 46
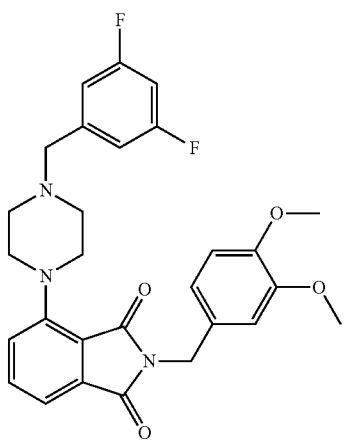
Cpd 47
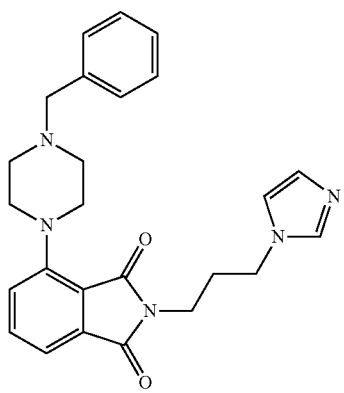
Cpd 48
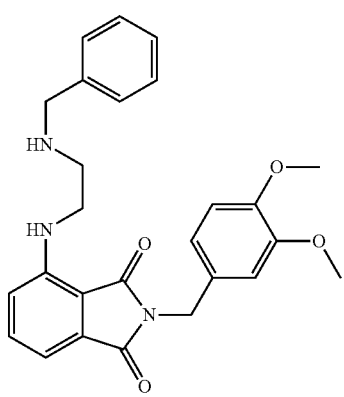

Cpd 49
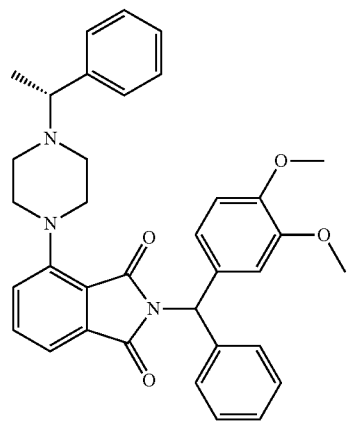
Cpd 50
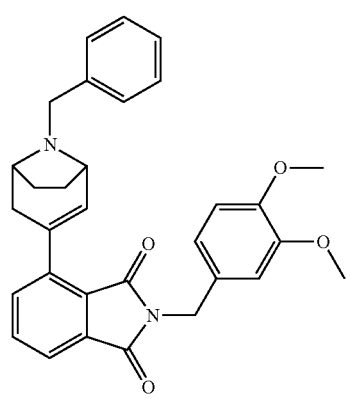
Cpd 51
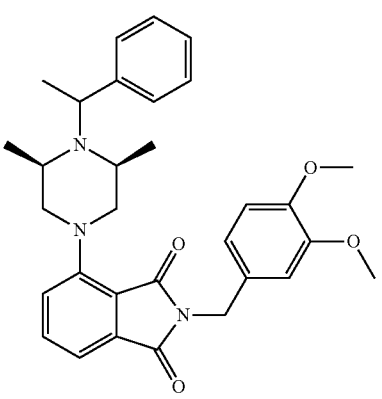
Cpd 52
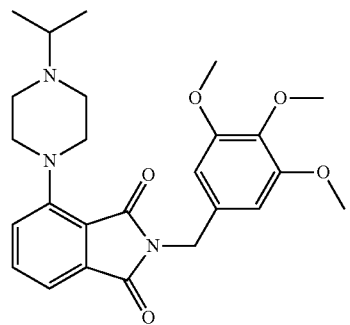
Cpd 53
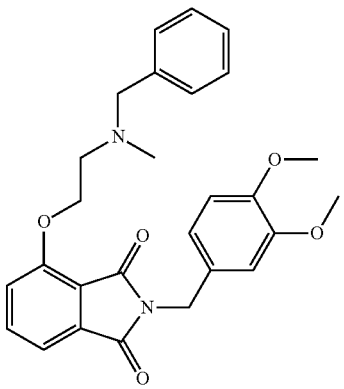
Cpd 54
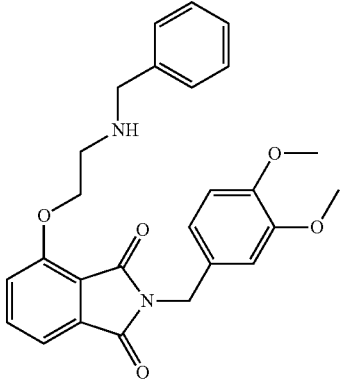
Cpd 55
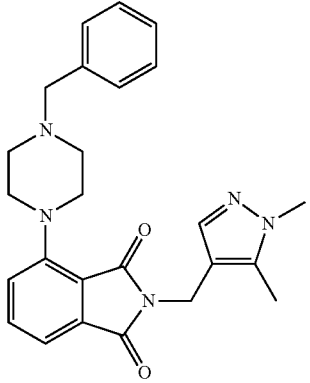
Cpd 56
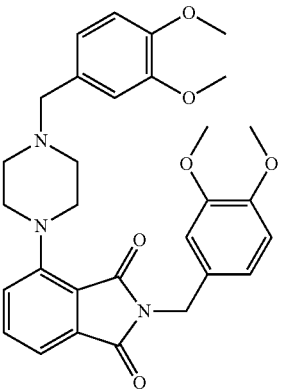

-continued
Cpd 57
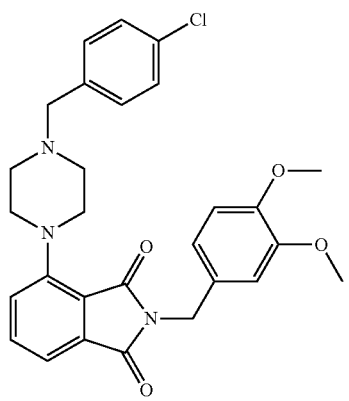
Cpd 58
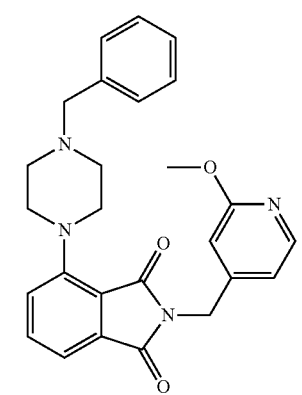
Cpd 59
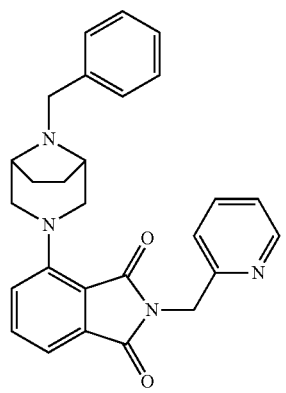
Cpd 60
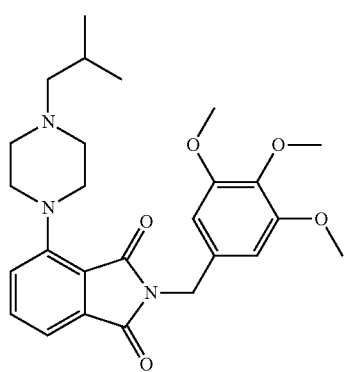
-continued
Cpd 61
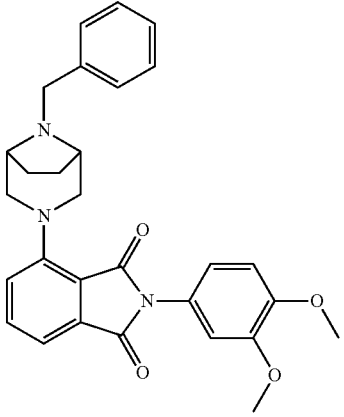
Cpd 62
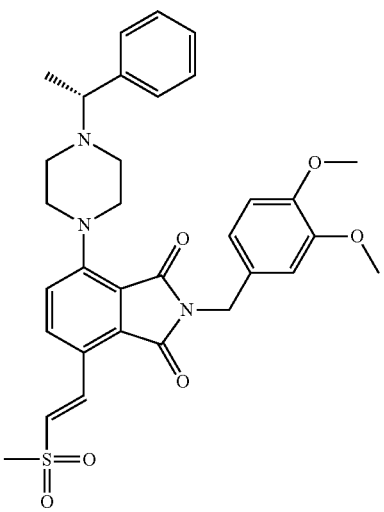
Cpd 63
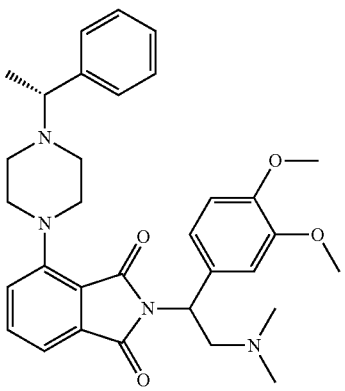

Cpd 64
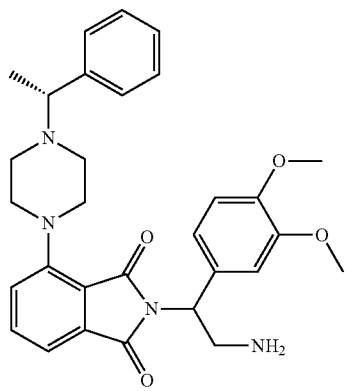
Cpd 65
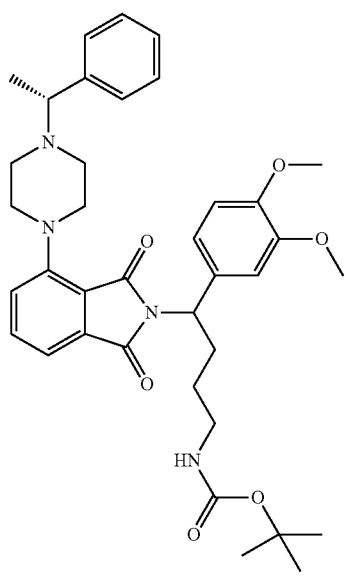
Cpd 66
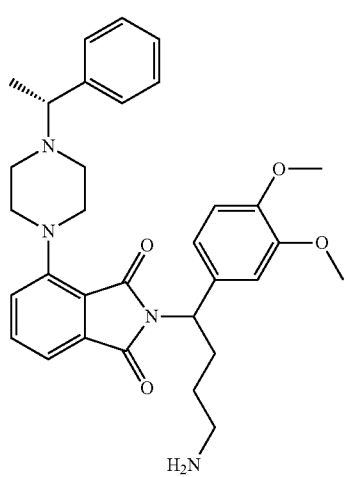
Cpd 67
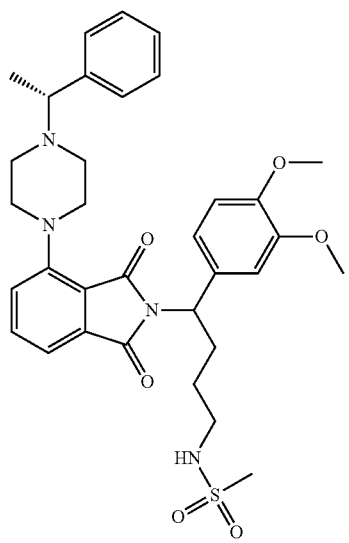
Cpd 68
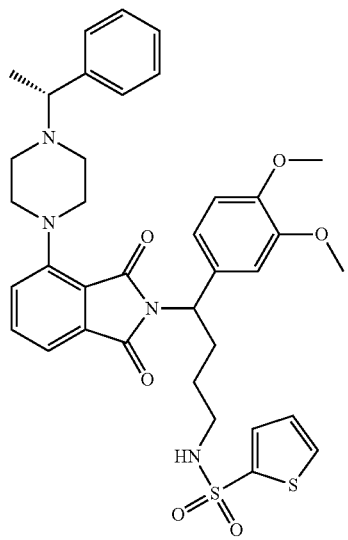
Cpd 69
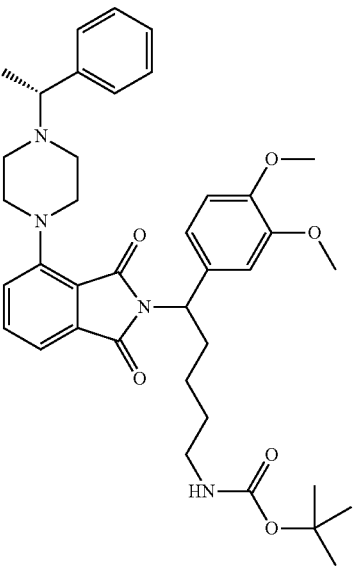

Cpd 70
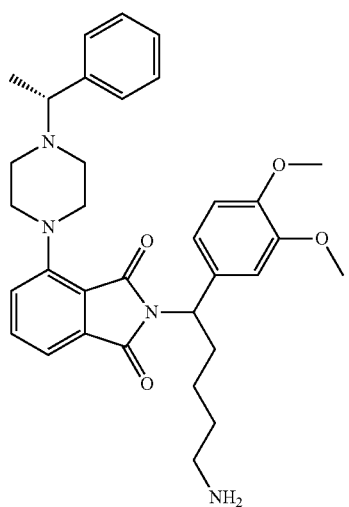
Cpd 71
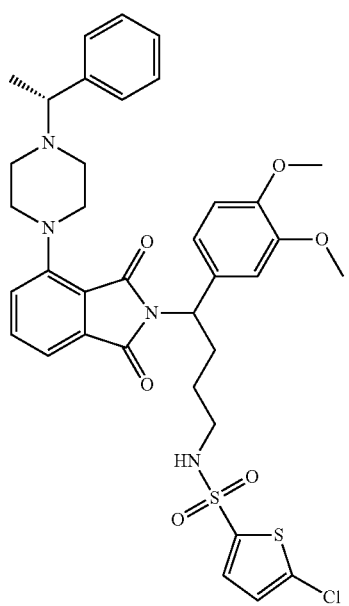
Cpd 72
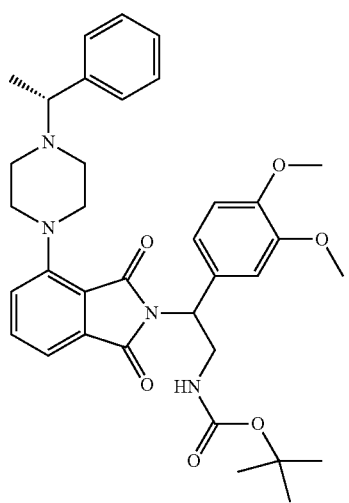
Cpd 73
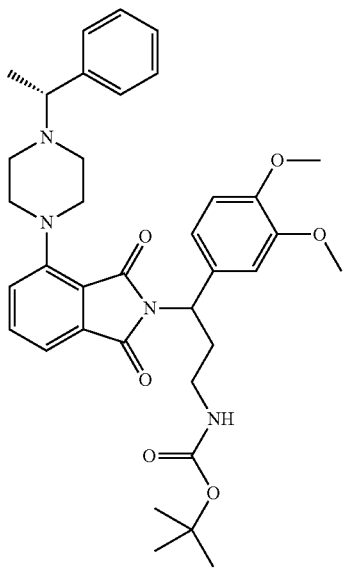
Cpd 74
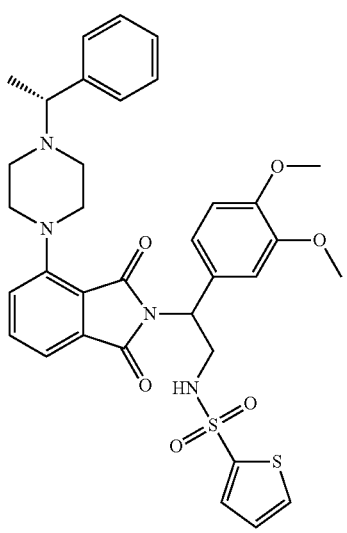
Cpd 75
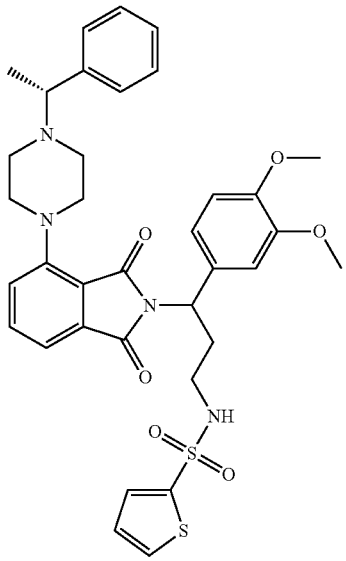

Cpd 76
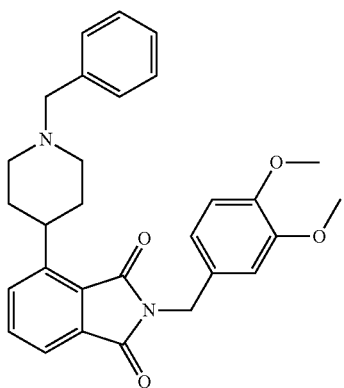
Cpd 80
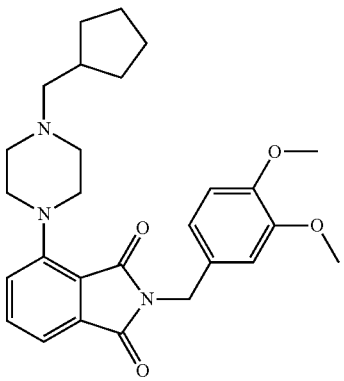
Cpd 77
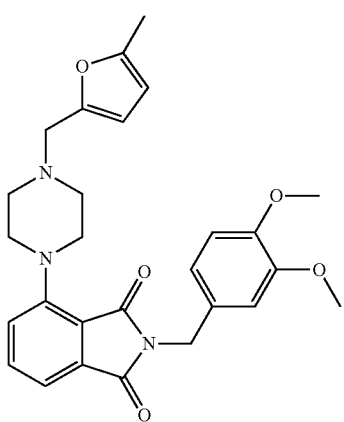
Cpd 81
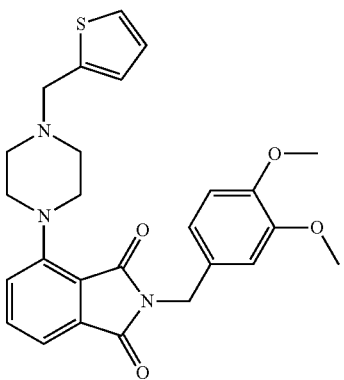
Cpd 78
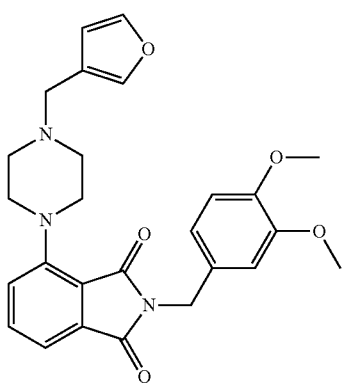
Cpd 82
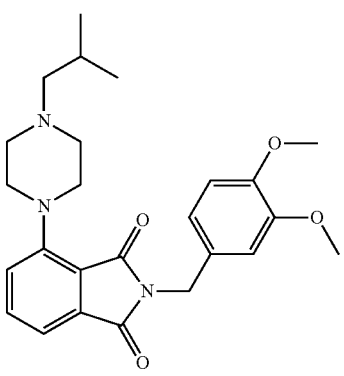
Cpd 79
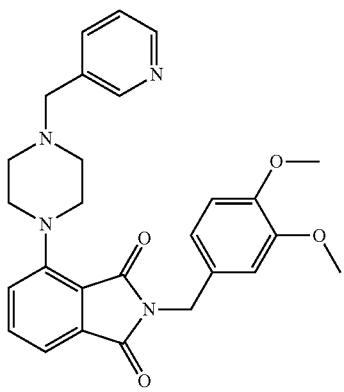
Cpd 83
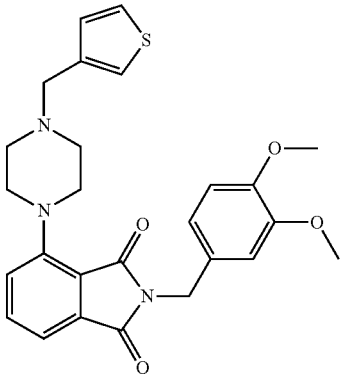

65
-continued
Cpd 84
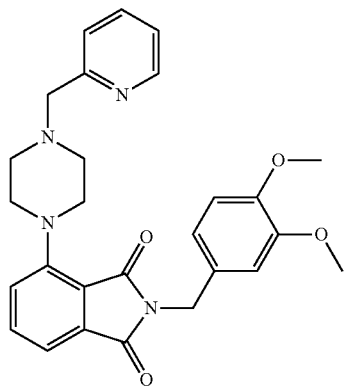
Cpd 85
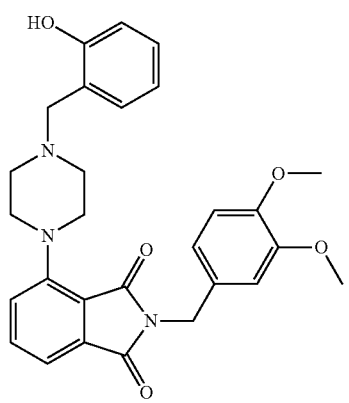
Cdp 86
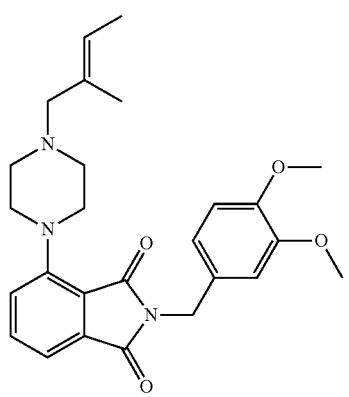
Cpd 87
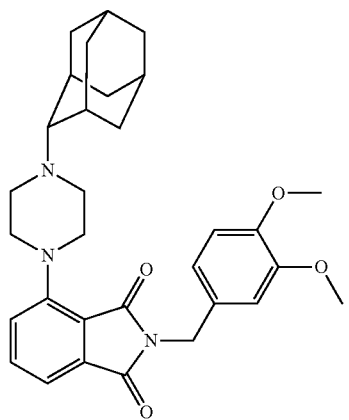
66
-continued
Cpd 88
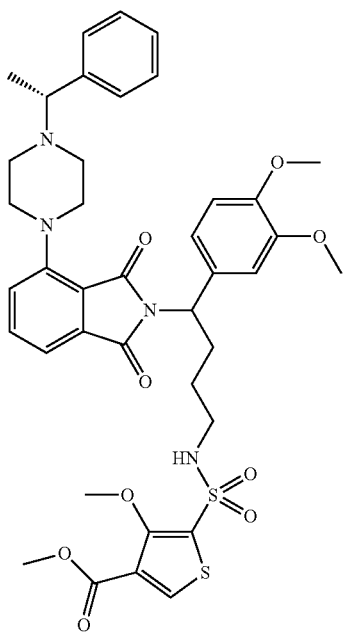
Cpd 89
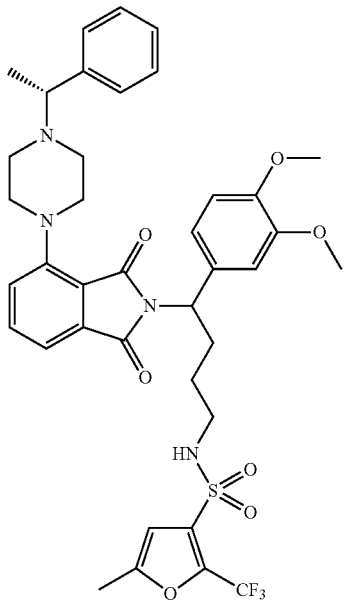

Cpd 90
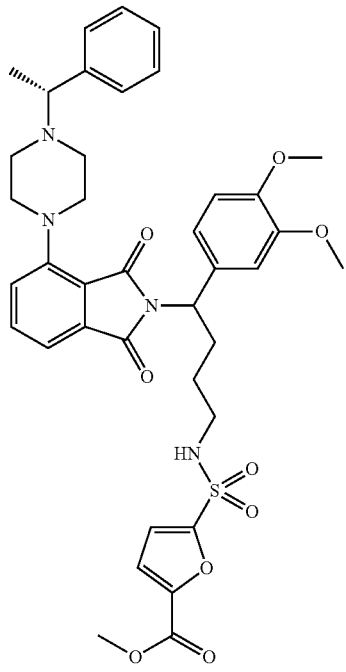
Cpd 92
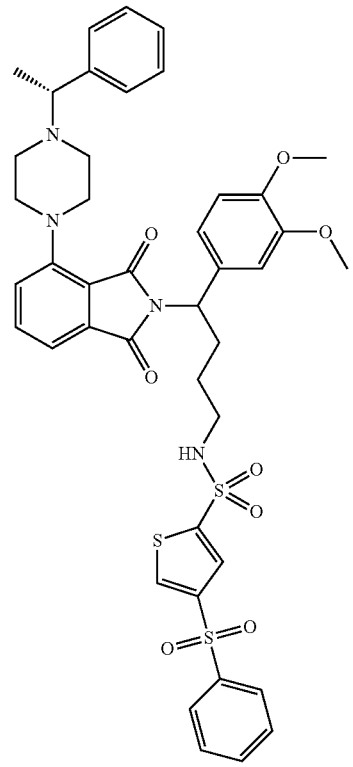
Cpd 91
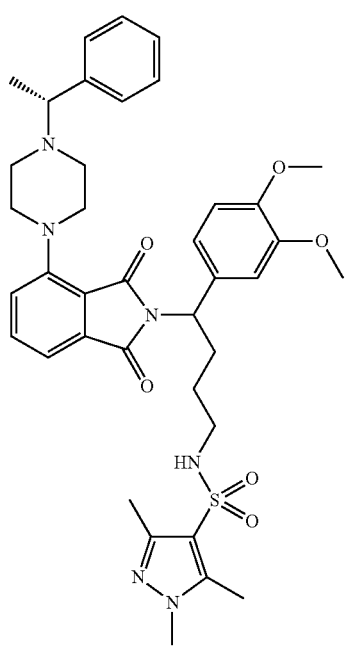
Cpd 93
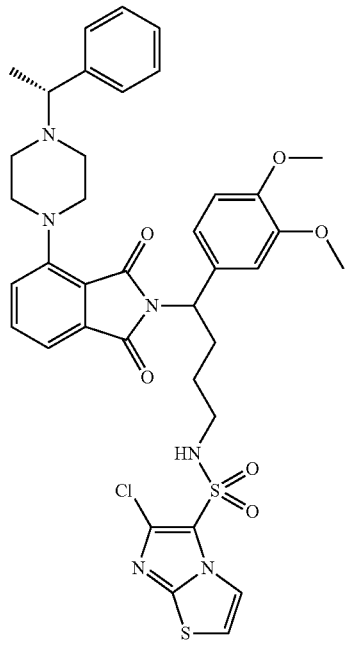

Cpd 94
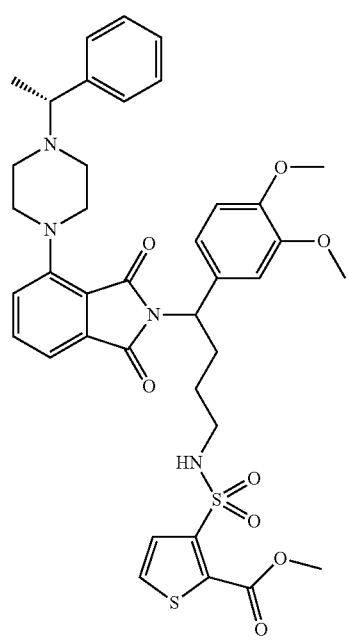
Cpd 96
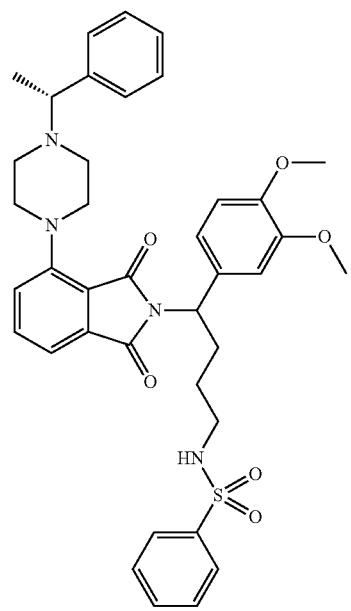
Cpd 95
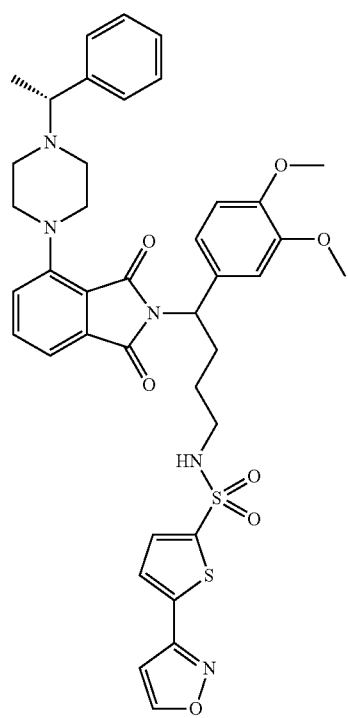
Cpd 97
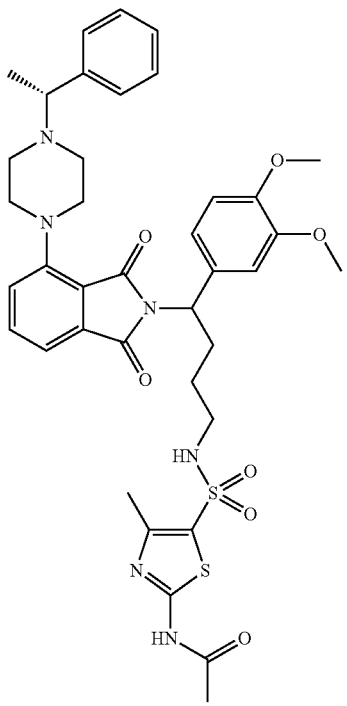

Cpd 98
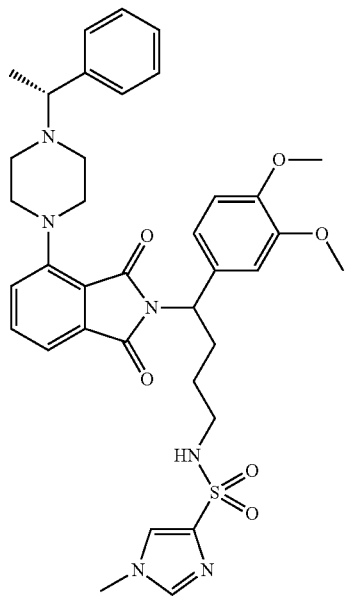
Cpd 100
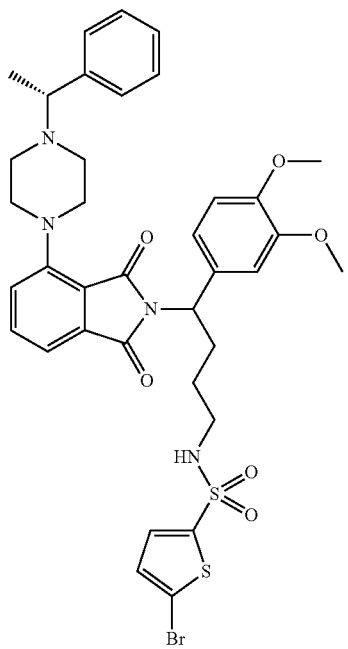
Cpd 99
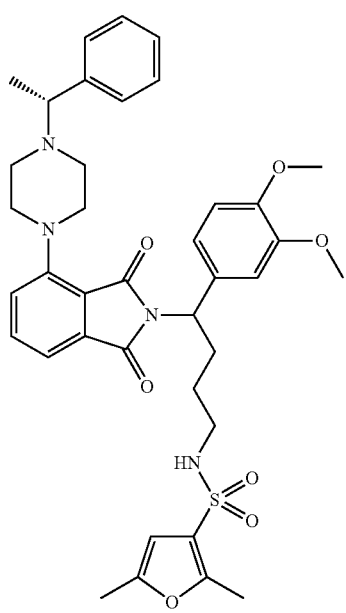
Cpd 101
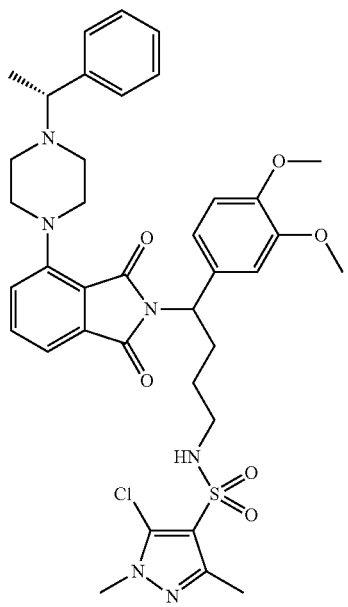

Cpd 102
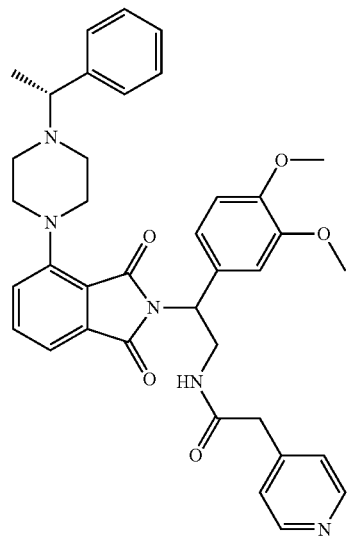
Cpd 103
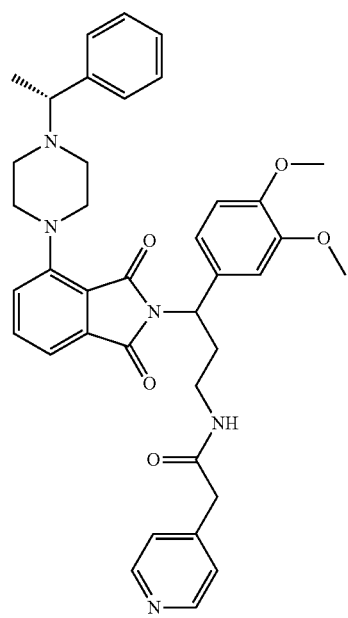
Cpd 104
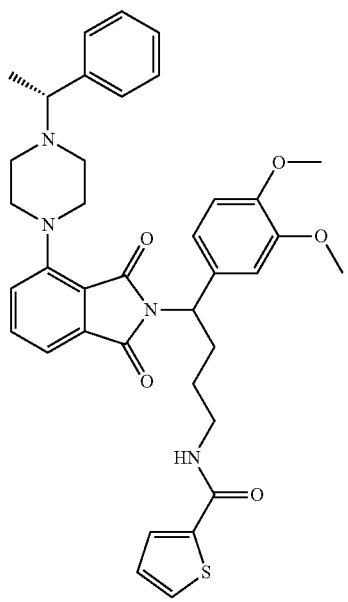
Cpd 105
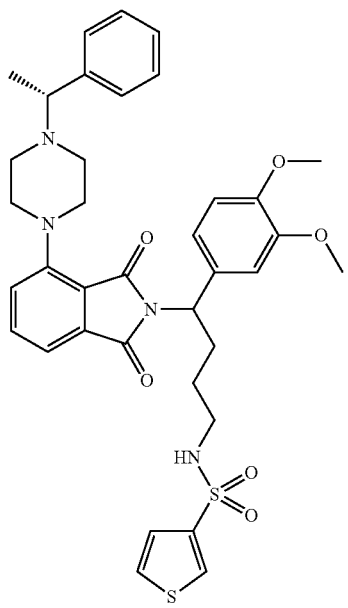

Cpd 106
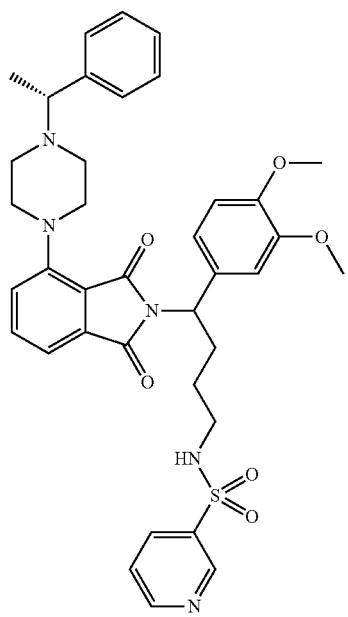
Cpd 108
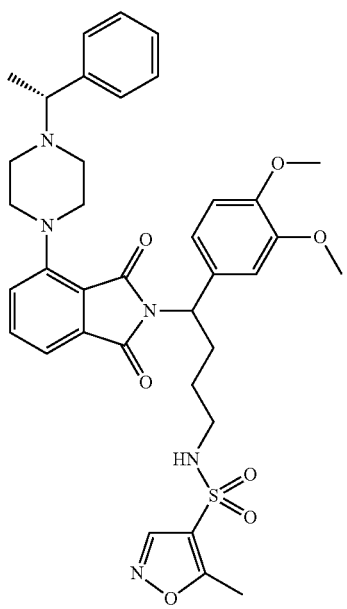
Cpd 107
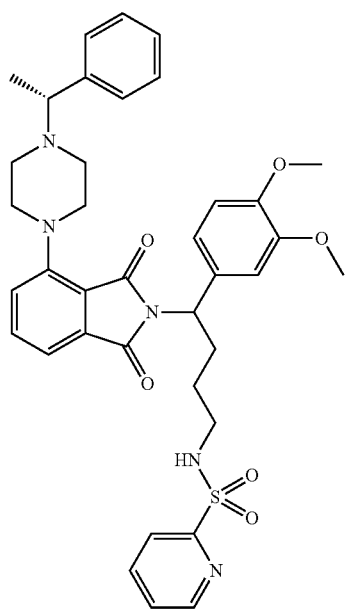
Cpd 109
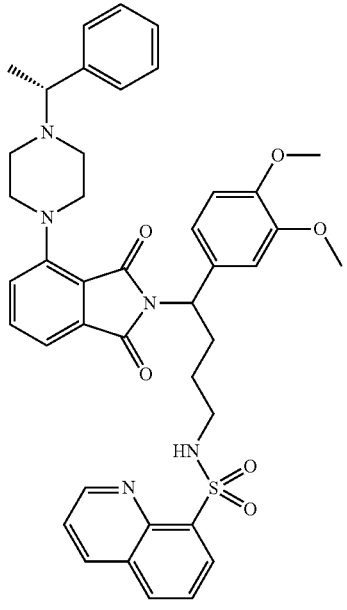

Cpd 110
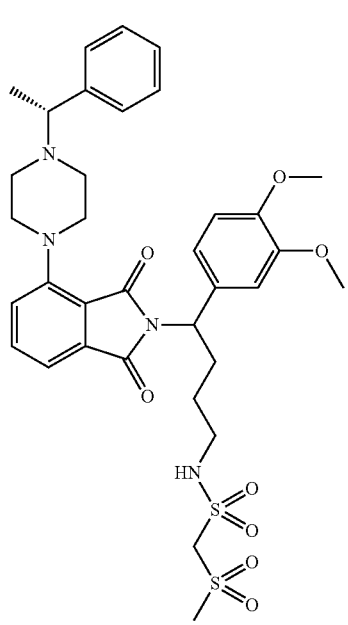
Cpd 111
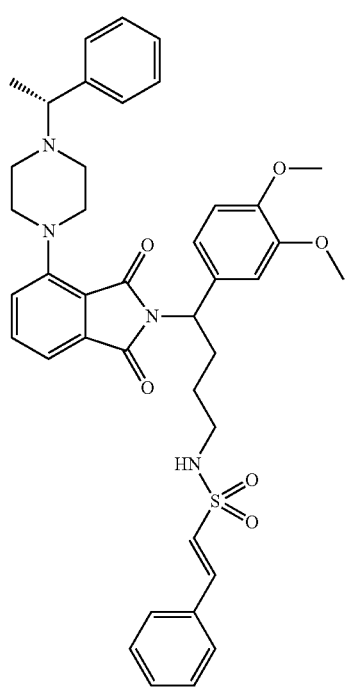
Cpd 112
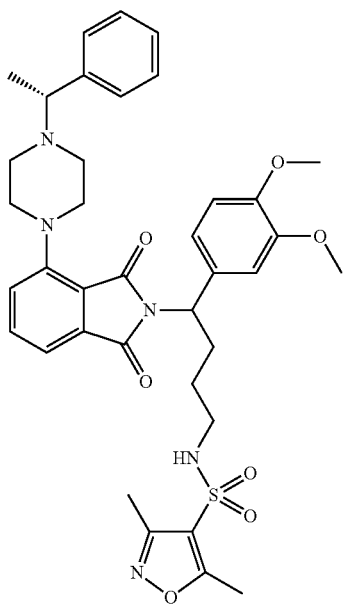
Cpd 113
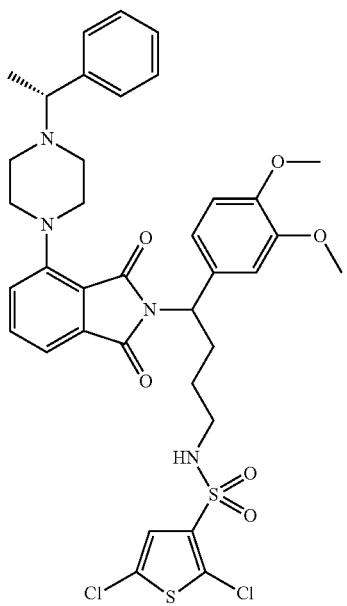

Cpd 114
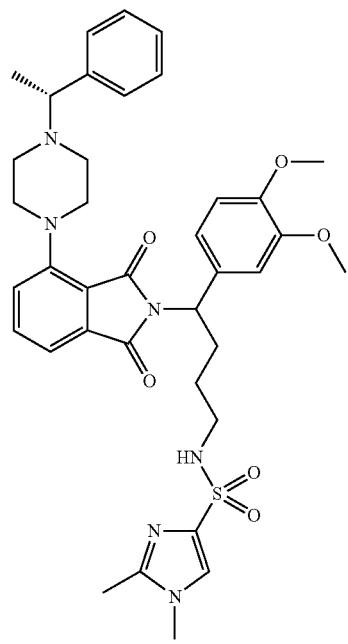
Cpd 116
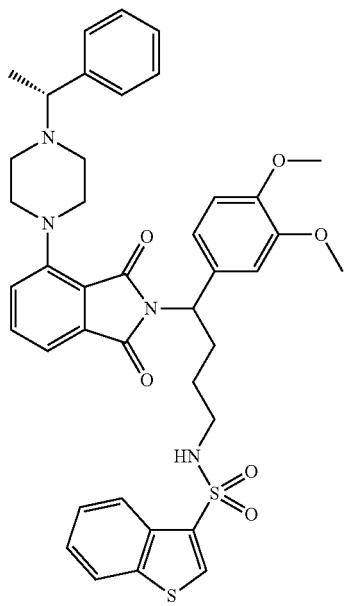
Cpd 115
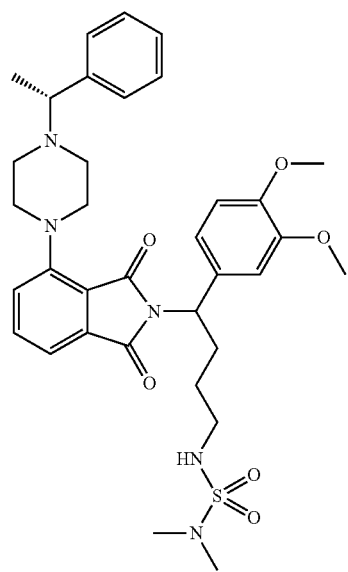
Cpd 117
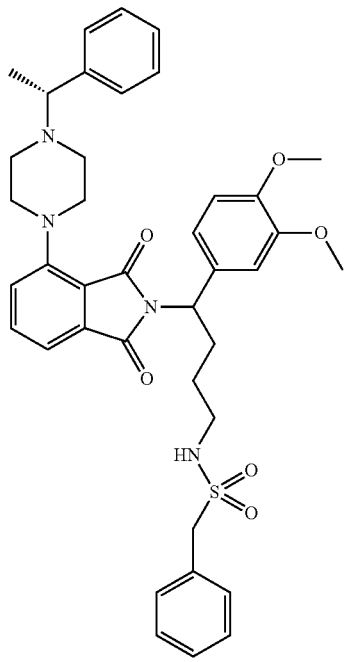

-continued
Cpd 118
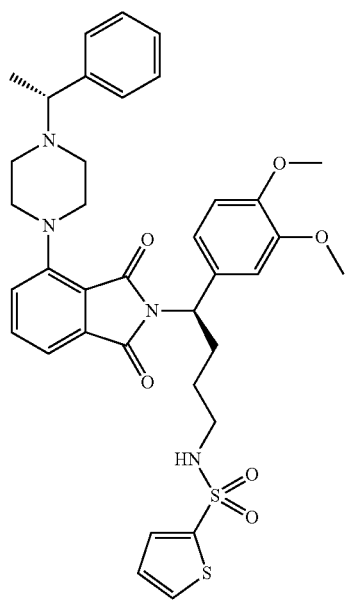
Cpd 119
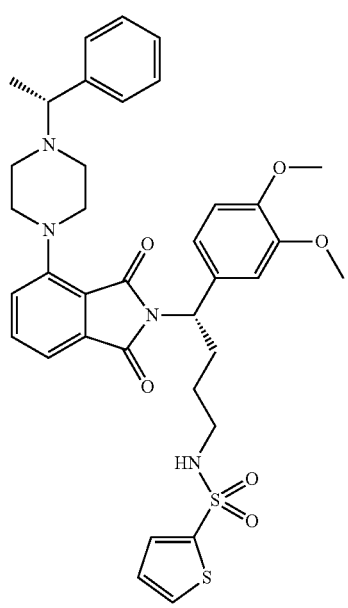
-continued
Cpd 120
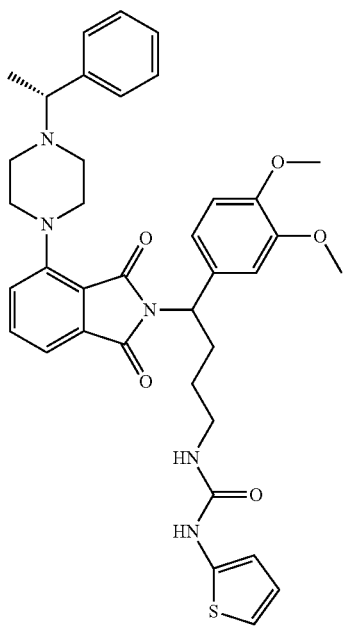
Cpd 121
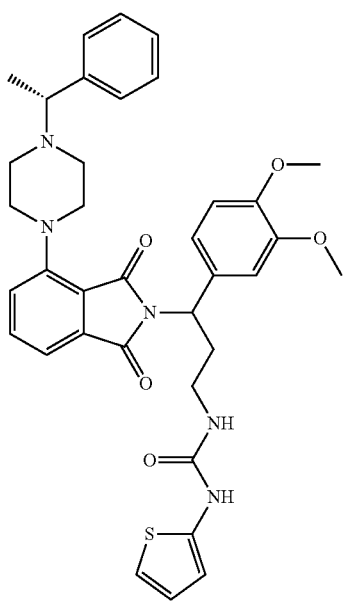

Cpd 122
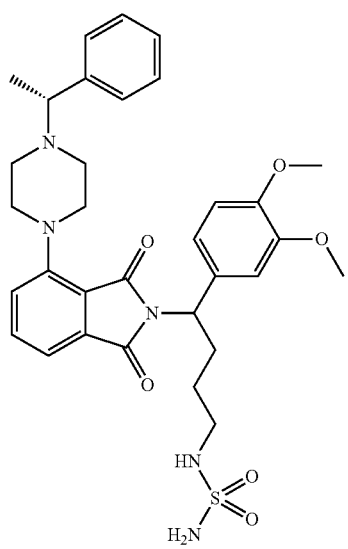
Cpd 123
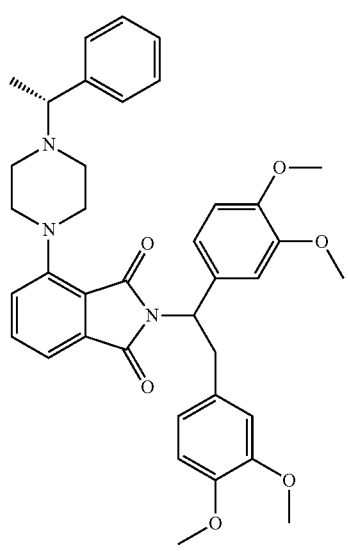
Cpd 124
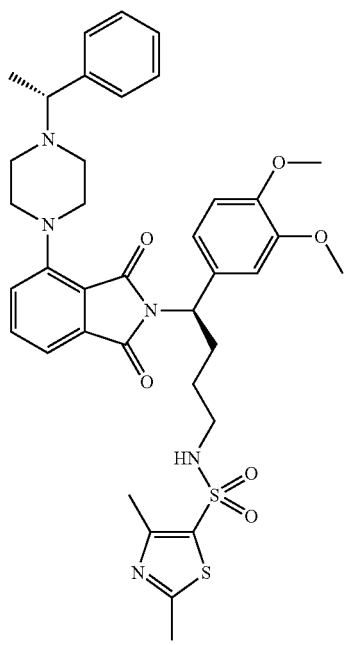
Cpd 125
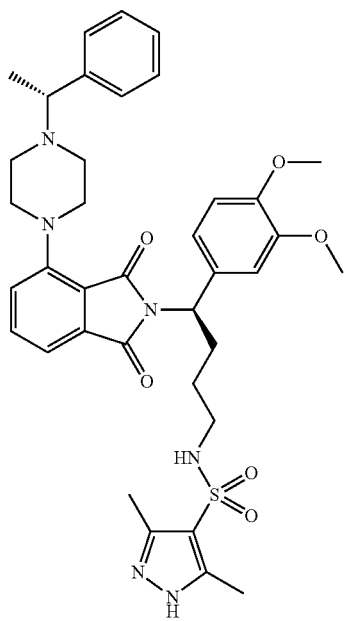

Cpd 126
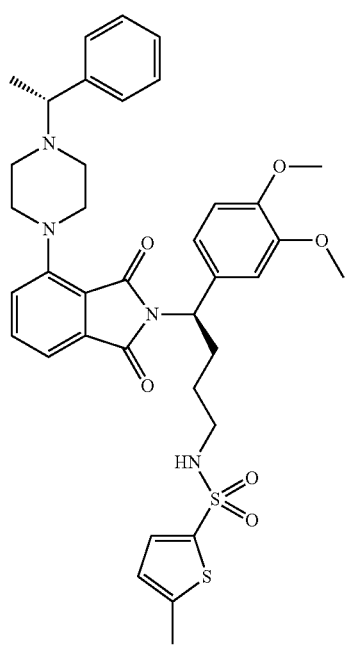
Cpd 127
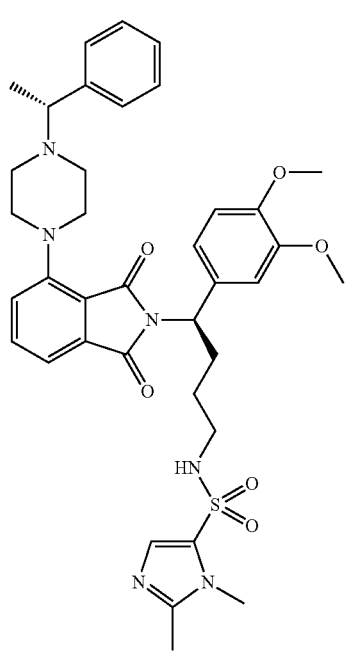
Cpd 128
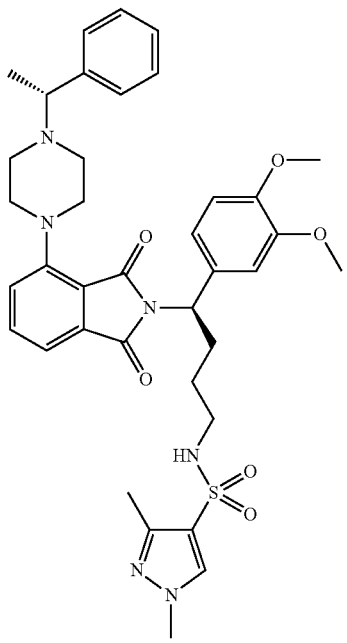
Cpd 129
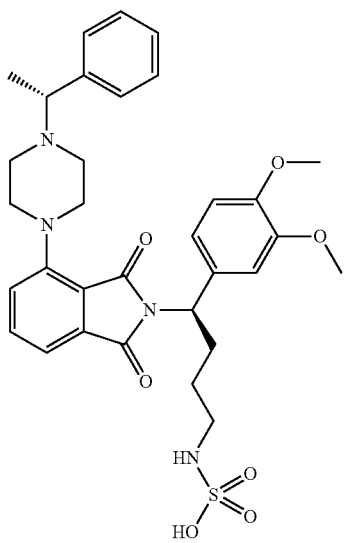

Cpd 130
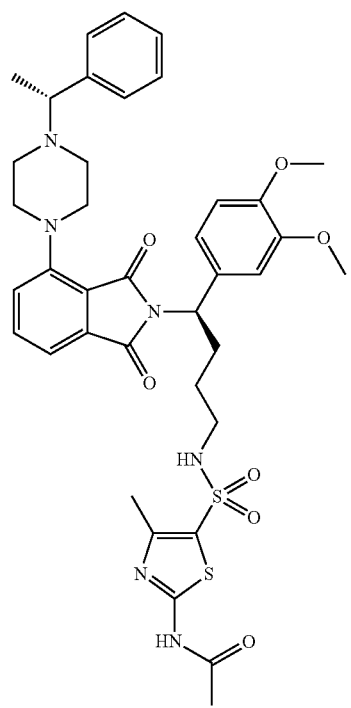
Cpd 131
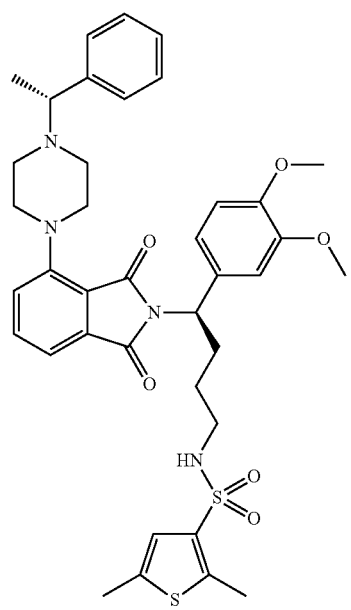
Cpd 132
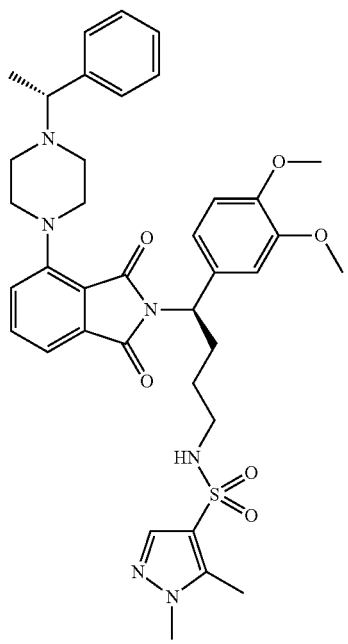
Cpd 133
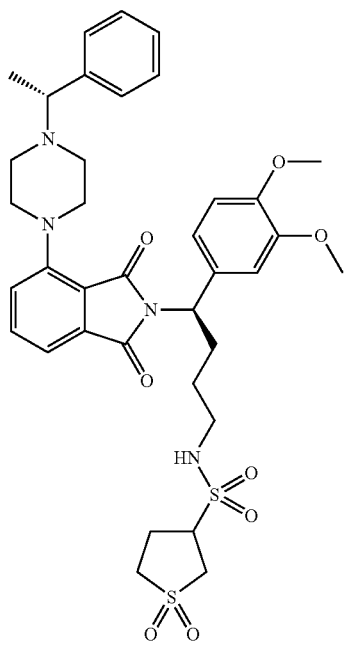

Cpd 134
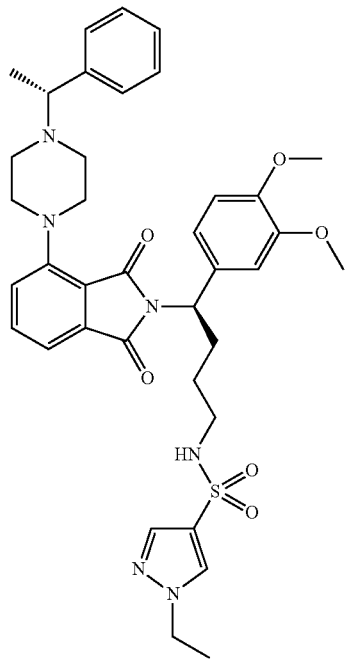
Cpd 135
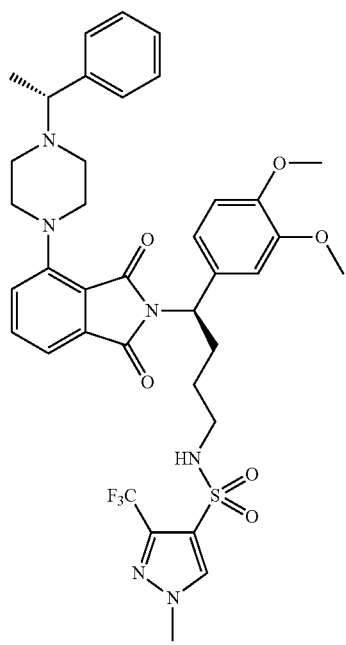
Cpd 136
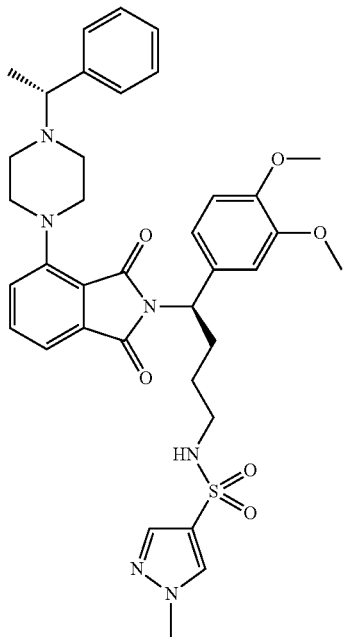
Cpd 137
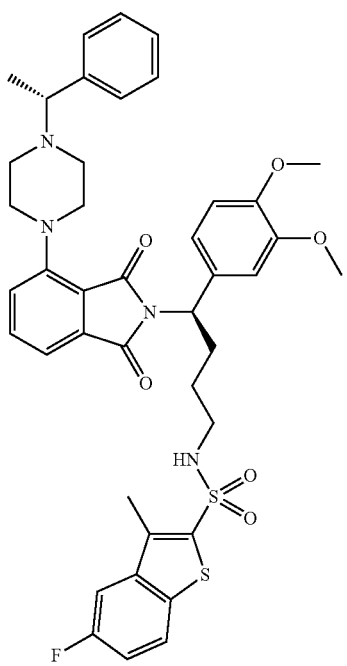

Cpd 138
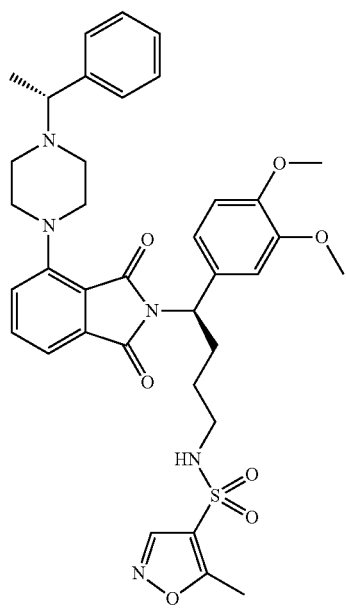
Cpd 139
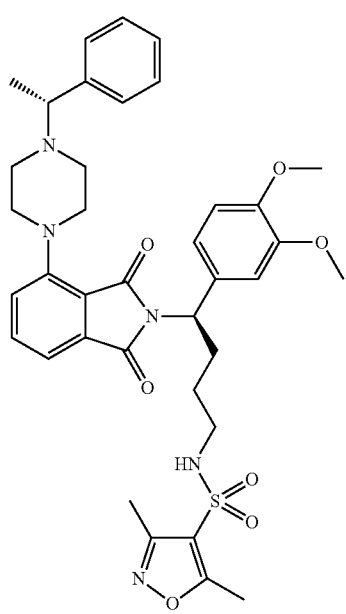
Cpd 140
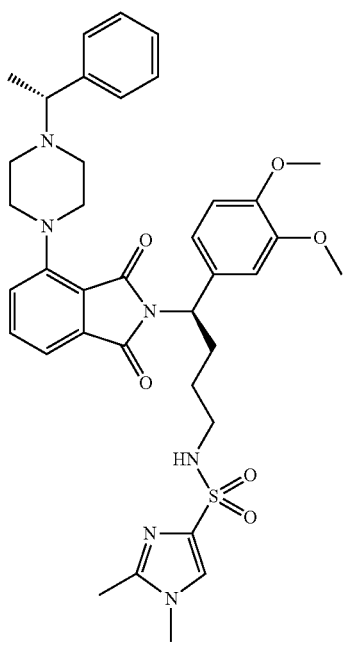
Cpd 141
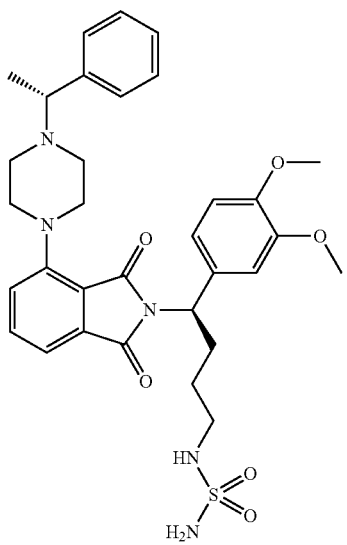

Cpd 142
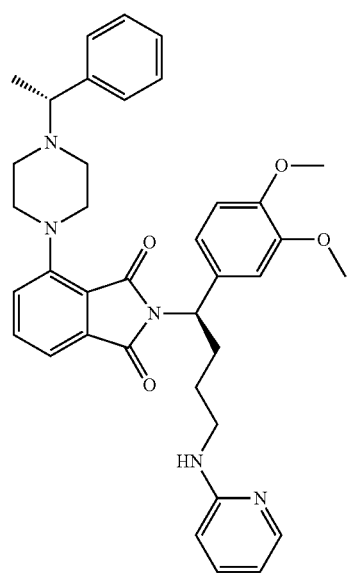
Cpd 144
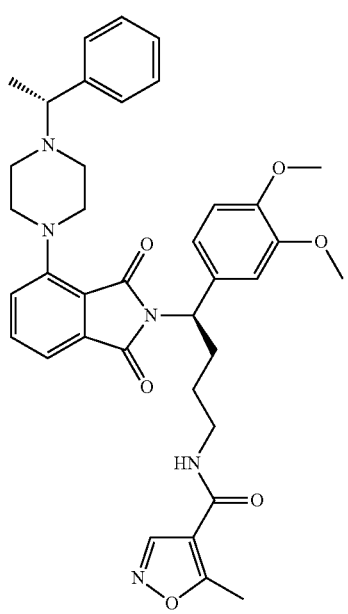
Cpd 143
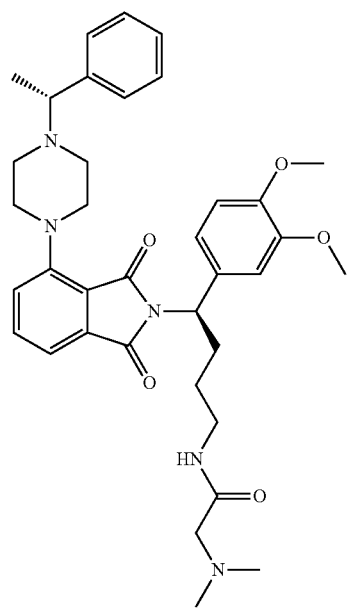
Cpd 145
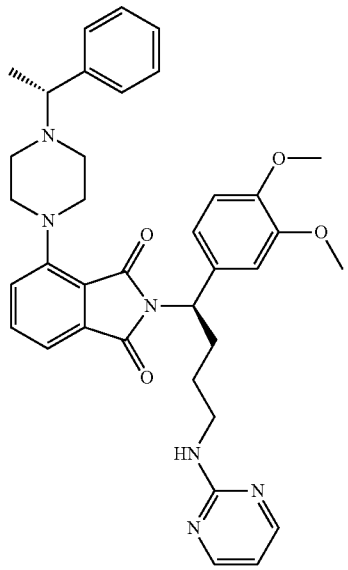

Cpd 146
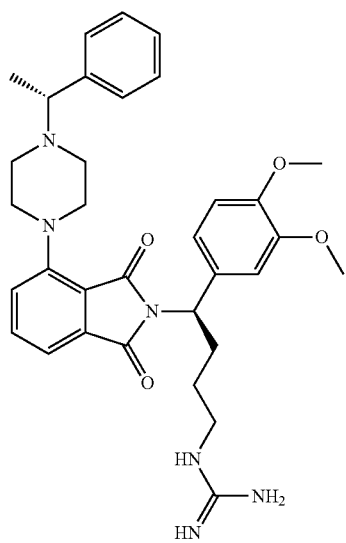
Cpd 147
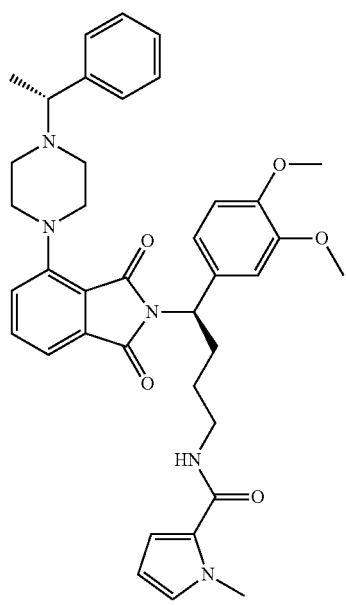
Cpd 148
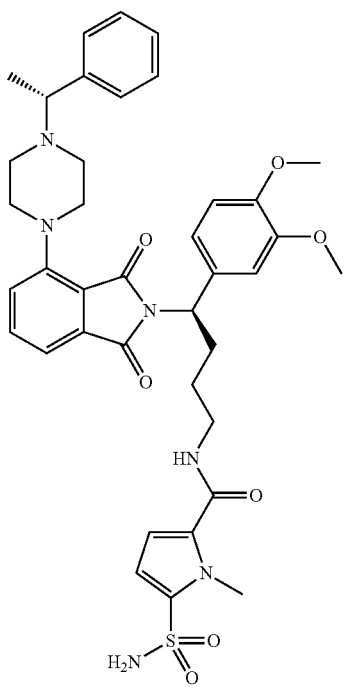
Cpd 149
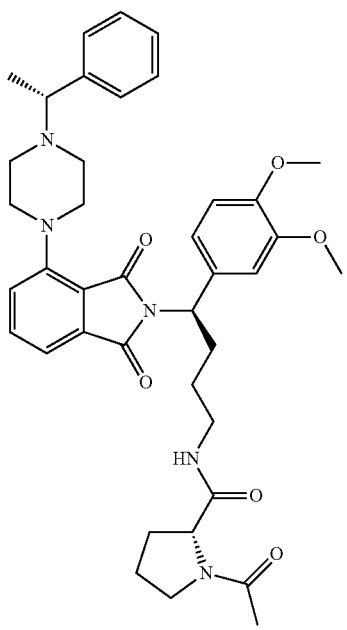

Cpd 150
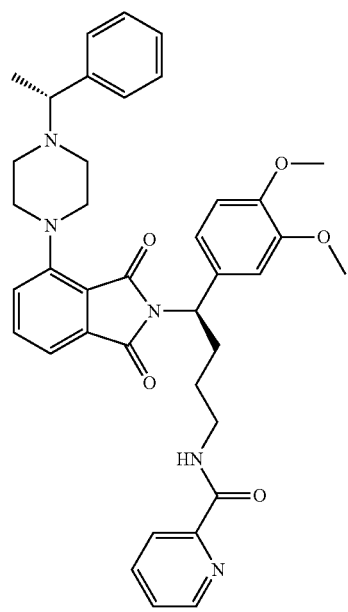
Cpd 151
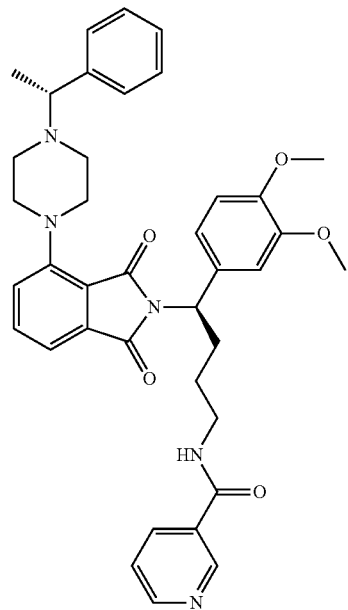
Cpd 152
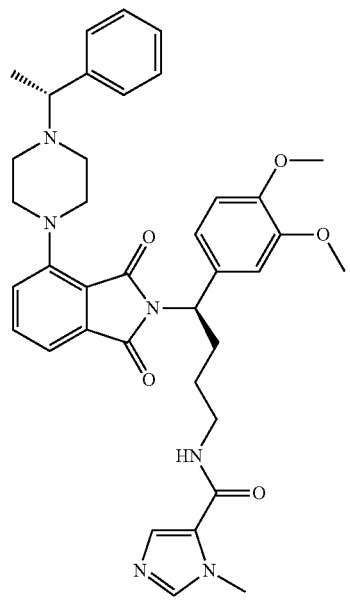
Cpd 153
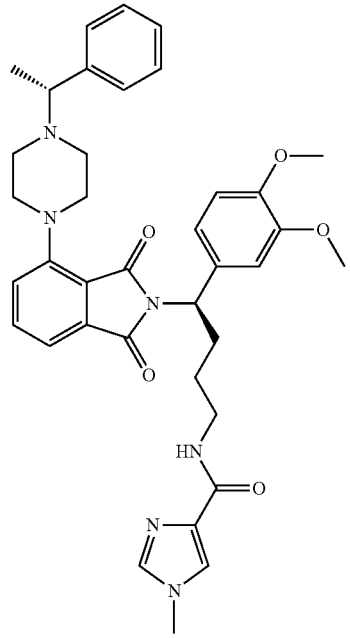

Cpd 154
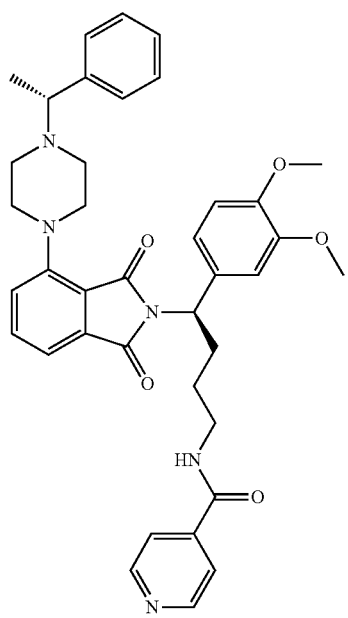
Cpd 155
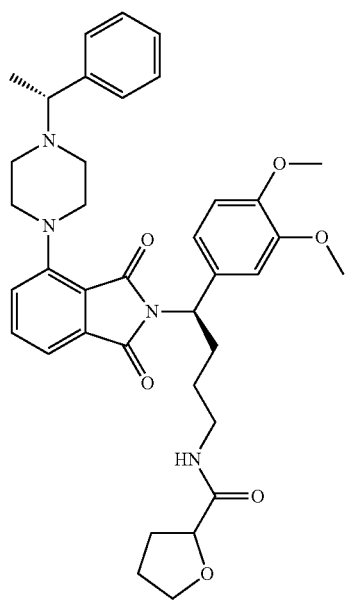
Cpd 156
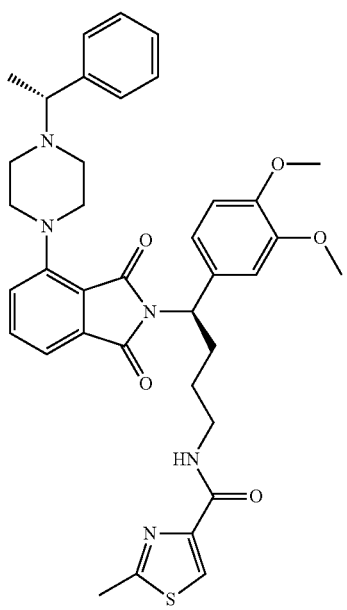
Cpd 157
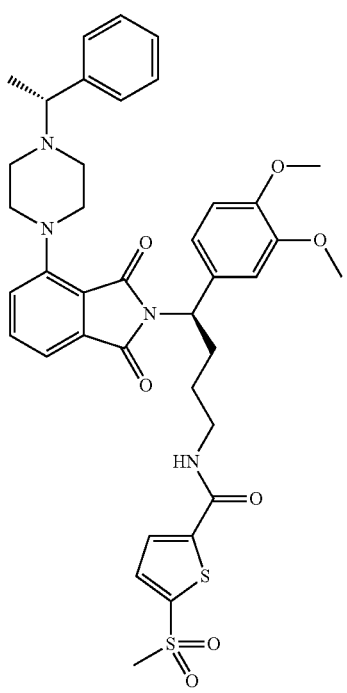

Cpd 158
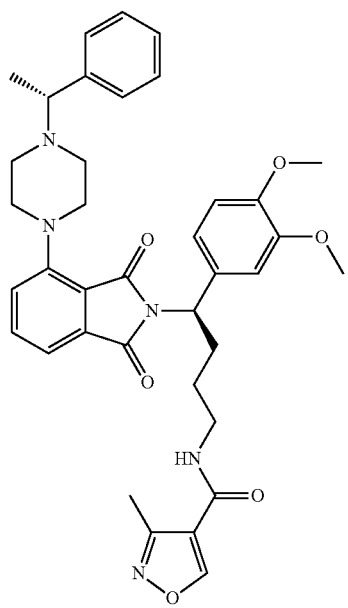
Cpd 159
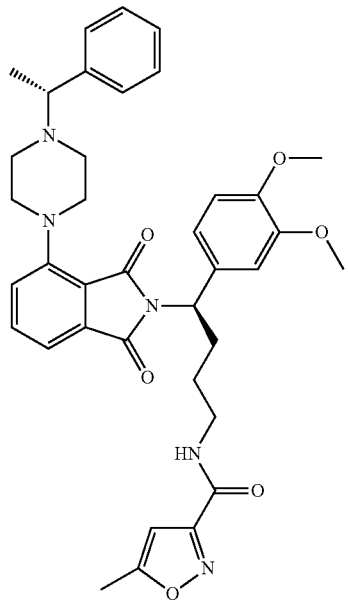
Cpd 160
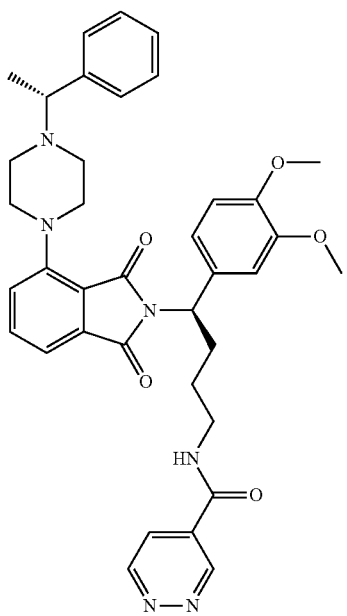
Cpd 161
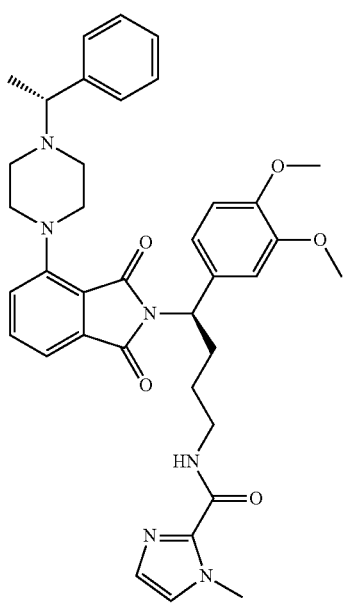

Cpd 162
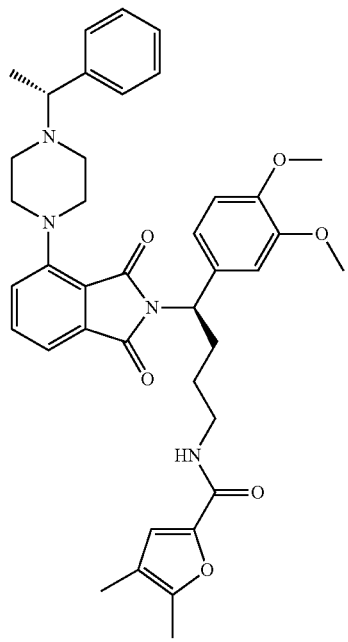
Cpd 163
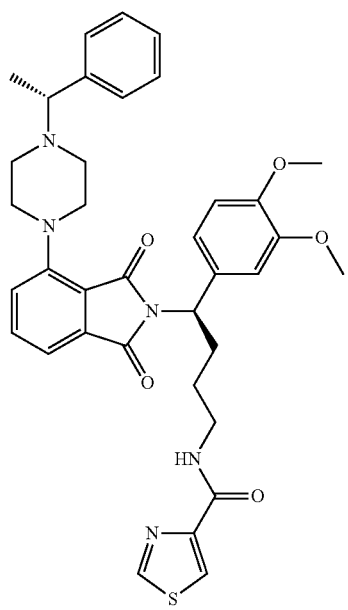
Cpd 164
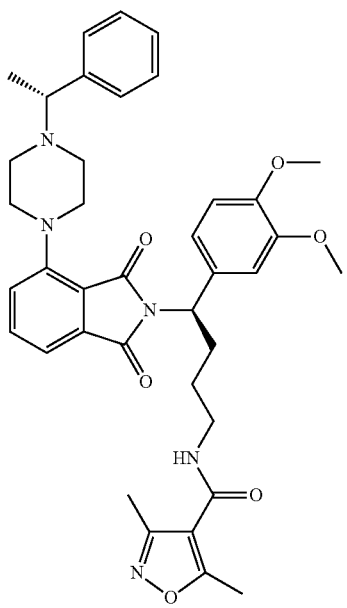
Cpd 165
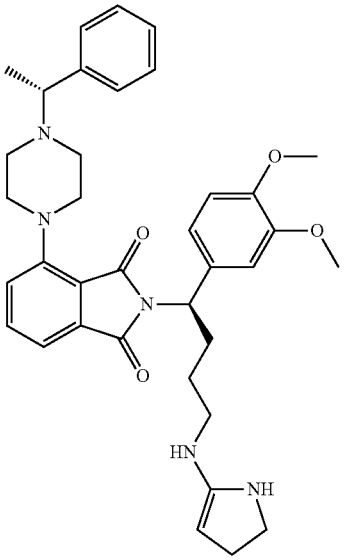

Cpd 166
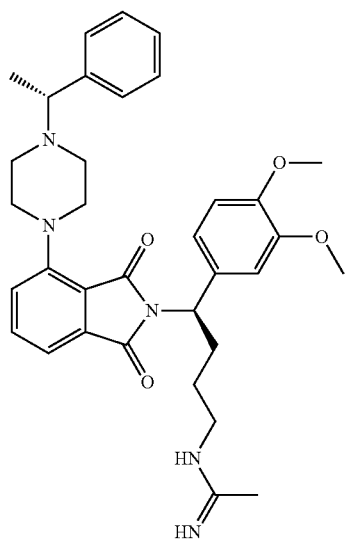
Cpd 167
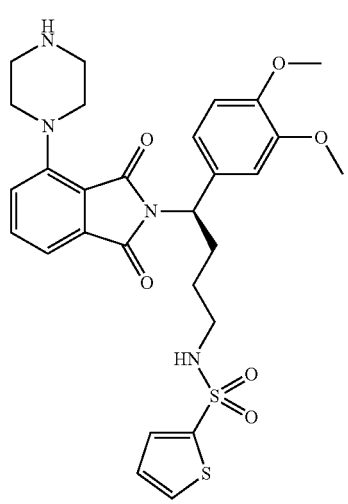
Cpd 168
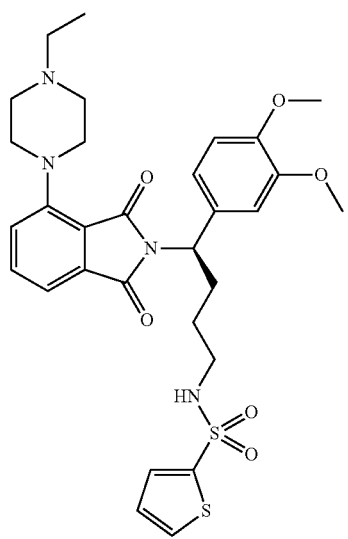
Cpd 169
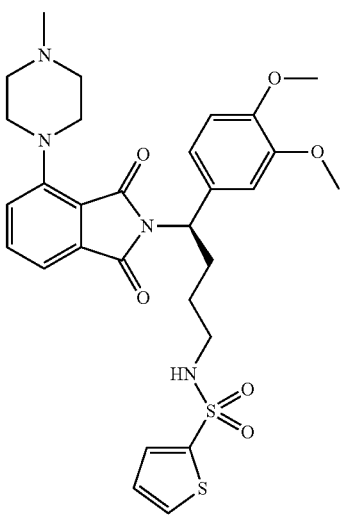
Cpd 170
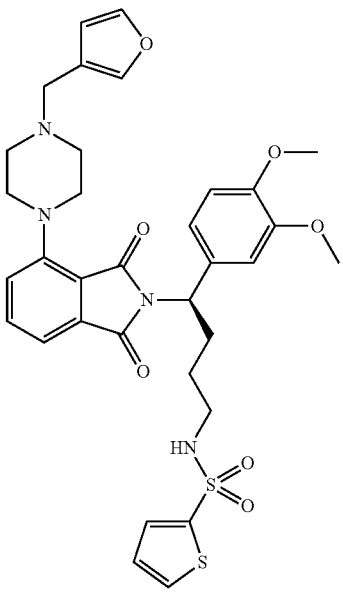

Cpd 171
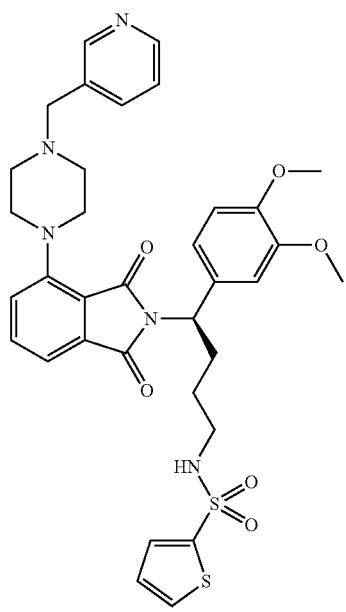
Cpd 172
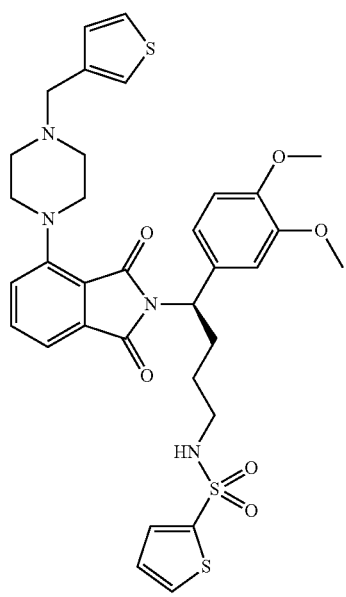
Cpd 173
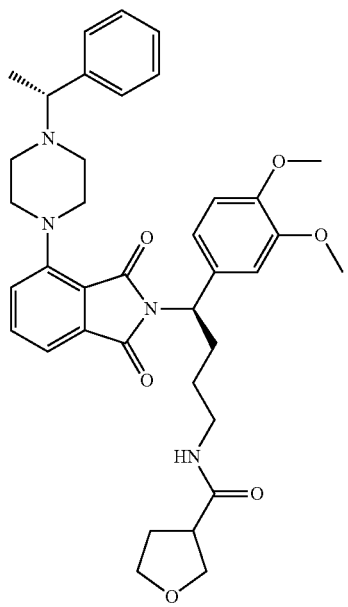
Cpd 174
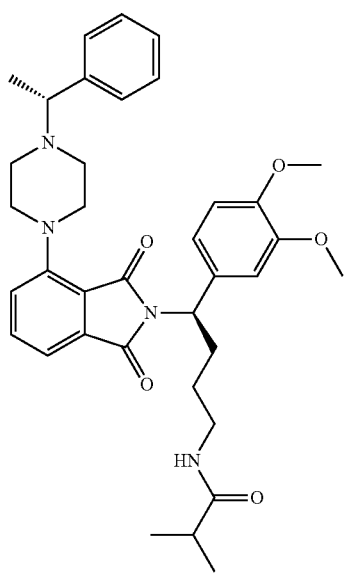

Cpd 175
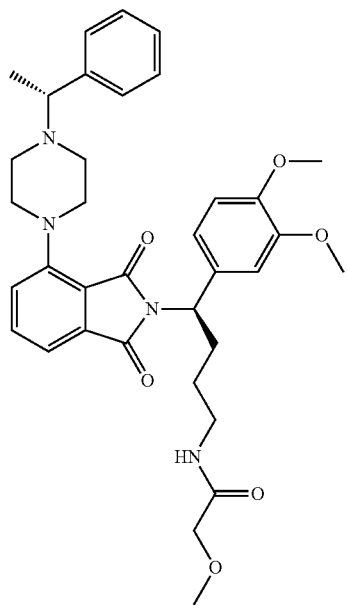
Cpd 176
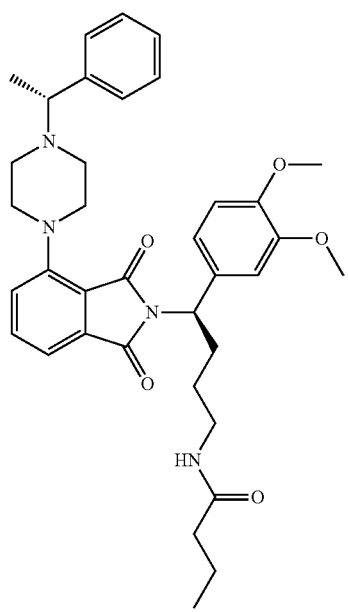
Cpd 177
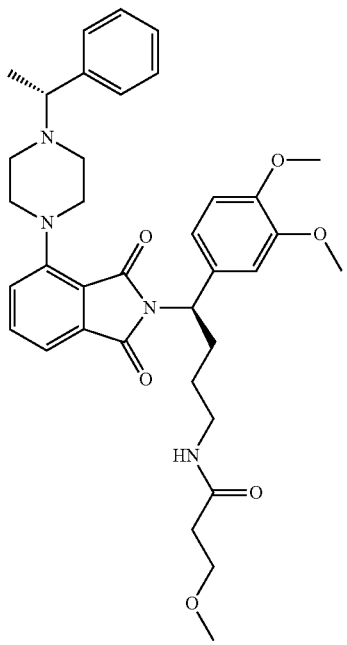
Cpd 178
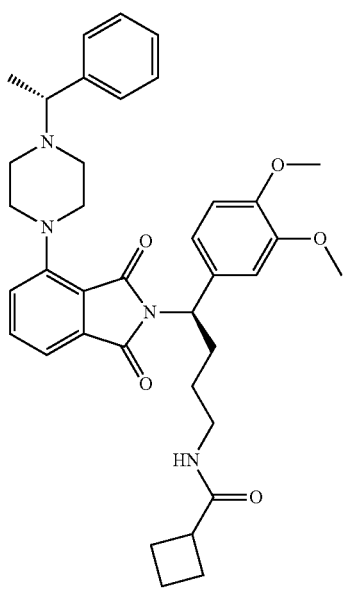

Cpd 179
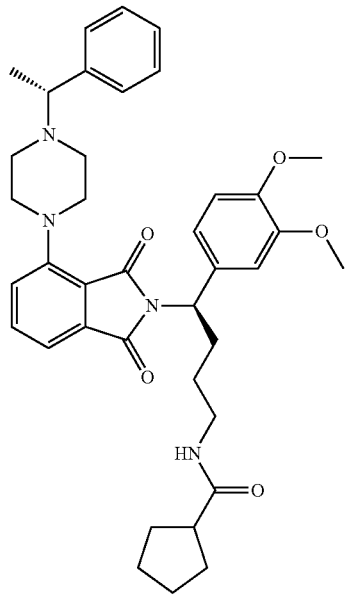
Cpd 181
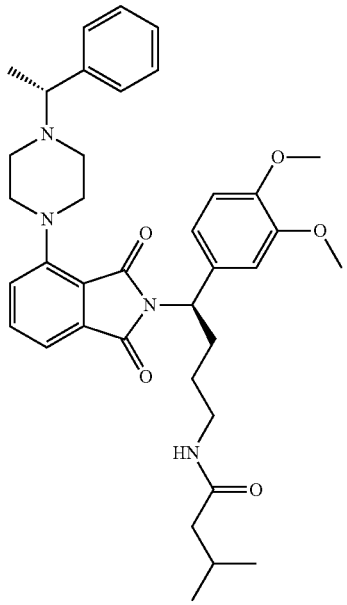
Cpd 180
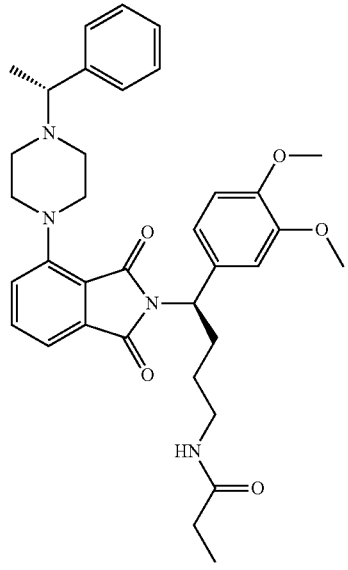
Cpd 182
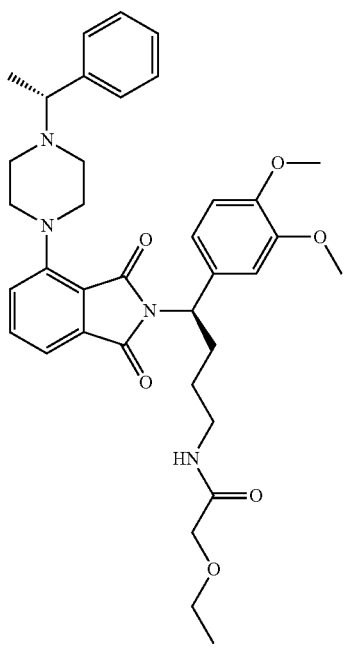

-continued
Cpd 183
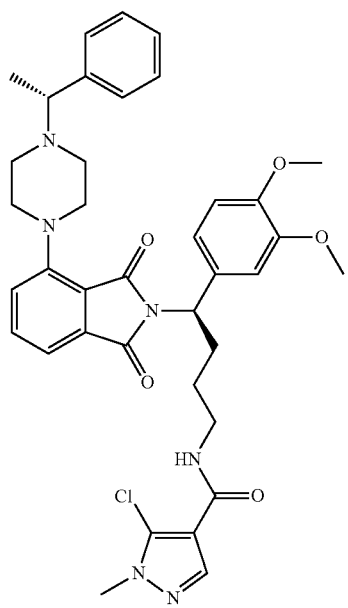
Cpd 184
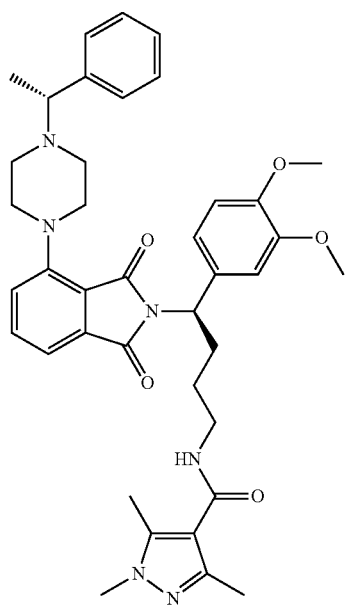
-continued
Cpd 185
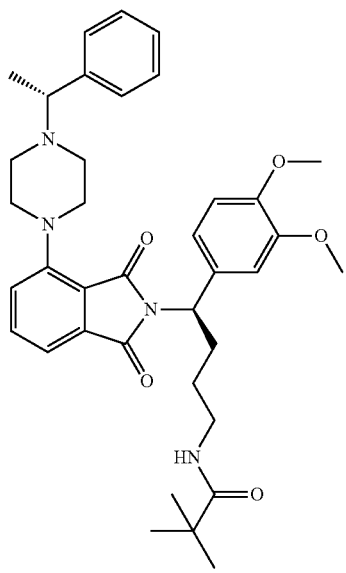
Cpd 186
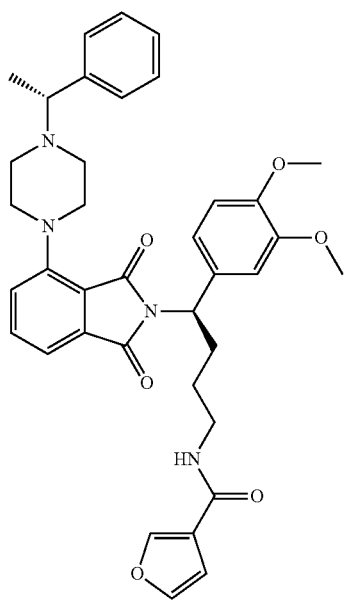

Cpd 187
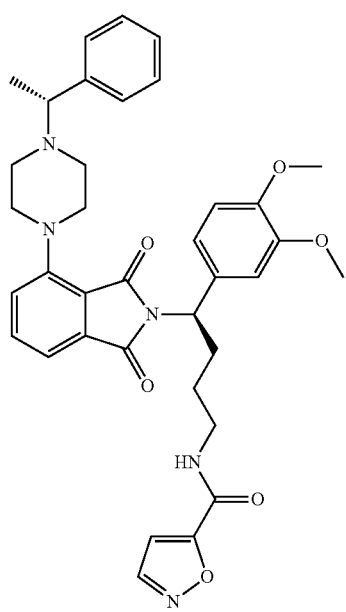
Cpd 188
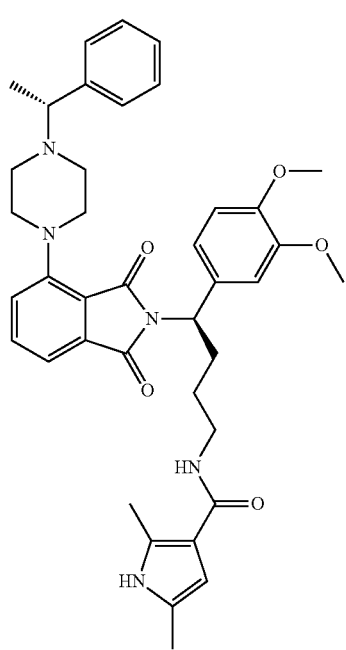
Cpd 189
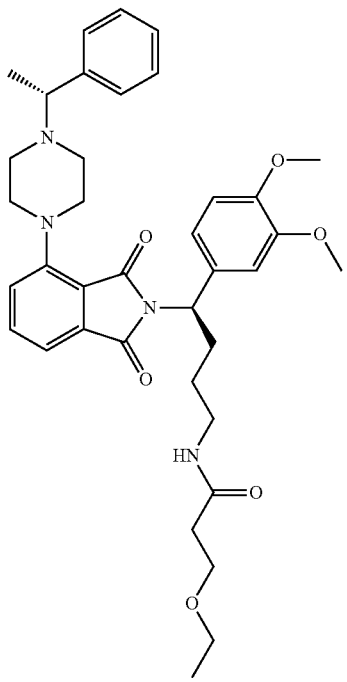
Cpd 190
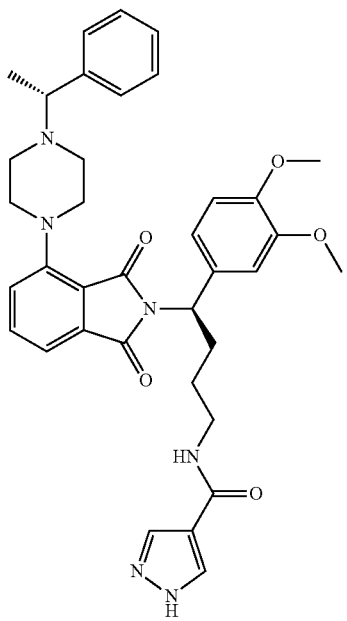

117
-continued
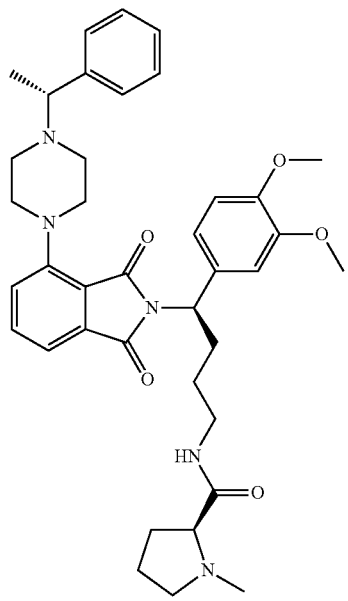
Cpd 191
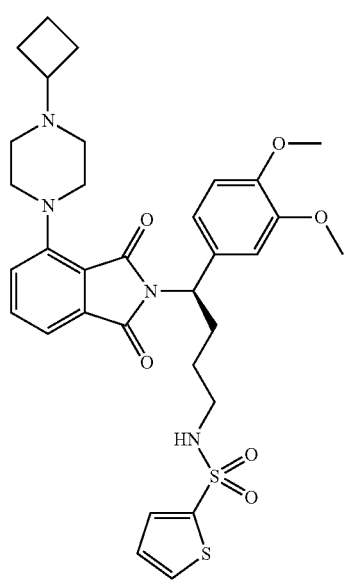
Cpd 192
118
-continued
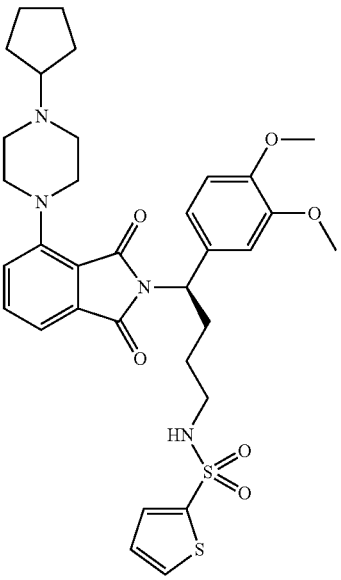
Cpd 193
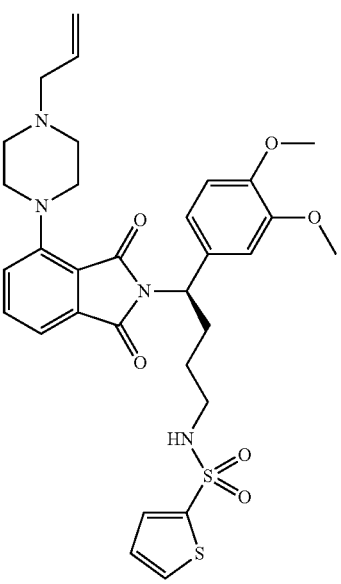
Cpd 194

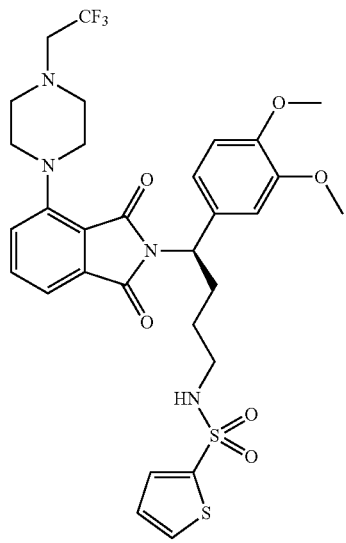
Cpd 195
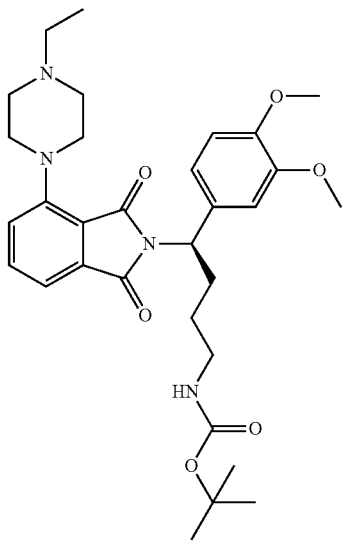
Cpd 197
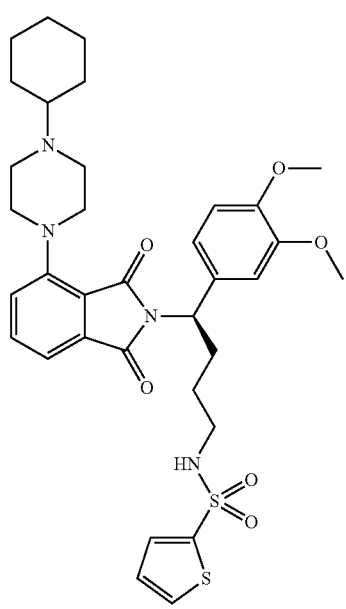
Cpd 196
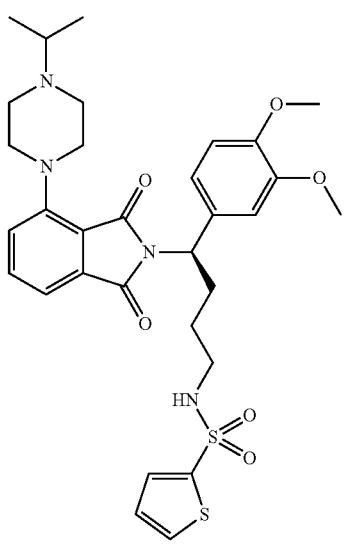
Cpd 198

Cpd 199
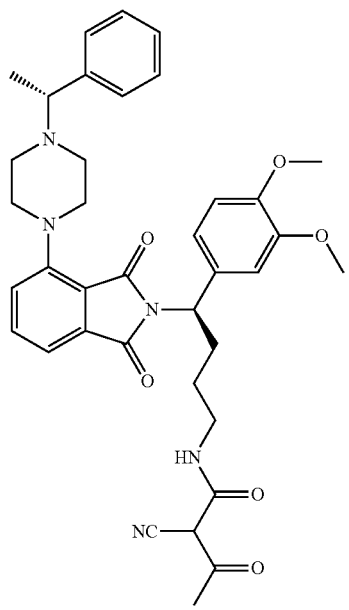
Cpd 200
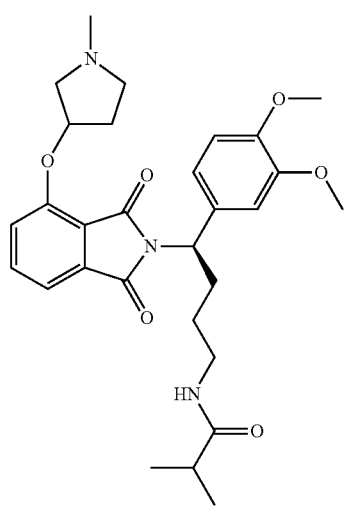
Cpd 201
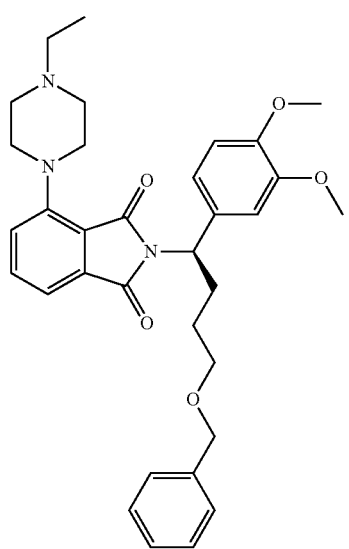
Cpd 202
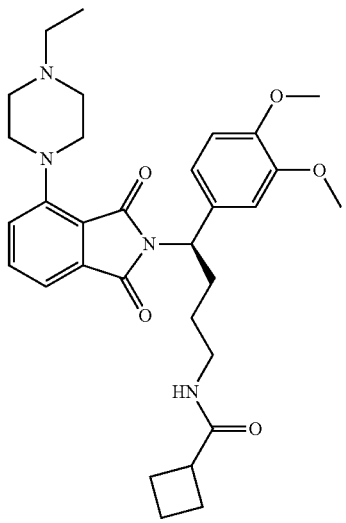
Cpd 203
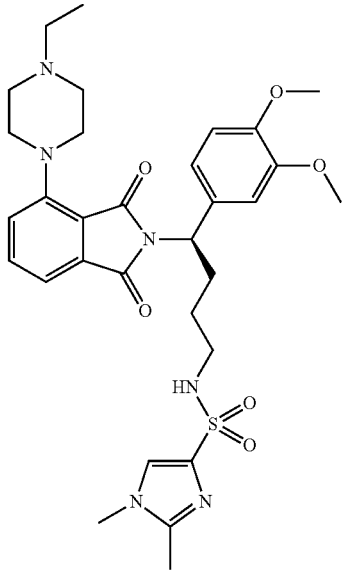
Cpd 204
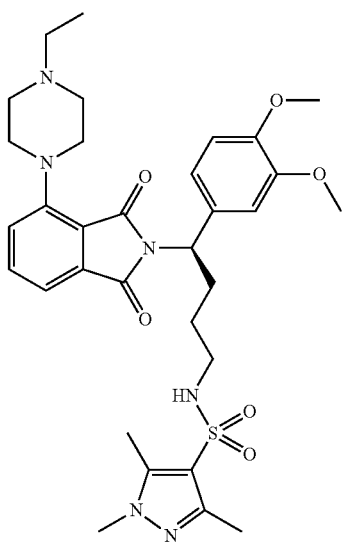

Cpd 205 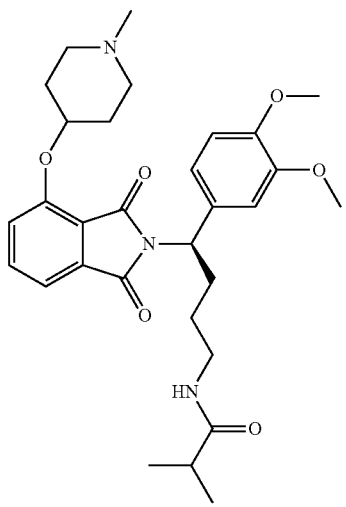
Cpd 208 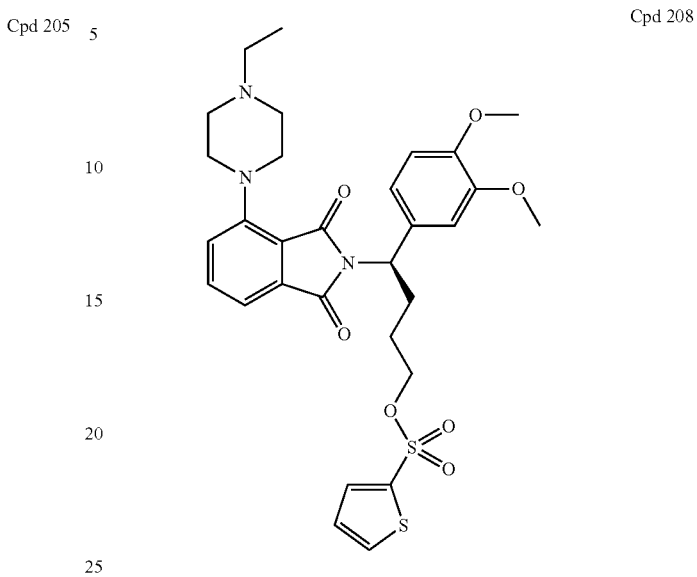
Cpd 206 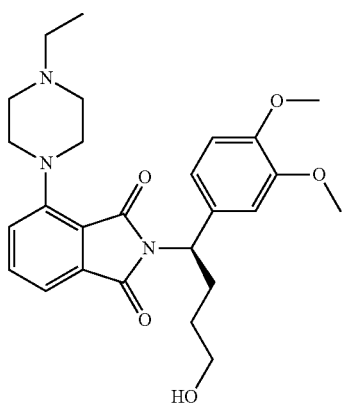
Cpd 209 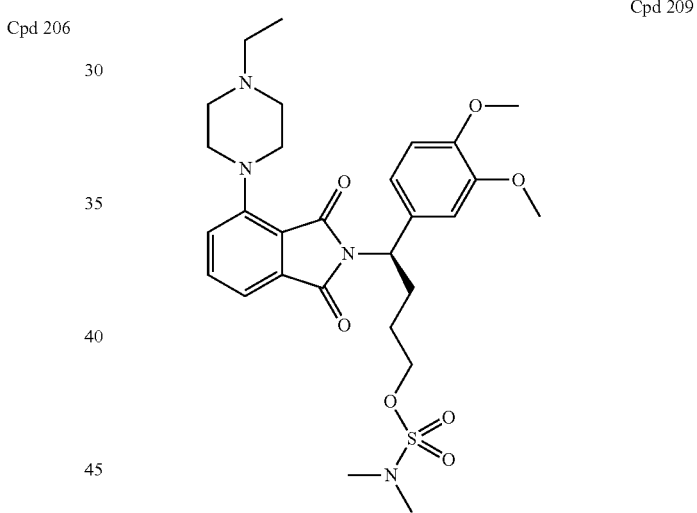
Cpd 207 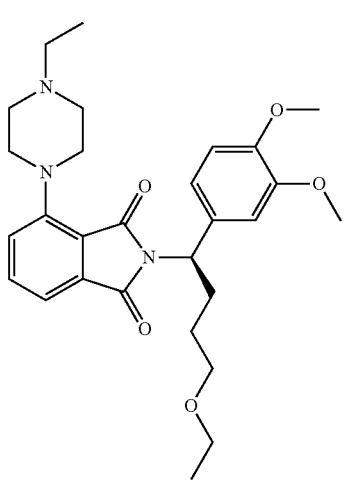
Cpd 210 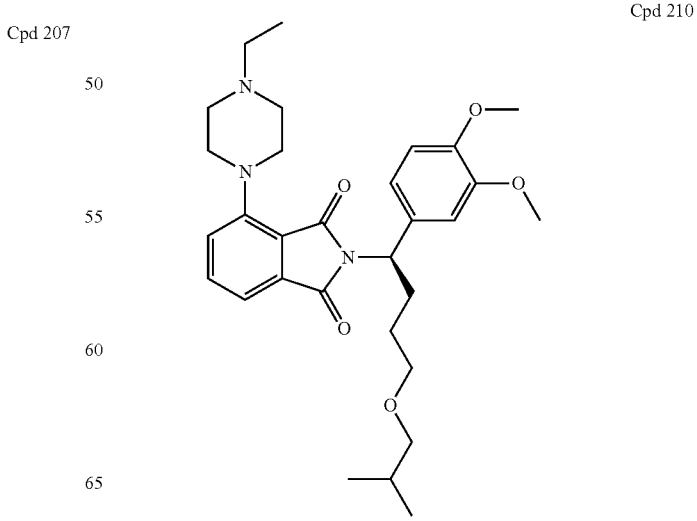

-continued
Cpd 211
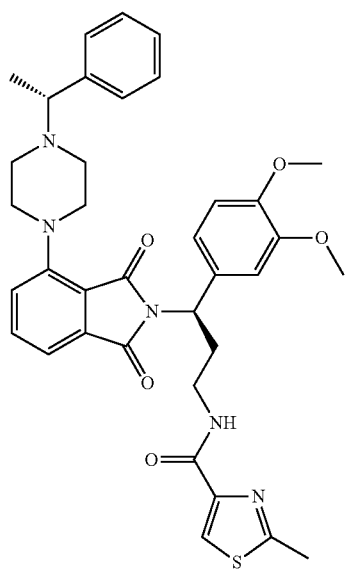
Cpd 212
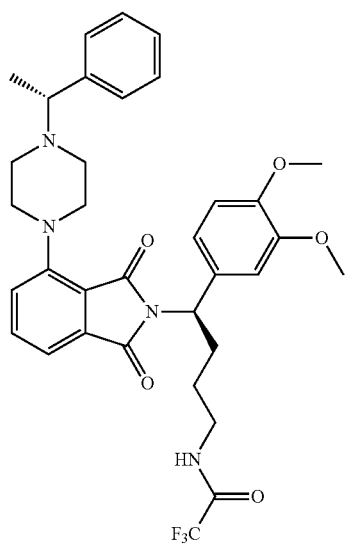
-continued
Cpd 213
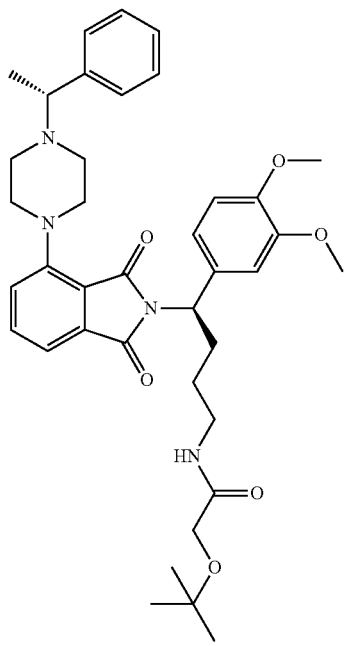
Cpd 214
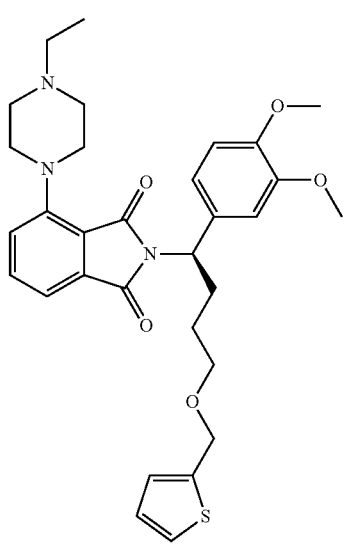

127
-continued
Cpd 215
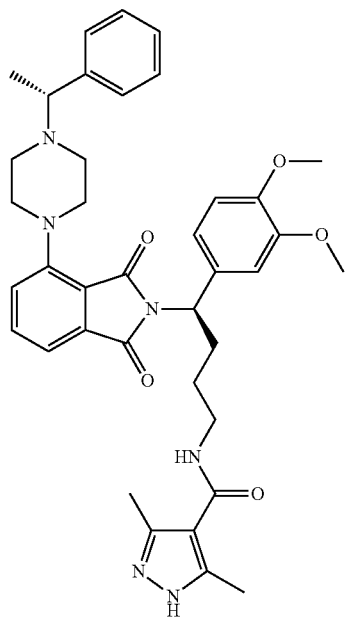
Cpd 216
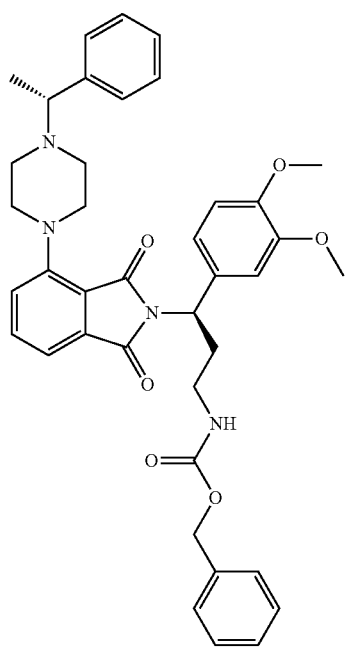
128
-continued
Cpd 217
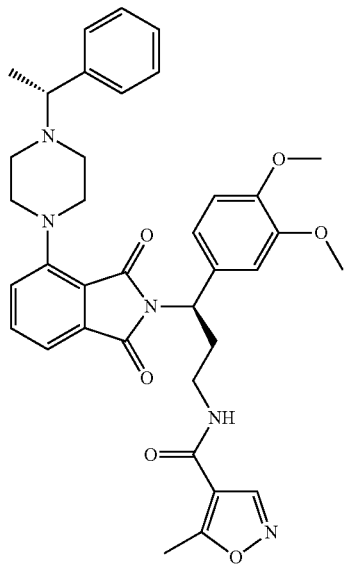
Cpd 218
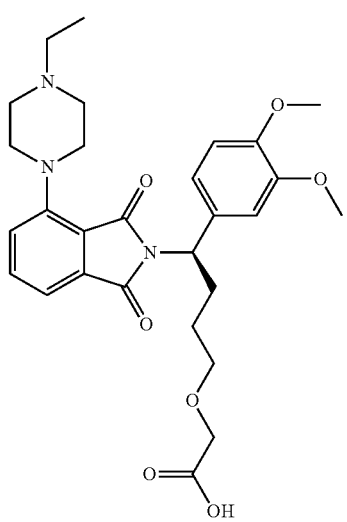

129
-continued
Cpd 219
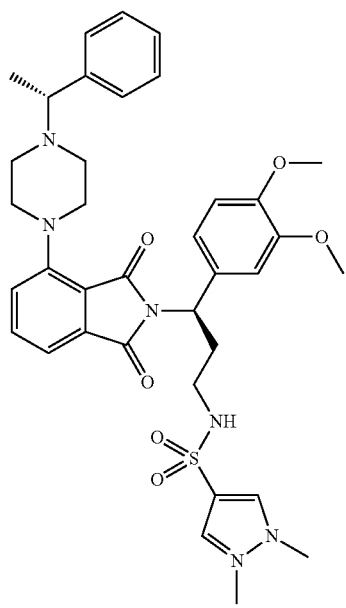
Cpd 220
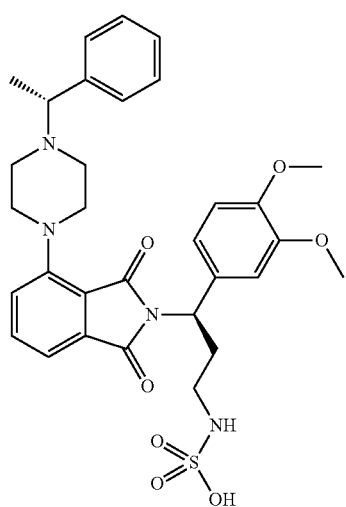
130
-continued
Cpd 221
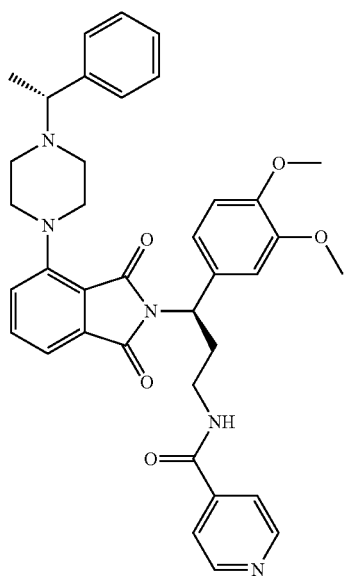
Cpd 222
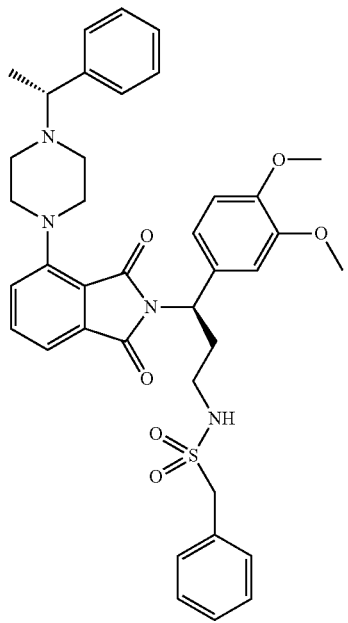

Cpd 223
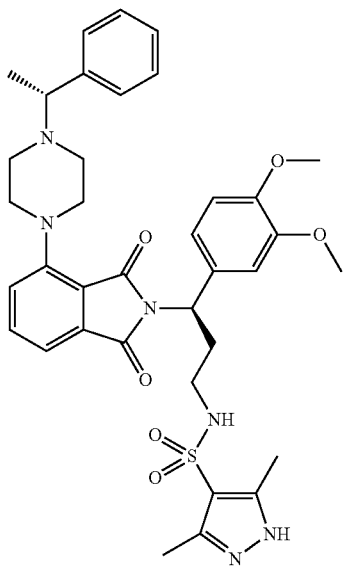
Cpd 224
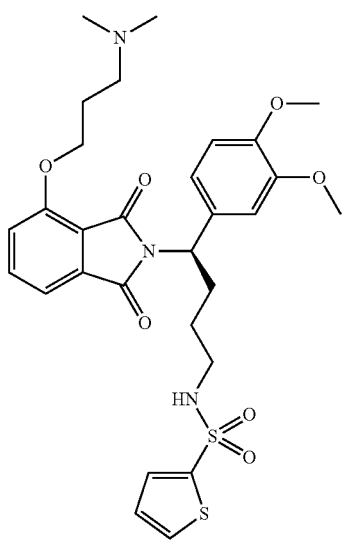
Cpd 225
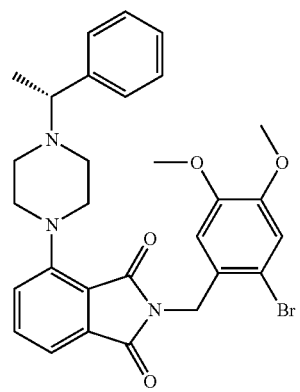
Cpd 226
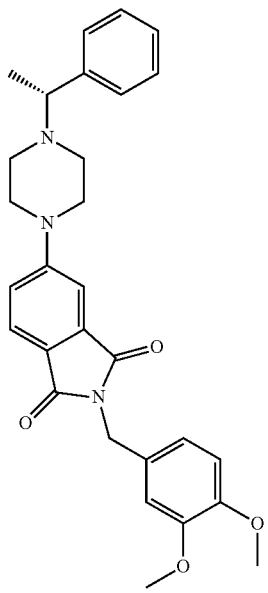
Cpd 227
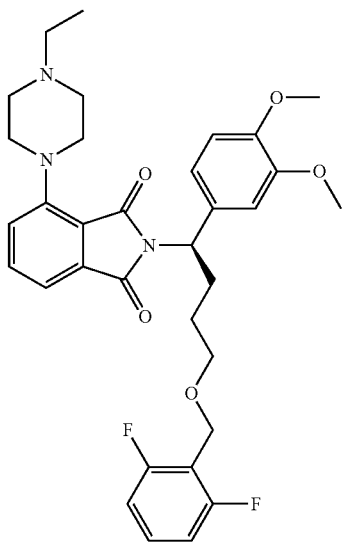
Cpd 228
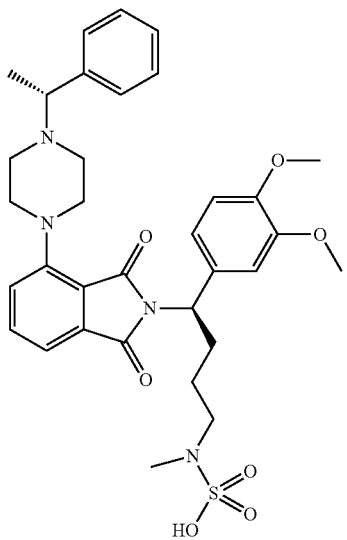

Cpd 229
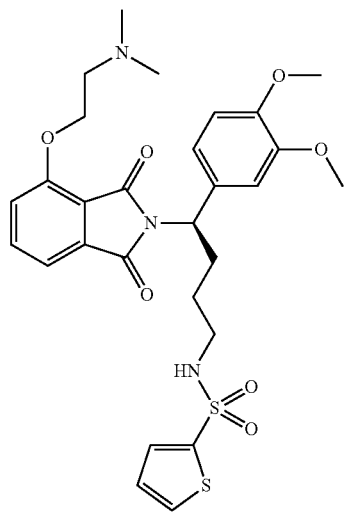
Cpd 230
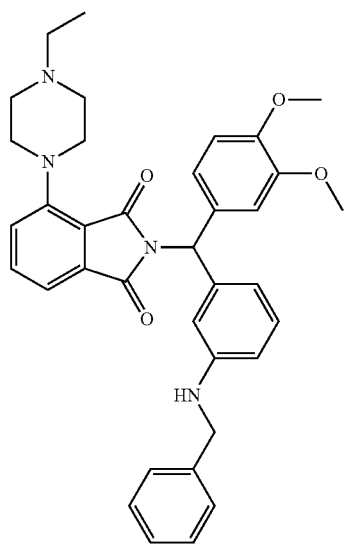
Cpd 231
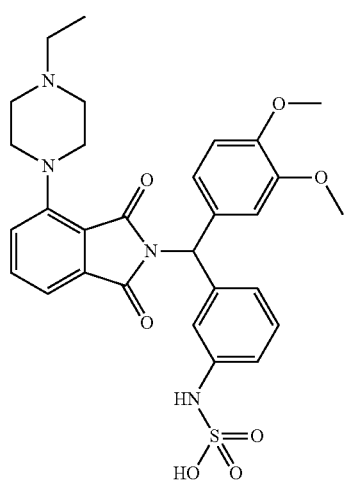
Cpd 232
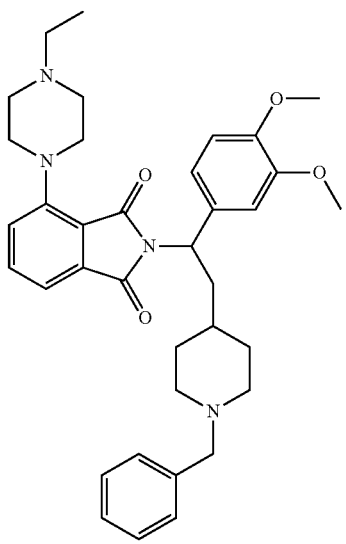
Cpd 233
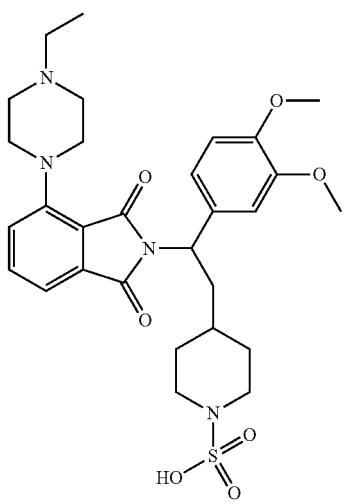
Cpd 234
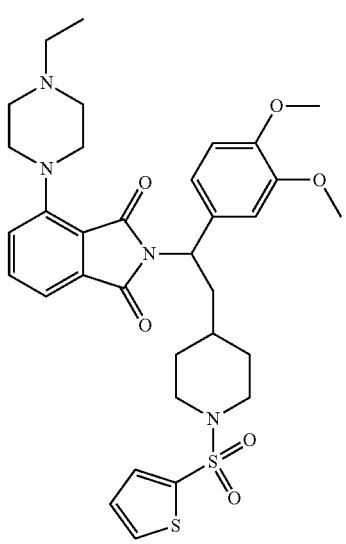

Cpd 235
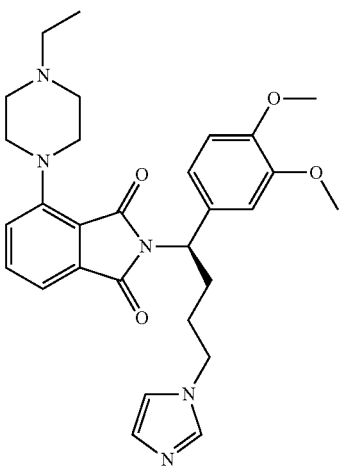

Cpd 236
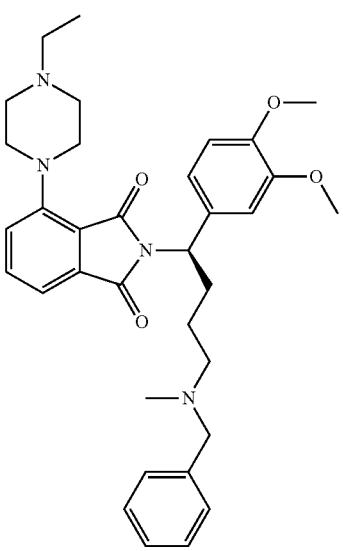

Cpd 237
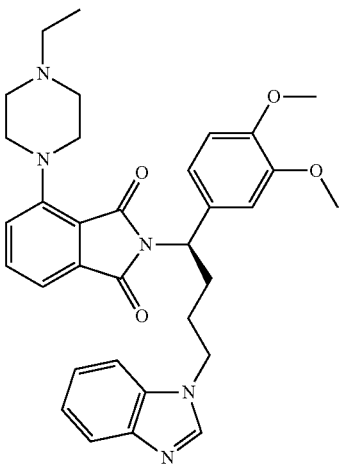

Example 40a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 40 described herein above.

Example 40b of the present invention is directed to an embodiment wherein compounds where $R_2$ is H are excluded from Example 40 described hereinabove.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Certain compounds of Formula (I) may exist in various stereoisomeric or tautomeric forms and mixtures thereof. The invention encompasses all such compounds, including active compounds in the form of essentially pure enantiomers, racemic mixtures and tautomers.

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The invention is considered to include the tautomeric forms of all compounds of Formula I. In addition, for chiral embodiments of the invention, the invention is considered to include pure enantiomers, racemic mixtures, as well as mixtures of enantiomers having 0.001% to 99.99% enantiomeric excess. In addition, some of the compounds represented by Formula I may be prodrugs, i.e., derivatives of a drug that possess superior delivery capabilities and therapeutic value as compared to the active drug. Prodrugs are transformed into active drugs by in vivo enzymatic or chemical processes.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

"Geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations relative to a core molecule and are intended to be used as defined in the literature.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Furthermore, compounds of the present invention may have at least one crystalline, polymorph or amorphous form. The plurality of such forms are included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention includes the use of an instant compound in the manufacture of a medicament for treating a Urotensin II-mediated disorder.

The present invention is also directed to a method for treating a Urotensin-II mediated disorder. An embodiment of the present invention is a method for treating a disorder including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke.

The present method of using Urotensin II receptor antagonists to reduce anti-neoplastic agent induced diarrhea and nephrotoxicity is applicable in any situations when anti-neoplastic agents (such as cisplatin, cis-diaminedichloroplatinum) are being administered to treat cancers or tumors. However, most often UII antagonists are used when tumors or cancers being treated are those of solid malignancies, notably those of the bladder, cervix, lung, ovary, and testis such as testicular tumor; bladder cancer; ureterpyelonephritic tumor; prostatic cancer; ovarian cancer; head and neck cancer; non-small-cell lung cancer; esophageal cancer; cervical cancer; neuroblastoma; gastric cancer; small cell lung cancer; bone cancer; non-Hodgkin's lymphomas; tumors of brain, endometrium, upper gastrointestinal tract, head and neck, and thymus; neuroblastoma; and sarcoma of bone and soft tissue.

Recent data (American Heart Association Scientific Sessions 2005, "SB-611812 in the treatment of heart failure", by Nicolas Bousette at Montreal General Hospital, Canada) has demonstrated that Urotensin II receptor antagonists may be useful for improving cardiac function and for cardiac remodeling associated with chronic heart failure (CHF).

A therapeutically effective amount for use of the instant compounds or a pharmaceutical composition thereof comprises a dose range from about 0.1 mg to about 3000 mg, from about 0.1 mg to about 1000 mg, from about 10 mg to about 500 mg or from about 1 mg to about 100 mg of active ingredient in a regimen of about 1 to 4 times per day for an average (70 kg) human; although, it is apparent to one skilled in the art that the therapeutically effective amount for active compounds of the invention will vary as will the conditions being treated.

Optimal dosages of the compounds of Formula (I) to be administered for the treatment of or prevention of Urotensin II mediated disorders may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Example 41 of the present invention is directed to compounds of Formula (I) or a form thereof as described herein selected from the group consisting of:

| Cpd | Name |
| --- | --- |
| 1 | 2-(3,4-dimethoxy-benzyl)-4-[4-(1R)-(1-phenyl-ethyl)-piperazin-1-yl]-isoindole-1,3-dione, |
| 2 | 2-[1-(3,4-dimethoxy-phenyl)-ethyl]-4-[4-(1R)-(1-phenyl-ethyl)-piperazin-1-yl]-isoindole-1,3-dione, |
| 3 | 2-[(S)-1-(3,4-dimethoxy-phenyl)-ethyl]-4-[4-(1R)-(1-phenyl-ethyl)-piperazin-1-yl]-isoindole-1,3-dione, |
| 4 | (R)-2-[1-(3,4-dimethoxy-phenyl)-ethyl]-4-[4-(1R)-(1-phenyl-ethyl)-piperazin-1-yl]-isoindole-1,3-dione, |
| 5 | 4-(4-benzyl-piperazin-1-yl)-2-(3,4-dimethoxy-benzyl)-isoindole-1,3-dione, |
| 6 | 2-(3,4-dimethoxy-benzyl)-4-[4-(1-phenyl-ethyl)-piperazin-1-yl]-isoindole-1,3-dione, |
| 7 | 4-(8-benzyl-3,8-diaza-bicyclo[3.2.1]oct-3-yl)-2-(3,4-dimethoxy-benzyl)-isoindole-1,3-dione, |
| 8 | 2-[1-(3,4-dimethoxy-phenyl)-propyl]-4-[4-(1R)-(1-phenyl-ethyl)-piperazin-1-yl]-isoindole-1,3-dione, |
| 9 | 4-(8-benzyl-3,8-diaza-bicyclo[3.2.1]oct-3-yl)-7-chloro-2-(3,4-dimethoxy-benzyl)-isoindole-1,3-dione, |
| 10 | 4-chloro-2-(3,4-dimethoxy-benzyl)-7-[4-(1R)-(1-phenyl-ethyl)-piperazin-1-yl]-isoindole-1,3-dione, |

| Cpd | Name |
|---|---|
| 11 | 4-(4-benzyl-piperazin-1-yl)-2-(5,6-dimethoxy-indan-1-yl)-isoindole-1,3-dione, |
| 12 | 2-(3,4-dimethoxy-benzyl)-4-[4-(4-fluoro-benzyl)-piperazin-1-yl]-isoindole-1,3-dione, |
| 13 | 2-(3,4-dimethoxy-benzyl)-4-[4-(1-phenyl-propyl)-piperazin-1-yl]-isoindole-1,3-dione, |
| 14 | 2-(3,4-dimethoxy-benzyl)-4-[4-(1S)-(1-phenyl-ethyl)-piperazin-1-yl]-isoindole-1,3-dione, |
| 15 | 2-(4-hydroxy-3-methoxy-benzyl)-4-[4-(1R)-(1-phenyl-ethyl)-piperazin-1-yl]-isoindole-1,3-dione, |
| 16 | 4-[4-(2,6-difluoro-benzyl)-piperazin-1-yl]-2-(3,4-dimethoxy-benzyl)-isoindole-1,3-dione, |
| 17 | 2-(3,4-dimethoxy-benzyl)-4-[4-(3-fluoro-benzyl)-piperazin-1-yl]-isoindole-1,3-dione, |
| 18 | 2-(4-ethoxy-3-methoxy-benzyl)-4-[4-(1R)-(1-phenyl-ethyl)-piperazin-1-yl]-isoindole-1,3-dione, |
| 19 | 4-(1-benzyl-1,2,3,6-tetrahydro-pyridin-4-yl)-2-(3,4-dimethoxy-benzyl)-isoindole-1,3-dione, |
| 20 | 2-(3,4-dimethoxy-benzyl)-4-(4-indan-1-yl-piperazin-1-yl)-isoindole-1,3-dione, |
| 21 | 2-(3-ethoxy-4-methoxy-benzyl)-4-[4-(1R)-(1-phenyl-ethyl)-piperazin-1-yl]-isoindole-1,3-dione, |
| 22 | 2-(3,4-dimethoxy-benzyl)-4-(4-phenethyl-piperazin-1-yl)-isoindole-1,3-dione |
| 23 | 4-(4-benzyl-piperazin-1-yl)-2-(1,3,5-trimethyl-1H-pyrazol-4-ylmethyl)-isoindole-1,3-dione, |
| 24 | 4-[4-(2,4-difluoro-benzyl)-piperazin-1-yl]-2-(3,4-dimethoxy-benzyl)-isoindole-1,3-dione, |
| 25 | 4-(8-benzyl-3,8-diaza-bicyclo[3.2.1]oct-3-yl)-2-[2-(3,4-dimethoxy-phenyl)-ethyl]-isoindole-1,3-dione, |
| 26 | 4-(8-benzyl-3,8-diaza-bicyclo[3.2.1]oct-3-yl)-2-(3,4,5-trimethoxy-benzyl)-isoindole-1,3-dione, |
| 27 | 4-[4-(cyclopropyl-phenyl-methyl)-piperazin-1-yl]-2-(3,4-dimethoxy-benzyl)-isoindole-1,3-dione, |
| 28 | 2-(3,4-dimethoxy-benzyl)-4-[4-(1-methyl-1-phenyl-ethyl)-piperazin-1-yl]-isoindole-1,3-dione, |
| 29 | 4-[4-(2,5-difluoro-benzyl)-piperazin-1-yl]-2-(3,4-dimethoxy-benzyl)-isoindole-1,3-dione, |
| 30 | (S)-3-(3,4-dimethoxy-phenyl)-3-{1,3-dioxo-4-[4-(1R)-(1-phenyl-ethyl)-piperazin-1-yl]-1,3-dihydro-isoindol-2-yl}-propionic acid, |
| 31 | 4-[4-(2-chloro-benzyl)-piperazin-1-yl]-2-(3,4-dimethoxy-benzyl)-isoindole-1,3-dione, |
| 32 | 2-(3,4-dimethoxy-benzyl)-4-[8-(1-phenyl-ethyl)-3,8-diaza-bicyclo[3.2.1]oct-3-yl]-isoindole-1,3-dione, |
| 33 | 2-(3,4-dimethoxy-benzyl)-4-[4-(2-methyl-benzyl)-piperazin-1-yl]-isoindole-1,3-dione, |
| 34 | 4-(4-benzyl-piperazin-1-yl)-2-(3,4,5-trimethoxy-benzyl)-isoindole-1,3-dione, |
| 35 | 2-(3,4-dimethoxy-benzyl)-4-[4-(1-phenyl-prop-2-ynyl)-piperazin-1-yl]-isoindole-1,3-dione, |
| 36 | 2-(3,4-dimethoxy-benzyl)-4-[4-(3-methyl-benzyl)-piperazin-1-yl]-isoindole-1,3-dione, |
| 37 | 4-(1R,2R)-(2-benzylamino-cyclohexylamino)-2-(3,4-dimethoxy-benzyl)-isoindole-1,3-dione, |
| 38 | 2-{4-[2-(3,4-dimethoxy-benzyl)-1,3-dioxo-2,3-dihydro-1H-isoindol-4-yl]-piperazin-1-ylmethyl}-benzonitrile, |
| 39 | 4-(8-benzyl-3,8-diaza-bicyclo[3.2.1]oct-3-yl)-2-pyridin-4-ylmethyl-isoindole-1,3-dione, |
| 40 | 2-(3,4-dimethoxy-benzyl)-4-[4-(4-methyl-benzyl)-piperazin-1-yl]-isoindole-1,3-dione, |
| 41 | 2-(3-methoxy-4-propoxy-benzyl)-4-[4-(1R)-(1-phenyl-ethyl)-piperazin-1-yl]-isoindole-1,3-dione, |
| 42 | (3R,5S)-4-(4-benzyl-3,5-dimethyl-piperazin-1-yl)-2-(3,4-dimethoxy-benzyl)-isoindole-1,3-dione, |
| 43 | 4-(4-benzyl-piperazin-1-yl)-2-(2-pyridin-4-yl-ethyl)-isoindole-1,3-dione, |
| 44 | 4-[4-(3-chloro-benzyl)-piperazin-1-yl]-2-(3,4-dimethoxy-benzyl)-isoindole-1,3-dione, |
| 45 | 4-(8-benzyl-3,8-diaza-bicyclo[3.2.1]oct-3-yl)-2-(3,5-dimethoxy-benzyl)-isoindole-1,3-dione, |
| 46 | 4-[4-(3,5-difluoro-benzyl)-piperazin-1-yl]-2-(3,4-dimethoxy-benzyl)-isoindole-1,3-dione, |
| 47 | 4-(4-benzyl-piperazin-1-yl)-2-(3-imidazol-1-yl-propyl)-isoindole-1,3-dione, |
| 48 | 4-(2-benzylamino-ethylamino)-2-(3,4-dimethoxy-benzyl)-isoindole-1,3-dione, |
| 49 | 2-[(3,4-dimethoxy-phenyl)-phenyl-methyl]-4-[4-(1R)-(1-phenyl-ethyl)-piperazin-1-yl]-isoindole-1,3-dione, |

| Cpd | Name |
| --- | --- |
| 50 | 4-(8-benzyl-8-aza-bicyclo[3.2.1]oct-2-en-3-yl)-2-(3,4-dimethoxy-benzyl)-isoindole-1,3-dione, |
| 51 | (3R,5S)-2-(3,4-dimethoxy-benzyl)-4-[3,5-dimethyl-4-(1-phenyl-ethyl)-piperazin-1-yl]-isoindole-1,3-dione, |
| 52 | 4-(4-isopropyl-piperazin-1-yl)-2-(3,4,5-trimethoxy-benzyl)-isoindole-1,3-dione, |
| 53 | 4-[2-(benzyl-methyl-amino)-ethoxy]-2-(3,4-dimethoxy-benzyl)-isoindole-1,3-dione, |
| 54 | 4-(2-benzylamino-ethoxy)-2-(3,4-dimethoxy-benzyl)-isoindole-1,3-dione, |
| 55 | 4-(4-benzyl-piperazin-1-yl)-2-(1,5-dimethyl-1H-pyrazol-4-ylmethyl)-isoindole-1,3-dione, |
| 56 | 2-(3,4-dimethoxy-benzyl)-4-[4-(3,4-dimethoxy-benzyl)-piperazin-1-yl]-isoindole-1,3-dione, |
| 57 | 4-[4-(4-chloro-benzyl)-piperazin-1-yl]-2-(3,4-dimethoxy-benzyl)-isoindole-1,3-dione, |
| 58 | 4-(4-benzyl-piperazin-1-yl)-2-(2-methoxy-pyridin-4-ylmethyl)-isoindole-1,3-dione, |
| 59 | 4-(8-benzyl-3,8-diaza-bicyclo[3.2.1]oct-3-yl)-2-pyridin-2-ylmethyl-isoindole-1,3-dione, |
| 60 | 4-(4-isobutyl-piperazin-1-yl)-2-(3,4,5-trimethoxy-benzyl)-isoindole-1,3-dione, |
| 61 | 4-(8-benzyl-3,8-diaza-bicyclo[3.2.1]oct-3-yl)-2-(3,4-dimethoxy-phenyl)-isoindole-1,3-dione |
| 62 | 2-(3,4-dimethoxy-benzyl)-4-(2-methanesulfonyl-vinyl)-7-[4-(1R)-(1-phenyl-ethyl)-piperazin-1-yl]-isoindole-1,3-dione, |
| 63 | 2-[1-(3,4-dimethoxy-phenyl)-2-dimethylamino-ethyl]-4-[4-(1R)-(1-phenyl-ethyl)-piperazin-1-yl]-isoindole-1,3-dione, |
| 64 | 2-[2-amino-1-(3,4-dimethoxy-phenyl)-ethyl]-4-[4-(1R)-(1-phenyl-ethyl)-piperazin-1-yl]-isoindole-1,3-dione, |
| 65 | (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-carbamic acid tert-butyl ester, |
| 66 | 2-[4-amino-1-(3,4-dimethoxy-phenyl)-butyl]-4-[4-(1R)-(1-phenyl-ethyl)-piperazin-1-yl]-isoindole-1,3-dione, |
| 67 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methanesulfonamide, |
| 68 | thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 69 | (5-(3,4-dimethoxy-phenyl)-5-{1,3-dioxo-4-[4-(1R)-(1-phenyl-ethyl)-piperazin-1-yl]-1,3-dihydro-isoindol-2-yl}-pentyl)-carbamic acid tert-butyl ester, |
| 70 | 2-[5-amino-1-(3,4-dimethoxy-phenyl)-pentyl]-4-[4-(1R)-(1-phenyl-ethyl)-piperazin-1-yl]-isoindole-1,3-dione, |
| 71 | 5-chloro-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 72 | (2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-carbamic acid tert-butyl ester, |
| 73 | (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-carbamic acid tert-butyl ester, |
| 74 | thiophene-2-sulfonic acid (2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-amide, |
| 75 | thiophene-2-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 76 | 4-(1-benzyl-piperidin-4-yl)-2-(3,4-dimethoxy-benzyl)-isoindole-1,3-dione, |
| 77 | 2-(3,4-dimethoxy-benzyl)-4-[4-(5-methyl-furan-2-ylmethyl)-piperazin-1-yl]-isoindole-1,3-dione, |
| 78 | 2-(3,4-dimethoxy-benzyl)-4-(4-furan-3-ylmethyl-piperazin-1-yl)-isoindole-1,3-dione, |
| 79 | 2-(3,4-dimethoxy-benzyl)-4-(4-pyridin-3-ylmethyl-piperazin-1-yl)-isoindole-1,3-dione, |
| 80 | 4-(4-cyclopentylmethyl-piperazin-1-yl)-2-(3,4-dimethoxy-benzyl)-isoindole-1,3-dione, |
| 81 | 2-(3,4-dimethoxy-benzyl)-4-(4-thiophen-2-ylmethyl-piperazin-1-yl)-isoindole-1,3-dione, |
| 82 | 2-(3,4-dimethoxy-benzyl)-4-(4-isobutyl-piperazin-1-yl)-isoindole-1,3-dione, |
| 83 | 2-(3,4-dimethoxy-benzyl)-4-(4-thiophen-3-ylmethyl-piperazin-1-yl)-isoindole-1,3-dione, |
| 84 | 2-(3,4-dimethoxy-benzyl)-4-(4-pyridin-2-ylmethyl-piperazin-1-yl)-isoindole-1,3-dione, |
| 85 | 2-(3,4-dimethoxy-benzyl)-4-[4-(2-hydroxy-benzyl)-piperazin-1-yl]-isoindole-1,3-dione, |

| Cpd | Name |
|---|---|
| 86 | (E)-2-(3,4-dimethoxy-benzyl)-4-[4-(2-methyl-but-2-enyl)-piperazin-1-yl]-isoindole-1,3-dione, |
| 87 | 4-(4-adamantan-2-yl-piperazin-1-yl)-2-(3,4-dimethoxy-benzyl)-isoindole-1,3-dione, |
| 88 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methoxy-thiophene-3-carboxylic acid methyl ester, |
| 89 | 5-methyl-2-trifluoromethyl-furan-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 90 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-furan-2-carboxylic acid methyl ester, |
| 91 | 1,3,5-trimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 92 | 4-benzenesulfonyl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 93 | 6-chloro-imidazo[2,1-b]thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 94 | 3-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-thiophene-2-carboxylic acid methyl ester, |
| 95 | 5-isoxazol-3-yl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 96 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-benzenesulfonamide, |
| 97 | N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide, |
| 98 | 1-methyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 99 | 2,5-dimethyl-furan-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 100 | 5-bromo-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 101 | 5-chloro-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 102 | N-(2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-2-pyridin-4-yl-acetamide, |
| 103 | N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-2-pyridin-4-yl-acetamide, |
| 104 | thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 105 | thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 106 | pyridine-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 107 | pyridine-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 108 | 5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 109 | quinoline-8-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 110 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-methanesulfonyl-methanesulfonamide, |
| 111 | 2-phenyl-ethenesulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 112 | 3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 113 | 2,5-dichloro-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 114 | 1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 115 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-N,N-dimethyl-sulfamide, |
| 116 | benzo[b]thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 117 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-phenyl-methanesulfonamide, |
| 118 | (R)-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 119 | (S)-thiophene-2-sulfonic acid 4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 120 | 1-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-thiophen-2-yl-urea, |
| 121 | 1-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-3-thiophen-2-yl-urea, |
| 122 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 123 | 2-[1,2-bis-(3,4-dimethoxy-phenyl)-ethyl]-4-[4-(1R)-(1-phenyl-ethyl)-piperazin-1-yl]-isoindole-1,3-dione, |
| 124 | (R)-2,4-dimethyl-thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 125 | (R)-3,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 126 | (R)-5-methyl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 127 | (R)-2,3-dimethyl-3H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 128 | (R)-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 129 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-sulfamic acid, |
| 130 | (R)-N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide, |
| 131 | (R)-2,5-dimethyl-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 132 | (R)-1,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 133 | (R)-1,1-dioxo-tetrahydro-1$\lambda^6$-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 134 | (R)-1-ethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 135 | (R)-1-methyl-3-trifluoromethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 136 | (R)-1-methyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 137 | (R)-5-fluoro-3-methyl-benzo[b]thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 138 | (R)-5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 139 | (R)-3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 140 | (R)-1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 141 | (R)-N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 142 | (R)-2-[1-(3,4-dimethoxy-phenyl)-4-(pyridin-2-ylamino)-butyl]-4-[4-(1R)-(1-phenyl-ethyl)-piperazin-1-yl]-isoindole-1,3-dione, |
| 143 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-dimethylamino-acetamide, |
| 144 | (R)-5-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 145 | (R)-2-[1-(3,4-dimethoxy-phenyl)-4-(pyrimidin-2-ylamino)-butyl]-4-[4-(1R)-(1-phenyl-ethyl)-piperazin-1-yl]-isoindole-1,3-dione, |
| 146 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-guanidine, |
| 147 | (R)-1-methyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 148 | (R)-1-methyl-5-sulfamoyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 149 | (R)-1-acetyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 150 | (R)-pyridine-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 151 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-nicotinamide, |
| 152 | (R)-3-methyl-3H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 153 | (R)-1-methyl-1H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 154 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isonicotinamide, |
| 155 | (R)-tetrahydro-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 156 | (R)-2-methyl-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 157 | (R)-5-methanesulfonyl-thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 158 | (R)-3-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 159 | (R)-5-methyl-isoxazole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 160 | (R)-pyridazine-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 161 | (R)-1-methyl-1H-imidazole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 162 | (R)-4,5-dimethyl-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 163 | (R)-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 164 | (R)-3,5-dimethyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 165 | (R)-2-[4-(4,5-dihydro-1H-pyrrol-2-ylamino)-1-(3,4-dimethoxy-phenyl)-butyl]-4-[4-(1R)-(1-phenyl-ethyl)-piperazin-1-yl]-isoindole-1,3-dione, |
| 166 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamidine, |
| 167 | (R)-thiophene-2-sulfonic acid [4-(3,4-dimethoxy-phenyl)-4-(1,3-dioxo-4-piperazin-1-yl-1,3-dihydro-isoindol-2-yl)-butyl]-amide, |
| 168 | (R)-thiophene-2-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 169 | (R)-thiophene-2-sulfonic acid {4-(3,4-dimethoxy-phenyl)-4-[4-(4-methyl-piperazin-1-yl)-1,3-dioxo-1,3-dihydro-isoindol-2-yl]-butyl}-amide, |

-continued

| Cpd | Name |
|---|---|
| 170 | (R)-thiophene-2-sulfonic acid {4-(3,4-dimethoxy-phenyl)-4-[4-(4-furan-3-ylmethyl-piperazin-1-yl)-1,3-dioxo-1,3-dihydro-isoindol-2-yl]-butyl}-amide, |
| 171 | (R)-thiophene-2-sulfonic acid {4-(3,4-dimethoxy-phenyl)-4-[1,3-dioxo-4-(4-pyridin-3-ylmethyl-piperazin-1-yl)-1,3-dihydro-isoindol-2-yl]-butyl}-amide, |
| 172 | (R)-thiophene-2-sulfonic acid {4-(3,4-dimethoxy-phenyl)-4-[1,3-dioxo-4-(4-thiophen-3-ylmethyl-piperazin-1-yl)-1,3-dihydro-isoindol-2-yl]-butyl}-amide, |
| 173 | (R)-tetrahydro-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 174 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isobutyramide, |
| 175 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-methoxy-acetamide, |
| 176 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-butyramide, |
| 177 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methoxy-propionamide, |
| 178 | (R)-cyclobutanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 179 | (R)-cyclopentanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 180 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-propionamide, |
| 181 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methyl-butyramide, |
| 182 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-ethoxy-acetamide, |
| 183 | (R)-5-chloro-1-methyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 184 | (R)-1,3,5-trimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 185 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2-dimethyl-propionamide, |
| 186 | (R)-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 187 | (R)-isoxazole-5-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 188 | (R)-2,5-dimethyl-1H-pyrrole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 189 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-ethoxy-propionamide, |
| 190 | (R)-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 191 | (S)-1-methyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 192 | (R)-thiophene-2-sulfonic acid [4-[4-(4-cyclobutyl-piperazin-1-yl)-1,3-dioxo-1,3-dihydro-isoindol-2-yl]-4-(3,4-dimethoxy-phenyl)-butyl]-amide, |
| 193 | (R)-thiophene-2-sulfonic acid [4-[4-(4-cyclopentyl-piperazin-1-yl)-1,3-dioxo-1,3-dihydro-isoindol-2-yl]-4-(3,4-dimethoxy-phenyl)-butyl]-amide, |
| 194 | (R)-thiophene-2-sulfonic acid [4-[4-(4-allyl-piperazin-1-yl)-1,3-dioxo-1,3-dihydro-isoindol-2-yl]-4-(3,4-dimethoxy-phenyl)-butyl]-amide, |
| 195 | (R)-thiophene-2-sulfonic acid (4-(3,4-dimethoxy-phenyl)-4-{1,3-dioxo-4-[4-(2,2,2-trifluoro-ethyl)-piperazin-1-yl]-1,3-dihydro-isoindol-2-yl}-butyl)-amide, |
| 196 | (R)-thiophene-2-sulfonic acid [4-[4-(4-cyclohexyl-piperazin-1-yl)-1,3-dioxo-1,3-dihydro-isoindol-2-yl]-4-(3,4-dimethoxy-phenyl)-butyl]-amide, |
| 197 | (R)-{4-(3,4-dimethoxy-phenyl)-4-[4-(4-ethyl-piperazin-1-yl)-1,3-dioxo-1,3-dihydro-isoindol-2-yl]-butyl}-carbamic acid tert-butyl ester, |
| 198 | (R)-thiophene-2-sulfonic acid {4-(3,4-dimethoxy-phenyl)-4-[4-(4-isopropyl-piperazin-1-yl)-1,3-dioxo-1,3-dihydro-isoindol-2-yl]-butyl}-amide, |
| 199 | (R)-2-cyano-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-oxo-butyramide, |

| Cpd | Name |
| --- | --- |
| 200 | (R)-N-{4-(3,4-dimethoxy-phenyl)-4-[4-(1-methyl-pyrrolidin-3-yloxy)-1,3-dioxo-1,3-dihydro-isoindol-2-yl]-butyl}-isobutyramide, |
| 201 | (R)-2-[4-benzyloxy-1-(3,4-dimethoxy-phenyl)-butyl]-4-(4-ethyl-piperazin-1-yl)-isoindole-1,3-dione, |
| 202 | (R)-cyclobutanecarboxylic acid {4-(3,4-dimethoxy-phenyl)-4-[4-(4-ethyl-piperazin-1-yl)-1,3-dioxo-1,3-dihydro-isoindol-2-yl]-butyl}-amide, |
| 203 | (R)-1,2-dimethyl-1H-imidazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 204 | (R)-1,3,5-trimethyl-1H-pyrazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 205 | (R)-N-{4-(3,4-dimethoxy-phenyl)-4-[4-(1-methyl-piperidin-4-yloxy)-1,3-dioxo-1,3-dihydro-isoindol-2-yl]-butyl}-isobutyramide, |
| 206 | (R)-2-[1-(3,4-dimethoxy-phenyl)-4-hydroxy-butyl]-4-(4-ethyl-piperazin-1-yl)-isoindole-1,3-dione, |
| 207 | (R)-2-[1-(3,4-dimethoxy-phenyl)-4-ethoxy-butyl]-4-(4-ethyl-piperazin-1-yl)-isoindole-1,3-dione, |
| 208 | (R)-thiophene-2-sulfonic acid 4-(3,4-dimethoxy-phenyl)-4-[4-(4-ethyl-piperazin-1-yl)-1,3-dioxo-1,3-dihydro-isoindol-2-yl]-butyl ester, |
| 209 | (R)-dimethyl-sulfamic acid 4-(3,4-dimethoxy-phenyl)-4-[4-(4-ethyl-piperazin-1-yl)-1,3-dioxo-1,3-dihydro-isoindol-2-yl]-butyl ester, |
| 210 | (R)-2-[1-(3,4-dimethoxy-phenyl)-4-isobutoxy-butyl]-4-(4-ethyl-piperazin-1-yl)-isoindole-1,3-dione, |
| 211 | (R)-2-methyl-thiazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 212 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2,2-trifluoro-acetamide, |
| 213 | (R)-2-tert-butoxy-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamide, |
| 214 | (R)-2-[1-(3,4-dimethoxy-phenyl)-4-(thiophen-2-ylmethoxy)-butyl]-4-(4-ethyl-piperazin-1-yl)-isoindole-1,3-dione, |
| 215 | (R)-3,5-dimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 216 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-carbamic acid benzyl ester, |
| 217 | (R)-5-methyl-isoxazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 218 | (R)-{4-(3,4-dimethoxy-phenyl)-4-[4-(4-ethyl-piperazin-1-yl)-1,3-dioxo-1,3-dihydro-isoindol-2-yl]-butoxy}-acetic acid, |
| 219 | (R)-1,2-dimethyl-1H-imidazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 220 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-sulfamic acid, |
| 221 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-isonicotinamide, |
| 222 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-C-phenyl-methanesulfonamide, |
| 223 | (R)-3,5-dimethyl-1H-pyrazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 224 | (R)-thiophene-2-sulfonic acid {4-(3,4-dimethoxy-phenyl)-4-[4-(3-dimethylamino-propoxy)-1,3-dioxo-1,3-dihydro-isoindol-2-yl]-butyl}-amide, |
| 225 | 2-(2-bromo-4,5-dimethoxy-benzyl)-4-[4-(1R)-(1-phenyl-ethyl)-piperazin-1-yl]-isoindole-1,3-dione, |
| 226 | 2-(3,4-dimethoxy-benzyl)-5-[4-(1R)-(1-phenyl-ethyl)-piperazin-1-yl]-isoindole-1,3-dione, |
| 227 | (R)-2-[4-(2,6-difluoro-benzyloxy)-1-(3,4-dimethoxy-phenyl)-butyl]-4-(4-ethyl-piperazin-1-yl)-isoindole-1,3-dione, |
| 228 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methyl-sulfamic acid, |
| 229 | (R)-thiophene-2-sulfonic acid {4-(3,4-dimethoxy-phenyl)-4-[4-(2-dimethylamino-ethoxy)-1,3-dioxo-1,3-dihydro-isoindol-2-yl]-butyl}-amide, |
| 230 | 2-[(3-benzylamino-phenyl)-(3,4-dimethoxy-phenyl)-methyl]-4-(4-ethyl-piperazin-1-yl)-isoindole-1,3-dione, |
| 231 | (3-{(3,4-dimethoxy-phenyl)-[4-(4-ethyl-piperazin-1-yl)-1,3-dioxo-1,3-dihydro-isoindol-2-yl]-methyl}-phenyl)-sulfamic acid, |
| 232 | 2-[2-(1-benzyl-piperidin-4-yl)-1-(3,4-dimethoxy-phenyl)-ethyl]-4-(4-ethyl-piperazin-1-yl)-isoindole-1,3-dione, |
| 233 | 4-{2-(3,4-dimethoxy-phenyl)-2-[4-(4-ethyl-piperazin-1-yl)-1,3-dioxo-1,3-dihydro-isoindol-2-yl]-ethyl}-piperidine-1-sulfonic acid, |

| Cpd | Name |
|---|---|
| 234 | 2-{1-(3,4-dimethoxy-phenyl)-2-[1-(thiophene-2-sulfonyl)-piperidin-4-yl]-ethyl}-4-(4-ethyl-piperazin-1-yl)-isoindole-1,3-dione, |
| 235 | (R)-2-[1-(3,4-dimethoxy-phenyl)-4-imidazol-1-yl-butyl]-4-(4-ethyl-piperazin-1-yl)-isoindole-1,3-dione, |
| 236 | (R)-2-[4-(benzyl-methyl-amino)-1-(3,4-dimethoxy-phenyl)-butyl]-4-(4-ethyl-piperazin-1-yl)-isoindole-1,3-dione, and |
| 237 | (R)-2-[4-benzoimidazol-1-yl-1-(3,4-dimethoxy-phenyl)-butyl]-4-(4-ethyl-piperazin-1-yl)-isoindole-1,3-dione. |

Example 41a of the present invention is directed to an embodiment wherein wherein Compounds 5, 12, 16, 17, 22, 23, 24, 29, 31, 33, 34, 36, 38, 40, 44, 46, 47, 52, 55, 56, 57, 60, 77, 78, 79, 80, 81, 82, 83, 84, 85, 86 and 87, as described herein, are excluded from Example 41 described herein above.

Example 41b of the present invention is directed to an embodiment wherein compounds where $R_2$ is H are excluded from Example 41 described hereinabove.

Example 42 of the present invention is directed to compounds of Formula (I) or a form thereof as described herein selected from the group consisting of:

| Cpd | Name |
|---|---|
| 1 | 2-(3,4-dimethoxy-benzyl)-4-[4-(1R)-(1-phenyl-ethyl)-piperazin-1-yl]-isoindole-1,3-dione, |
| 2 | 2-[1-(3,4-dimethoxy-phenyl)-ethyl]-4-[4-(1R)-(1-phenyl-ethyl)-piperazin-1-yl]-isoindole-1,3-dione, |
| 3 | 2-[(S)-1-(3,4-dimethoxy-phenyl)-ethyl]-4-[4-(1R)-(1-phenyl-ethyl)-piperazin-1-yl]-isoindole-1,3-dione, |
| 4 | (R)-2-[1-(3,4-dimethoxy-phenyl)-ethyl]-4-[4-(1R)-(1-phenyl-ethyl)-piperazin-1-yl]-isoindole-1,3-dione, |
| 5 | 4-(4-benzyl-piperazin-1-yl)-2-(3,4-dimethoxy-benzyl)-isoindole-1,3-dione, |
| 6 | 2-(3,4-dimethoxy-benzyl)-4-[4-(1-phenyl-ethyl)-piperazin-1-yl]-isoindole-1,3-dione, |
| 7 | 4-(8-benzyl-3,8-diaza-bicyclo[3.2.1]oct-3-yl)-2-(3,4-dimethoxy-benzyl)-isoindole-1,3-dione, |
| 8 | 2-[1-(3,4-dimethoxy-phenyl)-propyl]-4-[4-(1R)-(1-phenyl-ethyl)-piperazin-1-yl]-isoindole-1,3-dione, |
| 9 | 4-(8-benzyl-3,8-diaza-bicyclo[3.2.1]oct-3-yl)-7-chloro-2-(3,4-dimethoxy-benzyl)-isoindole-1,3-dione, |
| 10 | 4-chloro-2-(3,4-dimethoxy-benzyl)-7-[4-(1R)-(1-phenyl-ethyl)-piperazin-1-yl]-isoindole-1,3-dione, |
| 11 | 4-(4-benzyl-piperazin-1-yl)-2-(5,6-dimethoxy-indan-1-yl)-isoindole-1,3-dione, |
| 12 | 2-(3,4-dimethoxy-benzyl)-4-[4-(4-fluoro-benzyl)-piperazin-1-yl]-isoindole-1,3-dione, |
| 13 | 2-(3,4-dimethoxy-benzyl)-4-[4-(1-phenyl-propyl)-piperazin-1-yl]-isoindole-1,3-dione, |
| 14 | 2-(3,4-dimethoxy-benzyl)-4-[4-(1S)-(1-phenyl-ethyl)-piperazin-1-yl]-isoindole-1,3-dione, |
| 15 | 2-(4-hydroxy-3-methoxy-benzyl)-4-[4-(1R)-(1-phenyl-ethyl)-piperazin-1-yl]-isoindole-1,3-dione, |
| 16 | 4-[4-(2,6-difluoro-benzyl)-piperazin-1-yl]-2-(3,4-dimethoxy-benzyl)-isoindole-1,3-dione, |
| 62 | 2-(3,4-dimethoxy-benzyl)-4-(2-methanesulfonyl-vinyl)-7-[4-(1R)-(1-phenyl-ethyl)-piperazin-1-yl]-isoindole-1,3-dione, |
| 63 | 2-[1-(3,4-dimethoxy-phenyl)-2-dimethylamino-ethyl]-4-[4-(1R)-(1-phenyl-ethyl)-piperazin-1-yl]-isoindole-1,3-dione, |
| 64 | 2-[2-amino-1-(3,4-dimethoxy-phenyl)-ethyl]-4-[4-(1R)-(1-phenyl-ethyl)-piperazin-1-yl]-isoindole-1,3-dione, |
| 65 | (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-carbamic acid tert-butyl ester, |
| 66 | 2-[4-amino-1-(3,4-dimethoxy-phenyl)-butyl]-4-[4-(1R)-(1-phenyl-ethyl)-piperazin-1-yl]-isoindole-1,3-dione, |
| 67 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methanesulfonamide, |
| 68 | thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 70 | 2-[5-amino-1-(3,4-dimethoxy-phenyl)-pentyl]-4-[4-(1R)-(1-phenyl-ethyl)-piperazin-1-yl]-isoindole-1,3-dione, |
| 76 | 4-(1-benzyl-piperidin-4-yl)-2-(3,4-dimethoxy-benzyl)-isoindole-1,3-dione, |
| 77 | 2-(3,4-dimethoxy-benzyl)-4-[4-(5-methyl-furan-2-ylmethyl)-piperazin-1-yl]-isoindole-1,3-dione, |

| Cpd | Name |
|---|---|
| 78 | 2-(3,4-dimethoxy-benzyl)-4-(4-furan-3-ylmethyl-piperazin-1-yl)-isoindole-1,3-dione, |
| 83 | 2-(3,4-dimethoxy-benzyl)-4-(4-thiophen-3-ylmethyl-piperazin-1-yl)-isoindole-1,3-dione, |
| 86 | (E)-2-(3,4-dimethoxy-benzyl)-4-[4-(2-methyl-but-2-enyl)-piperazin-1-yl]-isoindole-1,3-dione, |
| 87 | 4-(4-adamantan-2-yl-piperazin-1-yl)-2-(3,4-dimethoxy-benzyl)-isoindole-1,3-dione, |
| 88 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methoxy-thiophene-3-carboxylic acid methyl ester, |
| 89 | 5-methyl-2-trifluoromethyl-furan-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 90 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-furan-2-carboxylic acid methyl ester, |
| 91 | 1,3,5-trimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 92 | 4-benzenesulfonyl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 93 | 6-chloro-imidazo[2,1-b]thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 94 | 3-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-thiophene-2-carboxylic acid methyl ester, |
| 95 | 5-isoxazol-3-yl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 96 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-benzenesulfonamide, |
| 97 | N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide, |
| 98 | 1-methyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 99 | 2,5-dimethyl-furan-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 100 | 5-bromo-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 101 | 5-chloro-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 102 | N-(2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-2-pyridin-4-yl-acetamide, |
| 103 | N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-2-pyridin-4-yl-acetamide, |
| 104 | thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 105 | thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 106 | pyridine-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 107 | pyridine-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 108 | 5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 109 | quinoline-8-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 110 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-methanesulfonyl-methanesulfonamide, |
| 111 | 2-phenyl-ethenesulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 112 | 3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 114 | 1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 115 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-N,N-dimethyl-sulfamide, |
| 117 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-phenyl-methanesulfonamide, |
| 118 | (R)-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 119 | (S)-thiophene-2-sulfonic acid 4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 120 | 1-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-thiophen-2-yl-urea, |
| 121 | 1-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-3-thiophen-2-yl-urea, |
| 122 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 123 | 2-[1,2-bis-(3,4-dimethoxy-phenyl)-ethyl]-4-[4-(1R)-(1-phenyl-ethyl)-piperazin-1-yl]-isoindole-1,3-dione, |
| 124 | (R)-2,4-dimethyl-thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 125 | (R)-3,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 126 | (R)-5-methyl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 127 | (R)-2,3-dimethyl-3H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 128 | (R)-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 129 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-sulfamic acid, |
| 130 | (R)-N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide, |
| 131 | (R)-2,5-dimethyl-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 132 | (R)-1,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 133 | (R)-1,1-dioxo-tetrahydro-1$\lambda^6$-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 134 | (R)-1-ethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 135 | (R)-1-methyl-3-trifluoromethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 136 | (R)-1-methyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 138 | (R)-5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 139 | (R)-3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 140 | (R)-1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 141 | (R)-N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 142 | (R)-2-[1-(3,4-dimethoxy-phenyl)-4-(pyridin-2-ylamino)-butyl]-4-[4-(1R)-(1-phenyl-ethyl)-piperazin-1-yl]-isoindole-1,3-dione, |

| Cpd | Name |
| --- | --- |
| 143 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-dimethylamino-acetamide, |
| 144 | (R)-5-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 145 | (R)-2-[1-(3,4-dimethoxy-phenyl)-4-(pyrimidin-2-ylamino)-butyl]-4-[4-(1R)-(1-phenyl-ethyl)-piperazin-1-yl]-isoindole-1,3-dione, |
| 146 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-guanidine, |
| 147 | (R)-1-methyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 148 | (R)-1-methyl-5-sulfamoyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 149 | (R)-1-acetyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 150 | (R)-pyridine-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 151 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-nicotinamide, |
| 152 | (R)-3-methyl-3H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 153 | (R)-1-methyl-1H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 154 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isonicotinamide, |
| 155 | (R)-tetrahydro-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 156 | (R)-2-methyl-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 157 | (R)-5-methanesulfonyl-thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 158 | (R)-3-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 159 | (R)-5-methyl-isoxazole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 160 | (R)-pyridazine-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 161 | (R)-1-methyl-1H-imidazole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 162 | (R)-4,5-dimethyl-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 163 | (R)-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 164 | (R)-3,5-dimethyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 165 | (R)-2-[4-(4,5-dihydro-1H-pyrrol-2-ylamino)-1-(3,4-dimethoxy-phenyl)-butyl]-4-[4-(1R)-(1-phenyl-ethyl)-piperazin-1-yl]-isoindole-1,3-dione, |
| 166 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamidine, |
| 167 | (R)-thiophene-2-sulfonic acid [4-(3,4-dimethoxy-phenyl)-4-(1,3-dioxo-4-piperazin-1-yl-1,3-dihydro-isoindol-2-yl)-butyl]-amide, |
| 168 | (R)-thiophene-2-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 169 | (R)-thiophene-2-sulfonic acid {4-(3,4-dimethoxy-phenyl)-4-[4-(4-methyl-piperazin-1-yl)-1,3-dioxo-1,3-dihydro-isoindol-2-yl]-butyl}-amide, |
| 170 | (R)-thiophene-2-sulfonic acid {4-(3,4-dimethoxy-phenyl)-4-[4-(4-furan-3-ylmethyl-piperazin-1-yl)-1,3-dioxo-1,3-dihydro-isoindol-2-yl]-butyl}-amide, |

| Cpd | Name |
|---|---|
| 171 | (R)-thiophene-2-sulfonic acid {4-(3,4-dimethoxy-phenyl)-4-[1,3-dioxo-4-(4-pyridin-3-ylmethyl-piperazin-1-yl)-1,3-dihydro-isoindol-2-yl]-butyl}-amide, |
| 172 | (R)-thiophene-2-sulfonic acid {4-(3,4-dimethoxy-phenyl)-4-[1,3-dioxo-4-(4-thiophen-3-ylmethyl-piperazin-1-yl)-1,3-dihydro-isoindol-2-yl]-butyl}-amide, |
| 173 | (R)-tetrahydro-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 174 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isobutyramide, |
| 175 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-methoxy-acetamide, |
| 176 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-butyramide, |
| 177 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methoxy-propionamide, |
| 178 | (R)-cyclobutanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 179 | (R)-cyclopentanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 180 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-propionamide, |
| 181 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methyl-butyramide, |
| 182 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-ethoxy-acetamide, |
| 183 | (R)-5-chloro-1-methyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 184 | (R)-1,3,5-trimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 185 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2-dimethyl-propionamide, |
| 186 | (R)-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 187 | (R)-isoxazole-5-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 188 | (R)-2,5-dimethyl-1H-pyrrole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 189 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-ethoxy-propionamide, |
| 190 | (R)-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 191 | (S)-1-methyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 192 | (R)-thiophene-2-sulfonic acid [4-[4-(4-cyclobutyl-piperazin-1-yl)-1,3-dioxo-1,3-dihydro-isoindol-2-yl]-4-(3,4-dimethoxy-phenyl)-butyl]-amide, |
| 193 | (R)-thiophene-2-sulfonic acid [4-[4-(4-cyclopentyl-piperazin-1-yl)-1,3-dioxo-1,3-dihydro-isoindol-2-yl]-4-(3,4-dimethoxy-phenyl)-butyl]-amide, |
| 194 | (R)-thiophene-2-sulfonic acid [4-[4-(4-allyl-piperazin-1-yl)-1,3-dioxo-1,3-dihydro-isoindol-2-yl]-4-(3,4-dimethoxy-phenyl)-butyl]-amide, |
| 196 | (R)-thiophene-2-sulfonic acid [4-[4-(4-cyclohexyl-piperazin-1-yl)-1,3-dioxo-1,3-dihydro-isoindol-2-yl]-4-(3,4-dimethoxy-phenyl)-butyl]-amide, |
| 197 | (R)-{4-(3,4-dimethoxy-phenyl)-4-[4-(4-ethyl-piperazin-1-yl)-1,3-dioxo-1,3-dihydro-isoindol-2-yl]-butyl}-carbamic acid tert-butyl ester, |
| 198 | (R)-thiophene-2-sulfonic acid {4-(3,4-dimethoxy-phenyl)-4-[4-(4-isopropyl-piperazin-1-yl)-1,3-dioxo-1,3-dihydro-isoindol-2-yl]-butyl}-amide, |
| 199 | (R)-2-cyano-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-oxo-butyramide, |
| 201 | (R)-2-[4-benzyloxy-1-(3,4-dimethoxy-phenyl)-butyl]-4-(4-ethyl-piperazin-1-yl)-isoindole-1,3-dione, |
| 202 | (R)-cyclobutanecarboxylic acid {4-(3,4-dimethoxy-phenyl)-4-[4-(4-ethyl-piperazin-1-yl)-1,3-dioxo-1,3-dihydro-isoindol-2-yl]-butyl}-amide, |

| Cpd | Name |
|---|---|
| 203 | (R)-1,2-dimethyl-1H-imidazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 204 | (R)-1,3,5-trimethyl-1H-pyrazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 206 | (R)-2-[1-(3,4-dimethoxy-phenyl)-4-hydroxy-butyl]-4-(4-ethyl-piperazin-1-yl)-isoindole-1,3-dione, |
| 207 | (R)-2-[1-(3,4-dimethoxy-phenyl)-4-ethoxy-butyl]-4-(4-ethyl-piperazin-1-yl)-isoindole-1,3-dione, |
| 208 | (R)-thiophene-2-sulfonic acid 4-(3,4-dimethoxy-phenyl)-4-[4-(4-ethyl-piperazin-1-yl)-1,3-dioxo-1,3-dihydro-isoindol-2-yl]-butyl ester, |
| 209 | (R)-dimethyl-sulfamic acid 4-(3,4-dimethoxy-phenyl)-4-[4-(4-ethyl-piperazin-1-yl)-1,3-dioxo-1,3-dihydro-isoindol-2-yl]-butyl ester, |
| 211 | (R)-2-methyl-thiazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 212 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2,2-trifluoro-acetamide, |
| 213 | (R)-2-tert-butoxy-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamide, |
| 215 | (R)-3,5-dimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 216 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-carbamic acid benzyl ester, |
| 217 | (R)-5-methyl-isoxazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 218 | (R)-{4-(3,4-dimethoxy-phenyl)-4-[4-(4-ethyl-piperazin-1-yl)-1,3-dioxo-1,3-dihydro-isoindol-2-yl]-butoxy}-acetic acid, |
| 219 | (R)-1,2-dimethyl-1H-imidazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 220 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-sulfamic acid, |
| 221 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-isonicotinamide, |
| 222 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-C-phenyl-methanesulfonamide, |
| 223 | (R)-3,5-dimethyl-1H-pyrazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 224 | (R)-thiophene-2-sulfonic acid {4-(3,4-dimethoxy-phenyl)-4-[4-(3-dimethylamino-propoxy)-1,3-dioxo-1,3-dihydro-isoindol-2-yl]-butyl}-amide, |
| 227 | (R)-2-[4-(2,6-difluoro-benzyloxy)-1-(3,4-dimethoxy-phenyl)-butyl]-4-(4-ethyl-piperazin-1-yl)-isoindole-1,3-dione, |
| 228 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methyl-sulfamic acid, |
| 229 | (R)-thiophene-2-sulfonic acid {4-(3,4-dimethoxy-phenyl)-4-[4-(2-dimethylamino-ethoxy)-1,3-dioxo-1,3-dihydro-isoindol-2-yl]-butyl}-amide, |
| 230 | 2-[(3-benzylamino-phenyl)-(3,4-dimethoxy-phenyl)-methyl]-4-(4-ethyl-piperazin-1-yl)-isoindole-1,3-dione, |
| 231 | (3-{(3,4-dimethoxy-phenyl)-[4-(4-ethyl-piperazin-1-yl)-1,3-dioxo-1,3-dihydro-isoindol-2-yl]-methyl}-phenyl)-sulfamic acid, |
| 232 | 2-[2-(1-benzyl-piperidin-4-yl)-1-(3,4-dimethoxy-phenyl)-ethyl]-4-(4-ethyl-piperazin-1-yl)-isoindole-1,3-dione, |
| 233 | 4-{2-(3,4-dimethoxy-phenyl)-2-[4-(4-ethyl-piperazin-1-yl)-1,3-dioxo-1,3-dihydro-isoindol-2-yl]-ethyl}-piperidine-1-sulfonic acid, |
| 234 | 2-{1-(3,4-dimethoxy-phenyl)-2-[1-(thiophene-2-sulfonyl)-piperidin-4-yl]-ethyl}-4-(4-ethyl-piperazin-1-yl)-isoindole-1,3-dione, |
| 235 | (R)-2-[1-(3,4-dimethoxy-phenyl)-4-imidazol-1-yl-butyl]-4-(4-ethyl-piperazin-1-yl)-isoindole-1,3-dione, |
| 236 | (R)-2-[4-(benzyl-methyl-amino)-1-(3,4-dimethoxy-phenyl)-butyl]-4-(4-ethyl-piperazin-1-yl)-isoindole-1,3-dione, and |
| 237 | (R)-2-[4-benzoimidazol-1-yl-1-(3,4-dimethoxy-phenyl)-butyl]-4-(4-ethyl-piperazin-1-yl)-isoindole-1,3-dione. |

Example 42a of the present invention is directed to an embodiment wherein wherein Compounds 5, 12, 16, 77, 78, 83, 86 and 87, as described herein, are excluded from Example 42 described herein above.

Example 42b of the present invention is directed to an embodiment wherein compounds where $R_2$ is H are excluded from Example 42 described hereinabove.

Example 43 of the present invention is directed to compounds of Formula (I) or a form thereof as described herein selected from the group consisting of:

| Cpd | Name |
|---|---|
| 1 | 2-(3,4-dimethoxy-benzyl)-4-[4-(1R)-(1-phenyl-ethyl)-piperazin-1-yl]-isoindole-1,3-dione, |
| 2 | 2-[1-(3,4-dimethoxy-phenyl)-ethyl]-4-[4-(1R)-(1-phenyl-ethyl)-piperazin-1-yl]-isoindole-1,3-dione, |
| 3 | 2-[(S)-1-(3,4-dimethoxy-phenyl)-ethyl]-4-[4-(1R)-(1-phenyl-ethyl)-piperazin-1-yl]-isoindole-1,3-dione, |
| 4 | (R)-2-[1-(3,4-dimethoxy-phenyl)-ethyl]-4-[4-(1R)-(1-phenyl-ethyl)-piperazin-1-yl]-isoindole-1,3-dione, |
| 5 | 4-(4-benzyl-piperazin-1-yl)-2-(3,4-dimethoxy-benzyl)-isoindole-1,3-dione, |
| 6 | 2-(3,4-dimethoxy-benzyl)-4-[4-(1-phenyl-ethyl)-piperazin-1-yl]-isoindole-1,3-dione, |
| 7 | 4-(8-benzyl-3,8-diaza-bicyclo[3.2.1]oct-3-yl)-2-(3,4-dimethoxy-benzyl)-isoindole-1,3-dione, |
| 8 | 2-[1-(3,4-dimethoxy-phenyl)-propyl]-4-[4-(1R)-(1-phenyl-ethyl)-piperazin-1-yl]-isoindole-1,3-dione, |
| 9 | 4-(8-benzyl-3,8-diaza-bicyclo[3.2.1]oct-3-yl)-7-chloro-2-(3,4-dimethoxy-benzyl)-isoindole-1,3-dione, |
| 10 | 4-chloro-2-(3,4-dimethoxy-benzyl)-7-[4-(1R)-(1-phenyl-ethyl)-piperazin-1-yl]-isoindole-1,3-dione, |
| 11 | 4-(4-benzyl-piperazin-1-yl)-2-(5,6-dimethoxy-indan-1-yl)-isoindole-1,3-dione, |
| 12 | 2-(3,4-dimethoxy-benzyl)-4-[4-(4-fluoro-benzyl)-piperazin-1-yl]-isoindole-1,3-dione, |
| 13 | 2-(3,4-dimethoxy-benzyl)-4-[4-(1-phenyl-propyl)-piperazin-1-yl]-isoindole-1,3-dione, |
| 14 | 2-(3,4-dimethoxy-benzyl)-4-[4-(1S)-(1-phenyl-ethyl)-piperazin-1-yl]-isoindole-1,3-dione, |
| 63 | 2-[1-(3,4-dimethoxy-phenyl)-2-dimethylamino-ethyl]-4-[4-(1R)-(1-phenyl-ethyl)-piperazin-1-yl]-isoindole-1,3-dione, |
| 64 | 2-[2-amino-1-(3,4-dimethoxy-phenyl)-ethyl]-4-[4-(1R)-(1-phenyl-ethyl)-piperazin-1-yl]-isoindole-1,3-dione, |
| 65 | (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-carbamic acid tert-butyl ester, |
| 66 | 2-[4-amino-1-(3,4-dimethoxy-phenyl)-butyl]-4-[4-(1R)-(1-phenyl-ethyl)-piperazin-1-yl]-isoindole-1,3-dione, |
| 67 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methanesulfonamide, |
| 68 | thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 70 | 2-[5-amino-1-(3,4-dimethoxy-phenyl)-pentyl]-4-[4-(1R)-(1-phenyl-ethyl)-piperazin-1-yl]-isoindole-1,3-dione, |
| 78 | 2-(3,4-dimethoxy-benzyl)-4-(4-furan-3-ylmethyl-piperazin-1-yl)-isoindole-1,3-dione, |
| 83 | 2-(3,4-dimethoxy-benzyl)-4-(4-thiophen-3-ylmethyl-piperazin-1-yl)-isoindole-1,3-dione, |
| 86 | (E)-2-(3,4-dimethoxy-benzyl)-4-[4-(2-methyl-but-2-enyl)-piperazin-1-yl]-isoindole-1,3-dione, |
| 87 | 4-(4-adamantan-2-yl-piperazin-1-yl)-2-(3,4-dimethoxy-benzyl)-isoindole-1,3-dione, |
| 88 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methoxy-thiophene-3-carboxylic acid methyl ester, |
| 90 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-furan-2-carboxylic acid methyl ester, |
| 91 | 1,3,5-trimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 93 | 6-chloro-imidazo[2,1-b]thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 94 | 3-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-thiophene-2-carboxylic acid methyl ester, |
| 95 | 5-isoxazol-3-yl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 96 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-benzenesulfonamide, |

| Cpd | Name |
| --- | --- |
| 97 | N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide, |
| 98 | 1-methyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 99 | 2,5-dimethyl-furan-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 101 | 5-chloro-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 102 | N-(2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-2-pyridin-4-yl-acetamide, |
| 103 | N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-2-pyridin-4-yl-acetamide, |
| 104 | thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 105 | thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 106 | pyridine-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 107 | pyridine-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 108 | 5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 109 | quinoline-8-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 110 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-methanesulfonyl-methanesulfonamide, |
| 111 | 2-phenyl-ethenesulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 112 | 3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 114 | 1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 115 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-N,N-dimethyl-sulfamide, |
| 117 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-phenyl-methanesulfonamide, |
| 118 | (R)-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 119 | (S)-thiophene-2-sulfonic acid 4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 120 | 1-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-thiophen-2-yl-urea, |
| 121 | 1-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-3-thiophen-2-yl-urea, |
| 122 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 123 | 2-[1,2-bis-(3,4-dimethoxy-phenyl)-ethyl]-4-[4-(1R)-(1-phenyl-ethyl)-piperazin-1-yl]-isoindole-1,3-dione, |
| 124 | (R)-2,4-dimethyl-thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 125 | (R)-3,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 126 | (R)-5-methyl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 127 | (R)-2,3-dimethyl-3H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 128 | (R)-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 129 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-sulfamic acid, |
| 130 | (R)-N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide, |
| 131 | (R)-2,5-dimethyl-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 132 | (R)-1,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 133 | (R)-1,1-dioxo-tetrahydro-1$\lambda^6$-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 134 | (R)-1-ethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 135 | (R)-1-methyl-3-trifluoromethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 136 | (R)-1-methyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 138 | (R)-5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 139 | (R)-3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 140 | (R)-1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 141 | (R)-N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 142 | (R)-2-[1-(3,4-dimethoxy-phenyl)-4-(pyridin-2-ylamino)-butyl]-4-[4-(1R)-(1-phenyl-ethyl)-piperazin-1-yl]-isoindole-1,3-dione, |
| 143 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-dimethylamino-acetamide, |
| 144 | (R)-5-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 145 | (R)-2-[1-(3,4-dimethoxy-phenyl)-4-(pyrimidin-2-ylamino)-butyl]-4-[4-(1R)-(1-phenyl-ethyl)-piperazin-1-yl]-isoindole-1,3-dione, |
| 146 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-guanidine, |
| 147 | (R)-1-methyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 148 | (R)-1-methyl-5-sulfamoyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 149 | (R)-1-acetyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 150 | (R)-pyridine-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 151 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-nicotinamide, |
| 152 | (R)-3-methyl-3H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 153 | (R)-1-methyl-1H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 154 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isonicotinamide, |
| 155 | (R)-tetrahydro-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 156 | (R)-2-methyl-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

-continued

| Cpd | Name |
|---|---|
| 157 | (R)-5-methanesulfonyl-thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 158 | (R)-3-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 159 | (R)-5-methyl-isoxazole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 160 | (R)-pyridazine-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 161 | (R)-1-methyl-1H-imidazole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 162 | (R)-4,5-dimethyl-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 163 | (R)-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 164 | (R)-3,5-dimethyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 165 | (R)-2-[4-(4,5-dihydro-1H-pyrrol-2-ylamino)-1-(3,4-dimethoxy-phenyl)-butyl]-4-[4-(1R)-(1-phenyl-ethyl)-piperazin-1-yl]-isoindole-1,3-dione, |
| 166 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamidine, |
| 167 | (R)-thiophene-2-sulfonic acid [4-(3,4-dimethoxy-phenyl)-4-(1,3-dioxo-4-piperazin-1-yl-1,3-dihydro-isoindol-2-yl)-butyl]-amide, |
| 168 | (R)-thiophene-2-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 169 | (R)-thiophene-2-sulfonic acid {4-(3,4-dimethoxy-phenyl)-4-[4-(4-methyl-piperazin-1-yl)-1,3-dioxo-1,3-dihydro-isoindol-2-yl]-butyl}-amide, |
| 170 | (R)-thiophene-2-sulfonic acid {4-(3,4-dimethoxy-phenyl)-4-[4-(4-furan-3-ylmethyl-piperazin-1-yl)-1,3-dioxo-1,3-dihydro-isoindol-2-yl]-butyl}-amide, |
| 171 | (R)-thiophene-2-sulfonic acid {4-(3,4-dimethoxy-phenyl)-4-[1,3-dioxo-4-(4-pyridin-3-ylmethyl-piperazin-1-yl)-1,3-dihydro-isoindol-2-yl]-butyl}-amide, |
| 172 | (R)-thiophene-2-sulfonic acid {4-(3,4-dimethoxy-phenyl)-4-[1,3-dioxo-4-(4-thiophen-3-ylmethyl-piperazin-1-yl)-1,3-dihydro-isoindol-2-yl]-butyl}-amide, |
| 173 | (R)-tetrahydro-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 174 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isobutyramide, |
| 175 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-methoxy-acetamide, |
| 176 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-butyramide, |
| 177 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methoxy-propionamide, |
| 178 | (R)-cyclobutanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 179 | (R)-cyclopentanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 180 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-propionamide, |
| 181 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methyl-butyramide, |
| 182 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-ethoxy-acetamide, |
| 183 | (R)-5-chloro-1-methyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 184 | (R)-1,3,5-trimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 185 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2-dimethyl-propionamide, |
| 186 | (R)-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 187 | (R)-isoxazole-5-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 188 | (R)-2,5-dimethyl-1H-pyrrole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 189 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-ethoxy-propionamide, |
| 190 | (R)-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 191 | (S)-1-methyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 192 | (R)-thiophene-2-sulfonic acid [4-[4-(4-cyclobutyl-piperazin-1-yl)-1,3-dioxo-1,3-dihydro-isoindol-2-yl]-4-(3,4-dimethoxy-phenyl)-butyl]-amide, |
| 193 | (R)-thiophene-2-sulfonic acid [4-[4-(4-cyclopentyl-piperazin-1-yl)-1,3-dioxo-1,3-dihydro-isoindol-2-yl]-4-(3,4-dimethoxy-phenyl)-butyl]-amide, |
| 194 | (R)-thiophene-2-sulfonic acid [4-[4-(4-allyl-piperazin-1-yl)-1,3-dioxo-1,3-dihydro-isoindol-2-yl]-4-(3,4-dimethoxy-phenyl)-butyl]-amide, |
| 196 | (R)-thiophene-2-sulfonic acid [4-[4-(4-cyclohexyl-piperazin-1-yl)-1,3-dioxo-1,3-dihydro-isoindol-2-yl]-4-(3,4-dimethoxy-phenyl)-butyl]-amide, |
| 197 | (R)-{4-(3,4-dimethoxy-phenyl)-4-[4-(4-ethyl-piperazin-1-yl)-1,3-dioxo-1,3-dihydro-isoindol-2-yl]-butyl}-carbamic acid tert-butyl ester, |
| 198 | (R)-thiophene-2-sulfonic acid {4-(3,4-dimethoxy-phenyl)-4-[4-(4-isopropyl-piperazin-1-yl)-1,3-dioxo-1,3-dihydro-isoindol-2-yl]-butyl}-amide, |
| 199 | (R)-2-cyano-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-oxo-butyramide, |
| 201 | (R)-2-[4-benzyloxy-1-(3,4-dimethoxy-phenyl)-butyl]-4-(4-ethyl-piperazin-1-yl)-isoindole-1,3-dione, |
| 202 | (R)-cyclobutanecarboxylic acid {4-(3,4-dimethoxy-phenyl)-4-[4-(4-ethyl-piperazin-1-yl)-1,3-dioxo-1,3-dihydro-isoindol-2-yl]-butyl}-amide, |
| 203 | (R)-1,2-dimethyl-1H-imidazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 204 | (R)-1,3,5-trimethyl-1H-pyrazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 206 | (R)-2-[1-(3,4-dimethoxy-phenyl)-4-hydroxy-butyl]-4-(4-ethyl-piperazin-1-yl)-isoindole-1,3-dione, |
| 207 | (R)-2-[1-(3,4-dimethoxy-phenyl)-4-ethoxy-butyl]-4-(4-ethyl-piperazin-1-yl)-isoindole-1,3-dione, |
| 208 | (R)-thiophene-2-sulfonic acid 4-(3,4-dimethoxy-phenyl)-4-[4-(4-ethyl-piperazin-1-yl)-1,3-dioxo-1,3-dihydro-isoindol-2-yl]-butyl ester, |
| 209 | (R)-dimethyl-sulfamic acid 4-(3,4-dimethoxy-phenyl)-4-[4-(4-ethyl-piperazin-1-yl)-1,3-dioxo-1,3-dihydro-isoindol-2-yl]-butyl ester, |
| 211 | (R)-2-methyl-thiazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 212 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2,2-trifluoro-acetamide, |
| 213 | (R)-2-tert-butoxy-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamide, |
| 215 | (R)-3,5-dimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 216 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-carbamic acid benzyl ester, |
| 217 | (R)-5-methyl-isoxazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 218 | (R)-{4-(3,4-dimethoxy-phenyl)-4-[4-(4-ethyl-piperazin-1-yl)-1,3-dioxo-1,3-dihydro-isoindol-2-yl]-butoxy}-acetic acid, |
| 219 | (R)-1,2-dimethyl-1H-imidazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 220 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-sulfamic acid, |
| 221 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-isonicotinamide, |
| 222 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-C-phenyl-methanesulfonamide, |

| Cpd | Name |
|---|---|
| 223 | (R)-3,5-dimethyl-1H-pyrazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 224 | (R)-thiophene-2-sulfonic acid {4-(3,4-dimethoxy-phenyl)-4-[4-(3-dimethylamino-propoxy)-1,3-dioxo-1,3-dihydro-isoindol-2-yl]-butyl}-amide, |
| 227 | (R)-2-[4-(2,6-difluoro-benzyloxy)-1-(3,4-dimethoxy-phenyl)-butyl]-4-(4-ethyl-piperazin-1-yl)-isoindole-1,3-dione, |
| 228 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methyl-sulfamic acid, |
| 229 | (R)-thiophene-2-sulfonic acid {4-(3,4-dimethoxy-phenyl)-4-[4-(2-dimethylamino-ethoxy)-1,3-dioxo-1,3-dihydro-isoindol-2-yl]-butyl}-amide, |
| 230 | 2-[(3-benzylamino-phenyl)-(3,4-dimethoxy-phenyl)-methyl]-4-(4-ethyl-piperazin-1-yl)-isoindole-1,3-dione, |
| 231 | (3-{(3,4-dimethoxy-phenyl)-[4-(4-ethyl-piperazin-1-yl)-1,3-dioxo-1,3-dihydro-isoindol-2-yl]-methyl}-phenyl)-sulfamic acid, |
| 232 | 2-[2-(1-benzyl-piperidin-4-yl)-1-(3,4-dimethoxy-phenyl)-ethyl]-4-(4-ethyl-piperazin-1-yl)-isoindole-1,3-dione, |
| 233 | 4-{2-(3,4-dimethoxy-phenyl)-2-[4-(4-ethyl-piperazin-1-yl)-1,3-dioxo-1,3-dihydro-isoindol-2-yl]-ethyl}-piperidine-1-sulfonic acid, |
| 234 | 2-{1-(3,4-dimethoxy-phenyl)-2-[1-(thiophene-2-sulfonyl)-piperidin-4-yl]-ethyl}-4-(4-ethyl-piperazin-1-yl)-isoindole-1,3-dione, |
| 235 | (R)-2-[1-(3,4-dimethoxy-phenyl)-4-imidazol-1-yl-butyl]-4-(4-ethyl-piperazin-1-yl)-isoindole-1,3-dione, |
| 236 | (R)-2-[4-(benzyl-methyl-amino)-1-(3,4-dimethoxy-phenyl)-butyl]-4-(4-ethyl-piperazin-1-yl)-isoindole-1,3-dione, and |
| 237 | (R)-2-[4-benzoimidazol-1-yl-1-(3,4-dimethoxy-phenyl)-butyl]-4-(4-ethyl-piperazin-1-yl)-isoindole-1,3-dione. |

Example 43a of the present invention is directed to an embodiment wherein wherein Compounds 5, 12, 78, 83, 86 and 87, as described herein, are excluded from Example 43 described herein above.

Example 43b of the present invention is directed to an embodiment wherein compounds where $R_2$ is H are excluded from Example 43 described hereinabove.

Example 44 of the present invention is directed to compounds of Formula (I) or a form thereof as described herein selected from the group consisting of:

| Cpd | Name |
|---|---|
| 1 | 2-(3,4-dimethoxy-benzyl)-4-[4-(1R)-(1-phenyl-ethyl)-piperazin-1-yl]-isoindole-1,3-dione, |
| 2 | 2-[1-(3,4-dimethoxy-phenyl)-ethyl]-4-[4-(1R)-(1-phenyl-ethyl)-piperazin-1-yl]-isoindole-1,3-dione, |
| 68 | thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 91 | 1,3,5-trimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 94 | 3-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-thiophene-2-carboxylic acid methyl ester, |
| 95 | 5-isoxazol-3-yl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 96 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-benzenesulfonamide, |
| 97 | N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide, |
| 98 | 1-methyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 101 | 5-chloro-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 102 | N-(2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-2-pyridin-4-yl-acetamide, |
| 103 | N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-2-pyridin-4-yl-acetamide, |

| Cpd | Name |
|---|---|
| 104 | thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 105 | thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 106 | pyridine-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 107 | pyridine-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 108 | 5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 109 | quinoline-8-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 110 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-methanesulfonyl-methanesulfonamide, |
| 112 | 3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 114 | 1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 115 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-N,N-dimethyl-sulfamide, |
| 117 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-phenyl-methanesulfonamide, |
| 118 | (R)-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 119 | (S)-thiophene-2-sulfonic acid 4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 122 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 124 | (R)-2,4-dimethyl-thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 140 | (R)-1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 141 | (R)-N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 142 | (R)-2-[1-(3,4-dimethoxy-phenyl)-4-(pyridin-2-ylamino)-butyl]-4-[4-(1R)-(1-phenyl-ethyl)-piperazin-1-yl]-isoindole-1,3-dione, |
| 143 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-dimethylamino-acetamide, |
| 144 | (R)-5-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 145 | (R)-2-[1-(3,4-dimethoxy-phenyl)-4-(pyrimidin-2-ylamino)-butyl]-4-[4-(1R)-(1-phenyl-ethyl)-piperazin-1-yl]-isoindole-1,3-dione, |
| 146 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-guanidine, |
| 147 | (R)-1-methyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 148 | (R)-1-methyl-5-sulfamoyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 149 | (R)-1-acetyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 150 | (R)-pyridine-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 151 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-nicotinamide, |
| 152 | (R)-3-methyl-3H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 153 | (R)-1-methyl-1H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 154 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isonicotinamide, |
| 155 | (R)-tetrahydro-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 156 | (R)-2-methyl-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 157 | (R)-5-methanesulfonyl-thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 158 | (R)-3-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 159 | (R)-5-methyl-isoxazole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 160 | (R)-pyridazine-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 161 | (R)-1-methyl-1H-imidazole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 162 | (R)-4,5-dimethyl-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 163 | (R)-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 164 | (R)-3,5-dimethyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 165 | (R)-2-[4-(4,5-dihydro-1H-pyrrol-2-ylamino)-1-(3,4-dimethoxy-phenyl)-butyl]-4-[4-(1R)-(1-phenyl-ethyl)-piperazin-1-yl]-isoindole-1,3-dione, |
| 166 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamidine, |
| 167 | (R)-thiophene-2-sulfonic acid [4-(3,4-dimethoxy-phenyl)-4-(1,3-dioxo-4-piperazin-1-yl-1,3-dihydro-isoindol-2-yl)-butyl]-amide, |
| 168 | (R)-thiophene-2-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 169 | (R)-thiophene-2-sulfonic acid {4-(3,4-dimethoxy-phenyl)-4-[4-(4-methyl-piperazin-1-yl)-1,3-dioxo-1,3-dihydro-isoindol-2-yl]-butyl}-amide, |
| 170 | (R)-thiophene-2-sulfonic acid {4-(3,4-dimethoxy-phenyl)-4-[4-(4-furan-3-ylmethyl-piperazin-1-yl)-1,3-dioxo-1,3-dihydro-isoindol-2-yl]-butyl}-amide, |
| 171 | (R)-thiophene-2-sulfonic acid {4-(3,4-dimethoxy-phenyl)-4-[1,3-dioxo-4-(4-pyridin-3-ylmethyl-piperazin-1-yl)-1,3-dihydro-isoindol-2-yl]-butyl}-amide, |
| 172 | (R)-thiophene-2-sulfonic acid {4-(3,4-dimethoxy-phenyl)-4-[1,3-dioxo-4-(4-thiophen-3-ylmethyl-piperazin-1-yl)-1,3-dihydro-isoindol-2-yl]-butyl}-amide, |
| 173 | (R)-tetrahydro-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 174 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isobutyramide, |
| 175 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-methoxy-acetamide, |
| 176 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-butyramide, |
| 177 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methoxy-propionamide, |
| 178 | (R)-cyclobutanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 179 | (R)-cyclopentanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 180 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-propionamide, |
| 181 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methyl-butyramide, |
| 182 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-ethoxy-acetamide, |

| Cpd | Name |
|---|---|
| 183 | (R)-5-chloro-1-methyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 184 | (R)-1,3,5-trimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 185 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2-dimethyl-propionamide, |
| 186 | (R)-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 187 | (R)-isoxazole-5-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 188 | (R)-2,5-dimethyl-1H-pyrrole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 189 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-ethoxy-propionamide, |
| 190 | (R)-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 191 | (S)-1-methyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 192 | (R)-thiophene-2-sulfonic acid [4-[4-(4-cyclobutyl-piperazin-1-yl)-1,3-dioxo-1,3-dihydro-isoindol-2-yl]-4-(3,4-dimethoxy-phenyl)-butyl]-amide, |
| 193 | (R)-thiophene-2-sulfonic acid [4-[4-(4-cyclopentyl-piperazin-1-yl)-1,3-dioxo-1,3-dihydro-isoindol-2-yl]-4-(3,4-dimethoxy-phenyl)-butyl]-amide, |
| 194 | (R)-thiophene-2-sulfonic acid [4-[4-(4-allyl-piperazin-1-yl)-1,3-dioxo-1,3-dihydro-isoindol-2-yl]-4-(3,4-dimethoxy-phenyl)-butyl]-amide, |
| 196 | (R)-thiophene-2-sulfonic acid [4-[4-(4-cyclohexyl-piperazin-1-yl)-1,3-dioxo-1,3-dihydro-isoindol-2-yl]-4-(3,4-dimethoxy-phenyl)-butyl]-amide, |
| 197 | (R)-{4-(3,4-dimethoxy-phenyl)-4-[4-(4-ethyl-piperazin-1-yl)-1,3-dioxo-1,3-dihydro-isoindol-2-yl]-butyl}-carbamic acid tert-butyl ester, |
| 198 | (R)-thiophene-2-sulfonic acid {4-(3,4-dimethoxy-phenyl)-4-[4-(4-isopropyl-piperazin-1-yl)-1,3-dioxo-1,3-dihydro-isoindol-2-yl]-butyl}-amide, |
| 199 | (R)-2-cyano-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-oxo-butyramide, |
| 201 | (R)-2-[4-benzyloxy-1-(3,4-dimethoxy-phenyl)-butyl]-4-(4-ethyl-piperazin-1-yl)-isoindole-1,3-dione |
| 203 | (R)-1,2-dimethyl-1H-imidazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 204 | (R)-1,3,5-trimethyl-1H-pyrazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 206 | (R)-2-[1-(3,4-dimethoxy-phenyl)-4-hydroxy-butyl]-4-(4-ethyl-piperazin-1-yl)-isoindole-1,3-dione, |
| 209 | (R)-dimethyl-sulfamic acid 4-(3,4-dimethoxy-phenyl)-4-[4-(4-ethyl-piperazin-1-yl)-1,3-dioxo-1,3-dihydro-isoindol-2-yl]-butyl ester, |
| 211 | (R)-2-methyl-thiazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 212 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2,2-trifluoro-acetamide, |
| 213 | (R)-2-tert-butoxy-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamide, |
| 215 | (R)-3,5-dimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 216 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-carbamic acid benzyl ester, |
| 217 | (R)-5-methyl-isoxazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 219 | (R)-1,2-dimethyl-1H-imidazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 220 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-sulfamic acid, |
| 221 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-isonicotinamide, |

| Cpd | Name |
|---|---|
| 222 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-C-phenyl-methanesulfonamide, |
| 223 | (R)-3,5-dimethyl-1H-pyrazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 228 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methyl-sulfamic acid, |
| 233 | 4-{2-(3,4-dimethoxy-phenyl)-2-[4-(4-ethyl-piperazin-1-yl)-1,3-dioxo-1,3-dihydro-isoindol-2-yl]-ethyl}-piperidine-1-sulfonic acid, |
| 234 | 2-{1-(3,4-dimethoxy-phenyl)-2-[1-(thiophene-2-sulfonyl)-piperidin-4-yl]-ethyl}-4-(4-ethyl-piperazin-1-yl)-isoindole-1,3-dione, |
| 235 | (R)-2-[1-(3,4-dimethoxy-phenyl)-4-imidazol-1-yl-butyl]-4-(4-ethyl-piperazin-1-yl)-isoindole-1,3-dione, |
| 236 | (R)-2-[4-(benzyl-methyl-amino)-1-(3,4-dimethoxy-phenyl)-butyl]-4-(4-ethyl-piperazin-1-yl)-isoindole-1,3-dione, and |
| 237 | (R)-2-[4-benzoimidazol-1-yl-1-(3,4-dimethoxy-phenyl)-butyl]-4-(4-ethyl-piperazin-1-yl)-isoindole-1,3-dione. |

Example 44a of the present invention is directed to an embodiment wherein compounds where $R_2$ is H are excluded from Example 44 described hereinabove.

Example 45 of the present invention is directed to compounds of Formula (I) or a form thereof as described herein selected from the group consisting of:

| Cpd | Name |
|---|---|
| 1 | 2-(3,4-dimethoxy-benzyl)-4-[4-(1R)-(1-phenyl-ethyl)-piperazin-1-yl]-isoindole-1,3-dione, |
| 91 | 1,3,5-trimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 94 | 3-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-thiophene-2-carboxylic acid methyl ester, |
| 98 | 1-methyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 101 | 5-chloro-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 102 | N-(2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-2-pyridin-4-yl-acetamide, |
| 103 | N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-2-pyridin-4-yl-acetamide, |
| 106 | pyridine-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 107 | pyridine-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 108 | 5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 109 | quinoline-8-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 110 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-methanesulfonyl-methanesulfonamide, |
| 112 | 3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 114 | 1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 115 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-N,N-dimethyl-sulfamide, |
| 117 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-phenyl-methanesulfonamide, |
| 118 | (R)-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 122 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 124 | (R)-2,4-dimethyl-thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 125 | (R)-3,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 127 | (R)-2,3-dimethyl-3H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 128 | (R)-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 129 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-sulfamic acid, |
| 132 | (R)-1,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 133 | (R)-1,1-dioxo-tetrahydro-1$\lambda^6$-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 134 | (R)-1-ethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 136 | (R)-1-methyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 138 | (R)-5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 139 | (R)-3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 140 | (R)-1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 141 | (R)-N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide, |
| 143 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-dimethylamino-acetamide, |
| 144 | (R)-5-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 145 | (R)-2-[1-(3,4-dimethoxy-phenyl)-4-(pyrimidin-2-ylamino)-butyl]-4-[4-(1R)-(1-phenyl-ethyl)-piperazin-1-yl]-isoindole-1,3-dione, |
| 146 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-guanidine, |
| 147 | (R)-1-methyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 148 | (R)-1-methyl-5-sulfamoyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 149 | (R)-1-acetyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 150 | (R)-pyridine-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 151 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-nicotinamide, |
| 152 | (R)-3-methyl-3H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 153 | (R)-1-methyl-1H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 154 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isonicotinamide, |
| 155 | (R)-tetrahydro-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 156 | (R)-2-methyl-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

-continued

| Cpd | Name |
|---|---|
| 157 | (R)-5-methanesulfonyl-thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 158 | (R)-3-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 159 | (R)-5-methyl-isoxazole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 160 | (R)-pyridazine-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 161 | (R)-1-methyl-1H-imidazole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 162 | (R)-4,5-dimethyl-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 163 | (R)-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 164 | (R)-3,5-dimethyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 165 | (R)-2-[4-(4,5-dihydro-1H-pyrrol-2-ylamino)-1-(3,4-dimethoxy-phenyl)-butyl]-4-[(1R)-(1-phenyl-ethyl)-piperazin-1-yl]-isoindole-1,3-dione, |
| 166 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamidine, |
| 167 | (R)-thiophene-2-sulfonic acid [4-(3,4-dimethoxy-phenyl)-4-(1,3-dioxo-4-piperazin-1-yl-1,3-dihydro-isoindol-2-yl)-butyl]-amide, |
| 168 | (R)-thiophene-2-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 169 | (R)-thiophene-2-sulfonic acid {4-(3,4-dimethoxy-phenyl)-4-[4-(4-methyl-piperazin-1-yl)-1,3-dioxo-1,3-dihydro-isoindol-2-yl]-butyl}-amide, |
| 170 | (R)-thiophene-2-sulfonic acid {4-(3,4-dimethoxy-phenyl)-4-[4-(4-furan-3-ylmethyl-piperazin-1-yl)-1,3-dioxo-1,3-dihydro-isoindol-2-yl]-butyl}-amide, |
| 171 | (R)-thiophene-2-sulfonic acid {4-(3,4-dimethoxy-phenyl)-4-[1,3-dioxo-4-(4-pyridin-3-ylmethyl-piperazin-1-yl)-1,3-dihydro-isoindol-2-yl]-butyl}-amide, |
| 172 | (R)-thiophene-2-sulfonic acid {4-(3,4-dimethoxy-phenyl)-4-[1,3-dioxo-4-(4-thiophen-3-ylmethyl-piperazin-1-yl)-1,3-dihydro-isoindol-2-yl]-butyl}-amide, |
| 173 | (R)-tetrahydro-furan-3-carboxylic acid (4-(3,4-dimethoxy-phenyl)-4-{1,3-dioxo-4-[(1R)-(1-phenyl-ethyl)-piperazin-1-yl]-1,3-dihydro-isoindol-2-yl}-butyl)-amide, |
| 174 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isobutyramide, |
| 175 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-methoxy-acetamide, |
| 176 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-butyramide, |
| 177 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methoxy-propionamide, |
| 178 | (R)-cyclobutanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 179 | (R)-cyclopentanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 180 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-propionamide, |
| 181 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methyl-butyramide, |
| 182 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-ethoxy-acetamide, |
| 183 | (R)-5-chloro-1-methyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 184 | (R)-1,3,5-trimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 185 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2-dimethyl-propionamide, |
| 186 | (R)-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

| Cpd | Name |
|---|---|
| 187 | (R)-isoxazole-5-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 188 | (R)-2,5-dimethyl-1H-pyrrole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 189 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-ethoxy-propionamide, |
| 190 | (R)-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 191 | (S)-1-methyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 192 | (R)-thiophene-2-sulfonic acid [4-[4-(4-cyclobutyl-piperazin-1-yl)-1,3-dioxo-1,3-dihydro-isoindol-2-yl]-4-(3,4-dimethoxy-phenyl)-butyl]-amide, |
| 193 | (R)-thiophene-2-sulfonic acid [4-[4-(4-cyclopentyl-piperazin-1-yl)-1,3-dioxo-1,3-dihydro-isoindol-2-yl]-4-(3,4-dimethoxy-phenyl)-butyl]-amide, |
| 194 | (R)-thiophene-2-sulfonic acid [4-[4-(4-allyl-piperazin-1-yl)-1,3-dioxo-1,3-dihydro-isoindol-2-yl]-4-(3,4-dimethoxy-phenyl)-butyl]-amide, |
| 196 | (R)-thiophene-2-sulfonic acid [4-[4-(4-cyclohexyl-piperazin-1-yl)-1,3-dioxo-1,3-dihydro-isoindol-2-yl]-4-(3,4-dimethoxy-phenyl)-butyl]-amide, |
| 198 | (R)-thiophene-2-sulfonic acid {4-(3,4-dimethoxy-phenyl)-4-[4-(4-isopropyl-piperazin-1-yl)-1,3-dioxo-1,3-dihydro-isoindol-2-yl]-butyl}-amide, |
| 199 | (R)-2-cyano-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-oxo-butyramide, |
| 201 | (R)-2-[4-benzyloxy-1-(3,4-dimethoxy-phenyl)-butyl]-4-(4-ethyl-piperazin-1-yl)-isoindole-1,3-dione, |
| 204 | (R)-1,3,5-trimethyl-1H-pyrazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 211 | (R)-2-methyl-thiazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 212 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2,2-trifluoro-acetamide, |
| 213 | (R)-2-tert-butoxy-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamide, |
| 215 | (R)-3,5-dimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 217 | (R)-5-methyl-isoxazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 219 | (R)-1,2-dimethyl-1H-imidazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 220 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-sulfamic acid, |
| 221 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-isonicotinamide, |
| 222 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-C-phenyl-methanesulfonamide, |
| 223 | (R)-3,5-dimethyl-1H-pyrazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide, |
| 228 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methyl-sulfamic acid, and |
| 236 | (R)-2-[4-(benzyl-methyl-amino)-1-(3,4-dimethoxy-phenyl)-butyl]-4-(4-ethyl-piperazin-1-yl)-isoindole-1,3-dione. |

Example 45a of the present invention is directed to an embodiment wherein compounds where $R_2$ is H are excluded from Example 45 described hereinabove.

Example 46 of the present invention is directed to compounds of Formula (I) or a form thereof as described herein selected from the group consisting of:

| Cpd | Name |
|---|---|
| 127 | (R)-2,3-dimethyl-3H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |

-continued

| Cpd | Name |
|---|---|
| 128 | (R)-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 129 | (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-sulfamic acid, |
| 132 | (R)-1,5-dimethyl-1 H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 136 | (R)-1-methyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 155 | (R)-tetrahydro-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 168 | (R)-thiophene-2-sulfonic acid {4-(3,4-dimethoxy-phenyl)-4-[4-(4-ethyl-piperazin-1-yl)-1,3-dioxo-1,3-dihydro-isoindol-2-yl]-butyl}-amide, |
| 170 | (R)-thiophene-2-sulfonic acid {4-(3,4-dimethoxy-phenyl)-4-[4-(4-furan-3-ylmethyl-piperazin-1-yl)-1,3-dioxo-1,3-dihydro-isoindol-2-yl]-butyl}-amide, |
| 175 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-methoxy-acetamide, |
| 177 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methoxy-propionamide, |
| 180 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-propionamide, |
| 182 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-ethoxy-acetamide, |
| 185 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2-dimethyl-propionamide, |
| 189 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-ethoxy-propionamide, |
| 190 | (R)-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide, |
| 192 | (R)-thiophene-2-sulfonic acid [4-[4-(4-cyclobutyl-piperazin-1-yl)-1,3-dioxo-1,3-dihydro-isoindol-2-yl]-4-(3,4-dimethoxy-phenyl)-butyl]-amide, |
| 193 | (R)-thiophene-2-sulfonic acid [4-[4-(4-cyclopentyl-piperazin-1-yl)-1,3-dioxo-1,3-dihydro-isoindol-2-yl]-4-(3,4-dimethoxy-phenyl)-butyl]-amide, |
| 198 | (R)-thiophene-2-sulfonic acid {4-(3,4-dimethoxy-phenyl)-4-[4-(4-isopropyl-piperazin-1-yl)-1,3-dioxo-1,3-dihydro-isoindol-2-yl]-butyl}-amide, |
| 199 | (R)-2-cyano-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-oxo-butyramide, and |
| 204 | (R)-1,3,5-trimethyl-1H-pyrazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide. |

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

Abbreviations used in the instant specification, particularly the Schemes and Examples, are as follows:

| Abbreviation | Meaning |
|---|---|
| Bn or Bzl | benzyl |
| Boc | tert-butoxycarbonyl |
| Bop-Cl | bis(2-oxo-3-oxazolidinyl)phosphinic chloride |
| BOP-reagent | benzotriazol-1-yloxy-tris(dimethylamino)phosphonium hexafluorophosphate |
| BSA | bovine serum albumin |
| CBZ | benzyloxycarbonyl |

-continued

| Abbreviation | Meaning |
|---|---|
| DBC | 2,6-dichlorobenzoylchloride |
| DCM | dichloromethane |
| DEAD | diethyl azodicarboxylate |
| DIC | 2-dimethylaminoisopropyl chloride hydrochloride |
| DMAP | 4-dimethylaminopyridine |
| DMF | N,N-dimethylformamide |
| DMSO | dimethylsulfoxide |
| DIPEA | diisopropylethylamine |
| dppf | 1,1'-bis(iphenylphosphino)ferrocene |
| EDC | ethyl-dimethylaminopropyl-carbodiimide |
| EDTA | ethylenediaminetetraacetic acid |
| Et$_3$N | triethylamine |
| EDAC | N-ethyl-N'-dimethylaminopropyl-carbodiimide hydrochloride |
| Et$_2$O | diethyl ether |
| EtOAc | ethyl acetate |
| EtOH | ethanol |
| h | hour |
| HBTU | O-benzotriazol-1-yl-N,N,N',N'-tetramethyl-uronium hexafluorophosphate |
| HOBt | hydroxybenzotriazole hydrate |

| Abbreviation | Meaning |
|---|---|
| HATU | O-(7-azabenzotriazol-1-yl)-1,1,3,3-tetramethyl-uronium hexafluorophosphate |
| HPLC | high performance liquid chromatography |
| HEPES | 4-(2-hydroxyethyl)-1-piperazine-ethanesulfonic acid |
| KOAc | potassium acetate |
| LAH | lithium aluminum hydride |
| Me | methyl |
| MeOH | methanol |
| min | minutes |
| Me | methyl |
| MeCN | acetonitrile |
| MPK | milligrams per kilogram |
| $NH_4OAc$ | ammonium acetate |
| NMM | N-methyl-morpholine |
| NT | not tested |
| PBS | phosphate buffer solution |
| $Pd(OH)_2/C$ | palladium hydroxide on carbon |
| Ph | phenyl |
| $(o\text{-}tolyl)_3P$ | tri-o-tolylphosphine |
| Pd/C | palladium on activated carbon |
| $Pd(dppf)_2Cl_2 \cdot CH_2Cl_2$ | dichloro(1,1'-bis(diphenylphosphino)ferrocene)palladium (ii) dichloromethane adduct |
| $Pd_2(dba)_3 \cdot CHCl_3$ | tris(dibenzylideneacetone)dipalladium (0) chloroform adduct |
| $Pd(OAc)_2$ | palladium(ii) acetate |
| $Ph_3P$ | triphenylphosphine |
| PS-HOBt | hydroxybenzotriazole, polymer bound 0.9 mmol/g (polystyrene resin) |
| PPT | precipitate |
| psi | pounds per square inch |
| rt | room temperature |
| SDS | sodium dodecasulfate |
| TBDMS-Cl | tert-butyldimethylsilyl chloride |
| $[(t\text{-}Bu)_3P]_2Pd$ | bis(tri-t-butylphophine)palladium (0) |
| TEA | triethylamine |
| THF | tetrahydrofuran |
| Thi | thienyl |
| TMS | tetramethylsilane |
| TFA | trifluoroacetic acid |
| Tol | toluene |
| (R)-tol-BINAP | (R)-(+)-2,2'-bis(di-p-tolylphosphino)-1,1'-binaphthyl |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

Scheme A describes the synthesis of compounds of the present invention wherein A is ring of formula a-1.

SCHEME A

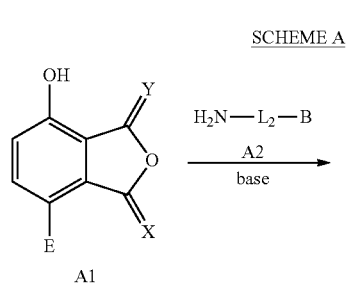

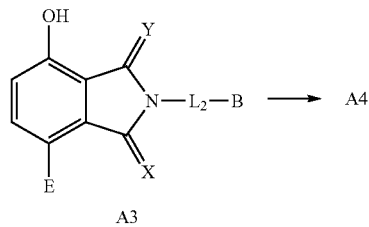

A commercially available or readily prepared phthalic anhydride of formula A1 may be reacted with an amine of formula A2 in the presence of a suitable base such as a tertiary amine to give a compound of formula A3, wherein the OH substituent may be converted to a triflate or other appropriate leaving group (LG) using conventional chemical reagents and methods to give a compound of formula A4. Examples of appropriate leaving groups include fluoride, bromide, iodide, triflate, mesylate, and the like.

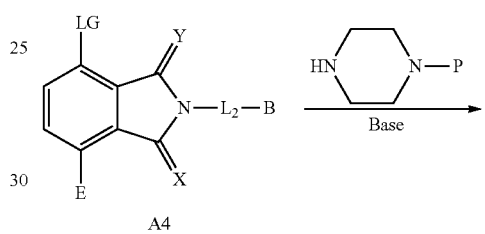

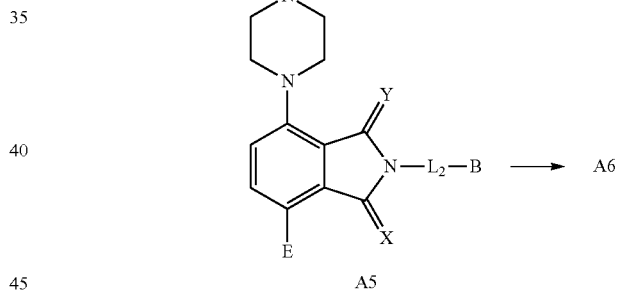

The leaving group of formula A4 may be displaced with a mono-protected piperazine (wherein P is an appropriate amino protecting group) to give a compound of formula A5. Removal of the protecting group P using conventional methods provides a compound of formula A6

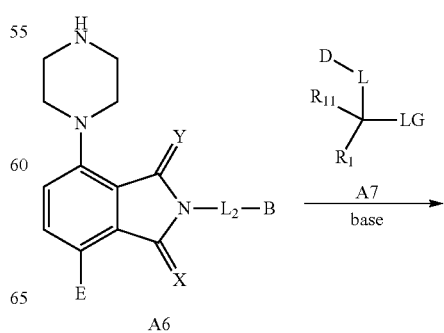

-continued

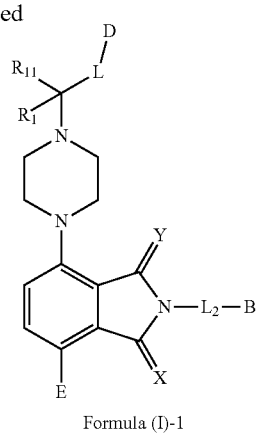

Formula (I)-1

Alkylation of the compound of formula A6 with a compound of formula A7 provides a compound of Formula (I)-1. The group LG is herein defined as a leaving group subject to nucleophilic displacement. Examples of appropriate leaving groups are described above.

Scheme B describes the synthesis of compounds of the present invention wherein substituent A is an optionally unsaturated ring of formula a-2 or a-5.

SCHEME B

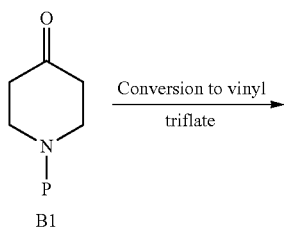

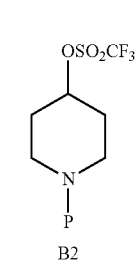

B2

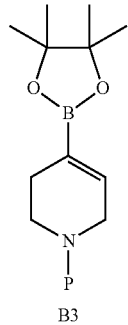

B3

A compound of formula B1 may be converted to its corresponding vinyl triflate, which may then be converted to a vinyl borate of formula B3 using methods known to those skilled in the art.

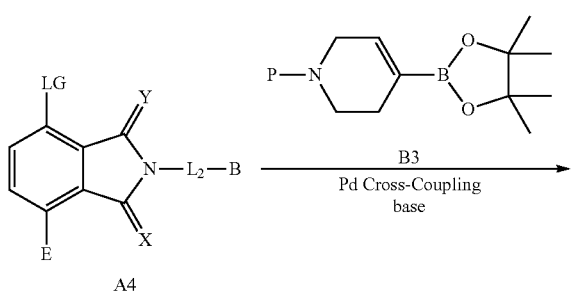

A4

-continued

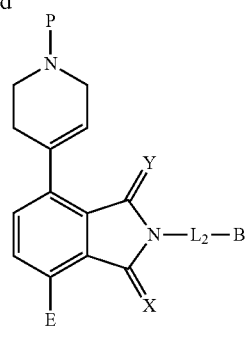

B4

Compound A4 may be coupled with a boronate of formula B3 using palladium catalysis to give a compound of formula B4.

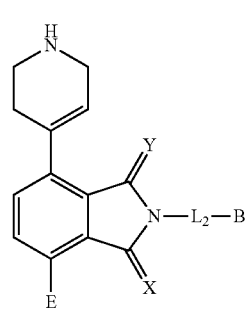 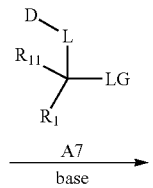

B5

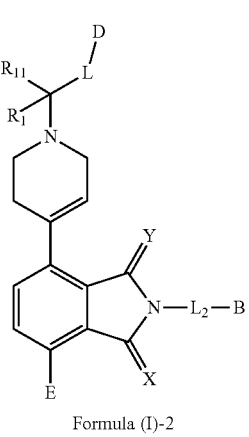

Formula (I)-2

Removal of the protecting group P followed by alkylation with a compound of formula A7, as described herein, provides a compound of Formula (I)-2, wherein substituent A is an unsaturated ring of formula a-2.

Other compounds representative of the present invention, wherein substituent A is a ring of formula a-2 or an optionally unsaturated ring of formula a-5, may be prepared using techniques known to those skilled in the art.

Scheme C describes the synthesis of certain compounds of the present invention.

SCHEME C

C1    C2

An alcohol of formula C1 is either commercially available or may be prepared using conventional methods and known reagents and starting materials. The hydroxy group of compound of formula C1 may be activated through conversion of the hydroxy group to an appropriate leaving group, LG (as defined previously) to provide a compound of formula C2.

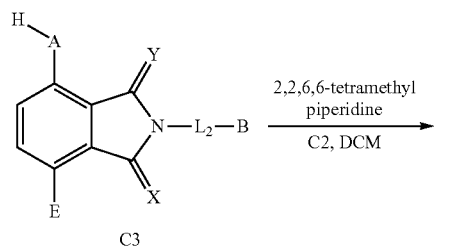

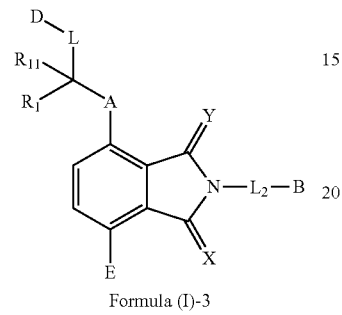

Formula (I)-3

Nucleophilic displacement of the leaving group by the amino portion of substituent A on a compound of formula C3, provides a compound of Formula (I)-3.

Scheme D describes the synthesis of compounds of the present invention wherein substituent A is absent and Rg represents either OH or LG (a previously defined leaving group).

SCHEME D

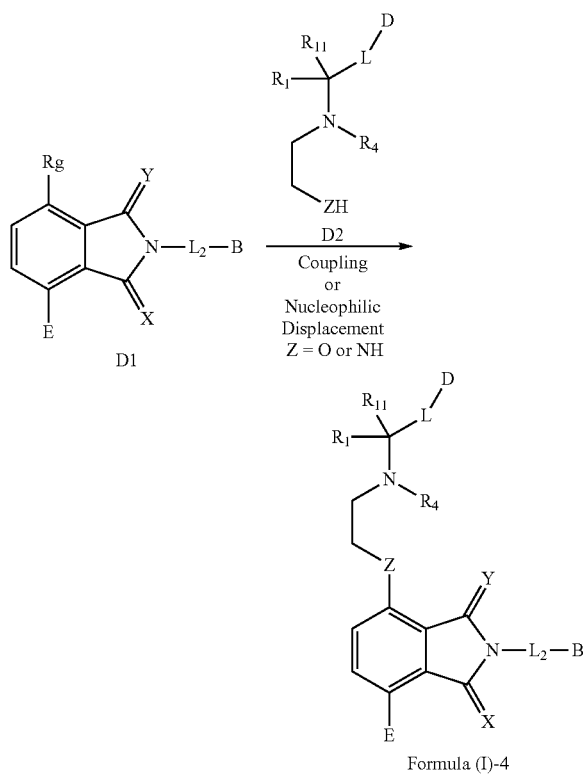

Formula (I)-4

A compound of formula D1 (wherein Rg is OH) may be coupled with a compound of formula D2 (when Z is O) to provide a compound of Formula (I)-4.

This transformation may be accomplished using a coupling reaction, such as a Mitsunobu reaction, in the presence of an appropriate coupling agent and activating agents such as triphenylphosphine in an aprotic solvent.

Alternatively, treatment of the compound of formula D2 with a base (such as sodium hydride and the like) forms a nucleophilic alkoxy group for displacing a leaving group on the compound of formula D1 (wherein Rg is an appropriate leaving group such as fluoride, bromide, iodide, triflate, mesylate, and the like).

A compound of formula D2 (when Z is NH) may be coupled with a compound of formula D1 (wherein Rg is a leaving group) to provide a compound of Formula (I)-4 by using a procedure adapted from Scheme A for preparing the compound of formula A5.

Scheme E describes the synthesis of compounds of the present invention wherein substituent A is ring of formula a-4.

SCHEME E

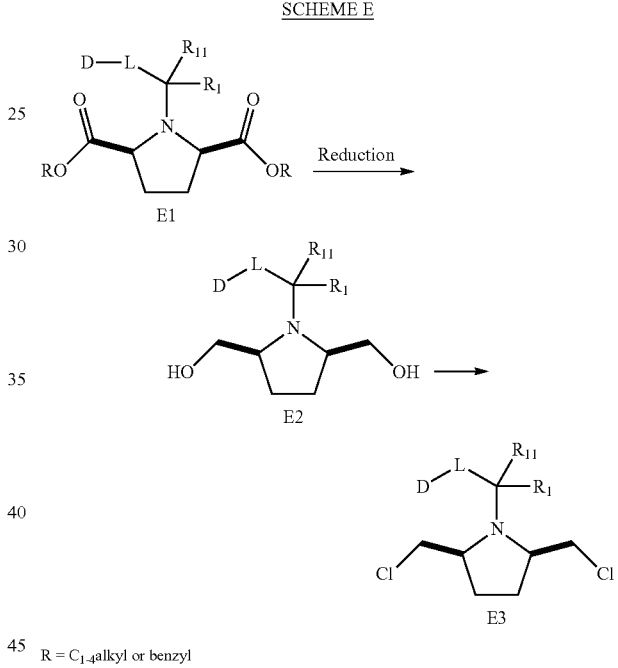

R = $C_{1-4}$ alkyl or benzyl

A diester of formula E1 may be reduced in the presence of a hydride source to diol E2, which may then be converted to the corresponding bis-chloride of formula E3 using thionyl chloride, oxalyl chloride, or the like.

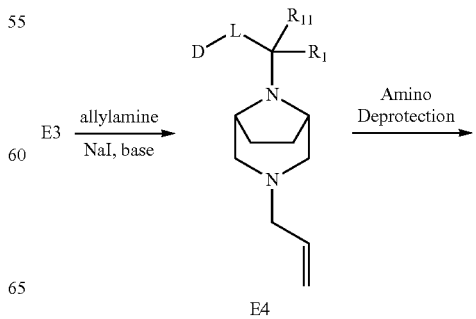

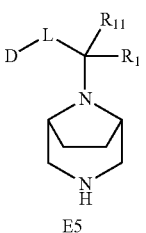

E5

Reaction of a compound of formula E3 with allylamine gives a compound of formula E4. Subsequent removal of the allyl group using conventional N-allylamino deprotection chemistry gives an amine of formula E5.

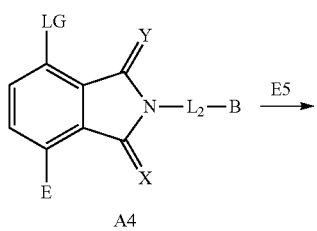

A4

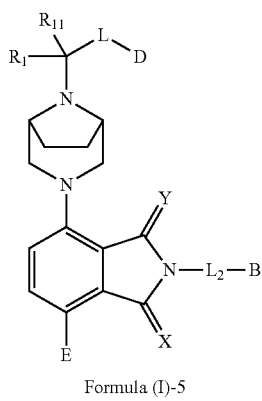

Formula (I)-5

Reaction of a compound of formula A4 with a compound of formula E5 provides a compound of Formula (I)-5.

Scheme F describes the preparation of certain compounds of the present invention.

SCHEME F

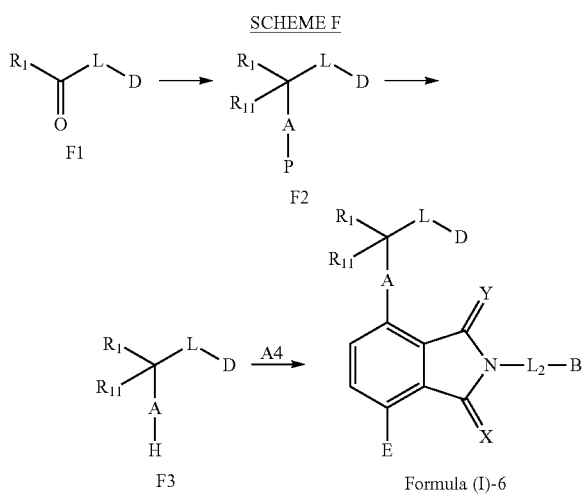

Reductive amination of a ketone of formula F1 with the amino group of a mono-protected substituent A gives a compound of formula F2 (wherein $R_{11}$ is hydrogen). Removal of the protecting group followed by reaction with Compound A4 as described herein gives a compound of Formula (I)-6.

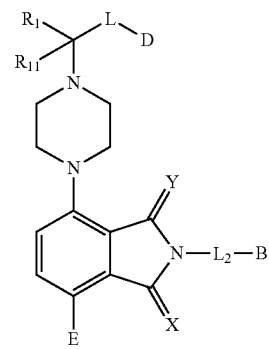

Formula (I)-6

Alternatively, reductive amination of a ketone of formula F1 with the compound of formula A6 as described herein gives a compound of Formula (I)-6 (wherein $R_{11}$ is hydrogen).

Scheme G describes the synthesis of certain intermediates of the present invention wherein B is a phenyl substituent independently substituted with two to three unbranched $C_{1-3}$alkoxy groups.

SCHEME G

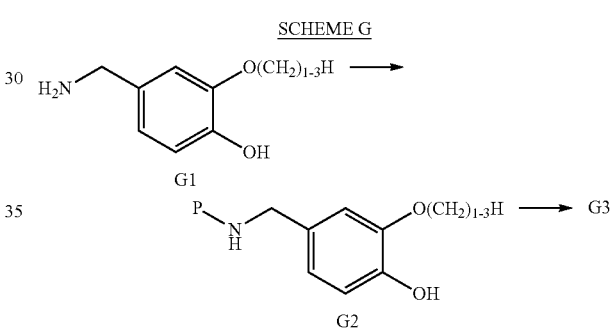

An aminophenol of formula G1 may be amino protected, and subsequently O-alkylated using conventional chemistry known to those skilled in the art to give a compound of formula G3.

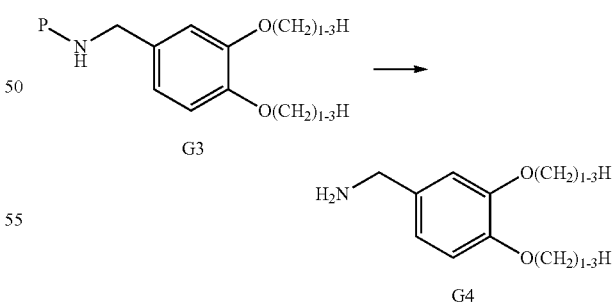

Removal of the amino-protecting group P provides a compound of formula G4. A compound of formula G4 may then be substituted for a compound of formula A2 of Scheme A to prepare certain compounds of the present invention.

Scheme H describes the preparation of certain amino intermediate compounds of formula A2 wherein $L_2$ is —CH($R_2$)—$(CR_6R_7)_r$—.

SCHEME H

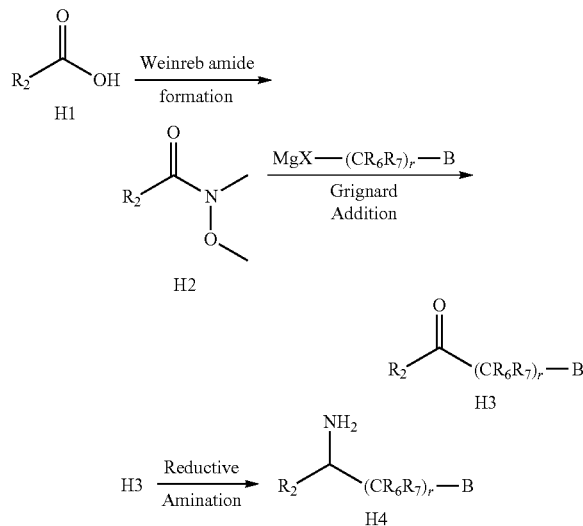

A compound of formula H1 may be converted to its corresponding Weinreb amide using chemical methods known to those skilled in the art. The Weinreb amide of formula H2 may be treated with a organometallic reagent, such as a Grignard reagent to give a ketone of formula H3. Reductive amination of the ketone functionality of a compound of formula H3 provides certain A2 intermediates.

Those skilled in the art will recognize that compounds of formula H4 may be prepared stereoselectively using an adaptation of methods referenced in the literature, such as Kadyrov, R. and Riermeier, T. *Angew. Chem. Int. Ed.* 2003, 42, 5472-5474.

Scheme I describes the preparation of certain compounds of the present invention wherein substituent E is —$C_{2-5}$alkyl-$R_E$ or —CH=CH—$C_{0-3}$alkyl-$R_E$.

SCHEME I

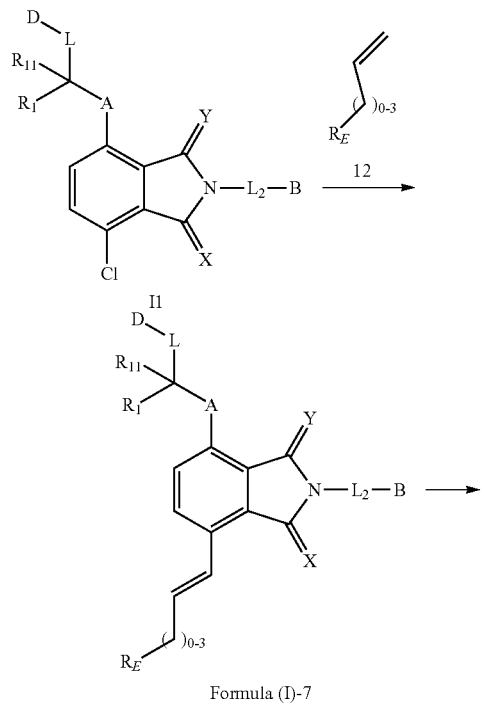

Formula (I)-7

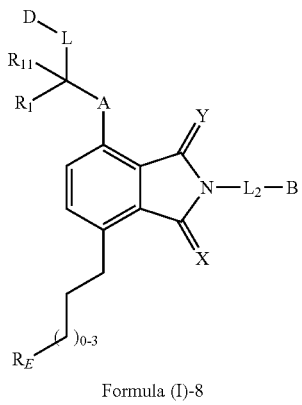

Formula (I)-8

An $R_E$-substituted alkenyl group may be installed via a palladium catalyzed carbon-carbon coupling reaction. In particular, a compound of formula II (wherein E is chloro) may be coupled with a compound of formula I2 to yield compounds of Formula (I)-7 of the present invention. Hydrogenation of a compound of formula (I)-7 accomplishes the conversion of the alkenyl functionality to its corresponding alkyl derivative, as depicted in the compounds of Formula (I)-8.

Scheme J describes the synthesis of compounds of the present invention wherein the biradical substituent A is a ring of formula a-2.

SCHEME J

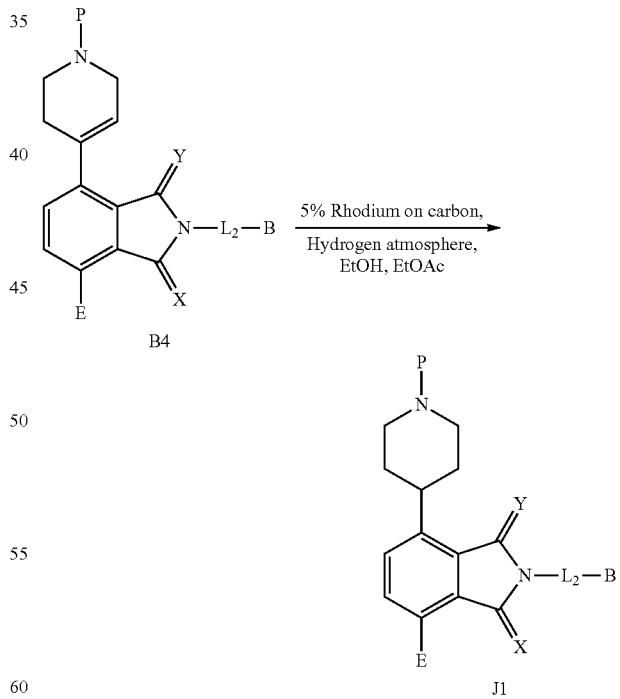

Compound B4 may be reduced in the presence of rhodium catalyst under a hydrogen atmosphere to give a compound of Formula J1. Removal of protecting group P, followed by the reactions described in Scheme B provide additional compounds representative of the compounds of Formula (I).

Scheme K describes the synthesis of certain compounds of the present invention.

SCHEME K

A compound of formula K1 may be reacted with a compound of formula K2 in the presence of a suitable base and a metal catalyst to give a compound of formula K3.

Scheme L describes the synthesis of certain compounds of the present invention.

SCHEME L

The alcohol of a compound of formula L1 may be converted to a leaving group of formula L2.

Nucleophilic displacement of the leaving group by the heteroatom portion of a heterocycle or heteroaryl of formula $R_{200}$, provides a compound of Formula (I)-9.

Scheme M describes the synthesis of certain compounds of the present invention.

SCHEME M

The alcohol of a compound of formula M1 may be eliminated to give the alkene of formula M2.

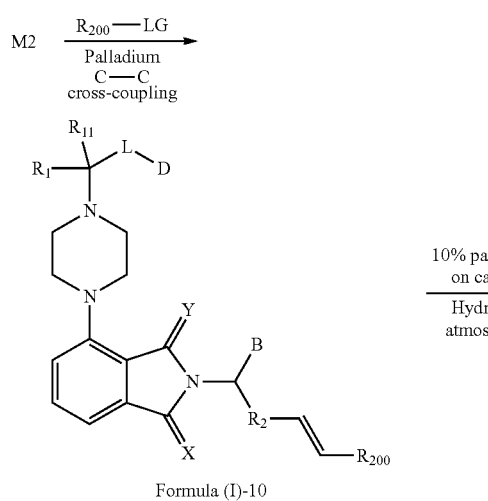

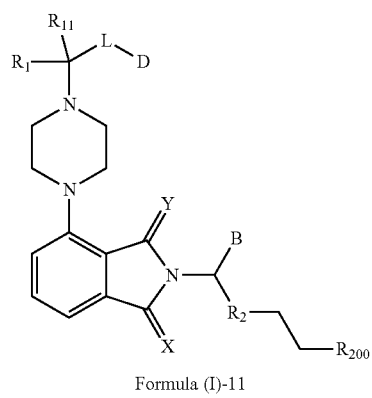

Coupling of a compound of formula M2 with $R_{200}$-LG may be accomplished by conventional transition metal catalyzed C—C coupling methodology to give a compound of Formula (I)-10.

The compound of Formula (I)-10 may be reacted with 10% palladium on carbon under a hydrogen atmosphere to give a compound of Formula (I)-11.

SPECIFIC EXAMPLES

Example 1

4-[4-(2,6-difluoro-benzyl)-piperazin-1-yl]-2-(3,4-dimethoxy-benzyl)-isoindole-1,3-dione Cpd 16

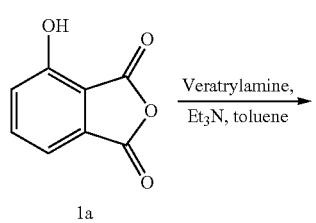

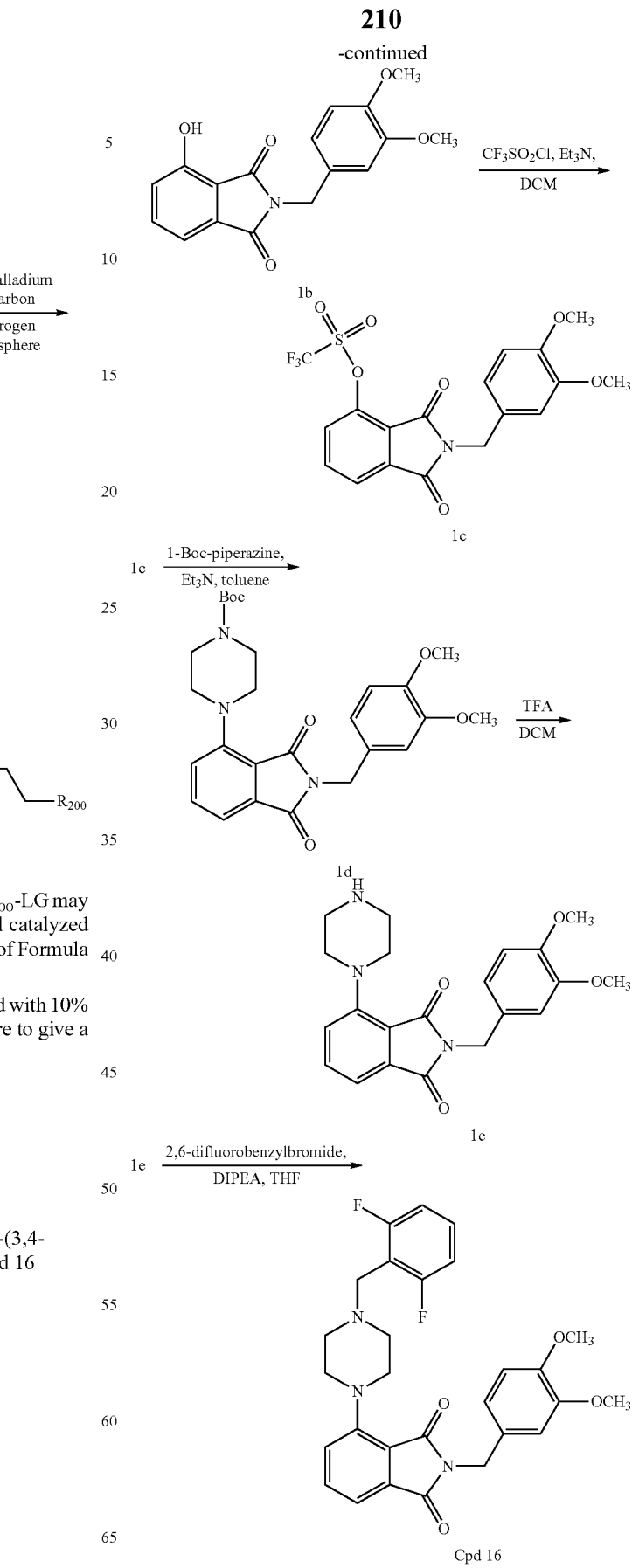

A. A 200 mL round bottom flask was charged with phthalic anhydride Compound 1a (3.07 g, 0.019 mol) and dry toluene (94 mL). Veratrylamine (2.8 mL, 0.019 mol) and TEA (3.6 mL, 0.026 mol) were added to the mixture. A Dean-Stark trap was attached to the flask and the mixture was refluxed for 24 h. The mixture was cooled to room temperature and diluted with DCM (200 mL) and washed with 1.0 N HCl (100 mL). The organic layers were combined and dried using $MgSO_4$, filtered through Celite®, and concentrated in vacuo to give 5.6 g (96%) of Compound 1b as a yellow solid. $^1$H NMR (300 MHz, $CDCl_3$) δ 7.70-7.86 (m, 1 H), 7.57 (ovdd, J=7.5 Hz, 1 H), 7.37 (d, J=7.3 Hz, 1 H), 7.15 (d, J=8.4 Hz, 1 H), 6.91-7.01 (m, 2 H), 6.81 (d, J=7.8 Hz, 1 H), 4.74 (s, 2 H), 3.88 (s, 3 H), and 3.85 (s, 3 H); MS ($ES^+$) 314 (M+1).

B. A 500 mL round bottom flask was charged with Compound 1b (5.90 g, 0.019 mol), DCM (80 mL), and $Et_3N$ (3.6 mL, 0.026 mol). The mixture was cooled using ice/water bath. A solution of trifluoromethanesulfonyl chloride (2.2 mL, 0.021 mol) in DCM (20 mL) was added dropwise via an addition funnel. The mixture was then stirred for 1 h in an ice/water bath. The mixture was then diluted with DCM (200 mL) and washed with 1.0 N HCl (100 mL) solution. The organic layer was dried using $MgSO_4$, filtered through Celite®, and concentrated in vacuo to give 8.20 g (97%) of Compound 1c as a yellow solid. $^1$H NMR (300 MHz, $CDCl_3$) δ 7.78-7.87 (m, 2 H), 7.53 (d, J=8.3 Hz, 1 H), 6.99-7.02 (m, 2 H), 6.79 (d, J=8.1 Hz, 1 H), 4.79 (s, 2 H), 3.87 (s, 3 H), and 3.84 (s, 3 H); MS ($ES^+$) 446 (M+1).

C. A 10 mL sealed tube was charged with Compound 1c (0.50 g, 1.12 mmol), 1-Boc-piperazine (0.22 g, 1.18 mmol), toluene (1.3 mL), and $Et_3N$ (0.2 mL, 1.43 mmol). The tube was sealed under argon and heated to 110° C. for 18 h. The mixture was cooled to room temperature and purified via flash silica gel chromatography (230-400 mesh silica gel 60, 80:20 hexanes:EtOAc) to give 0.33 g (61%) of Compound 1d as a yellow solid. $^1$H NMR (300 MHz, MeOH) δ 7.61-7.67 (ovdd, J=7.2 Hz, 1 H), 7.38 (d, J=7.2 Hz, 1 H), 7.28 (d, J=8.2 Hz, 1 H), 6.99 (s, 1 H), 6.86-6.93 (m, 2 H), 4.71 (s, 2 H), 3.81 (s, 3 H), 3.79 (s, 3 H), 3.61-3.65 (m, 4 H), 3.27-3.31 (m, 4 H), and 1.48 (s, 9 H); MS ($ES^+$) 482 (M+1).

D. A 50 mL round bottom flask was charged with Compound 1d (0.33 g, 0.69 mmol) and DCM (3.0 mL). TFA (0.7 mL) was added and the mixture was stirred at room temperature for 1 h. The mixture was concentrated in-vacuo. The crude oil (Compound 1e) was dissolved in THF (3.4 mL). 2,6-Difluorobenzyl bromide (0.20 g, 0.97 mmol) and DIPEA (0.26 mL, 1.49 mmol) were added. The mixture was heated to reflux for 24 h and evaporated. The crude oil was purified on a Gilson HPLC with a reversed phase Kromasil column (10 u, 100 Å C18, column length 250×50 mm, gradient 80:20-0:100 $H_2O$:MeCN) to give 369.0 mg (87%) of the title Compound 16 as a yellow solid. $^1$H NMR (300 MHz, $CDCl_3$) δ 7.62 (ovdd, J=7.5 Hz, 1 H), 7.46-7.54 (m, 2 H), 7.13 (d, J=8.2 Hz, 1 H), 7.07 (ovdd, J=8.2 Hz, 1 H), 6.93-6.96 (m, 3 H), 6.80 (d, J=6.2 Hz, 1 H), 4.72 (s, 2 H), 4.42 (s, 2 H), 3.87 (s, 3 H), 3.84 (s, 3 H), 3.53-3.62 (m, 4 H), and 3.27-3.47 (m, 4 H); MS ($ES^+$) 508 (M+1); Anal. Calcd for $C_{28}H_{27}F_2N_3O_4 \cdot 1.4 CF_3CO_2H \cdot 0.3H_2O$: C, 55.00; H, 4.35; N, 6.25; F, 17.51; $H_2O$, 0.80. Found: C, 54.83; H, 3.96; N, 6.09; F, 17.30; $H_2O$, 0.60.

Other compounds of the present invention may be prepared by those skilled in the art by varying the starting materials, reagent(s) and conditions used. Using the procedure of Example 1, the following compounds were prepared:

| Cpd | Name |
|---|---|
| 23 | 4-(4-benzyl-piperazin-1-yl)-2-(1,3,5-trimethyl-1H-pyrazol-4-ylmethyl)-isoindole-1,3-dione<br>$^1$H NMR (400 MHz, $CDCl_3$) δ 7.65 (t, J = 8 Hz, 1H), 7.32 (d, J = 7 Hz, 1H), 7.27 (d, J = 8 Hz, 1H), 6.92 (s, 1H), 6.87 (d, J = 8 Hz, 1H), 6.77 (d, J = 8 Hz, 1H), 6.17 (br s, 1H), 5.99 (br s, 1H), 4.64 (s, 2H), 3.73 (br s, 6H), 3.50 (s, 2H), 3.3 (m, 4H), 2.6 (m, 4H), 2.23 (s, 3H). Observed Parent Peak 444; MS calc'd 443.6 |
| 77 | 2-(3,4-dimethoxy-benzyl)-4-[4-(5-methyl-furan-2-ylmethyl)-piperazin-1-yl]-isoindole-1,3-dione<br>$^1$H NMR (400 MHz, $CDCl_3$) δ 7.65 (t, J = 8 Hz, 1H), 7.32 (d, J = 7 Hz, 1H), 7.27 (d, J = 8 Hz, 1H), 6.92 (s, 1H), 6.87 (d, J = 8 Hz, 1H), 6.77 (d, J = 8 Hz, 1H), 6.17 (br s, 1H), 5.99 (br s, 1H), 4.64 (s, 2H), 3.73 (br s, 6H), 3.50 (s, 2H), 3.3 (m, 4H), 2.6 (m, 4H), 2.23 (s, 3H). |
| 78 | 2-(3,4-dimethoxy-benzyl)-4-(4-furan-3-ylmethyl-piperazin-1-yl)-isoindole-1,3-dione<br>$^1$H NMR (400 MHz, $CDCl_3$) δ 7.64 (t, J = 7 Hz, 1H), 7.58 (d, J = 8 Hz, 2H), 7.32 (d, J = 7 Hz, 1H), 7.28 (d, J = 7 Hz, 1H), 6.92 (s, 1H), 6.88 (d, J = 8 Hz, 1H), 6.77 (d, J = 8 Hz, 1H), 6.45 (s, 1H), 4.63 (s, 2H), 3.73 (br s, 6H), 3.40 (s, 2H), 3.3 (m, 4H), 2.6 (m, 4H). |
| 79 | 2-(3,4-dimethoxy-benzyl)-4-(4-pyridin-3-ylmethyl-piperazin-1-yl)-isoindole-1,3-dione<br>$^1$H NMR (400 MHz, $CDCl_3$) δ 8.54 (s, 1H), 8.48 (m, 1H), 7.74 (d, J = 7 Hz, 1H), 7.65 (t, J = 7 Hz, 1H), 7.37 (m, 1H), 7.32 (d, J = 7 Hz, 1H), 7.28 (d, J = 8 Hz, 1H), 6.91(s, 1H), 6.87 (d, J = 8 Hz, 1H), 6.77 (d, J = 8 Hz, 1H), 4.63 (s, 2H), 3.73 (br s, 6H), 3.6 (s, 2H), 3.3 (m, 4H), 2.6 (m, 4H). |
| 80 | 4-(4-cyclopentylmethyl-piperazin-1-yl)-2-(3,4-dimethoxy-benzyl)-isoindole-1,3-dione<br>$^1$H NMR (400 MHz, $CDCl_3$) δ 7.65 (t, J = 7 Hz, 1H), 7.32 (d, J = 7 Hz, 1H), 7.28 (d, J = 8 Hz, 1H), 6.92 (s, 1H), 6.87 (d, J = 8 Hz, 1H), 6.77 (d, J = 8 Hz, 1H), 4.63 (s, 2H), 3.72 (s, 3H), 3.71(s, 3H), 3.3 (m, 4H), 2.6 (m, 4H), 2.25 (m, 2H), 2.11 (m, 1H), 1.8-1.1 (m, 8H). |
| 81 | 2-(3,4-dimethoxy-benzyl)-4-(4-thiophen-2-ylmethyl-piperazin-1-yl)-isoindole-1,3-dione<br>$^1$H NMR (400 MHz, $CDCl_3$) δ 7.65 (t, J = 7 Hz, 1H), 7.43 (m, 1H), 7.32 (d, J = 7 Hz, 1H), 7.28 (d, J = 8 Hz, 1H), 7.0 (m, 2H), 6.92 (s, 1H), 6.87 (d, J = 8 Hz, 1H), 6.77 (d, J = 8 Hz, 1H), 4.63 (s, 2H), 3.77 (s, 2H), 3.72 (s, 3H), 3.71 (s, 3H), 3.3 (m, 4H), 2.6 (m, 4H). |

| Cpd | Name |
|---|---|
| 82 | 2-(3,4-dimethoxy-benzyl)-4-(4-isobutyl-piperazin-1-yl)-isoindole-1,3-dione<br>$^1$H NMR (400 MHz, CDCl$_3$) δ 7.65 (t, J = 8 Hz, 1H), 7.32 (d, J = 7 Hz, 1H), 7.28 (d, J = 8 Hz, 1H), 6.92 (s, 1H), 6.88 (d, J = 8 Hz, 1H), 6.78 (d, J = 8 Hz, 1H), 4.64 (s, 2H), 3.72 (br s, 6H), 3.3 (m, 4H), 2.5 (m, 4H), 2.10 (m, 2H), 1.81 (m, 1H), 0.91 (d, J = 7 Hz, 6H). |
| 83 | 2-(3,4-dimethoxy-benzyl)-4-(4-thiophen-3-ylmethyl-piperazin-1-yl)-isoindole-1,3-dione<br>$^1$H NMR (400 MHz, CDCl$_3$) δ 7.6-7.4 (m, 2H), 7.35 (d, J = 7 Hz, 1H), 7.3-6.9 (m, 5H), 6.78 (m, J = 8 Hz, 1H), 4.73 (s, 2H), 3.87 (s, 3H), 3.83 (s, 3H), 3.62 (s, 2H), 3.4 (m, 4H), 2.7 (m, 4H). |
| 84 | 2-(3,4-dimethoxy-benzyl)-4-(4-pyridin-2-ylmethyl-piperazin-1-yl)-isoindole-1,3-dione<br>MS (ES+) 473.3 (M + 1). |
| 85 | 2-(3,4-dimethoxy-benzyl)-4-[4-(2-hydroxy-benzyl)-piperazin-1-yl]-isoindole-1,3-dione<br>MS (ES+) 488.4 (M + 1). |
| 86 | (E)-2-(3,4-dimethoxy-benzyl)-4-[4-(2-methyl-but-2-enyl)-piperazin-1-yl]-isoindole-1,3-dione<br>MS (ES+) 450.4 (M + 1). |
| 87 | 4-(4-adamantan-2-yl-piperazin-1-yl)-2-(3,4-dimethoxy-benzyl)-isoindole-1,3-dione<br>MS (ES+) 516.4 (M + 1). |
| 225 | 2-(2-bromo-4,5-dimethoxy-benzyl)-4-[4-(1R)-(1-phenyl-ethyl)-piperazin-1-yl]-isoindole-1,3-dione<br>$^1$H NMR (300 MHz, CDCl$_3$) δ 7.65 (ovdd, J = 8.1 Hz, 1 H), 7.43-7.52 (m, 6 H), 7.16 (d, J = 8.2 Hz, 1 H), 7.01 (s, 1 H), 6.77 (s, 1 H), 4.85 (s, 2 H), 4.30-4.37 (m, 1 H), 3.74-4.00 (m, 10 H), 3.41-3.57 (m, 2 H), 3.02-3.19 (m, 2 H), and 1.84 (d, J = 7.0 Hz, 6 H); MS (ES+) 564.2 (M), 566.2 (M + 2). |

Example 2

2-(3,4-dimethoxy-benzyl)-4-[4-(4-fluoro-benzyl)-piperazin-1-yl]-isoindole-1,3-dione Cpd 12

Compound 12 was prepared by the methods described in Example 1 for the synthesis of Compound 1, substituting 4-fluorobenzyl bromide (0.03 mL) for 2,6-difluorobenzyl-bromide and substituting K$_2$CO$_3$ (0.084 g) for DIEA in Example 1, Step D. Compound 12 was isolated as a yellow solid. MS (ES$^+$) 490 (M+1); HRMS (FAB$^+$) m/z 490.2127 (490.2142 calcd for C$_{28}$H$_{28}$N$_3$O$_4$F+H$^+$).

Other compounds of the present invention may be prepared by those skilled in the art by varying the starting materials, reagent(s) and conditions used. Using the procedure of Example 2, the following compounds were prepared:

| Cpd | Name |
|---|---|
| 5 | 4-(4-benzyl-piperazin-1-yl)-2-(3,4-dimethoxy-benzyl)-isoindole-1,3-dione<br>Isolated as a yellow solid. $^1$H NMR (300 MHz, CDCl$_3$) δ 7.23-7.60 (ovdd, J = 7.4 Hz, 1 H), 7.39-7.50 (m, 6 H), 7.12 (d, J = 8.2 Hz, 1 H), 6.90-6.97 (m, 2 H), 6.37 (d, J = 8.7 Hz, 1 H), 4.72 (s, 2 H), 4.27 (s, 2 H), 3.87 (s, 3 H), 3.83 (s, 3 H), 3.66-3.77 (m, 4 H), 3.41-3.48 (m, 2 H), and 3.14-3.18 (m, 2 H); MS (ES$^+$) 472 (M + 1). |
| 6 | 2-(3,4-dimethoxy-benzyl)-4-[4-(1-phenyl-ethyl)-piperazin-1-yl]-isoindole-1,3-dione<br>Isolated as a yellow solid. $^1$H NMR (300 MHz, CDCl$_3$) δ 7.51 (ovdd, J = 7.2 Hz, 1H), 7.31-7.38 (m, 6 H), 7.08 (d, J = 8.2 Hz, 1 H), 6.96-7.00 (m, 2 H), 6.80 (d, J = 8.8 Hz, 1 H), 4.72 (s, 2 H), 3.86 (s, 3 H), 3.83 (s, 3 H), 3.44 (q, J = 6.6 Hz, 1 H), 3.30-3.33 (m, 4 H), 2.70-2.76 (m, 2 H), 2.60-2.65 (m, 2 H), and 1.41 (d, J = 6.7 Hz, 3 H); MS (ES$^+$) 486 (M + 1); Anal. Calcd for C$_{29}$H$_{31}$N$_3$O$_4$: C, 71.73; H, 6.43; N, 8.65. Found: C, 71.40; H, 6.45; N, 8.42. |
| 11 | 4-(4-benzyl-piperazin-1-yl)-2-(5,6-dimethoxy-indan-1-yl)-isoindole-1,3-dione<br>$^1$H NMR (300 MHz, CDCl$_3$) δ 7.62 (ovdd, J = 8.2 Hz, 1H), 7.50 (d, J = 7.2 Hz, 1 H), 7.28-7.34 (m, 1 H), 7.12-7.19 (m, 3 H), 6.91-6.98 (m, 2 H), 6.80 (d, J = 8.7 Hz, 1 H), 4.73 (s, 2 H), 4.34 (s, 2 H), 3.88 (s, 3 H), 3.84 (s, 3 H), and 3.13-3.75 (m, 8 H); MS (ES$^+$) 498.0 (M + 1). |
| 13 | 2-(3,4-dimethoxy-benzyl)-4-[4-(1-phenyl-propyl)-piperazin-1-yl]-isoindole-1,3-dione<br>$^1$H NMR (300 MHz, CDCl$_3$) δ 7.36-7.63 (m, 7 H), 7.11 (d, J = 8.2 Hz, 1 H), 6.82-7.02 (m, 2 H), 6.78 (d, J = 8.7 Hz, 1 H), 4.71 (s, 2 H), 4.10-4.17 (m, 1 H), 3.75-3.98 (m, 9 H), 3.38-3.62 (m, 3 H), 3.08-3.22 (m, 2 H), 2.21-2.31 (m, 2 H), and 0.81 (t, J = 7.1 Hz, 3 H); MS (ES$^+$) 500 (M + 1). |

-continued

| Cpd | Name |
|---|---|
| 17 | 2-(3,4-dimethoxy-benzyl)-4-[4-(3-fluoro-benzyl)-piperazin-1-yl]-isoindole-1,3-dione<br>Isolated as a yellow solid. MS (ES$^+$) 490 (M+1); HRMS (FAB$^+$) m/z 490.2129 (490.2142 calcd for $C_{28}H_{28}N_3O_4F$ + H$^+$). |
| 22 | 2-(3,4-dimethoxy-benzyl)-4-(4-phenethyl-piperazin-1-yl)-isoindole-1,3-dione<br>Isolated as a yellow solid. $^1$H NMR (300 MHz, CDCl$_3$) δ 7.63 (ovdd, J = 7.4 Hz, 1 H), 7.50 (d, J = 7.0 Hz, 1 H), 7.21-7.37 (m, 5 H), 7.13 (d, J = 8.2 Hz, 1 H), 6.96-6.98 (m, 2H), 6.79 (d, J = 8.7 Hz, 1 H), 4.74 (s, 2 H), 3.88 (s, 3 H), 3.84 (s, 3 H), 2.77-3.81 (m, 4 H), 3.46-3.52 (m, 2 H), 3.23-3.32 (m, 2 H), and 3.11-3.20 (m, 4 H); MS (ES$^+$) 486 (M + 1); Anal. Calcd for $C_{29}H_{31}N_3O_4$•1.2 CF$_3$CO$_2$H•0.1 H$_2$O: C, 60.42; H, 5.23; N, 6.73; F, 10.95; H$_2$O, 0.29. Found: C, 60.32; H, 5.25; N, 6.60; F, 10.55; H$_2$O, 0.31. |
| 24 | 4-[4-(2,4-difluoro-benzyl)-piperazin-1-yl]-2-(3,4-dimethoxy-benzyl)-isoindole-1,3-dione<br>Isolated as a yellow solid. $^1$H NMR (300 MHz, CDCl$_3$) δ 7.49-7.65 (m, 3 H), 7.13 (d, J = 8.0 Hz, 1 H), 6.92-7.04 (m, 4 H), 6.78-6.86 (m, 1 H), 4.73 (s, 2 H), 4.35 (s, 2 H), 3.87 (s, 3 H), 3.84 (s, 3 H), 3.60-3.81 (m, 4 H), and 3.24-3.46 (m, 4 H); MS (ES$^+$) 508 (M + 1). |
| 27 | 4-[4-(cyclopropyl-phenyl-methyl)-piperazin-1-yl]-2-(3,4-dimethoxy-benzyl)-isoindole-1,3-dione<br>$^1$H NMR (300 MHz, CDCl$_3$) δ 7.38-7.68 (m, 7 H), 7.12 (d, J = 8.2 Hz, 1 H), 6.87-7.05 (m, 2 H), 6.78 (d, J = 8.2 Hz, 1 H), 4.72 (s, 2 H), 4.16-4.20 (m, 1 H), 3.71-3.95 (m, 8 H), 3.33-3.62 (m, 2 H), 3.02-3.18 (m, 2 H), 2.48-2.54 (m, 2 H), 1.00-1.10 (m, 1 H), and 0.73-0.88 (m, 4 H); MS (ES$^+$) 512 (M + 1). |
| 28 | 2-(3,4-dimethoxy-benzyl)-4-[4-(1-methyl-1-phenyl-ethyl)-piperazin-1-yl]-isoindole-1,3-dione<br>Isolated as a yellow solid. $^1$H NMR (300 MHz, CDCl$_3$) δ 7.56-7.61(m, 2 H), 7.38-7.53 (m, 5 H), 7.04 (d, J = 8.2 Hz, 1 H), 6.85-6.87 (m, 2 H), 6.71 (d, J = 8.7 Hz, 1 H), 4.64 (s, 2 H), 3.80 (s, 3 H), 3.77 (s, 3 H), 3.42-3.63 (m, 6 H), 3.01-3.34 (m, 2 H), and 1.88 (s, 6 H); MS (ES$^+$) 500 (M + 1). |
| 29 | 4-[4-(2,5-difluoro-benzyl)-piperazin-1-yl]-2-(3,4-dimethoxy-benzyl)-isoindole-1,3-dione<br>$^1$H NMR (300 MHz, CDCl$_3$) δ 7.63 (dd, J = 8.1 Hz, J = 7.6 Hz, 1 H), 7.40-7.51 (m, 6 H), 7.15 (d, J = 8.2 Hz, 1 H), 6.81 (s, 1 H), 6.56 (s, 1 H), 5.76-5.81 (m, 1 H), 4.29 (s, 2 H), 3.88 (s, 3 H), 3.64-3.81 (m, 7 H), 3.16-3.45 (m, 5 H), 2.88-2.98 (m, 1 H), 2.48-2.60 (m, 1 H), and 2.34-2.45 (m, 1 H); MS (ES$^+$) 508.8 (M + 1). |
| 31 | 4-[4-(2-chloro-benzyl)-piperazin-1-yl]-2-(3,4-dimethoxy-benzyl)-isoindole-1,3-dione<br>Isolated as a yellow solid. MS (ES$^+$) 507 (M + 1); HRMS (FAB$^+$) m/z 528.1682 (528.1666 calcd for $C_{28}H_{28}N_3O_4Cl$ + Na$^+$). |
| 33 | 2-(3,4-dimethoxy-benzyl)-4-[4-(2-methyl-benzyl)-piperazin-1-yl]-isoindole-1,3-dione<br>Isolated as a yellow solid. MS (ES$^+$) 486 (M + 1); HRMS (FAB$^+$) m/z 486.2375 (486.2393 calcd for $C_{29}H_{31}N_3O_4$ + H$^+$). |
| 34 | 4-(4-benzyl-piperazin-1-yl)-2-(3,4,5-trimethoxy-benzyl)-isoindole-1,3-dione<br>Observed Parent Peak 502; MS calc'd 501.6 |
| 35 | 2-(3,4-dimethoxy-benzyl)-4-[4-(1-phenyl-prop-2-ynyl)-piperazin-1-yl]-isoindole-1,3-dione<br>$^1$H NMR (300 MHz, CDCl$_3$) δ 7.48-7.67 (m, 7 H), 7.12 (d, J = 8.1 Hz, 1 H), 6.96-7.00 (m, 2 H), 6.79 (d, J = 8.3 Hz, 1 H), 5.60 (s, 1 H), 4.74 (s, 2 H), 3.72-3.91 (m, 8 H), 3.34-3.68 (m, 4 H), and 3.00 (s, 1 H); MS (ES$^+$) 496 (M + 1). |
| 36 | 2-(3,4-dimethoxy-benzyl)-4-[4-(3-methyl-benzyl)-piperazin-1-yl]-isoindole-1,3-dione<br>Isolated as a yellow solid. MS (ES$^+$) 486 (M + 1); HRMS (FAB) m/z 486.2377 (486.2393 calcd for $C_{29}H_{31}N_3O_4$ + H$^+$). |
| 38 | 2-{4-[2-(3,4-dimethoxy-benzyl)-1,3-dioxo-2,3-dihydro-1H-isoindol-4-yl]-piperazin-1-ylmethyl}-benzonitrile<br>Isolated as a yellow solid. MS (ES$^+$) 497 (M + 1); HRMS (FAB$^+$) m/z 497.2181 (497.2189 calcd for $C_{29}H_{28}N_4O_4$ + H$^+$). |
| 40 | 2-(3,4-dimethoxy-benzyl)-4-[4-(4-methyl-benzyl)-piperazin-1-yl]-isoindole-1,3-dione<br>Isolated as a yellow solid. MS (ES$^+$) 486 (M + 1); HRMS (FAB$^+$) m/z 486.2378 (486.2393 calcd for $C_{29}H_{31}N_3O_4$ + H$^+$). |
| 43 | 4-(4-benzyl-piperazin-1-yl)-2-(2-pyridin-4-yl-ethyl)-isoindole-1,3-dione<br>Observed Parent Peak 427; MS calc'd 426.5 |
| 44 | 4-[4-(3-chloro-benzyl)-piperazin-1-yl]-2-(3,4-dimethoxy-benzyl)-isoindole-1,3-dione<br>Isolated as a yellow solid. MS (ES$^+$) 507 (M + 1); HRMS (FAB$^+$) m/z 506.1839 (506.1847 calcd for $C_{28}H_{28}N_3O_4Cl$ + H$^+$). |

| Cpd | Name |
|---|---|
| 46 | 4-[4-(3,5-difluoro-benzyl)-piperazin-1-yl]-2-(3,4-dimethoxy-benzyl)-isoindole-1,3-dione<br>Isolated as a yellow solid. $^1$H NMR (300 MHz, CDCl$_3$) δ 7.60-7.65 (ovdd, J = 7.4 Hz, 1 H), 7.50 (d, J = 7.1 Hz, 1 H), 7.13 (d, J = 8.2 Hz, 1 H), 6.92-7.04 (m, 5 H), 6.79 (d, J = 8.7 Hz, 1 H), 4.73 (s, 2 H), 4.28 (s, 2 H), 3.87 (s, 3 H), 3.84 (s, 3 H), 3.77-3.81 (m, 4 H), 3.45-3.51 (m, 2 H), and 3.16-3.22 (m, 2 H); MS (ES$^+$) 508 (M + 1). |
| 47 | 4-(4-benzyl-piperazin-1-yl)-2-(3-imidazol-1-yl-propyl)-isoindole-1,3-dione<br>Observed Parent Peak 430; MS calc'd 429.5 |
| 52 | 4-(4-isopropyl-piperazin-1-yl)-2-(3,4,5-trimethoxy-benzyl)-isoindole-1,3-dione<br>Observed Parent Peak 466; MS calc'd 453.5 |
| 55 | 4-(4-benzyl-piperazin-1-yl)-2-(1,5-dimethyl-1 H-pyrazol-4-ylmethyl)-isoindole-1,3-dione<br>Observed Parent Peak 430; MS calc'd 429.5 |
| 56 | 2-(3,4-dimethoxy-benzyl)-4-[4-(3,4-dimethoxy-benzyl)-piperazin-1-yl]-isoindole-1,3-dione<br>Observed Parent Peak 532; MS calc'd 531.6 |
| 57 | 4-[4-(4-chloro-benzyl)-piperazin-1-yl]-2-(3,4-dimethoxy-benzyl)-isoindole-1,3-dione<br>Isolated as a yellow solid. MS (ES$^+$) 507 (M + 1). |
| 58 | 4-(4-benzyl-piperazin-1-yl)-2-(2-methoxy-pyridin-4-ylmethyl)-isoindole-1,3-dione<br>$^1$H NMR (300 MHz, CDCl$_3$) δ 8.19 (d, J = 8.5 Hz, 1 H), 7.66 (dd, J = 8.2 Hz, J = 7.5 Hz, 1 H), 7.42-7.54 (m, 6 H), 7.17 (d, J = 8.2 Hz, 1 H), 6.92 (d, J = 5.6 Hz, 1 H), 6.74 (s, 1 H), 4.77 (s, 2 H), 4.29 (s, 2 H), 3.96 (s, 3 H), 3.69-3.77 (m, 4 H), 3.43-3.51 (m, 2 H), and 3.12-3.22 (m, 2 H); MS (ES$^+$) 443.0 (M + 1). |
| 60 | 4-(4-isobutyl-piperazin-1-yl)-2-(3,4,5-trimethoxy-benzyl)-isoindole-1,3-dione<br>Observed Parent Peak 467; MS calc'd 467.6 |

Example 3

4-(1-benzyl-1,2,3,6-tetrahydro-pyridin-4-yl)-2-(3,4-dimethoxy-benzyl)-isoindole-1,3-dione Cpd 19

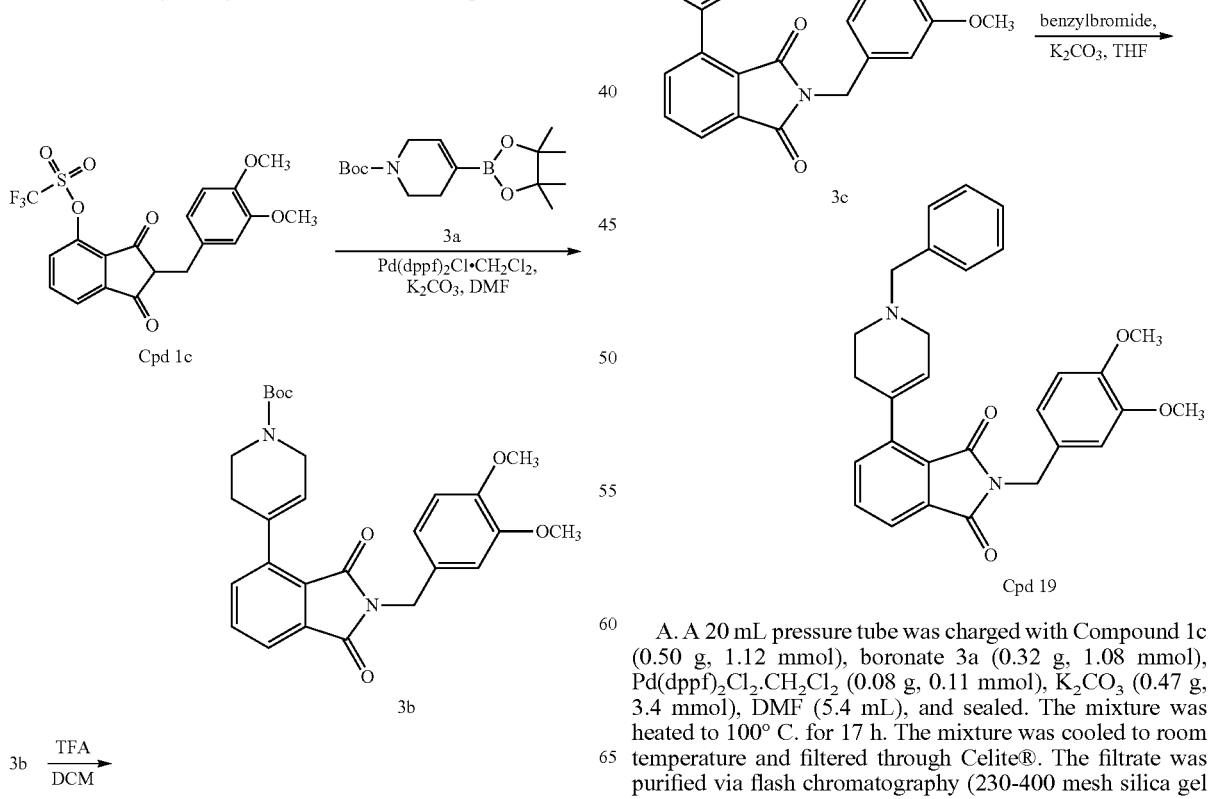

A. A 20 mL pressure tube was charged with Compound 1c (0.50 g, 1.12 mmol), boronate 3a (0.32 g, 1.08 mmol), Pd(dppf)$_2$Cl$_2$·CH$_2$Cl$_2$ (0.08 g, 0.11 mmol), K$_2$CO$_3$ (0.47 g, 3.4 mmol), DMF (5.4 mL), and sealed. The mixture was heated to 100° C. for 17 h. The mixture was cooled to room temperature and filtered through Celite®. The filtrate was purified via flash chromatography (230-400 mesh silica gel 60, 70:30 hexanes:EtOAc) to give 0.53 g (98%) of Compound 3b as a yellow solid. $^1$H NMR (300 MHz, CDCl$_3$) δ 7.76 (d, J=6.5 Hz, 1 H), 7.63 (ovdd, J=7.6 Hz, 1 H), 7.46 (d, J=6.8 Hz, 1 H), 6.99-7.01 (m, 2 H), 6.80 (d, J=8.7 Hz, 1 H), 5.85-5.99 (m, 1 H), 4.75 (s, 2 H), 4.09-4.14 (m, 2 H), 3.88 (s, 3 H), 3.84 (s, 3 H), 3.68-3.71 (m, 2 H), 2.54-2.62 (m, 2 H), and 1.51 (s, 9 H); MS (ES$^+$) 479 (M+1).

B. A 50 mL round bottom flask was charged with Compound 3b (0.53 g, 1.10 mmol) and DCM (4.4 mL). A portion of TFA (1.1 mL) was added and the mixture was stirred at room temperature for 1 h. The mixture was concentrated in vacuo and then dissolved in THF (5.6 mL). Benzyl bromide (0.15 mL, 1.26 mmol), and K$_2$CO$_3$ (0.49 g, 3.54 mmol) were added and the mixture was heated to reflux for 24 h. The crude oil was purified on a Gilson HPLC with a reversed phase Kromasil column (10μ, 100 Å C18, column length 250×50 mm, gradient 80:20-0:100 H$_2$O:MeCN) to give 250.0 mg (48%) of the title Compound 19 as a yellow solid. $^1$H NMR (300 MHz, CDCl$_3$) δ 7.77-7.88 (m, 2 H), 7.52-7.62 (m, 6 H), 7.00 (s, 1 H), 6.86-6.93 (m, 2 H), 5.84-5.91 (m, 1 H), 4.75 (s, 2 H), 4.55 (s, 2 H), 3.89.3.94 (m, 2 H), 3.79 (s, 3 H), 3.78 (s, 3 H), 3.29-3.32 (m, 2 H), and 2.75-2.95 (m, 2 H); MS (ES$^+$) 469 (M+1); Anal. Calcd for C$_{29}$H$_{28}$N$_2$O$_4$·1.4 CF$_3$CO$_2$H·0.4H$_2$O: C, 60.11; H, 4.79; N, 4.11; F, 12.56; H$_2$O, 1.13. Found: C, 59.97; H, 4.67; N, 4.33; F, 12.57; H$_2$O, 0.98.

Example 4

2-(3,4-dimethoxy-benzyl)-4-[4-(1S)-(1-phenyl-ethyl)-piperazin-1-yl]-isoindole-1.3 dione Cpd 14

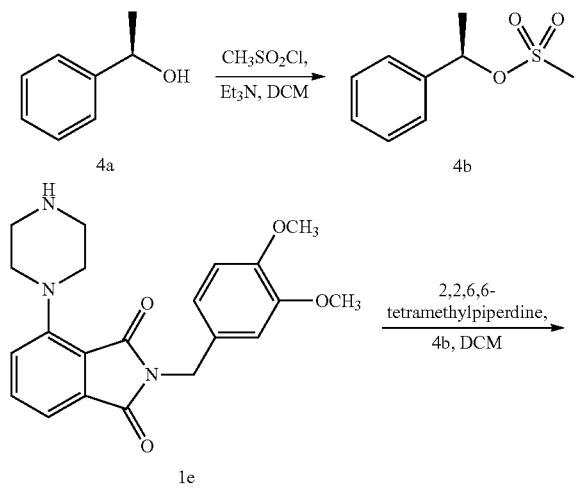

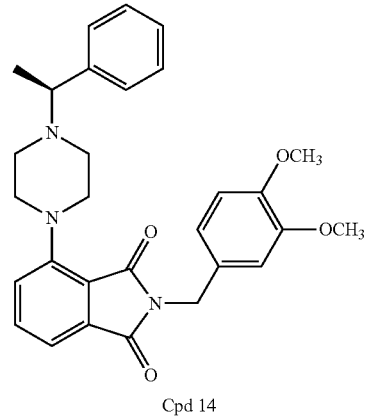 [SMILES: COc1ccc(CN2C(=O)c3cccc(N4CC5CCC(C4)N5Cc4ccccc4)c3C2=O)cc1OC]

Cpd 14

A. A 100 mL round bottom flask was charged with R-phenethylalcohol (0.87 g, 7.12 mmol) and DCM (36.0 mL). The mixture was cooled using an ice/water bath. Triethylamine (1.2 mL, 8.61 mmol) was added to the mixture followed by the dropwise addition methanesulfonyl chloride (0.61 mL, 7.88 mmol). The mixture was stirred for 1 h in the ice/water bath and then washed with 1N HCl (50 mL). The organic layer was dried using MgSO$_4$, and filtered through Celite®. Compound 1e (3.52 g, 7.11 mmol) and 2,2,6,6-tetramethylpiperidine (2.7 mL, 15.9 mmol) were added to the crude DCM solution. The mixture was refluxed for 24 h, cooled to room temperature and concentrated in vacuo. The crude oil was purified purified via flash chromatography (230-400 mesh silica gel 60, gradient 99:1-95:5 DCM:MeOH) to give 2.4 g (70%) of Compound 14 as a yellow solid. $^1$H NMR (300 MHz, CDCl$_3$) δ 7.52 (ovdd, J=7.2 Hz, 1 H), 7.26-7.37 (m, 6 H), 7.09 (d, J=8.4 Hz, 1 H), 6.95-7.00 (m, 2 H), 6.77 (d, J=8.7 Hz, 1 H), 4.72 (s, 2 H), 3.86 (s, 3 H), 3.83 (s, 3 H), 3.44 (q, J=6.6 Hz, 1 H), 3.30-3.39 (m, 4 H), 2.73-2.75 (m, 2 H), 2.62-2.65 (m, 2 H), and 1.42 (d, J=6.6 Hz, 3 H); MS (ES$^+$) 486 (M+1); (α)$_D$–18.3 (c 1.04, CHCl$_3$, 23° C.).

Other compounds of the present invention may be prepared by those skilled in the art by varying the starting materials, reagent(s) and conditions used. Using the procedure of Example 4, the following compounds were prepared:

| Cpd | Name |
|---|---|
| 1 | 2-(3,4-dimethoxy-benzyl)-4-[4-(1R)-(1-phenyl-ethyl)-piperazin-1-yl]-isoindole-1,3-dione<br>Isolated as a yellow solid. $^1$H NMR (300 MHz, CDCl$_3$) δ 7.53 (ovdd, J = 7.2 Hz, 1 H), 7.24-7.37 (m, 6 H), 7.09 (d, J = 8.2 Hz, 1 H), 6.97-7.00 (m, 2 H), 6.77 (d, J = 8.7 Hz, 1 H), 4.72 (s, 2 H), 3.86 (s, 3 H), 3.83 (s, 3 H), 3.46 (q, J = 6.6 Hz, 1 H), 3.28-3.38 (m, 4 H), 2.72-2.76 (m, 2 H), 2.60-2.66 (m, 2 H), and 1.42 (d, J = 6.6 Hz, 3 H); MS (ES$^+$) 486 (M + 1); (α)$_D$ + 18.6 (c 1.00, CHCl$_3$, 23° C.); Anal. Calcd for C$_{29}$H$_{31}$N$_3$O$_4$•1.2 HCl•0.6 H$_2$O: C, 64.49; H, 6.23; N, 7.78; Cl, 7.88; H$_2$O, 2.00. Found: C, 64.71; H, 5.97; N, 7.58; Cl, 8.04; H$_2$O, 2.20. |
| 30 | (S)-3-(3,4-dimethoxy-phenyl)-3-{1,3-dioxo-4-[4-(1R)-(1-phenyl-ethyl)-piperazin-1-yl]-1,3-dihydro-isoindol-2-yl}-propionic acid<br>$^1$H NMR (300 MHz, CDCl$_3$) δ 7.53 (dd, J = 8.3 Hz, J = 7.3 Hz, 1 H), 7.41-7.47 (m, 4 H), 7.35-7.39 (m, 2 H), 7.12 (d, J = 8.4 Hz, 1 H), 6.98-7.07 (m, 2 H), 6.78-6.81 (m, 1 H), 5.65-5.71 (m, 1 H), 4.30-4.37 (m, 1 H), 3.59-3.98 (m, 11 H), 2.96-3.22 (m, 4 H), and 1.78 (d, J = 7.0 Hz, 3 H); MS (ES$^+$) 544.2 (M + 1). |

Example 5

(3R,5S)-4-(4-benzyl-3,5-dimethyl-piperazin-1-yl)-2-(3,4-dimethoxy-benzyl)-isoindole-1,3-dione Cpd 42

Compound 42 was prepared by the methods described in Example 1 for the synthesis of Compound 16, substituting 2,6-dimethylpiperazine (26 mg) for 1-Boc-piperazine in Example 1, Step C; and substituting benzylbromide (0.05 mL) for 2,6-difluorobenzylbromide and $K_2CO_3$ (0.09 g) for DIEA in Example1, Step D. Compound 42 was isolated as a yellow solid. $^1$H NMR (300 MHz, CDCl$_3$) δ 7.51-7.87 (m, 7 H), 7.10 (d, J=8.2 Hz, 1 H), 6.91-6.94 (m, 2 H), 6.76 (d, J=8.2 Hz, 1H), 4.70 (s, 2 H), 4.62 (s, 2 H), 3.85 (s, 3 H), 3.83 (s, 3 H), 3.71-3.75 (m, 2 H), 3.43-3.52 (m, 4 H), and 1.71 (d, J=5.9 Hz, 6 H); MS (ES$^+$) 500 (M+1); Anal. Calcd for $C_{30}H_{33}N_3O_4 \cdot 1.67\ CF_3CO_2H \cdot 0.3H_2O$: C, 57.58; H, 5.11; N, 6.04; F, 13.69; $H_2O$, 0.78. Found: C, 57.24; H, 5.08; N, 6.27; F, 13.33; $H_2O$, 0.45.

Other compounds of the present invention may be prepared by those skilled in the art by varying the starting materials, reagent(s) and conditions used. Using the procedure of Example 5, the following compounds were prepared:

| Cpd | Name |
|-----|------|
| 37 | 4-(1R,2R)-(2-benzylamino-cyclohexylamino)-2-(3,4-dimethoxy-benzyl)-isoindole-1,3-dione<br>Isolated as a yellow solid. $^1$H NMR (300 MHz, CDCl$_3$) δ 7.38-7.43 (m, 1 H), 7.26-7.28 (m, 5 H), 6.94-7.01 (m, 3 H), 6.79-6.82 (m, 1 H), 6.17-6.21 (m, 1 H), 4.72 (s, 2 H), 3.88 (s, 2 H), 3.87 (s, 3 H), 3.84 (s, 3 H), 3.31-3.41 (m, 1 H), 2.48-2.55 (m, 1 H), 2.00-2.19 (m, 2 H), 1.64-1.76 (m, 2 H), and 1.18-1.38 (m, 4 H): MS (ES$^+$) 500 (M + 1). |
| 48 | 4-(2-benzylamino-ethylamino)-2-(3,4-dimethoxy-benzyl)-isoindole-1,3-dione<br>isolated as a yellow solid. $^1$H NMR (300 MHz, CDCl$_3$) δ 7.42-7.59 (m, 7 H), 6.88-7.14 (m, 4 H), 4.70 (s, 2 H), 4.26 (s, 2 H), 3.80 (s, 3 H), 3.79 (s, 3 H), 3.71-3.75 (m, 2 H), and 3.30-3.36 (m, 2 H); MS (ES$^+$) 446 (M + 1). |
| 51 | (3R,5S)-2-(3,4-dimethoxy-benzyl)-4-[3,5-dimethyl-4-(1-phenyl-ethyl)-piperazin-1-yl]-isoindole-1,3-dione<br>Isolated as a yellow solid.<br>$^1$H NMR (300 MHz, CD$_3$OD) δ 7.49-7.69 (m, 7 H), 6.96-7.18 (m, 3 H), 6.84-6.93 (m, 1 H), 4.72 (s, 2 H), 3.90-4.19 (m, 2 H), 3.72-3.87 (m, 7 H), 3.33-3.69 (m, 4 H), 1.94 (d, J = 7.3 Hz, 3 H), 1.63 (d, J = 6.6 Hz, 3 H), and 1.38 (d, J = 6.2 Hz, 3 H); MS (ES$^+$) 514 (M + 1). |

Example 6

4-(8-benzyl-8-aza-bicyclo[3.2.1]oct-2-en-3-yl)-2-(3,4-dimethoxy-benzyl)isoindole-1,3-dione Cpd 50

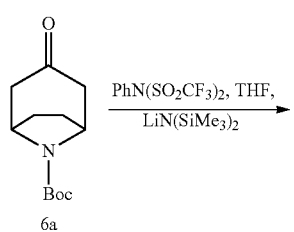

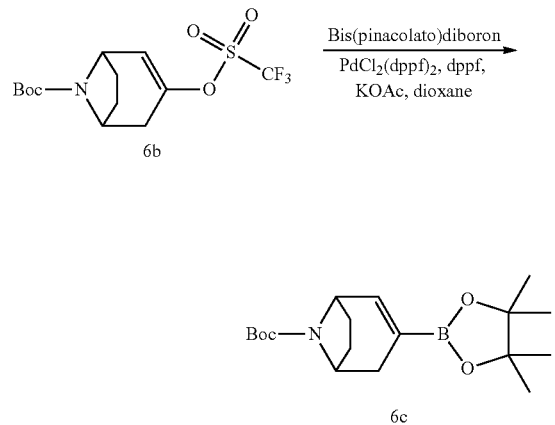

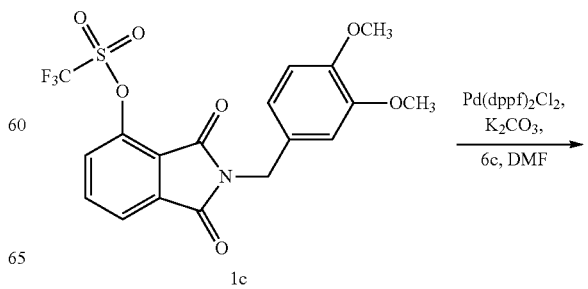

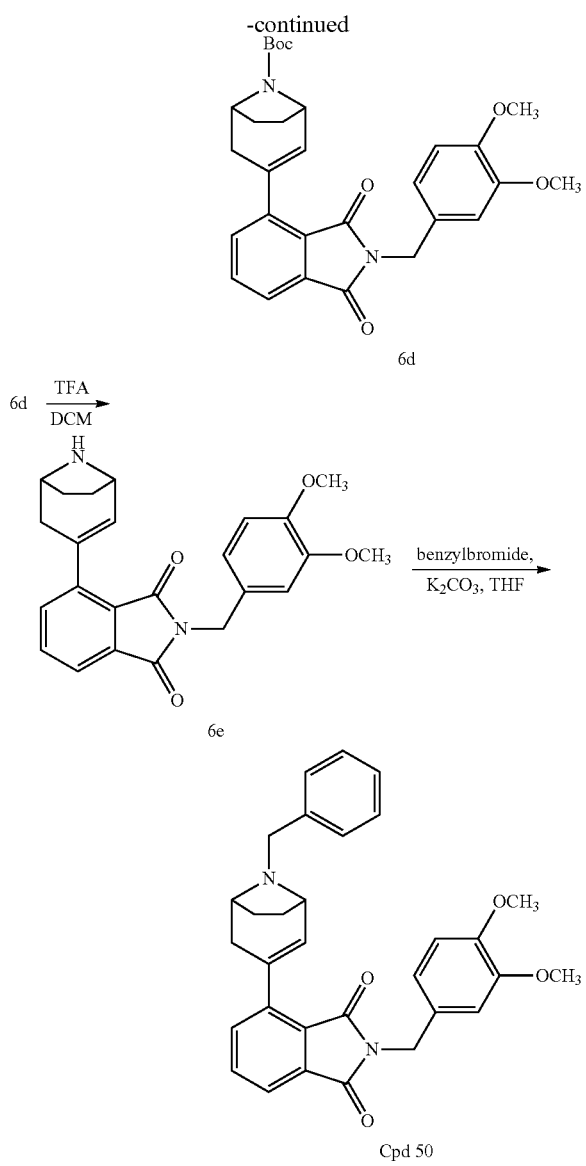

δ 6.76 (d, J=5.3 Hz, 1 H), 4.27-4.35 (m, 2 H), 2.80-2.90 (m, 1 H), 2.03-2.12 (m, 1 H), 1.88-1.94 (m, 4 H), 1.44 (s, 9 H), and 1.26 (s, 12 H).

C. A 20 mL sealed tube was charged with Compound 1c (0.10 g, 0.22 mmol), Cpd 6c (0.8 g, 0.24 mmol), Pd(dppf)$_2$Cl$_2$ (0.025 g, 0.03 mmol), K$_2$CO$_3$ (0.13 g, 0.94 mmol), and DMF (1.2 mL). The mixture was heated to 100° C. for 17 h. The mixture was cooled to room temperature and filtered through Celite®. The filtrate was purified via flash chromatography (230-400 mesh silica gel 60, 99:1 DCM:MeOH) to give 80.0 mg (71%) of Compound 6d as a yellow solid. $^1$H NMR (300 MHz, CDCl$_3$) δ 7.92 (d, J=7.4 Hz, 1 H), 7.73-7.81 (m, 2 H), 6.71-6.84 (m, 3 H), 6.08 (d, J=4.7 Hz, 1 H), 4.74 (s, 2 H), 4.12-4.20 (m, 1 H), 3.84 (s, 3 H), 3.81 (s, 3 H), 3.28-3.35 (m, 1 H), 2.30-2.38 (m, 2 H), 2.03-2.21 (m, 4 H), and 1.50 (s, 9 H).

D. A 50 mL round bottom flask was charged with Compound 6d (0.05 g, 0.099 mmol) and DCM (0.4 mL). A portion of TFA (0.1 mL) was added and the mixture was stirred at room temperature for 1 h. The mixture was concentrated in vacuo to give crude Compound 6e. Compound 6e was dissolved in THF (0.5 mL). Benzyl bromide (0.15 mL, 1.26 mmol) and K$_2$CO$_3$ (0.05 g, 3.54 mmol) were added and the mixture was heated to reflux for 24 h. The crude oil was purified on a Gilson HPLC with a reversed phase Kromasil column (10μ, 100 Å C18, column length 250×50 mm, gradient 80:20-0:100 H$_2$O:MeCN) to give the 35.8 mg (73%) of the title Compound 50 as a yellow solid. $^1$H NMR (300 MHz, CDCl$_3$) δ 7.48-7.86 (m, 8 H), 6.83-7.04 (m, 3 H), 6.02-6.07 (m, 1 H), 4.74 (s, 2 H), 3.78 (s, 3 H), 3.75 (s, 3 H), 3.72 (s, 2 H), 3.30-3.32 (m, 2 H), 2.88-3.03 (m, 1 H), and 2.23-2.64 (m, 5 H); MS (ES$^+$) 495 (M+1).

Example 7

4-[2-(benzyl-methyl-amino)-ethoxy]-2-(3,4-dimethoxy-benzyl)-isoindole-1,3-dione Cpd 53

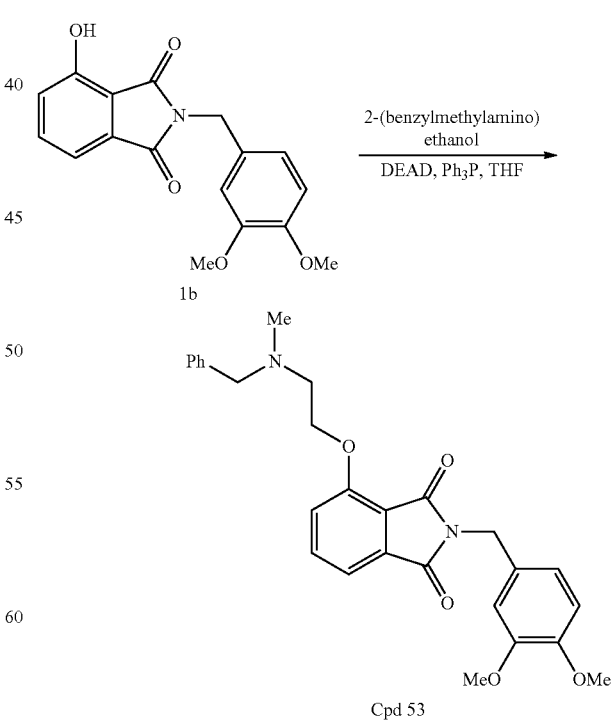

A. A 300 mL round bottom flask was charged with Compound 6a (1.0 g, 4.44 mmol) and THF (30 mL). The mixture was cooled to −78° C. using a dry ice/acetone bath. A 20% solution of LiN(SiMe$_3$)$_2$ in THF (5.0 mL, 5.32 mmol) was added dropwise over 15 min. The mixture was stirred at −78° C. for 40 min. A solution of PhN(SO$_2$CF$_3$)$_2$ (1.6 g, 4.48 mmol) in THF (33 mL) was added dropwise via addition funnel. The mixture was stirred for 18 h with gradual warming to room temperature. The mixture was concentrated in vacuo and purified via flash chromatography (230-400 mesh silica gel 60, 95:5 hexanes:EtOAc) to give 1.0 g (63%) of Compound 6b as a white solid. $^1$H NMR (300 MHz, CDCl$_3$) δ 6.08 (d, J=5.3 Hz, 1 H), 4.31-4.45 (m, 2 H), 3.04-3.21 (m, 2 H), 1.97-2.24 (m, 4 H), and 1.46 (s, 9 H).

B. A 200 mL round bottom flask was charged with Compound 6b (1.4 g, 3.92 mmol), Pd(dppf)$_2$Cl$_2$ (0.09 g, 0.12 mmol), K$_2$CO$_3$ (1.15 g, 11.7 mmol), and dioxane (23.0 mL). Bis(pinacolato)diboron (1.1 g, 4.33 mmol) was added and the mixture was heated to 80° C. for 20 h. The mixture was concentrated in-vacuo and purified via flash chromatography (230-400 mesh silica gel 60, DCM) to give 1.0 g (76%) of Compound 6c as a white solid. $^1$H NMR (300 MHz, CDCl$_3$)

A 40 mL round bottom flask was charged with Compound 1b (254 mg, 0.812 mmol), 2-(benzylmethylamino)ethanol (126 µL, 0.812 mmol), PPh$_3$ (231 mg, 0.881 mmol), and THF (4.0 mL). The mixture was cooled using an ice/water bath and DEAD (138 µL, 0.877 mmol) was added dropwise via addition funnel as a solution in THF (3.0 mL) over 20 min. The mixture was stirred at room temperature for 48 h, concentrated in vacuo, and dissolved in EtOAc (25 mL). The solution was washed with 1 N NaOH (2×50 mL) and brine (50 mL). The organic layer was dried using Na$_2$SO$_4$, filtered through Celite®, and concentrated in vacuo. The crude oil was purified on a Gilson HPLC with a reversed phase Kromasil column (10µ, 100 Å C18, column length 250×50 mm, gradient 80:20-0:100 H$_2$O:MeCN) to give 52.3 mg (14%) of Compound 53 as a glass-like oil. $^1$H NMR (300 MHz, CDCl$_3$) δ 7.61 (t, J=7.0 Hz, 1 H), 7.38-7.46 (m, 6 H), 7.13 (d, J=9.0 Hz, 1 H), 6.88-6.91 (m, 2 H), 6.71 (d, J=7.0 Hz, 1 H), 4.65 (s, 2 H), 4.65 (bs, 2 H), 4.10-4.55 (m, 4 H), 3.76 (s, 6 H), 2.90 (s, 3 H); MS (ES$^+$) 461 (M+1).

Example 8

4-(2-benzylamino-ethoxy)-2-(3,4-dimethoxy-benzyl)-isoindole-1,3-dione Cpd 54

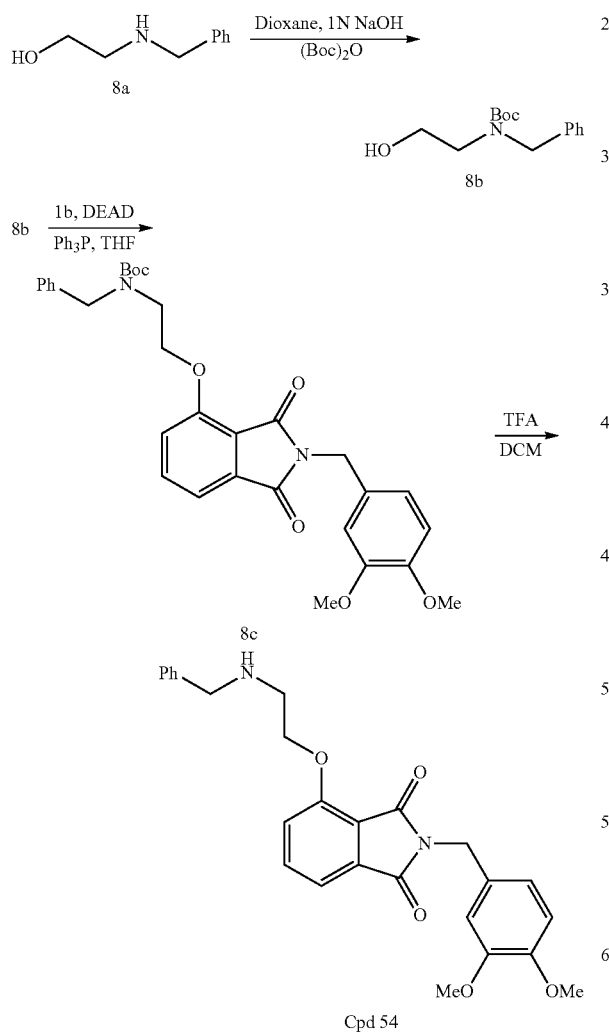

A. A 50 mL round bottom was charge with 2-benzylamino-ethanol 8a (284 mg, 1.85 mmol), dioxane (4.0 mL), and 1 N NaOH (4.0 mL); and cooled with an ice/water bath. A portion of di-tert-butyl dicarbonate (500 mg, 2.29 mmol) was added to the mixture, which was stirred for 18 h at room temperature. The pH was adjusted to 4 with 1 N HCl and extract with DCM (3×50 mL). The organic layer was dried using Na$_2$SO$_4$, filtered through Celite®, and concentrated in vacuo to give 330 mg (70%) of Compound 8b as a clear glass-like oil. $^1$H NMR (300 MHz, CDCl$_3$) δ 7.24-7.33 (m, 5 H), 4.48 (bs, 2 H), 3.56-3.74 (bs, 2 H), 3.29-3.44 (bs, 2 H), 1.42 (s, 9 H).

B. Compound 8c was prepared using the methods described in Example 8 for the preparation of Compound 53, substituting Compound 8b (330 mg) for 2-(benzylmethylamino)ethanol. Compound 8c was isolated as a clear glass-like oil. $^1$H NMR (300 MHz, CDCl$_3$) 7.64 (t, J=7.0 Hz, 1 H), 7.01-7.33 (m, 9 H), 6.79 (d, J=9.0 Hz, 1 H), 4.76 (s, 2 H), 4.75 (s, 2 H), 4.22-4.30 (m, 2 H), 3.87 (s, 3 H), 3.84 (s, 3 H), 3.58-3.65 (m, 2 H), 1.46 (s, 9 H).

C. A 50 mL round bottom was charged with Compound 8c (50 mg, 0.09 mmol) and DCM (4.8 mL). A portion of TFA (1.2 mL) was added and the mixture was stirred for 30 min and concentrated in vacuo to give 48.1 mg (98%) of Compound 54 as a clear oil. $^1$H NMR (300 MHz, CDCl$_3$) δ 7.56 (t, J=7.0 Hz, 1H), 7.19-7.43 (m, 6 H), 7.07 (d, J=9.0 Hz, 1 H), 6.86-6.87 (m, 2 H), 6.70 (d, J=9.0 Hz, 1 H), 4.63 (s, 2 H), 4.13-4.36 (bs, 4 H), 3.76 (s, 3 H), 3.76 (s, 3 H), 2.82-3.35 (bs, 2 H); MS (ES$^+$) 447 (M+1).

Example 9

4-(8-benzyl-3,8-diaza-bicyclo[3.2.1]oct-3-yl)-2-(3,4-dimethoxy-benzyl)-isoindole-1,3-dione Cpd 7

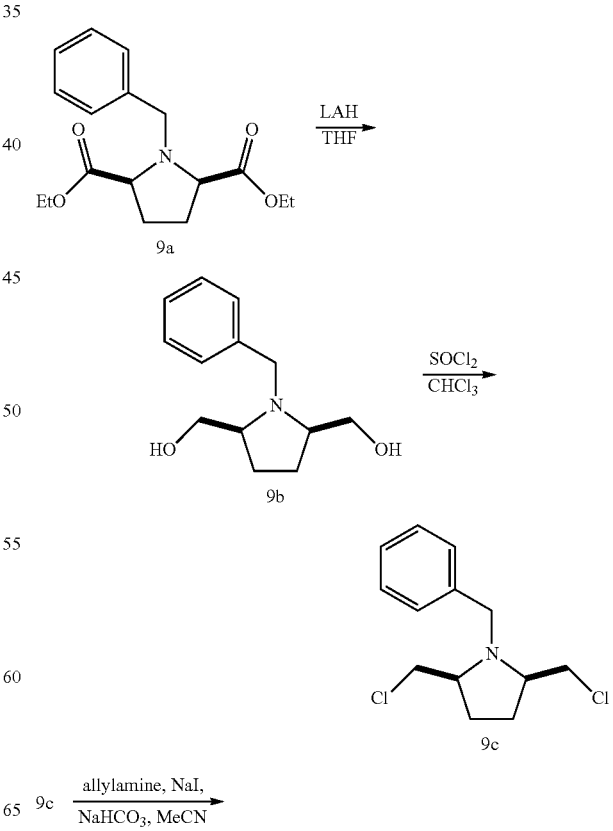

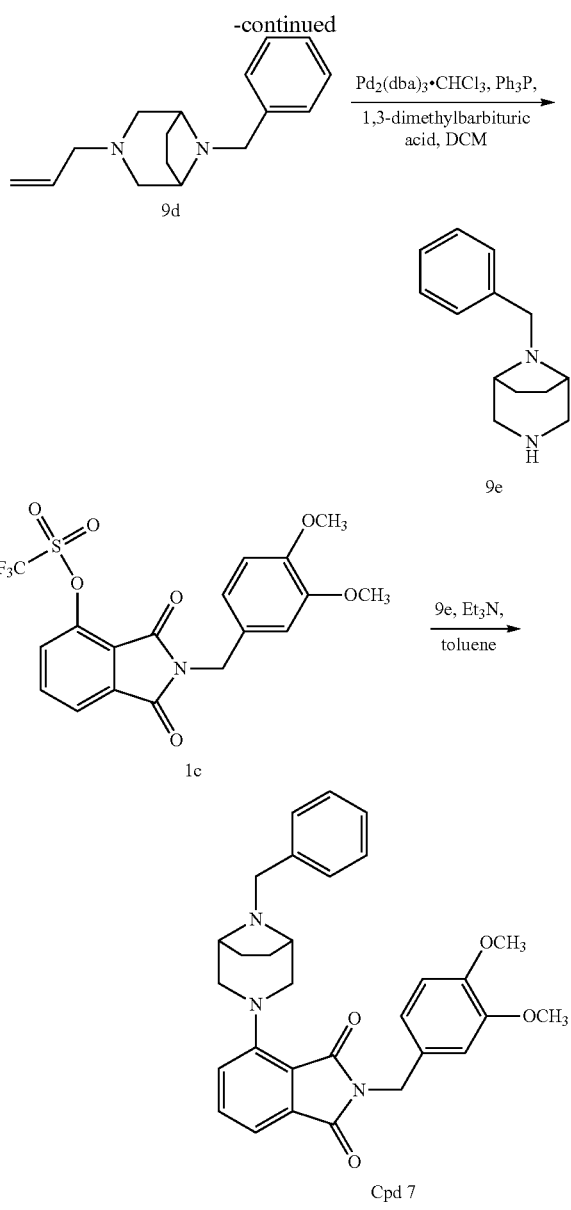

mmol), NaI (6.1 g, 40.7 mmol), and NaHCO$_3$ (13.5 g, 160.7 mmol) were added and the mixture was heated to reflux for 5 h. The mixture was cooled to room temperature, diluted with EtOAc (400 mL), and washed with 1N NaOH (300 mL). The organic layer was dried using MgSO$_4$, filtered through Celite®, and concentrated in vacuo. The crude oil was purified via flash chromatography (230-400 mesh silica gel 60, gradient 98:2-95:5 DCM:MeOH) to yield 1.53 g (39%) of Compound 9d as a white solid. MS (ES$^+$) 243 (M+1).

C. A 250 mL round bottom flask was charged with Compound 9d (1.53 g, 6.32 mmol) and DCM (32 mL). A portion of Pd$_2$(dba)$_3$·CHCl$_3$ (0.65 g, 0.63 mmol), Ph$_3$P (0.66 g, 2.51 mmol), and 1,3-dimethylbarbituric acid (1.48 g, 9.48 mmol) were added and the mixture refluxed for 3 h. The mixture was cooled to room temperature and extracted with 1N HCl (200 mL). The aqueous layer was basified with 3N NaOH and extracted with EtOAc (300 mL). The organic layer was dried using MgSO$_4$, filtered through Celite®, and concentrated in vacuo to give 1.22 g (96%) of Compound 9e as a white solid. $^1$H NMR (300 MHz, CDCl$_3$) δ 7.23-7.40 (m, 5 H), 3.48 (s, 2 H), 2.99-3.06 (m, 3 H), 2.57-2.62 (m, 2 H), 2.00-2.09 (m, 4 H), and 1.72-1.77 (m, 2 H): MS (ES$^+$) 203 (M+1).

D. A 20 mL pressure tube was charged with Compound 1c (0.20 g, 0.45 mmol), Compound 9e (0.1 g, 0.50 mmol), Et$_3$N (0.15 mL, 1.08 mmol), toluene (0.45 mL), and sealed. The mixture was heated to 110° C. for 72 h. The mixture was cooled to room temperature and purified via flash chromatography (230-400 mesh silica gel 60, DCM) to give 179.4 mg (80%) of Compound 7 as a yellow solid. $^1$H NMR (300 MHz, CDCl$_3$) δ 7.40-7.51 (m, 7 H), 6.98-7.06 (m, 3 H), 6.77-6.80 (m, 1 H), 4.73 (s, 2 H), 3.87 (s, 3 H), 3.83 (s, 3 H), 3.58-3.64 (m, 4 H), 3.29 (bs, 2 H), 3.12-3.16 (m, 2 H), and 2.06-2.15 (m, 4 H); MS (ES$^+$) 498 (M+1).

Example 10

2-(3,4-dimethoxy-benzyl)-4-[8-(1-phenyl-ethyl)-3,8-diaza-bicyclo[3.2.1]oct-3-yl]-isoindole-1,3-dione
Cpd 32

Compound 7 (50 mg, 0.10 mmol) was hydrogenated (50 psi H$_2$) with 10% Pd/C (5 mg) in EtOAc (1.0 mL) for 5 h. The mixture was filtered through Celite®, and concentrated in vacuo. The crude oil was dissolved in THF (0.4 mL). A portion of 1-bromoethylbenzene (0.03 mL, 0.22 mmol) and K$_2$CO$_3$ (36 mg, 0.26 mmol) were added. The mixture was heated to 50° C. for 4 h. The mixture was cooled to room temperature, filtered through Celite®, and concentrated in vacuo. The crude oil was purified on a Gilson HPLC with a reversed phase Kromasil column (10μ, 100 Å C18, column length 250×50 mm, gradient 90:10-0:100 H$_2$O:MeCN) to give the 19.7 mg (38%) of the title Compound 32 as a yellow solid. $^1$H NMR (300 MHz, CDCl$_3$) δ 7.71 (ovdd, J=7.6 Hz, 1 H), 7.49-7.60 (m, 6 H), 7.30 (d, J=8.2 Hz, 1 H), 6.94-7.00 (m, 1 H), 6.86-6.91 (m, 2 H), 4.73 (s, 2 H), 4.00-4.11 (m, 1 H), 3.81 (s, 3 H), 3.80 (s, 3 H), 3.43-3.60 (m, 4 H), 2.67-2.75 (m, 2 H), 2.43-2.51 (m, 2 H), 2.17-2.25 (m, 2 H), and 1.82 (d, J=6.7 Hz, 3 H); MS (ES$^+$) 512.

A. A 300 mL round bottom flask was charged with Compound 9a (7.1 g, 23.3 mmol) and THF (24 mL). The mixture was cooled to −78° C. using a dry ice/acetone bath. A 1.0M THF solution of LAH (100 mL, 100 mmol) was added dropwise via addition funnel. The mixture was stirred at −78° C. for 1 h. The dry ice/acetone bath was removed and the mixture stirred at room temperature for 4 h. The mixture was then cooled using an ice/water bath and the reaction was quenched by adding water slowly until all hydrogen evolution ceased. The mixture was diluted with DCM (500 mL) and washed water (300 mL). The organic layer was dried using MgSO$_4$, filtered through Celite®, and concentrated in vacuo to give 3.59 g (70%) of Compound 9b as a white solid. MS (ES$^+$) 222 (M+1).

B. A 500 mL round bottom flask was charged with Compound 9b (3.59 g, 23.3 mmol) and CHCl$_3$ (160 mL). A portion of thionyl chloride (6.0 mL, 82.2 mmol) was added and the mixture was heated to reflux for 18 h. The mixture was concentrated in vacuo to give crude Compound 9c. Compound 9c was dissolved in MeCN (230 mL). Allylamine (1.2 mL, 16.0

Example 11

2-(3,4-dimethoxy-benzyl)-4-(4-indan-1-yl-piperazin-1-yl)-isoindole-1,3-dione Cpd 20

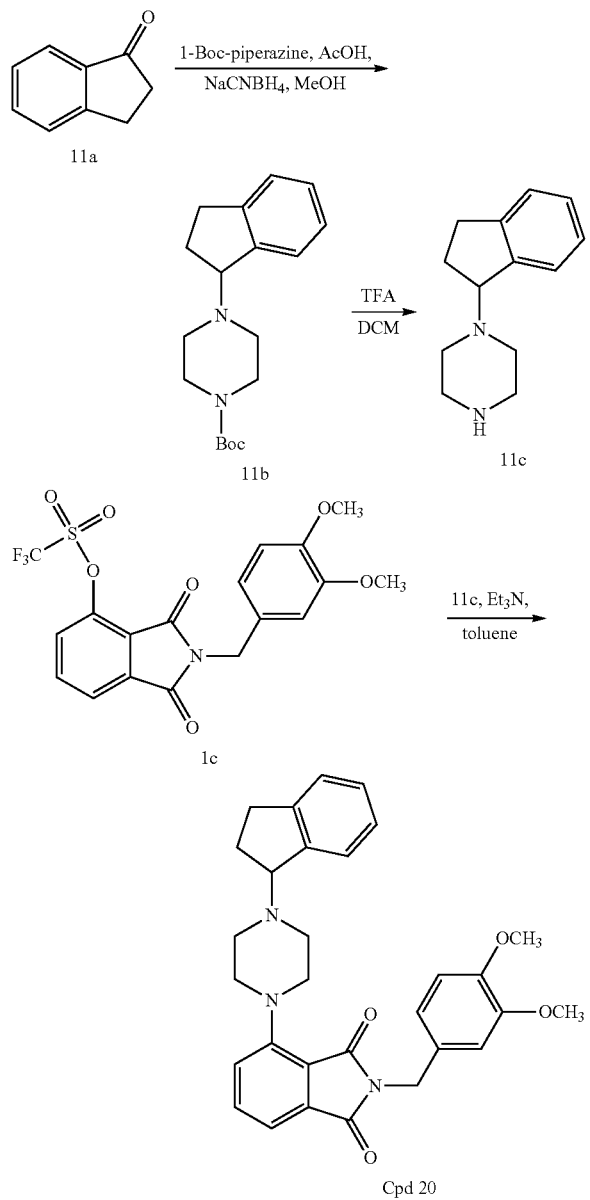 [SMILES: O=C1CCc2ccccc21 ; CC(C)(C)OC(=O)N1CCN(C2CCc3ccccc32)CC1 ; c1ccc2c(c1)CCC2N1CCNCC1 ; COc1ccc(CN2C(=O)c3cccc(OS(=O)(=O)C(F)(F)F)c3C2=O)cc1OC ; COc1ccc(CN2C(=O)c3cccc(N4CCN(C5CCc6ccccc65)CC4)c3C2=O)cc1OC]

A. A 500 mL round bottom flask was charged with N-Boc-piperazine (4.25 g, 22.8 mmol), Compound 11a (1.04 g, 7.87 mmol), and MeOH (140 mL). Acetic acid (1.8 mL, 31.4 mmol) and NaCNBH$_4$ (0.72 g, 11.5 mmol) were added and the mixture refluxed for 20 h. The mixture was cooled to room temperature, diluted with DCM (300 mL), and washed with H$_2$O (100 mL). The organic layer was dried using MgSO$_4$, filtered through Celite®, and concentrated in vacuo to give 1.68 g (73%) of Compound 11b as a white solid. $^1$H NMR (300 MHz, CDCl$_3$) δ 7.76-7.88 (m, 1 H), 7.56-7.68 (m, 1 H), 7.37-7.47 (m, 1 H), 7.16-7.26 (m, 1 H), 4.31-4.45 (m, 1 H), 3.41-3.52 (m, 4 H), 3.17-3.21 (m, 2 H), 2.69-3.01 (m, 2 H), 2.39-2.57 (m, 2 H), 2.08-2.13 (m, 2 H), and 1.48 (s, 9 H); MS (ES$^+$) 303 (M+1).

B. A 50 mL round bottom flask was charged with Compound 11b (1.68 g, 5.56 mmol) and DCM (24.0 mL). Upon addition of TFA (6.0 mL), the mixture was stirred at room temperature for 1 h and concentrated in vacuo to afford a crude mixture of Compound 11c. A 20 mL pressure tube was charged with Compound 1c (0.10 g, 0.22 mmol), crude Compound 11c (78 mg, 0.25 mmol), Et$_3$N (0.08 mL, 0.57 mmol), and toluene (0.22 mL), and sealed. After the mixture was heated to 110° C. for 20 h, it was cooled to room temperature and concentrated in vacuo. The crude oil was purified on a Gilson HPLC with a reversed phase Kromasil column (10μ, 100 Å C18, column length 250×50 mm, gradient 90:10-0:100 H$_2$O:MeCN) to give 17.9 mg (15%) of the title Compound 20 as a yellow solid. $^1$H NMR (300 MHz, CDCl$_3$) δ 7.62 (ovdd, J=7.2 Hz, 1 H), 7.20-7.43 (m, 6 H), 6.85-6.99 (m, 3 H), 4.70 (s, 2 H), 4.38-4.40 (m, 1 H), 3.80 (s, 3 H), 3.78 (s, 3 H), 3.29-3.37 (m, 4 H), 2.64-2.94 (m, 6 H), and 2.15-2.24 (m, 2 H); MS (ES$^+$) 498 (M+1).

Example 12

4-(8-benzyl-3,8-diaza-bicyclo[3.2.1]oct-3-yl)-2-pyridin-2-ylmethyl-isoindole-1,3-dione Cpd 59

Compound 59 was prepared by the methods described in Example 1 for the synthesis of Compound 16, substituting 2-(aminomethyl)pyridine (0.07 mL) for veratrylamine in Example 1, Step A, and substituting Compound 9e (120.0 mg) for N-Boc-piperazine in Example 1, Step C. Compound 59 was isolated as a yellow solid. $^1$H NMR (300 MHz, CDCl$_3$) δ 8.76 (d, J=4.7 Hz, 1 H), 8.05 (ovdd, J=6.6 Hz, 1 H), 7.28-7.65 (m, 9 H), 7.15 (d, J=8.2 Hz, 1 H), 5.13 (s, 2 H), 4.21 (s, 2 H), 3.88-4.04 (m, 2 H), 3.64-3.74 (m, 4 H), 2.62-2.65 (m, 2 H), and 2.25-2.29 (m, 2 H); MS (ES$^+$) 439 (M+1); Anal. Calcd for C$_{27}$H$_{26}$N$_4$O$_2$.2.1 CF$_3$CO$_2$H.0.4H$_2$O: C, 54.69; H, 4.25; N, 8.18; F, 17.47; H$_2$O, 1.05. Found: C, 54.47; H, 4.31; N, 8.09; F, 17.27; H$_2$O, 0.85.

Other compounds of the present invention may be prepared by those skilled in the art by varying the starting materials, reagent(s) and conditions used. Using the procedure of Example 12, the following compounds were prepared:

| Cpd | Name |
|---|---|
| 25 | 4-(8-benzyl-3,8-diaza-bicyclo[3.2.1]oct-3-yl)-2-[2-(3,4-dimethoxy-phenyl)-ethyl]-isoindole-1,3-dione Isolated as a yellow solid. $^1$H NMR (300 MHz, CDCl$_3$) δ 7.28-7.61 (m, 7 H), 7.07 (d, J = 8.2 Hz, 1 H), 6.77-6.81 (m, 3 H), 3.85-3.89 (m, 2 H), 3.84 (s, 3 H), 3.83 (s, 3 H), 3.61 (s, 2 H), 3.54-3.58 (m, 2 H), 3.21-3.31 (m, 2 H), 3.09-3.18 (m, 2 H), 2.89-2.98 (m, 2 H), and 2.07-2.19 (m, 4 H); MS (ES$^+$) 512 (M + 1). |

-continued

| Cpd | Name |
|---|---|
| 26 | 4-(8-benzyl-3,8-diaza-bicyclo[3.2.1]oct-3-yl)-2-(3,4,5-trimethoxy-benzyl)-isoindole-1,3-dione<br>Isolated as a yellow solid. $^1$H NMR (300 MHz, CDCl$_3$) δ 7.62 (ovdd, J = 7.6 Hz, 1 H), 7.46-7.51 (m, 6 H), 7.11 (d, J = 8.2 Hz, 1 H), 6.62-6.69 (m, 2 H), 4.70 (s, 2 H), 4.20-4.23 (m, 2 H), 4.01-4.04 (m, 2 H), 3.84 (s, 6 H), 3.81 (s, 3 H), 3.72-3.77 (m, 2 H), 3.61-3.65 (m, 2 H), 2.68-2.72 (m, 2 H), and 2.29-2.33 (m, 2 H); MS (ES$^+$) 528 (M + 1). |
| 39 | 4-(8-benzyl-3,8-diaza-bicyclo[3.2.1]oct-3-yl)-2-pyridin-4-ylmethyl-isoindole-1,3-dione<br>Isolated as a yellow solid. $^1$H NMR (300 MHz, CDCl$_3$) δ 8.79 (d, J = 6.4 Hz, 2 H), 7.76 (d, J = 6.0 Hz, 2 H), 7.69 (ovdd, J = 8.0 Hz, 1 H), 7.40-7.55 (m, 7 H), 4.97 (s, 2 H), 3.70 (s, 2 H), 3.42-3.55 (m, 4 H), 2.61-2.70 (m, 2 H), and 2.28-2.39 (m, 4 H); MS (ES$^+$) 439 (M + 1). |
| 45 | 4-(8-benzyl-3,8-diaza-bicyclo[3.2.1]oct-3-yl)-2-(3,5-dimethoxy-benzyl)-isoindole-1,3-dione<br>Isolated as a yellow solid. $^1$H NMR (300 MHz, CDCl$_3$) δ 7.60 (ovdd, J = 7.6 Hz, 1 H), 7.45-7.50 (m, 6 H), 7.10 (d, J = 8.2 Hz, 1 H), 6.51-6.53 (m, 2 H), 6.34-6.36 (m, 1 H), 4.72 (s, 2 H), 4.20-4.26 (m, 2 H), 4.01-4.06 (m, 2 H), 3.76-3.88 (m, 8 H), 3.57-3.72 (m, 2 H), 2.69-2.73 (m, 2 H), and 2.28-2.32 (m, 2 H); MS (ES$^+$) 498 (M + 1). |
| 61 | 4-(8-benzyl-3,8-diaza-bicyclo[3.2.1]oct-3-yl)-2-(3,4-dimethoxy-phenyl)-isoindole-1,3-dione<br>Isolated as a yellow solid. $^1$H NMR (300 MHz, CDCl$_3$) δ 7.71 (ovdd, J = 7.6 Hz, 1 H), 7.61(d, J = 7.2 Hz, 1 H), 7.47-7.57 (m, 6 H), 7.21 (d, J = 8.2 Hz, 1 H), 6.94-7.01 (m, 2 H), 4.23 (s, 2 H), 3.99-4.07 (m, 2 H), 3.94 (s, 3 H), 3.91 (s, 3 H), 3.79-3.83 (m, 2 H), 3.65-3.69 (m, 2 H), 2.73-2.76 (m, 2 H), and 2.29-2.32 (m, 2 H); MS (ES$^+$) 484 (M + 1). |

Example 13

2-(4-ethoxy-3-methoxy-benzyl)-4-[4-(1R)-(1-phenyl-ethyl)-piperazin-1-yl]-isoindole-1,3-dione Cpd 18

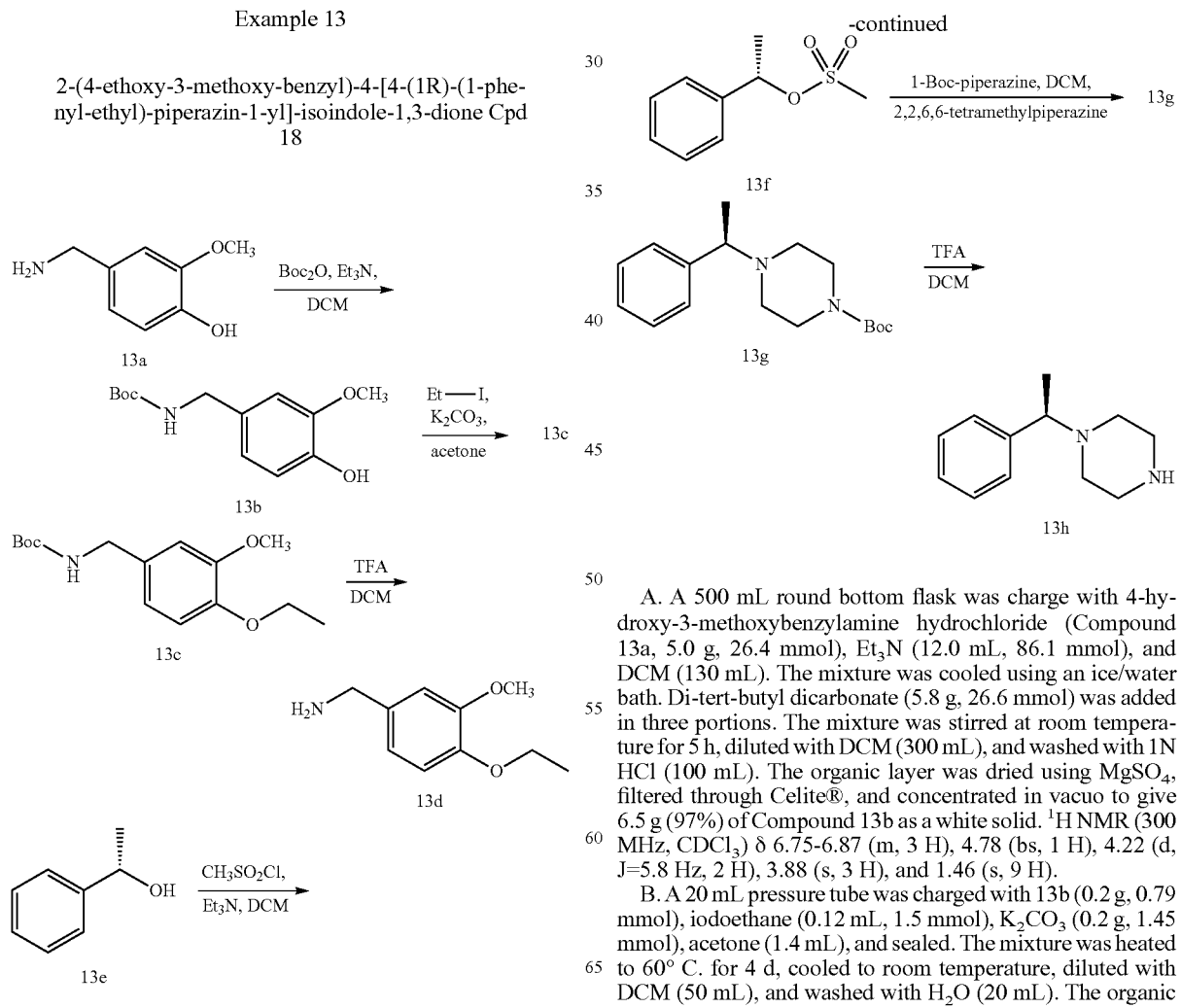

A. A 500 mL round bottom flask was charge with 4-hydroxy-3-methoxybenzylamine hydrochloride (Compound 13a, 5.0 g, 26.4 mmol), Et$_3$N (12.0 mL, 86.1 mmol), and DCM (130 mL). The mixture was cooled using an ice/water bath. Di-tert-butyl dicarbonate (5.8 g, 26.6 mmol) was added in three portions. The mixture was stirred at room temperature for 5 h, diluted with DCM (300 mL), and washed with 1N HCl (100 mL). The organic layer was dried using MgSO$_4$, filtered through Celite®, and concentrated in vacuo to give 6.5 g (97%) of Compound 13b as a white solid. $^1$H NMR (300 MHz, CDCl$_3$) δ 6.75-6.87 (m, 3 H), 4.78 (bs, 1 H), 4.22 (d, J=5.8 Hz, 2 H), 3.88 (s, 3 H), and 1.46 (s, 9 H).

B. A 20 mL pressure tube was charged with 13b (0.2 g, 0.79 mmol), iodoethane (0.12 mL, 1.5 mmol), K$_2$CO$_3$ (0.2 g, 1.45 mmol), acetone (1.4 mL), and sealed. The mixture was heated to 60° C. for 4 d, cooled to room temperature, diluted with DCM (50 mL), and washed with H$_2$O (20 mL). The organic layer was dried using MgSO$_4$, filtered through Celite®, and concentrated in vacuo to give 0.22 g (98%) of Compound 13c as a white solid. $^1$H NMR (300 MHz, CDCl$_3$) δ 6.79-6.82 (m, 3 H), 4.23 (d, J=5.8 Hz, 2 H), 4.23 (q, J=7.0 Hz, 2 H), 3.85 (s, 3 H), and 1.42-1.47 (m, 12 H).

C. A 50 mL round bottom flask was charged with Compound 13c (0.22 g, 0.79 mmol) and DCM (3.2 mL). TFA (0.8 mL) was added and the mixture was stirred at room temperature for 1 h. The mixture was concentrated in vacuo to give 0.23 g (99%) of Compound 13d as a white solid. $^1$H NMR (300 MHz, CDCl$_3$) δ 6.86-6.90 (m, 3 H), 4.05-4.15 (m, 4 H), 3.83 (s, 3 H), and 1.44 (t, J=7.0 Hz, 3 H).

D. A 100 mL round bottom flask was charged with S-phenethylalcohol (Compound 13e, 5.0 mL, 41.3 mmol) and DCM (210 mL). The mixture was cooled using an ice/water bath. Triethylamine (7.0 mL, 50.2 mmol) was added to the mixture followed by the dropwise addition methanesulfonyl chloride (3.6 mL, 46.5 mmol). The mixture was stirred for 4 h in the ice/water bath and then washed with 1N HCl (50 mL). The organic layer was dried with MgSO$_4$ and filtered through Celite® to give Compound 13f. A portion of 1-Boc-piperazine (7.70 g, 41.3 mmol) and 2,2,6,6-tetramethylpiperidine (15.4 mL, 90.7 mmol) were added to the crude DCM solution of Compound 13f. The mixture was refluxed for 24 h, cooled to room temperature, and concentrated in vacuo. The crude oil was purified via flash chromatography (230-400 mesh silica gel 60, gradient 100:0-90:10 DCM:MeOH) to give 8.92 g (74%) of Compound 13g as a white solid. $^1$H NMR (300 MHz, CDCl$_3$) δ 7.29-7.32 (m, 5 H), 3.34-3.41 (m, 5 H), 2.29-2.44 (m, 4 H), 1.43 (s, 9 H), and 1.36 (d, J=6.7 Hz, 3 H).

E. A 50 mL round bottom flask was charged with Compound 13g (8.92 g, 30.8 mmol) and DCM (120 mL). A portion of TFA (30 mL) was added and the mixture was stirred at room temperature for 1 h. The mixture was concentrated in vacuo. The crude oil was dissolved in DCM (400 mL) and washed with 1N NaOH (200 mL). The organic layer was dried using MgSO$_4$, filtered through Celite®, and concentrated in vacuo to give Compound 13h as a white solid. $^1$H NMR (300 MHz, CDCl$_3$) δ 7.36-7.40 (m, 5 H), 4.98 (q, J=6.8 Hz, 1 H), 3.45-3.48 (m, 4 H), 3.24-3.33 (m, 2 H), 3.09-3.13 (m, 2 H), and 1.64 (d, J=6.7 Hz, 3 H).

F. Compound 18 was prepared by the methods described in Example 1 for the synthesis of Compound 1, substituting Compound 13d (233 mg) for veratrylamine in Example 1, Step A, and substituting Compound 13h (200 mg) for N-Boc-piperazine in Example 1, Step C. Compound 18 was isolated as a yellow solid. $^1$H NMR (300 MHz, CDCl$_3$) δ 7.50-7.59 (m, 1 H), 7.30-7.38 (m, 6 H), 7.22-7.27 (m, 1 H), 6.90-6.98 (m, 2 H), 6.76-6.81 (m, 1 H), 4.71 (s, 2 H), 4.01-4.10 (m, 2 H), 3.85 (s, 3 H), 3.28-3.57 (m, 5 H), 2.71-2.75 (m, 2 H), 2.58-2.65 (m, 2 H), and 1.38-1.46 (m, 6 H); MS (ES$^+$) 500.

Other compounds of the present invention may be prepared by those skilled in the art by varying the starting materials, reagent(s) and conditions used. Using the procedure of Example 13, the following compounds were prepared:

| Cpd | Name |
| --- | --- |
| 21 | 2-(3-ethoxy-4-methoxy-benzyl)-4-[4-(1R)-(1-phenyl-ethyl)-piperazin-1-yl]-isoindole-1,3-dione<br>Isolated as a yellow solid. $^1$H NMR (300 MHz, CDCl$_3$) δ 7.49-7.59 (m, 1 H), 7.25-7.38 (m, 6 H), 7.08-7.15 (m, 1H), 6.96-7.00 (m, 2 H), 6.76-6.82 (m, 1H), 4.72 (s, 2 H), 4.05-4.13 (m, 2 H), 3.83 (s, 3 H), 3.63-3.67 (m, 1 H), 3.30-3.59 (m, 4 H), 2.71-2.77 (m, 2 H), 2.58-2.65 (m, 2 H), and 1.36-1.48 (m, 6 H); MS (ES$^+$) 500 (M + 1). |
| 41 | 2-(3-methoxy-4-propoxy-benzyl)-4-[4-(1R)-(1-phenyl-ethyl)-piperazin-1-yl]-isoindole-1,3-dione<br>Isolated as a yellow solid. $^1$H NMR (300 MHz, CDCl$_3$) δ 7.50-7.59 (m, 1 H), 7.26-7.38 (m, 6 H), 7.08-7.15 (m, 1H), 6.94-6.98 (m, 2 H), 6.76-6.82 (m, 1H), 4.71 (s, 2 H), 3.84-3.96 (m, 5 H), 3.32-3.59 (m, 5 H), 2.71-2.76 (m, 2 H), 2.60-2.65 (m, 2 H), 1.79-1.87 (m, 2 H), 1.42 (d, J = 6.6 Hz, 3 H), and 0.98-1.03 (m, 3 H); MS (ES$^+$) 514 (M + 1). |

Example 14

2-[1-(3,4-dimethoxy-phenyl)-ethyl]-4-[4-(1R)-(1-phenyl-ethyl)-piperazin-1-yl]-isoindole-1,3-dione
Cpd 2

Compound 2 was prepared by the methods described in Example 1 for the synthesis of Compound 1, substituting 1-(3,4-dimethoxyphenyl)-ethylamine hydrochloride (175.0 mg) for veratrylamine in Example 1, Step A, and substituting Compound 13h (200.0 mg) for N-Boc-piperazine in Example 1, Step C. Compound 2 was isolated as a yellow solid. $^1$H NMR (300 MHz, CDCl$_3$) δ 7.51-7.55 (m, 1 H), 7.24-7.36 (m, 6 H), 7.06-7.14 (m, 3 H), 6.77-6.87 (m, 1 H), 5.41-5.49 (m, 1 H), 3.86 (s, 3 H), 3.84 (s, 3 H), 3.31-3.59 (m, 5 H), 2.73-2.76 (m, 2 H), 2.60-2.64 (m, 2 H), 1.86 (d, J=7.3 Hz, 3 H), and 1.41 (d, J=6.6 Hz, 3 H); MS (ES$^+$) 500 (M+1).

Other compounds of the present invention may be prepared by those skilled in the art by varying the starting materials, reagent(s) and conditions used. Using the procedure of Example 14, the following compounds were prepared:

| Cpd | Name |
| --- | --- |
| 8 | 2-[1-(3,4-dimethoxy-phenyl)-propyl]-4-[4-(1R)-(1-phenyl-ethyl)-piperazin-1-yl]-isoindole-1,3-dione<br>$^1$H NMR (300 MHz, CDCl$_3$) δ 7.58 (dd, J = 8.1 Hz, J = 7.6 Hz, 1 H), 7.42-7.53 (m, 6 H), 7.02-7.11 (m, 3 H), 6.79 (d, J = 8.3 Hz, 1 H), 5.06-5.12 (m, 1 H), 4.35 (q, J = 7.0 Hz, 2 H), 3.87 (s, 3 H), 3.84 (s, 3 H), 3.62-3.72 (m, 3 H), 3.01-3.49 (m, 4 H), 2.40-2.65 (m, 1H), 2.21-2.35 (m, 1 H), 1.85 (d, J = 7.0 Hz, 3 H), and 0.92 (t, J = 7.3 Hz, 3 H); MS (ES$^+$) 514.1 (M + 1). |

-continued

| Cpd | Name |
|---|---|
| 49 | 2-[(3,4-dimethoxy-phenyl)-phenyl-methyl]-4-[4-(1R)-(1-phenyl-ethyl)-piperazin-1-yl]-isoindole-1,3-dione<br>Observed Parent Peak 562; MS calc'd 561.7 |
| 63 | 2-[1-(3,4-dimethoxy-phenyl)-2-dimethylamino-ethyl]-4-[4-(1R)-(1-phenyl-ethyl)-piperazin-1-yl]-isoindole-1,3-dione<br>$^1$H NMR (300 MHz, CDCl$_3$) δ 7.57 (ovdd, J = 7.9 Hz, 1 H), 7.40-7.48 (m, 6 H), 7.04-7.09 (m, 3 H), 6.81 (d, J = 8.0 Hz, 1 H), 5.62-5.66 (m, 1 H), 4.71-4.79 (m, 1H), 3.65-4.09 (m, 10 H), 3.22-3.49 (m, 2 H), 2.54-3.06 (m, 10 H), and 1.85 (d, J = 6.7 Hz, 3 H); MS (ES$^+$) 543.9 (M + 1). |

Example 15

4-chloro-2-(3,4-dimethoxy-benzyl)-7-[4-(1R)-(1-phenyl-ethyl)-piperazin-1-yl]-isoindole-1,3-dione Cpd 10

Compound 10 was prepared by the methods described in Example 1 for the synthesis of Compound 1, substituting 3,6-dichlorophthalic anhydride (3.30 g) for 3-hydroxyphthalic anhydride in Example 1, Step A, and substituting Compound 13h (4.30 g) for N-Boc-piperazine in Example 1, Step C. Compound 10 was isolated as a yellow solid. $^1$H NMR (300 MHz, CDCl$_3$) δ 7.43 (d, J=8.8, 1 H), 7.24-7.36 (m, 5 H), 6.98-7.06 (m, 3 H), 6.78 (d, J=8.6 Hz, 1 H), 4.71 (s, 2 H), 3.87 (s, 3 H), 3.84 (s, 3 H), 3.44 (q, J=6.7 Hz, 1 H), 3.28-3.33 (m, 4 H), 2.69-2.77 (m, 2 H), 2.58-2.65 (m, 2 H), and 1.41 (d, J=6.6 Hz, 3 H); MS (ES$^+$) 521 (M+1).

Other compounds of the present invention may be prepared by those skilled in the art by varying the starting materials, reagent(s) and conditions used. Using the procedure of Example 15, the following compounds were prepared:

| Cpd | Name |
|---|---|
| 9 | 4-(8-benzyl-3,8-diaza-bicyclo[3.2.1]oct-3-yl)-7-chloro-2-(3,4-dimethoxy-benzyl)-isoindole-1,3-dione<br>$^1$H NMR (300 MHz, CDCl$_3$) δ 7.43-7.57 (m, 6 H), 7.07 (d, J = 8.9 Hz, 1 H), 6.95-6.99 (m, 2 H), 6.79 (d, J = 8.7 Hz, 1 H), 4.71 (s, 2 H), 4.21 (s, 2 H), 3.92-3.96 (m, 2 H), 3.87 (s, 3 H), 3.84 (s, 3 H), 3.75-3.80 (m, 2 H), 3.61-3.66 (m, 2 H), 2.67-2.70 (m, 2 H), and 2.28-2.31 (m, 2 H); MS (ES$^+$) 532 (M + 1). |

Example 16

2-(3,4-dimethoxy-benzyl)-4-(2-methanesulfonyl-vinyl)-7-[4-(1R)-(1-phenyl-ethyl)-piperazin-1-yl]-isoindole-1,3-dione Cpd 62

A 10 mL sealed tube was charged with Compound 10 (100.0 mg, 0.19 mmol), sodium acetate (22.0 mg, 0.27 mmol), bis(tri-t-butylphosphine)palladium (0) (13.0 mg, 0.03 mmol), methyl vinylsulfone (0.02 ml, 0.23 mmol), and dimethylacetamide (1.0 mL). The tube was charge with argon and sealed. The mixture was heated at 150° C. for 24 h. The mixture was cooled to room temperature and purified via flash chromatography (230-400 mesh silica gel 60, gradient 90:10-50:50 hexanes:ethyl acetate) to give 21.7 mg (19%) of Compound 62 as a yellow solid. $^1$H NMR (300 MHz, CDCl$_3$) δ 8.44 (d, J=15.6, 1 H), 7.48-7.53 (m, 5 H), 7.01-7.08 (m, 3 H), 6.70-6.90 (m, 3 H), 4.64 (s, 2 H), 4.42 (q, J=6.9 Hz, 1 H), 3.94 (s, 3 H), 3.86 (s, 3 H), 3.33-3.80 (m, 8 H), 3.07 (s, 3 H), and 1.86 (d, J=6.7 Hz, 3 H); MS (ES$^+$) 590 (M+1).

Example 17

4-(1-benzyl-piperidin-4-yl)-2-(3,4-dimethoxy-benzyl)-isoindole-1,3-dione Cpd 76

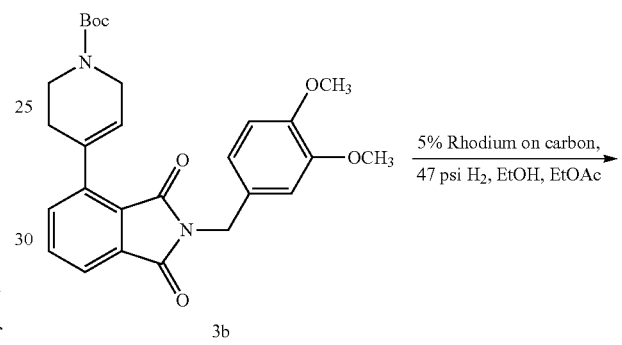

3b

-continued

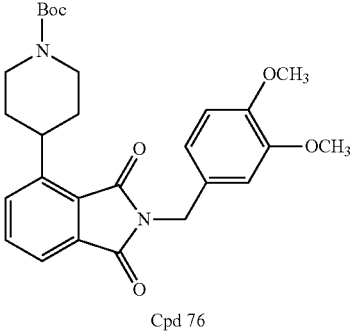

Cpd 76

A. 4-(1-Benzyl-piperidin-4-yl)-2-(3,4-dimethoxy-benzyl)-isoindole-1,3-dione. A Parr hydrogenation bottle was charge with Compound 3b (130 mg, 0.27 mmol), 5% rhodium on carbon (100 mg), ethanol (12 mL), and ethyl acetate (8 mL). The vessel was placed under 47 psi hydrogen and shaken for 16 h. The mixture was then filtered through Celite®, and concentrated in vacuo to give Compound 76. $^1$H NMR (300 MHz, CDCl$_3$) δ 7.64-7.76 (m, 3 H), 7.45-7.49 (m, 5 H), 6.95-7.00 (m, 2 H), 6.78-6.82 (m, 1 H), 4.73 (s, 2 H), 4.24 (s, 2 H), 3.87 (s, 3 H), 3.84 (s, 3 H), 3.67-3.71 (m, 1 H), 2.82-3.20 (m, 3 H), 2.28-2.40 (m, 2 H), and 1.91-2.11 (m, 2 H); MS (ES$^+$) 471 (M+1).

Example 18

2-[(S)-1-(3,4-dimethoxy-phenyl)ethyl]-4-[4-(1R)-(1-phenyl-ethyl)-piperazin-1-yl]-isoindole-1,3-dione
Cpd 3

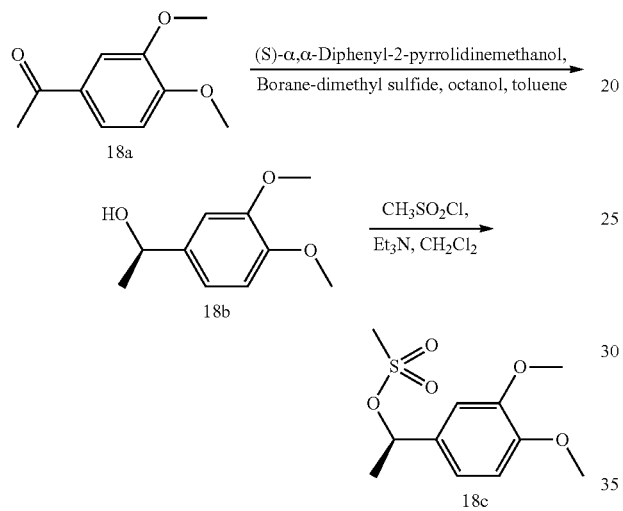

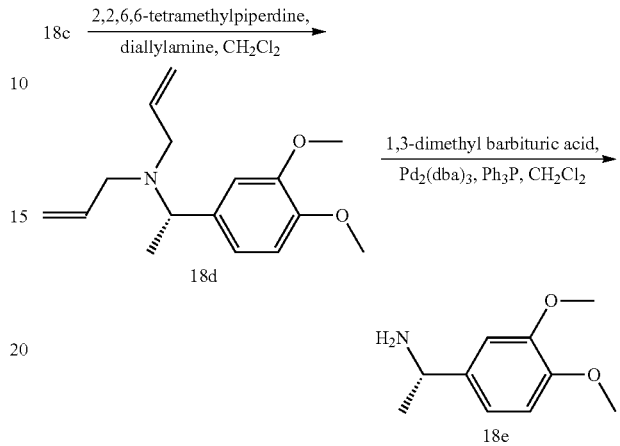

A. A 50-mL round bottom flask was charge with borane-dimethyl sulfide solution in toluene (0.4 mL, 0.8 mmol) and toluene (6.0 mL). Octanol (0.32 mL, 2.01 mmol) was added dropwise to the mixture. The mixture was stirred at 34° C. for 1 h. (S)-α, α-diphenyl-2-pyrrolidinemethanol (0.14 g, 0.55 mmol) was dissolved in toluene (6.0 mL) and added to the mixture followed by stirring for 1 h at 34° C. Borane-dimethyl sulfide solution in toluene (2.8 mL, 1.40 mmol) was added followed by dropwise addition of a solution of 3,4-dimethoxyacetophenone (Compound 18a, 1.0 g, 5.55 mmol) in toluene (6.0 mL) over 1 h via addition funnel. The mixture was cooled to room temperature and quench with 1N HCl (20 mL). The mixture was transferred to a separatory funnel and extracted with ethyl acetate (200 mL). The organic layer was washed with sodium bicarbonate (50 mL) and sodium chloride (50 mL). The organic layer was dried using MgSO$_4$, filtered through Celite®, and concentrated in vacuo to give 820 mg of Compound 18b as a white solid. $^1$H NMR (300 MHz, CDCl$_3$) δ 6.82-6.95 (m, 3 H), 4.86 (q, J=3.3 Hz, 2 H), 3.90 (s, 3 H), 3.88 (s, 3 H), 1.83 (s, 1 H), and 1.49 (d, J=6.4 Hz, 3 H).

B. A 100-mL round bottom flask was charged with Compound 18b (0.40 g, 2.20 mmol) and dichlormethane (11.0 mL). The mixture was cooled using an ice/water bath. Triethylamine (0.37 mL, 2.65 mmol) was added to the mixture followed by the dropwise addition methanesulfonyl chloride (0.19 mL, 2.45 mmol). The mixture was stirred for 4 h in the ice/water bath and then washed with 1N HCl (5 mL). The organic layer was dried with MgSO$_4$ and filtered through Celite® to give Compound 18c.

C. Diallylamine (0.27 mL, 2.19 mmol) and 2,2,6,6-tetramethylpiperidine (0.82 mL, 4.83 mmol) were added to the crude dichloromethane solution of Compound 18c. The mixture was refluxed for 24 h, cooled to room temperature, and concentrated in vacuo. The crude oil was purified via flash chromatography (230-400 mesh silica gel 60, gradient 100:0-98:2 CH$_2$Cl$_2$:MeOH) to give 0.4 g of Compound 18d as a white solid. $^1$H NMR (300 MHz, CDCl$_3$) δ 6.78-6.87 (m, 3 H), 5.78-5.91 (m, 2 H), 5.09-5.20 (m, 4 H), 4.18 (q, J=6.4 Hz, 2 H), 3.90 (m, 3 H), 3.86 (m, 3 H), 3.00-3.17 (m, 4 H), and 1.45 (d, J=6.4 Hz, 3 H).

D. A 50-mL round bottom flask was charged with Compound 18d (0.40 g, 1.53 mmol) and dichloromethane (8.0 mL). Pd$_2$(dba)$_3$.CHCl$_3$ (0.16 g, 0.15 mmol), triphenylphosphine (0.16 g, 6.1 mmol), and 1,3-dimethylbarbituric acid (0.79 g, 5.06 mmol) were added and the mixture was heated to reflux for 3 h. The mixture was cooled to room temperature, transferred to a separatory funnel, and extracted with 1N HCl (50 mL). The aqueous layer was basified with 3N NaOH and extracted with ethyl acetate (200 mL). The organic layer was dried with MgSO$_4$ and filtered through Celite® to give Compound 18e as a white solid. $^1$H NMR (300 MHz, CDCl$_3$) δ 6.74-6.85 (m, 3 H), 3.96-4.08 (m, 1 H), 3.83 (m, 3 H), 3.80 (m, 3 H), 1.87-1.97 (bs, 2 H), and 1.31 (d, J=6.6 Hz, 3 H).

E. Compound 3 was prepared by the methods described in Example 13 for the synthesis of Compound 18, substituting Compound 18e (0.14 g) for Compound 13d. Compound 3 was isolated as a yellow solid. [α]$_D$+13.8° (c=1.18, MeOH; 23° C.); $^1$H NMR (300 MHz, CDCl$_3$) δ 7.35-7.54 (m, 7 H), 6.93-7.07 (m, 3 H), 6.73 (d, J=8.6 Hz, 1 H), 5.36 (q, J=7.2 Hz, 1 H), 4.21 (q, J=5.2 Hz, 1 H), 3.79 (s, 3 H), 3.77 (s, 3 H), 3.36-3.64 (m, 6 H), 3.79-3.16 (m, 2 H), 1.83 (d, J=7.0 Hz, 3 H), and 1.79 (d, J=7.4 Hz, 3 H); MS (ES$^+$) 500 (M+1).

Other compounds of the present invention may be prepared by those skilled in the art by varying the starting materials, reagent(s) and conditions used. Using the procedure of Example 18, the following compounds were prepared:

| Cpd | Name |
|---|---|
| 4 | (R)-2-[1-(3,4-dimethoxy-phenyl)-ethyl]-4-[4-(1R)-(1-phenyl-ethyl)-piperazin-1-yl]-isoindole-1,3-dione<br>(R)-α,α-diphenyl-2-pyrrolidinemethanol (0.14 g) was substituted for (S)-α,α-diphenyl-2-pyrrolidinemethanol. Compound 4 was isolated as a yellow solid.<br>$[\alpha]_D$ + 11.6° (c = 1.17, MeOH; 23° C.); $^1$H NMR (300 MHz, CDCl$_3$) δ 7.56-7.61 (m, 1 H), 7.42-7.52 (m, 6 H), 7.10 (d, J = 8.2 Hz, 1 H), 7.00-7.02 (m, 2 H), 6.79 (d, J = 8.8 Hz, 1 H), 5.43 (q, J = 7.3 Hz, 1 H), 4.36 (q, J = 7.0 Hz, 1 H), 3.86 (s, 3 H), 3.84 (s, 3 H), 3.71-3.78 (m, 2 H), 3.40-3.60 (m, 2 H), 2.81-3.25 (m, 4 H), 1.87 (d, J = 7.3 Hz, 3 H), and 1.76 (d, J = 7.0 Hz, 3 H); MS (ES$^+$) 500 (M + 1). |

Example 19

2-(4-hydroxy-3-methoxy-benzyl)-4-[4-(1R)-(1-phenyl-ethyl)-piperazin-1-yl]-isoindole-1,3-dione Cpd 15

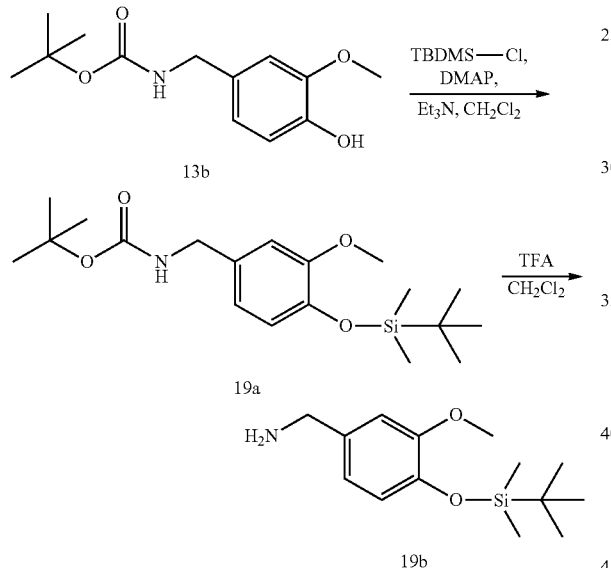

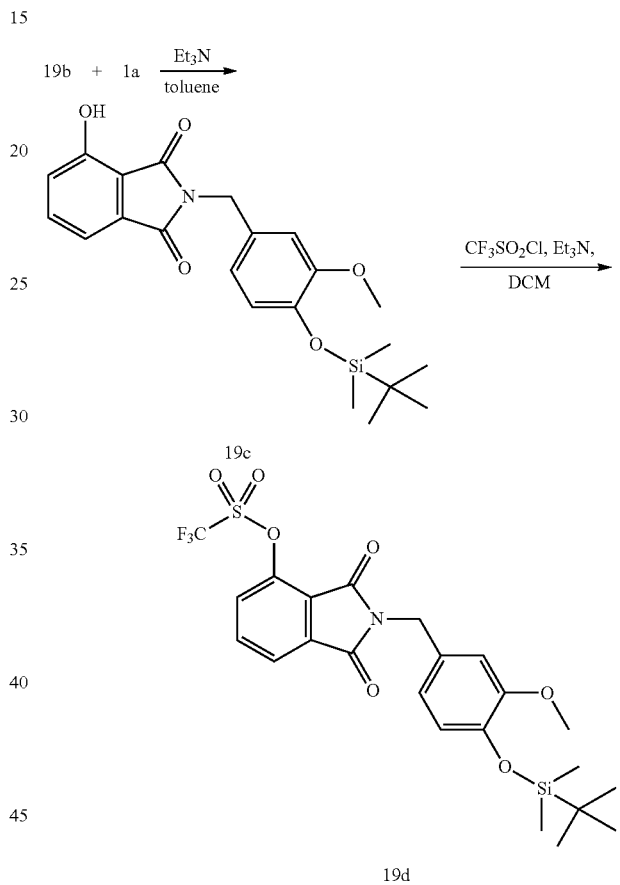

A. A 100-mL round bottom flask was charge with Compound 13b (0.5 g, 2.0 mmol) and dichloromethane (16 mL). Dimethylaminopyridine (10 mg, 0.08 mmol), triethylamine (0.7 mL, 5.0 mmol), and tert-butyldimethylsilyl chloride (0.47 g, 3.1 mmol) were added and the mixture was stirred at room temperature for 18 h. The mixture was transferred to a separatory funnel and extracted with dichloromethane (100 mL). The organic layer was washed with 1N HCl (50 mL). The organic layer was dried using MgSO$_4$, filtered through Celite®, and concentrated in vacuo to give Compound 19a as a white solid. $^1$H NMR (300 MHz, CDCl$_3$) δ 6.56-6.70 (m, 3 H), 4.08-4.10 (s, 2 H), 3.65 (s, 3 H), 1.32 (s, 9 H), 0.85 (s, 9 H), and 0.01 (m, 6 H).

B. Compound 19a was dissolved in dichloromethane (8.0 mL) and trifluoroacetic acid (2.0 mL) was added. The mixture was stirred at room temperature for 1 h and concentrated in vacuo to give Compound 19b as a white solid. $^1$H NMR (300 MHz, CDCl$_3$) δ 6.65-6.78 (m, 3 H), 3.88-4.06 (s, 2 H), 3.64 (s, 3 H), 0.84 (s, 9 H), and 0.01 (m, 6 H).

C. A 50-mL sealed tube was charged with Compound 19b (0.75 g, 2.81 mmol), Compound 1a (0.32 g, 1.95 mmol), and toluene (10.0 mL). Triethylamine (0.7 mL, 5.02 mmol) and 4 Å molecular sieves (0.64 g) were added and the tube was flushed with argon and sealed. The mixture was heated to 125° C. for 22 h. The mixture was cooled to room temperature, diluted with dichlormethane (100 mL), and transferred to a separatory funnel. The organic layer was washed with 1N HCl (40 mL), dried using MgSO$_4$, filtered through Celite®, and concentrated in vacuo to give Compound 19c as a crude oil. A 50-mL round bottom flask was charged with crude Compound 19c (0.88 g, 2.13 mmol), dichloromethane (10 mL), and triethylamine (0.33 mL, 2.37 mmol). The mixture was cooled using an ice/water bath. Trifluoromethanesulfonyl chloride (0.25 mL, 2.35 mmol) added dropwise. The mixture was then stirred for 1 h in an ice/water bath. The mixture was then diluted with dichloromethane (100 mL) and washed with 1.0 N HCl (100 mL) solution. The organic layer was dried using MgSO₄, filtered through Celite®, and concentrated in vacuo to give Compound 19d as a crude yellow solid.

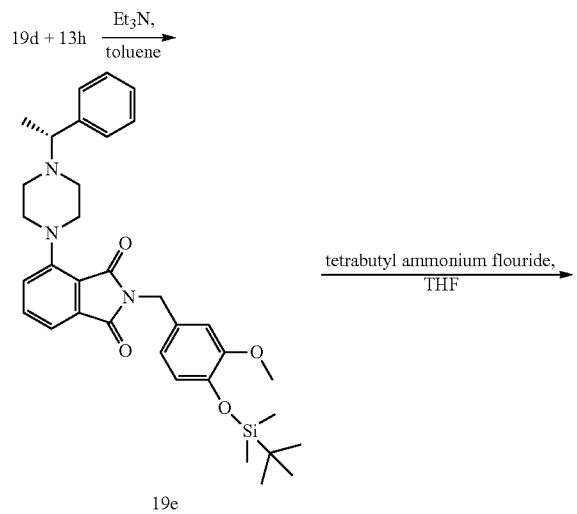

D. A 10 mL sealed tube was charged with crude Compound 19d (1.1 g, 2.02 mmol), Compound 13h (0.40 g, 2.11 mmol), toluene (2.0 mL), and triethylamine (0.65 mL, 4.66 mmol). The tube was sealed under argon and heated to 110° C. for 22 h. The mixture was cooled to room temperature. The crude mixture was concentrated in vacuo and dissolved in tetrahydrofuran (10 mL). Tetrabutylammonium fluoride (4.6 mL) was added and the mixture was stirred at room temperature for 1 h. The mixture was concentrated in vacuo to give a crude oil that was purified on a Gilson HPLC with a reversed phase Kromasil column (10μ, 100 Å C18, column length 250×50 mm, gradient 90:10-0:100 H₂O:MeCN) to give the 122.0 mg of the title Compound 15 as a yellow solid. ¹H NMR (300 MHz, CDCl₃) δ 7.52-7.57 (m, 1 H), 7.44-7.49 (m, 6 H), 7.04 (d, J=8.2 Hz, 1 H), 6.75-6.93 (m, 3 H), 4.65 (d, 2 H), 4.36 (q, J=7.0 Hz, 1 H), 3.82 (s, 3 H), 368-3.75 (m, 2 H), 3.52-3.68 (m, 2 H), 3.01-3.08 (m, 4 H), and 1.84 (d, J=6.8 Hz, 3 H); MS (ES⁺) 472 (M+1).

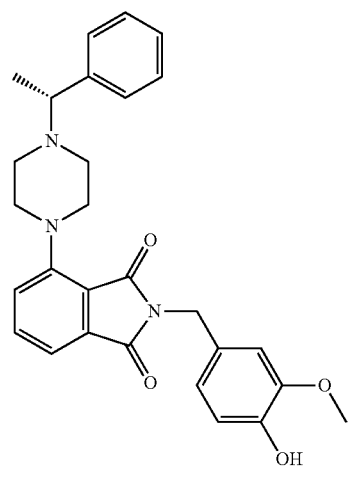

Cpd 15

Example 20

(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-carbamic acid tert-butyl ester Cpd 65

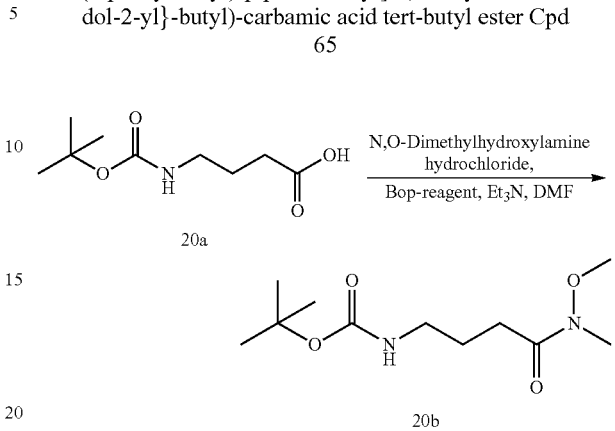

A. A 500-mL round bottom flask was charge with Compound 20a (4.2 g, 20.6 mmol) and dimethylformamide (207 mL). The mixture was cooled using an ice/water bath. Triethylamine (8.8 mL, 63.1 mmol) was added to the mixture followed by the benzotriazol-1-yloxy-tris(dimethylamino) phosphonium hexafluorophosphate (10.0 g, 22.6 mmol). N,O-dimethylhydroxylamine hydrochloride (3.1 g, 31.8 mmol) was added and the mixture was stirred at room temperature for 24 h. The mixture was diluted with dichloromethane (500 mL) and transferred to a separatory funnel. The organic layer was washed with 1N HCl (300 mL) and water (2×300 mL). The organic layer was dried using MgSO₄, filtered through Celite®, concentrated in vacuo, and purified via flash chromatography (230-400 mesh silica gel 60, gradient 100:0-90:10 DCM:MeOH) to give 5.08 g of Compound 20b as a white solid. ¹H NMR (300 MHz, CDCl₃) δ 3.65 (s, 3 H), 3.22-3.21 (m, 2 H), 3.16 (s, 3 H), 2.45-2.54 (m, 2 H), 1.80-1.89 (m, 2 H), and 1.42 (s, 9 H).

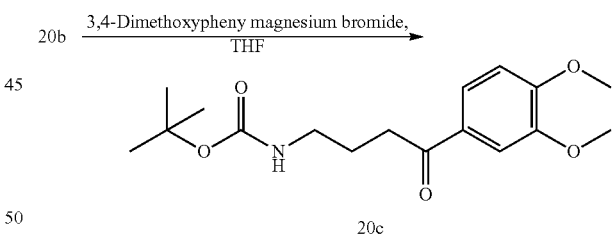

B. A 1-L round bottom flask was charged with Compound 20b (5.08 g, 20.7 mmol) and tetrahydrofuran (415 mL). The mixture was cooled using an ice/water bath. A solution of 3,4-Dimethoxyphenyl magnesium bromide in tetrahydrofuran (207 mL, 104 mmol) was added dropwise via addition funnel over 30 minutes. The mixture was allowed to warm to room temperature and stirred for 20 h. Water (150 mL) was added to the mixture and concentrated in vacuo. The mixture was extracted with dichloromethane (600 mL) and washed with water (2×300 mL). The organic layer was dried with MgSO₄, filtered through Celite®, concentrated in vacuo, and purified via flash chromatography (230-400 mesh silica gel 60, gradient 90:10-50:50 Hexanes:Ethyl Acetate) to give 4.0 g of Compound 20c as a white solid. ¹H NMR (300 MHz, CDCl₃) δ 7.57 (d, J=8.2 Hz, 1 H), 7.52 (s, 1 H), 6.88 (d, J=8.6

Hz, 1 H), 3.95 (s, 3 H), 3.92 (s, 3 H), 3.27-3.34 (m, 2 H), 2.97-3.02 (m, 2 H), 1.92-1.99 (m, 2 H), and 1.42 (s, 9 H).

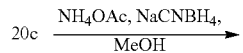

6.76-6.80 (m, 1 H), 5.17-5.23 (m, 1 H), 4.47-4.52 (m, 1 H), 3.87 (s, 3 H), 3.84 (s, 3 H), 3.40-3.57 (m, 2 H), 3.41-3.47 (m, 4 H), 3.14-3.19 (m, 2 H), 2.52-2.88 (m, 6 H), 2.21-2.30 (m, 2 H), 1.74 (d, J=7.0 Hz, 3 H), and 1.41 (s, 9 H); MS (ES$^+$) 643 (M+1).

Other compounds of the present invention may be prepared by those skilled in the art by varying the starting materials, reagent(s) and conditions used. Using the procedure of Example 20, the following compounds were prepared:

| Cpd | Name |
|---|---|
| 69 | (5-(3,4-dimethoxy-phenyl)-5-{1,3-dioxo-4-[4-(1R)-(1-phenyl-ethyl)-piperazin-1-yl]-1,3-dihydro-isoindol-2-yl}-pentyl)-carbamic acid tert-butyl ester<br>$^1$H NMR (300 MHz, CDCl$_3$) δ 7.29-7.79 (m, 8 H), 6.68-6.96 (m, 3 H), 5.28-5.35 (m, 1 H), 4.59-4.74 (m, 1 H), 3.75-4.06 (m, 8 H), 3.20-3.53 (m, 6 H), 2.16-2.41 (m, 7 H), and 1.21-1.59 (m, 12 H); MS (ES$^+$) 643.4 (M + 1). |
| 72 | (2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-carbamic acid tert-butyl ester<br>$^1$H NMR (300 MHz, CDCl$_3$) δ 7.59 (ovdd, J = 8.0 Hz, 1 H), 7.41-7.54 (m, 6 H), 7.10 (d, J = 8.2 Hz, 1 H), 6.97-7.11 (m, 2 H), 6.79 (d, J = 8.1 Hz, 1 H), 5.24-5.39 (m, 1 H), 4.59-4.71 (m, 1 H), 4.34-4.41 (m, 1 H), 4.08-4.19 (m, 1 H), 3.74-3.91 (m, 8 H), 3.37-3.60 (m, 6 H), 2.98-3.17 (m, 2 H), 1.85 (d, J = 6.9 Hz, 3 H), and 1.38 (s, 9 H); MS (ES$^+$) 615.4 (M + 1). |
| 73 | (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-carbamic acid tert-butyl ester<br>$^1$H NMR (300 MHz, CDCl$_3$) δ 7.61 (ovdd, J = 7.9 Hz, 1 H), 7.44-7.51 (m, 6 H), 6.97-7.13 (m, 3 H), 6.79 (d, J = 8.2 Hz, 1 H), 5.35-5.40 (m, 1 H), 4.60-4.77 (m, 1 H), 4.28-4.39 (m, 1 H), 3.68-3.94 (m, 8 H), 3.38-3.54 (m, 3 H), 2.92-3.27 (m, 5 H), 2.62-2.71 (m, 1 H), 2.33-2.45 (m, 1 H), 1.86 (d, J = 6.9 Hz, 3 H), and 1.38 (s, 9 H); MS (ES$^+$) 629.8 (M + 1). |
| 123 | 2-[1,2-bis-(3,4-dimethoxy-phenyl)-ethyl]-4-[4-(1R)-(1-phenyl-ethyl)-piperazin-1-yl]-isoindole-1,3-dione<br>$^1$H NMR (300 MHz, CDCl$_3$) δ 7.51-7.74 (m, 6 H), 7.37 (d, J = 7.2 Hz, 1 H), 7.03-7.14 (m, 3 H), 6.81 (d, J = 8.2 Hz, 1 H), 6.66-6.72 (m, 3 H), 5.43-5.49 (m, 1 H), 4.32-4.38 (m, 1 H), 3.88 (s, 3 H), 3.85 (s, 3 H), 3.78 (s, 3 H), 3.71 (s, 3 H), 3.35-3.64 (m, 8 H), 2.85-3.16 (m, 2 H), and 1.85 (d, J = 6.8 Hz, 3 H); MS (ES+) 636.2 (M + 1). |

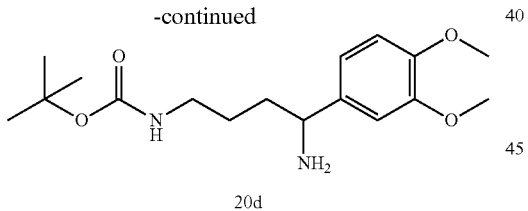

20d

C. A 300-mL round bottom flask was charged with Compound 20c (4.0 g, 12.4 mmol), ammonium acetate (9.5 g, 123.2 mmol), and methanol (42.0 mL). Sodium cyanoborohydride (0.55 g, 8.8 mmol) was added and the mixture was heated to 40° C. for 22 h. The mixture was cooled to room temperature and 1N NaOH (200 mL) was added. The mixture was transferred to a separatory funnel and extracted with dichloromethane (3×200 mL). The organic layer was dried with MgSO$_4$, filtered through Celite®, concentrated in vacuo, and purified via flash chromatography (230-400 mesh silica gel 60, gradient 100:0-90:10 CH$_2$Cl$_2$:methanol) to give 2.0 g of Compound 20d as a white solid. $^1$H NMR (300 MHz, CDCl$_3$) δ 6.83-6.87 (m, 3 H), 4.53-4.60 (m, 1 H), 3.90 (s, 3 H), 3.87 (s, 3 H), 3.10-3.15 (m, 2 H), 1.63-1.71 (m, 5 H), and 1.43 (s, 9 H).

D. Compound 65 was prepared by the methods described in Example 13 for the synthesis of Compound 18, substituting Compound 20d (0.65 g) for Compound 13d. Compound 65 was isolated as a yellow solid. $^1$H NMR (300 MHz, CDCl$_3$) δ 7.49-7.54 (m, 2 H), 7.30-7.41 (m, 6 H), 7.07-7.10 (m, 2 H), Example 21

2-[4-amino-1-(3,4-dimethoxy-phenyl)-butyl]-4-[4-(1R)-(1-phenyl-ethyl)-piperazin-1-yl]-isoindole-1,3-dione Cpd 66

A 10-mL round bottom flask was charge with Compound 65 (0.15 g, 2.0 mmol) and dichloromethane (2.0 mL). Trifluoroacetic acid (0.5 mL) was added and the mixture was stirred at room temperature for 3 h. The mixture was concentrated in vacuo to give Compound 66 (113 mg) as a yellow solid. $^1$H NMR (300 MHz, CDCl$_3$) δ 7.63-7.69 (m, 1 H), 7.50-7.56 (m, 5 H), 7.40-7.42 (m, 1 H), 7.26-7.29 (m, 1 H), 7.13-7.18 (m, 1 H), 7.02-7.06 (m, 1 H), 6.88-6.92 (m, 1 H), 5.25 (q, J=7.0 Hz, 1 H), 4.47 (q, J=6.8 Hz, 1 H), 3.85 (s, 3 H), 3.80 (s, 3 H), 3.47-3.60 (m, 3 H), 3.32-3.36 (m, 4 H), 2.96-3.07 (m, 3 H), 2.54-2.67 (m, 1 H), 2.32-2.42 (m, 1 H), 1.80 (d, J=6.8 Hz, 3 H), and 1.64-1.69 (s, 2 H); MS (ES$^+$) 543 (M+1).

Other compounds of the present invention may be prepared by those skilled in the art by varying the starting materials, reagent(s) and conditions used. Using the procedure of Example 21, the following compounds were prepared:

| Cpd | Name |
|---|---|
| 64 | 2-[2-amino-1-(3,4-dimethoxy-phenyl)-ethyl]-4-[4-(1R)-(1-phenyl-ethyl)-piperazin-1-yl]-isoindole-1,3-dione<br>$^1$H NMR (300 MHz, CD$_3$OD) δ 7.61 (ovdd, J = 8.3 Hz, 1 H), 7.23-7.39 (m, 7 H), 7.08-7.11 (m, 1 H), 7.01-7.04 (m, 1 H), 6.90 (d, J = 8.3 Hz, 1 H), 5.22-5.32 (m, 1 H), 3.82 (s, 3 H), 3.80 (s, 3 H), 3.43-3.56 (m, 4 H), 3.31-3.34 (m, 3 H), 2.59-2.77 (m, 4 H), and 1.46 (d, J = 6.7 Hz, 3 H); MS (ES$^+$) 515.8 (M + 1). |
| 70 | 2-[5-amino-1-(3,4-dimethoxy-phenyl)-pentyl]-4-[4-(1R)-(1-phenyl-ethyl)-piperazin-1-yl]-isoindole-1,3-dione<br>$^1$H NMR (300 MHz, CDCl$_3$) δ 7.31-7.75 (m, 8 H), 6.88-7.13 (m, 3 H), 5.21-5.26 (m, 1 H), 4.50-4.61 (m, 1 H), 3.66-3.89 (m, 7 H), 3.47-3.58 (m, 3 H), 2.92-3.33 (m, 6 H), 2.53-2.61 (m, 1 H), 2.25-2.33 (m, 1 H), 1.82 (d, J = 6.8 Hz, 3 H), 1.61-1.75 (m, 2 H), and 1.29-1.49 (m, 2 H); MS (ES$^+$) 542.3 (M + 1). |

Example 22 thiophene-2-sulfonic acid(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide Cpd 68

A 10-mL round bottom flask was charge with Compound 66 (20.0 mg, 0.04 mmol), potassium carbonate (8.0 mg, 0.06 mmol), and dichloromethane (0.5 mL). Thiophene-2-sulfonyl chloride (8.0 mg, 0.04 mmol) was added and the mixture was stirred at room temperature for 4 h. The mixture was concentrated in vacuo and purified via flash chromatography (230-400 mesh silica gel 60, gradient 100:0-95:5 CH$_2$Cl$_2$: methanol) to give 9.8 mg of Compound 68 as a yellow solid. $^1$H NMR (300 MHz, CDCl$_3$) δ 7.71-7.74 (m, 1 H), 7.51-7.61 (m, 3 H), 7.29-7.38 (m, 6 H), 7.02-7.18 (m, 3 H), 6.73-6.80 (m, 1 H), 5.10-5.17 (m, 1 H), 4.50-4.57 (m, 1 H), 3.86 (s, 3 H), 3.83 (s, 3 H), 3.31-3.39 (m, 4 H), 3.06-3.11 (m, 4 H), 2.65-2.74 (m, 2 H), 2.45-2.55 (m, 1 H), 2.20-2.31 (m, 1 H), 1.58-1.63 (m, 2 H), and 1.49 (d, J=6.8 Hz, 3 H); MS (ES$^+$) 689 (M+1).

Other compounds of the present invention may be prepared by those skilled in the art by varying the starting materials, reagent(s) and conditions used. Using the procedure of Example 22, the following compounds were prepared:

| Cpd | Name |
|---|---|
| 67 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methanesulfonamide<br>$^1$H NMR (300 MHz, CDCl$_3$) δ 7.58 (ovdd, J = 8.0 Hz, 1 H), 7.42-7.51 (m, 7 H), 7.02-7.12 (m, 2 H), 6.79 (d, J = 8.1 Hz, 1 H), 5.16-5.21 (m, 1 H), 4.29-4.36 (m, 1 H), 3.87 (s, 3 H), 3.84 (s, 3 H), 3.42-3.73 (m, 6 H), 3.06-3.26 (m, 4 H), 2.93 (s, 3 H), 2.52-2.59 (m, 1 H), 2.28-2.38 (m, 1 H), and 1.59-1.89 (m, 5 H); MS (ES$^+$) 621.9 (M + 1). |
| 71 | 5-chloro-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.51-7.61 (m, 1 H), 7.29-7.48 (m, 7 H), 6.74-7.16 (m, 5 H), 5.10-5.27 (m, 1 H), 4.62-4.73 (m, 1 H), 3.86 (s, 3 H), 3.84 (s, 3 H), 3.40-3.78 (m, 6 H), 2.70--3.25 (m, 4 H), 2.51-2.58 (m, 1 H), 2.23-2.47 (m, 1 H), and 1.53-1.94 (m, 5 H); MS (ES$^+$) 723.7 (M + 1). |
| 74 | thiophene-2-sulfonic acid (2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-amide<br>$^1$H NMR (300 MHz, CDCl$_3$) δ 7.49-7.63 (m, 9 H), 7.11-7.13 (m, 1 H), 7.02-7.05 (m, 1 H), 6.92-6.97 (m, 2 H), 6.78 (d, J = 8.9 Hz, 1 H), 5.32-5.37 (m, 1 H), 4.97-5.05 (m, 1 H), 4.36-4.39 (m, 1 H), 4.10-4.24 (m, 1 H), 3.60-3.92 (m, 8 H), 3.34-3.51 (m, 4 H), 2.93-3.06 (m, 2 H), and 1.86 (d, J = 6.8 Hz, 3 H); MS (ES$^+$) 661.8 (M + 1). |
| 75 | thiophene-2-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide<br>$^1$H NMR (300 MHz, CDCl$_3$) δ 7.48-7.61 (m, 8 H), 7.41 (d, J = 8.4 Hz, 1 H), 7.12 (d, J = 8.2 Hz, 1 H), 6.98-7.05 (m, 3 H), 6.77 (d, J = 8.5 Hz, 1 H), 5.31-5.39 (m, 1 H), 4.74-4.82 (m, 1 H), 4.36-4.42 (m, 1 H), 3.63-3.91 (m, 8 H), 3.39-3.57 (m, 3 H), 2.95-3.18 (m, 4 H), 2.63-2.81 (m, 1 H), 2.37-2.72 (m, 1 H), and 1.86 (d, J = 6.9 Hz, 3 H); MS (ES$^+$) 675.8 (M + 1). |
| 88 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methoxy-thiophene-3-carboxylic acid methyl ester<br>$^1$H NMR (300 MHz, CDCl$_3$) δ 8.16 (s, 1 H), 7.57 (dd, J = 8.2 Hz, J = 7.4 Hz, 1 H), 7.23-7.39 (m, 6 H), 7.01-7.14 (m, 3 H), 6.77 (d, J = 8.2 Hz, 1 H), 5.07-5.19 (m, 1 H), 4.81-4.90 (m, 1 H), 4.01 (s, 3 H), 3.87 (s, 3 H), 3.83 (s, 3 H), 3.81 (s, 3 H), 3.40-3.51 (m, 1 H), 3.23-3.38 (m, 4 H), 2.98-3.05 (m, 2 H), 2.41-2.80 (m, 4 H), 2.19-2.33 (m, 1 H), and 1.40-1.59 (m, 5 H); MS (ES+) 755.8 (M + 1). |

-continued

| Cpd | Name |
|---|---|
| 89 | 5-methyl-2-trifluoromethyl-furan-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.59 (dd, J = 8.2 Hz, J = 7.4 Hz, 1 H), 7.23-7.37 (m, 6 H), 6.96-7.19 (m, 3 H), 6.92 (s, 1 H), 6.77 (d, J = 8.2 Hz, 1 H), 5.07-5.19 (m, 1 H), 4.61-4.79 (m, 1 H), 3.43-3.52 (m, 1 H), 3.19-3.31 (m, 4 H), 2.48-2.78 (m, 7 H), 2.21-2.34 (m, 1 H), 1.49-1.58 (m, 2 H), and 1.43 (d, J = 6.6 Hz, 1 H); MS (ES+) 755.8 (M + 1) |
| 90 | 5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-furan-2-carboxylic acid methyl ester<br>MS (ES+) 731.7 (M + 1). |
| 91 | 1,3,5-trimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.59 (ovdd, J = 7.4 Hz, 1 H), 7.27-7.42 (m, 6 H), 6.98-7.13 (m, 3 H), 6.75 (d, J = 8.2 Hz, 1 H), 5.04-5.13 (m, 1 H), 4.29-4.38 (m, 1 H), 3.86 (s, 3 H), 3.83 (s, 3 H), 3.43 (s, 3 H), 3.21-3.52 (m, 5 H), 2.89-2.98 (m, 3 H), 2.44-2.53 (m, 3 H), 2.41 (s, 3 H), 2.33 (s, 3 H), 2.18-2.29 (m, 1 H), and 1.41-1.72 (m, 5 H); MS (ES+) 715.7 (M + 1). |
| 92 | 4-benzenesulfonyl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.20 (s, 1 H), 7.95 (d, J = 8.0 Hz, 2 H), 7.74 (s, 1 H), 7.28-7.67 (m, 13 H), 6.96-7.19 (m, 3 H), 6.78 (d, J = 8.3 Hz, 1 H), 5.11-5.18 (m, 1 H), 3.86 (s, 3 H), 3.84 (s, 3 H), 3.46-3.68 (m, 4 H), 2.79-3.18 (m, 5 H), 2.48-2.65 (m, 1 H), 2.19-2.40 (m, 1 H), and 1.44-1.93 (m, 5 H); MS (ES+) 701.8 (M + 1). |
| 93 | 6-chloro-imidazo[2,1-b]thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.92 (d, J = 6.9 Hz, 1 H), 7.33-7.58 (m, 8 H), 6.98-7.12 (m, 3 H), 6.76 (d, J = 8.4 Hz, 1 H), 5.09-5.23 (m, 2 H), 3.87 (s, 3 H), 3.84 (s, 3 H), 3.34-3.62 (m, 6 H), 2.76-3.09 (m, 4 H), 2.48-2.67 (m, 1 H), 2.13-2.31 (m, 1 H), and 1.48-1.86 (m, 5 H); MS (ES$^+$) 764.7 (M + 1). |
| 94 | 3-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-thiophene-2-carboxylic acid methyl ester<br>$^1$H NMR (300 MHz, CDCl$_3$) δ 7.41-7.53 (m, 3 H), 7.21-7.40 (m, 6 H), 6.98-7.12 (m, 3 H), 6.78 (d, J = 8.0 Hz, 1 H), 6.19-6.24 (m, 1 H), 5.04-5.13 (m, 1 H), 3.86 (s, 3 H), 3.84 (m, 3 H), 3.76 (s, 3 H), 3.27-3.51 (m, 5 H), 2.96-3.05 (m, 2 H), 2.58-2.83 (m, 3 H), 2.41-2.52 (m, 1 H), 2.18-2.32 (m, 1 H), and 1.37-1.65 (m, 5 H); MS (ES+) 746.7 (M). |
| 95 | 5-isoxazol-3-yl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>MS (ES$^+$) 756 (M + 1). |
| 96 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-benzenesulfonamide<br>$^1$H NMR (300 MHz, CDCl$_3$) δ 7.68-7.75 (m, 2 H), 7.39-7.58 (m, 3 H), 7.28-7.37 (m, 7 H), 6.97-7.12 (m, 3 H), 6.74 (d, J = 8.0 Hz, 1 H), 5.07-5.14 (m, 1 H), 4.39-4.47 (m, 1 H), 3.86 (s, 3 H), 3.84 (s, 3 H), 3.42-3.61 (m, 1 H), 3.27-3.35 (m, 4 H), 2.62-2.85 (m, 3 H), 2.39-2.57 (m, 1 H), 2.11-2.28 (m, 1 H), and 1.45-1.72 (m, 5 H); MS (ES+) 683.8 (M + 1). |
| 97 | N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide<br>$^1$H NMR (300 MHz, CDCl$_3$) δ 7.54 (ovdd, J = 7.8 Hz, 1 H), 7.36-7.42 (m, 6 H), 7.02-7.13 (m, 3 H), 6.77 (d, J = 8.1 Hz, 1 H), 6.03 (s, 1 H), 5.01-5.24 (m, 2 H), 3.86 (s, 3 H), 3.84 (m, 3 H), 3.27-3.61 (m, 3 H), 3.05-3.17 (m, 2 H), 2.59-2.83 (m, 3 H), 2.40-2.56 (m, 4 H), 2.19-2.35 (m, 4 H), and 1.40-1.58 (m, 5 H); MS (ES+) 761.7 (M + 1). |
| 98 | 1-methyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.58 (ovdd, J = 7.4 Hz, 1 H), 7.28-7.43 (m, 8 H), 6.99-7.12 (m, 3 H), 6.77 (d, J = 8.2 Hz, 1 H), 5.05-5.16 (m, 1 H), 3.92-4.02 (m, 1 H), 3.86 (s, 3 H), 3.83 (s, 3 H), 3.71 (s, 3 H), 3.21-3.50 (m, 1 H), 3.26-3.39 (m, 4 H), 2.97-3.07 (m, 2 H), 2.58-2.81 (m, 3 H), 2.41-2.55 (m, 1 H), 2.19-2.33 (m, 1 H), and 1.0-1.67 (m, 5 H); MS (ES+) 687.8 (M + 1). |
| 99 | 2,5-dimethyl-furan-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.59 (ovdd, J = 7.8 Hz, 1 H), 7.46-7.53 (m, 5 H), 7.42 (d, J = 8.0 Hz, 1 H), 7.16 (d, J = 8.2 Hz, 1 H), 6.99-7.04 (m, 2 H), 6.79 (d, J = 8.1 Hz, 1 H), 6.03 (s, 1 H), 5.06-5.21 (m, 1 H), |

| Cpd | Name |
|---|---|
| | 4.43-4.58 (m, 1 H), 4.26-4.41 (m, 1 H), 3.82-4.01 (m, 7 H), 3.63-3.78 (m, 2 H), 3.24-3.48 (m, 3 H), 2.98-3.17 (m, 4 H), 2.41-2.68 (m, 6 H), 2.19-2.37 (m, 4 H), 1.85 (d, J = 8.3 Hz, 1 H), and 1.42-1.61 (m, 2 H); MS (ES+) 701.8 (M + 1). |
| 100 | 5-bromo-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.58 (ovdd, J = 7.7 Hz, 1 H), 7.19-7.38 (m, 7 H), 6.95-7.10 (m, 4 H), 6.74 (d, J = 8.0 Hz, 1 H), 5.10-5.16 (m, 1 H), 4.52-4.61 (m, 1 H), 3.86 (s, 3 H), 3.84 (s, 3 H), 3.44-3.59 (m, 1 H), 3.26-3.35 (m, 4 H), 3.01-3.11 (m, 2 H), 2.62-2.85 (m, 3 H), 2.42-2.58 (m, 1 H), 2.11-2.28 (m, 1 H), and 1.43-1.74 (m, 5 H); MS (ES+) 689.8 (M + 1). |
| 101 | 5-chloro-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.52 (ovdd, J = 8.0 Hz, 1 H), 7.23-7.39 (m, 6 H), 7.02-7.12 (m, 3 H), 6.78 (d, J = 8.2 Hz, 1 H), 5.09-5.21 (m, 1 H), 4.51-4.62 (m, 1 H), 3.86 (s, 3 H), 3.84 (s, 3 H), 3.77 (s, 3 H), 3.27-3.60 (m, 5 H), 2.97-3.05 (m, 2 H), 2.61-2.82 (m, 3 H), 2.49-2.55 (m, 1 H), 2.37 (s, 3 H), 2.18-2.30 (m, 1 H), and 1.42-1.73 (m, 5 H); MS (ES$^+$) 736.7 (M + 1). |
| 105 | thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.93 (s, 1 H), 7.60 (ovdd, J = 7.7 Hz, 1 H), 7.45-7.50 (m, 5 H), 7.42 (d, J = 7.2 Hz, 1 H), 7.34-7.38 (m, 1 H), 7.28-7.31 (m, 1 H), 7.11 (d, J = 8.2 Hz, 1 H), 6.91-7.02 (m, 3 H), 6.78 (d, J = 8.0 Hz, 1 H), 5.10-5.15 (m, 1 H), 4.60-4.71 (m, 1 H), 4.36-4.40 (m, 1 H), 3.92-3.95 (m, 1 H), 3.86 (s, 3 H), 3.84 (s, 3 H), 3.69-3.77 (m, 2 H), 3.40-3.60 (m, 3 H), 2.85-3.26 (m, 4 H), 2.41-2.60 (m, 1 H), 2.01-2.32 (m, 1 H), 1.85 (d, J = 6.8 Hz, 1 H), and 1.47-1.54 (m, 2 H); MS (ES+) 689.8 (M + 1). |
| 106 | pyridine-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 9.05 (s, 1 H), 8.75 (d, J = 4.8 Hz, 1 H), 8.10 (d, J = 8.1 Hz, 1 H), 7.53 (ovdd, J = 8.2 Hz, 1 H), 7.29-7.43 (m, 7 H), 7.00-7.11 (m, 3 H), 6.77 (d, J = 8.1 Hz, 1 H), 5.11-5.20 (m, 1 H), 4.62-4.72 (m, 1 H), 3.86 (s, 3 H), 3.84 (s, 3 H), 3.31-3.62 (m, 5 H), 3.01-3.08 (m, 2 H), 2.44-2.73 (m, 4 H), 2.17-2.29 (m, 1 H), and 1.42-1.62 (m, 5 H); MS (ES+) 684.7 (M |
| 107 | pyridine-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.58-8.63 (m, 1 H), 7.87-8.02 (m, 2 H), 7.40-7.62 (m, 9 H), 7.11 (d, J = 8.4 Hz, 1 H), 6.91-7.03 (m, 2 H), 6.77 (d, J = 8.1 Hz, 1 H), 5.11-5.16 (m, 1 H), 4.97-5.03 (m, 1 H), 4.79-4.83 (m, 1 H), 4.31-4.38 (m, 1 H), 3.86 (s, 3 H), 3.84 (s, 3 H), 3.68-3.75 (m, 2 H), 3.46-3.51 (m, 4 H), 3.05-3.19 (m, 4 H), 2.55-2.62 (m, 1 H), 2.22-2.36 (m, 1 H), 1.85 (d, J = 6.9 Hz, 1 H), and 1.40-1.46 (m, 2 H); MS (ES+) 684.7 (M + 1). |
| 108 | 5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.59 (ovdd, J = 7.6 Hz, 1 H), 7.44-7.50 (m, 5 H), 7.41 (d, J = 7.2 Hz, 1 H), 7.28 (s, 1 H), 7.02-7.20 (m, 3 H), 6.79 (d, J = 8.0 Hz, 1 H), 5.16-5.21 (m, 1 H), 4.32-4.40 (m, 1 H), 3.94-4.00 (m, 1 H), 3.87 (s, 3 H), 3.84 (s, 3 H), 3.72-3.80 (m, 2 H), 3.41-3.65 (m, 5 H), 3.05-3.21 (m, 2 H), 2.69-2.82 (m, 1 H), 2.24-2.47 (m, 4 H), 1.85 (d, J = 6.9 Hz, 1 H), and 1.57-1.74 (m, 2 H); MS (ES+) 688.8 (M + 1). |
| 109 | quinoline-8-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>MS (ES$^+$) 734.8 (M + 1). |
| 110 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-methanesulfonyl-methanesulfonamide<br>$^1$H NMR (300 MHz, CDCl$_3$) δ 7.28-7.61 (m, 7 H), 7.01-7.12 (m, 3 H), 6.79 (d, J = 8.2 Hz, 1 H), 5.16-5.26 (m, 2 H), 4.36-4.71 (m, 2 H), 3.63-3.94 (m, 9 H), 3.27-3.48 (m, 5 H), 3.02-3.19 (m, 5 H), 2.23-2.76 (m, 2 H), 1.85 (d, J = 6.7 Hz, 2 H), and 1.58-1.64 (m, 2 H); MS (ES+) 699.7 (M + 1). |
| 111 | 2-phenyl-ethenesulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.28-7.61 (m, 14 H), 6.91-7.10 (m, 3 H), 6.69-6.83 (m, 1 H), 5.15-5.21 (m, 1 H), 4.31-4.39 (m, 1 H), 3.84 (s, 3 |

-continued

| Cpd | Name |
|---|---|
| | H), 3.82 (s, 3 H), 3.35-3.72 (m, 5 H), 3.04-3.14 (m, 2 H), 2.45-2.97 (m, 4 H), 2.25-2.37 (m, 1 H), and 1.32-1.94 (m, 5 H); MS (ES+) 709.8 (M + 1). |
| 112 | 3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 7.53 (ovdd, J = 7.3 Hz, 1 H), 7.31-7.48 (m, 6 H), 7.02-7.20 (m, 3 H), 6.78 (d, J = 8.1 Hz, 1 H), 5.12-5.21 (m, 1 H), 4.54-4.58 (m, 1 H), 3.87 (s, 3 H), 3.84 (s, 3 H), 3.32-3.63 (m, 5 H), 2.88-3.04 (m, 2 H), 2.49-2.83 (m, 7 H), 2.37 (s, 3 H), 2.17-2.30 (m, 1 H), and 1.36-1.75 (m, 5 H); MS (ES+) 702.8 (M + 1). |
| 113 | 2,5-dichloro-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 7.55 (ovdd, J = 7.7 Hz, 1 H), 7.35-7.43 (m, 6 H), 7.01-7.16 (m, 4 H), 6.78 (d, J = 8.1 Hz, 1 H), 5.12-5.33 (m, 1 H), 4.80-4.94 (m, 1 H), 3.86 (s, 3 H), 3.84 (s, 3 H), 3.24-3.48 (m, 4 H), 2.68-3.20 (m, 6 H), 2.49-2.62 (m, 1 H), 2.17-2.33 (m, 1 H), and 1.29-1.64 (m, 5 H); MS (ES+) 758.7 (M + 1). |
| 114 | 1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 7.53 (dd, J = 8.2 Hz, J = 7.5 Hz, 1 H), 7.31-7.40 (m, 7 H), 7.01-7.10 (m, 3 H), 6.76 (d, J = 8.2 Hz, 1 H), 5.10-5.15 (m, 1 H), 4.91-4.95 (m, 1 H), 3.86 (s, 3 H), 3.83 (s, 3 H), 3.59 (s, 3 H), 3.40-3.49 (m, 5 H), 2.98-3.03 (m, 2 H), 2.62-2.94 (m, 3 H), 2.40-2.55 (m, 1 H), 2.33 (s, 13 H), 2.17-2.28 (m, 1 H), and 1.44-1.69 (m, 5 H); MS (ES+) 701.8 (M + 1). |
| 115 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-N,N-dimethyl-sulfamide<br>¹H NMR (300 MHz, CDCl₃) δ 7.53 (ovdd, J = 7.3 Hz, 1 H), 7.29-7.51 (m, 6 H), 7.06-7.11 (m, 3 H), 6.78 (d, J = 8.1 Hz, 1 H), 5.17-5.22 (m, 1 H), 4.06-4.14 (m, 1 H), 3.87 (s, 3 H), 3.84 (s, 3 H), 3.37-3.49 (m, 6 H), 3.06-3.13 (m, 4 H), 2.76 (s, 6 H), 2.49-2.59 (m, 1 H), 2.17-2.33 (m, 1 H), and 1.49-1.62 (m, 5 H); MS (ES+) 650.8 (M + 1). |
| 116 | benzo[b]thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 8.20 (s, 1 H), 8.14 (d, J = 7.4 Hz, 1 H), 7.83 (d, J = 7.9 Hz, 1 H), 7.28-7.54 (m, 9 H), 7.08 (d, J = 8.3 Hz, 1 H), 6.89-6.99 (m, 2 H), 6.73 (d, J = 8.3 Hz, 1 H), 5.02-5.12 (m, 1 H), 4.65-4.69 (m, 1 H), 3.87 (s, 6 H), 3.55-3.60 (m, 1 H), 3.20-3.38 (m, 4 H), 2.94-3.04 (m, 2 H), 2.59-2.83 (m, 3 H), 2.36-2.45 (m, 1 H), 2.07-2.19 (m, 1 H), and 1.29-1.65 (m, 5 H); MS (ES+) 739.7 (M + 1). |
| 117 | N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-C-phenyl-methanesulfonamide<br>¹H NMR (300 MHz, CDCl₃) δ 7.54 (ovdd, J = 8.1 Hz, 1 H), 7.30-7.49 (m, 11 H), 7.03-7.15 (m, 3 H), 6.78 (d, J = 8.1 Hz, 1 H), 5.12-5.18 (m, 1 H), 4.22 (s, 2 H), 4.07-4.19 (m, 1 H), 3.86 (s, 3 H), 3.84 (s, 3 H), 3.26-3.62 (m, 5 H), 2.96-3.05 (m, 2 H), 2.55-2.80 (m, 3 H), 2.39-2.52 (m, 1 H), 2.16-2.28 (m, 1 H), and 1.33-1.61 (m, 5 H); MS (ES+) 697.8 (M + 1). |

Example 23

(R)-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide Cpd 118

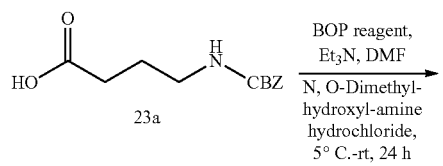

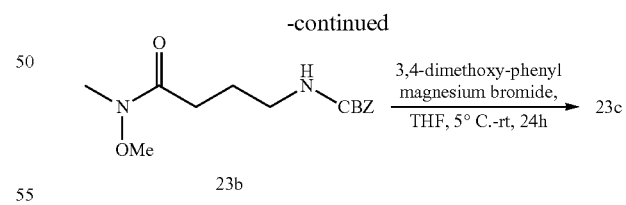

A 500-mL round bottom flask was charge with Compound 23a (4.2 g, 20.6 mmol) and dimethylformamide (207 mL). The mixture was cooled using an ice/water bath. Triethylamine (8.8 mL, 63.1 mmol) was added to the mixture followed by the benzotriazol-1-yloxy-tris(dimethylamino) phosphonium hexafluorophosphate (10.0 g, 22.6 mmol). N,O-dimethyl-hydroxyl-amine hydrochloride (3.1 g, 31.8 mmol) was added and the mixture was stirred at room temperature for 24 h. The mixture was concentrated in vacuo. The crude oil was diluted with ethyl acetate (500 mL) and transferred to a separatory funnel. The organic layer was washed with 1N HCl (2×300 mL), 1N NaOH (2×300 mL), and water (2×300 mL). The organic layer was dried using MgSO4, filtered through Celite®, and concentrated in vacuo to give 5.08 g of Compound 23b as a clear oil. $^1$H NMR (300 MHz, CDCl$_3$) δ 7.26-7.41 (m, 5 H), 5.09 (s, 2 H), 3.19-3.37 (m, 2 H), 3.16 (s, 3 H), 2.87-2.97 (m, 2 H), 2.85 (s, 3 H), and 1.83-1.90 (m, 2 H).

A 1 L round bottom flask was charged with Compound 23b (5.08 g, 20.7 mmol) and tetrahydrofuran (415 mL). The mixture was cooled using an ice/water bath. A solution of 3,4-Dimethoxy-phenyl magnesium bromide in tetrahydrofuran (207 mL, 104 mmol) was added dropwise via addition funnel over 30 minutes. The mixture was allowed to warm to room temperature and stirred for 20 h. Water (150 mL) was added to the mixture and concentrated in vacuo. The mixture was extracted with dichloromethane (600 mL) and washed with water (2×300 mL). The organic layer was dried with MgSO4, filtered through Celite®, concentrated in vacuo, and purified via flash chromatography (230-400 mesh silica gel 60, gradient 90:10-50:50 Hexanes:Ethyl Acetate) to give 4.0 g of Compound 23c as a white solid. $^1$H NMR (300 MHz, CDCl$_3$) δ 7.57 (d, J=8.4 Hz, 1 H), 7.51 (s, 1 H), 7.29-7.44 (m, 5 H), 6.88 (d, J=8.4 Hz, 1 H), 5.08 (s, 2 H), 3.95 (s, 3 H), 3.93 (s, 3 H), 3.27-3.34 (m, 2 H), 2.97-3.02 (m, 2 H), and 1.92-2.01 (m, 2 H); MS (ES$^+$) 358 (M+1).

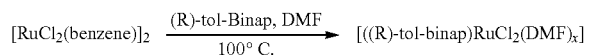

A 200-mL Schlenk tube was charged with [RuCl$_2$(benzene)]$_2$ (2.0 g, 4.0 mmol) and R-tol-BINAP (5.7 g, 8.4 mmol). The tube was put under vacuum for 15 minutes and then back flushed with argon. Dimethylformamide (133 mL, degassed with argon) was added to the tube and the mixture was flushed with argon. The tube was closed and heated to 100° C. for 10 minutes (stirring). The DMF was then removed under high vacuum at 70° C. to give [((R)-tol-binap)RuCl2(DMF)x] as a reddish/brown solid (See, Org. Syn. 71, 1993, 1-13).

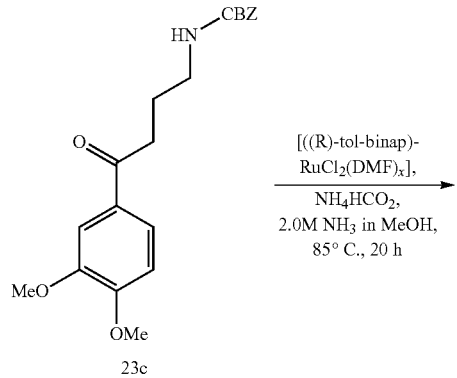

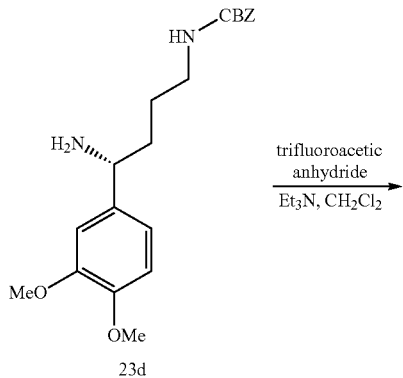

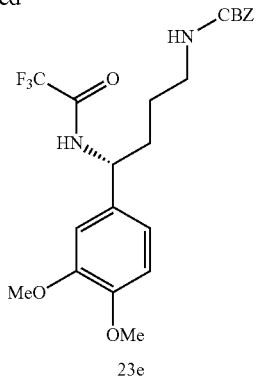

A 200-mL sealed tube was charged with Compound 23c (8.66 g, 24.2 mmol), [((R)-tol-binap)RuCl2(DMF)x] (2.1 g, 2.5 mmol), ammonium formate (15.3 g, 242.6 mmol), and a 2.0M solution of ammonia in methanol (97 mL). The tube was flushed with argon and sealed. The mixture was heated to 85° C. for 22 h. The mixture was cooled to room temperature and the sealed tube was opened carefully due to the release of pressure from excess ammonia. The mixture was concentrated in vacuo and diluted with 1N HCl (300 mL) and ethanol (150 mL). Heat to reflux for 2 h, then cool to room temperature and washed with diethyl ether (1×500 mL). The aqueous layer was basified with 3N NaOH to pH>10. Extraction using dichloromethane (3×400 mL) followed by drying of the organic layers with MgSO4, filtered through Celite®, and concentrated in vacuo to give 15.66 g of Compound 23d as a white solid. $^1$H NMR (300 MHz, CDCl$_3$) δ 7.30-7.34 (m, 5 H), 6.81-6.87 (m, 3 H), 5.08 (s, 2 H), 3.83-3.90 (m, 7 H), 3.16-3.22 (m, 2 H), and 1.38-1.71 (m, 6 H); MS (ES$^+$) 359 (M+1); Daicel Chiralpak AD-H, 4.6 mm×15 cm, Hex:IPA: 0.1% DEA (86:14), 1.0 ml/min, S-enantiomer 13.57 min, R-enantiomer 15.67 min (23d), 96% ee.

A 500-mL round bottom flask was charged with Compound 23d (15.66 g, 0.044 mol) and dichlormethane (220 mL). The mixture was cooled using an ice/water bath. Triethylamine (7.4 mL, 0.053 mol) was added followed by the dropwise addition of trifluoroaceticanhydride (6.8 mL, 0.049 mol). After 3 hours the mixture was extracted with dichloromethane (200 mL) and washed with 1N HCl (1×100 mL), 1N NaOH (1×100 mL), and water (1×100 mL). The organic layer was dried with MgSO4, filtered through Celite®, concentrated in vacuo to give 19.49 g (98%) of Compound 23e as a white solid. $^1$H NMR (300 MHz, CDCl$_3$) δ 7.31-7.35 (m, 5 H), 6.80-6.89 (m, 3 H), 5.10 (s, 2 H), 4.81-4.93 (m, 1 H), 3.87 (ovs, 6 H), 3.13-3.28 (m, 2 H), 1.80-2.00 (m, 2 H), and 1.42-1.59 (m, 2 H); MS (ES$^+$) 455 (M+1).

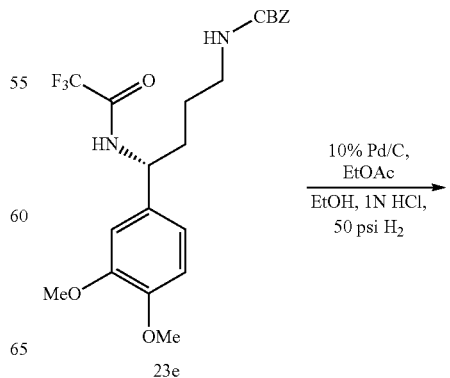

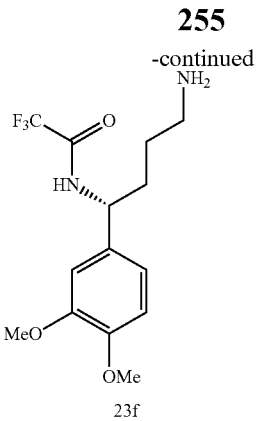

23f

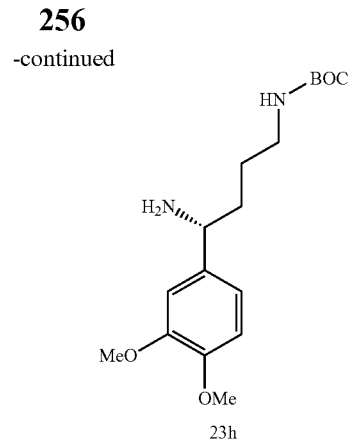

23h

A 500-mL round bottom flash was charge with Compound 23g (12.78 g, 0.030 mol), tetrahydrofuran (150 mL), methanol (40 mL), and 3N sodium hydroxide (30 mL). After 3 hours the mixture was diluted with dichloromethane (500 mL) and washed with water (1×100 mL). The organic layer was dried with MgSO$_4$, filtered through Celite®, and concentrated in vacuo. The crude material was purified via flash silica gel chromatography (230-400 mesh silica gel 60, gradient 90:10-40:60 hexanes:EtOAc) to give 9.73 g (99%) of Compound 23h as a white solid. $^1$H NMR (300 MHz, CDCl$_3$) δ 6.87 (s, 1 H), 6.82-6.84 (m, 2 H), 3.84-3.90 (m, 7 H), 3.08-3.14 (m, 2 H), 1.62-1.71 (m, 4 H), and 1.43 (s, 9 H); MS (ES$^+$) 325 (M+1).

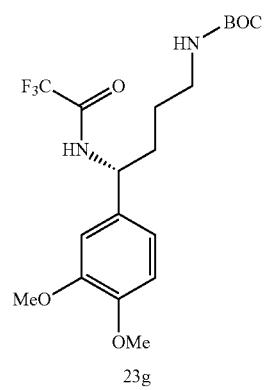

23g

A 500-mL hydrogenation vessel was charge with Compound 23e (19.49 g, 0.043 mol), ethyl acetate (80 mL), ethanol (70 mL), 1N HCl (20 mL), and 10% palladium on carbon (2.0 g). The mixture was hydrogenated at 50 psi hydrogen for 24 hours. The mixture was filtered through Celite® and concentrated in vacuo to give 13.77 g (90%) of Compound 23f as a white solid. $^1$H NMR (300 MHz, CDCl$_3$) δ 7.29-7.33 (m, 5 H), 6.81-6.86 (m, 3 H), 5.07 (s, 2 H), 4.80-4.89 (m, 1 H), 3.86 (ovs, 6 H), 3.15-3.25 (m, 2 H), and 1.35-1.64 (m, 6 H); MS (ES$^+$) 321 (M+1).

A 500-mL round bottom flash was charge with Compound 23f (16.85 g, 0.047 mol), dichloromethane (220 mL), and triethylamine (14.0 mL, 0.10 mol). The mixture was cooled using an ice/water bath. Di-tert-butyl dicarbonate (9.77 g, 0.045 mol) was added in one portion. The mixture was stirred at room temperature for 18 hours. The mixture was diluted with dichloromethane (300 mL) and washed with 1N HCl (1×100 mL), 1N NaOH (1×100 mL), and water (1×100 mL). The organic layer was dried with MgSO$_4$, filtered through Celite®, and concentrated in vacuo to give 12.78 g (64%) of Compound 23g as a white solid.

$^1$H NMR (300 MHz, CDCl$_3$) δ 6.81-6.85 (m, 2 H), 6.78 (s, 1 H), 4.86-4.94 (m, 1 H), 3.89 (s, 3 H), 3.87 (s, 1 H), 3.09-3.24 (m, 2 H), 1.82-2.00 (m, 2 H), 1.47-1.57 (m, 2 H), and 1.44 (s, 9 H).

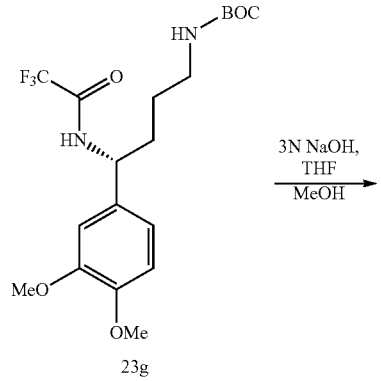

23g

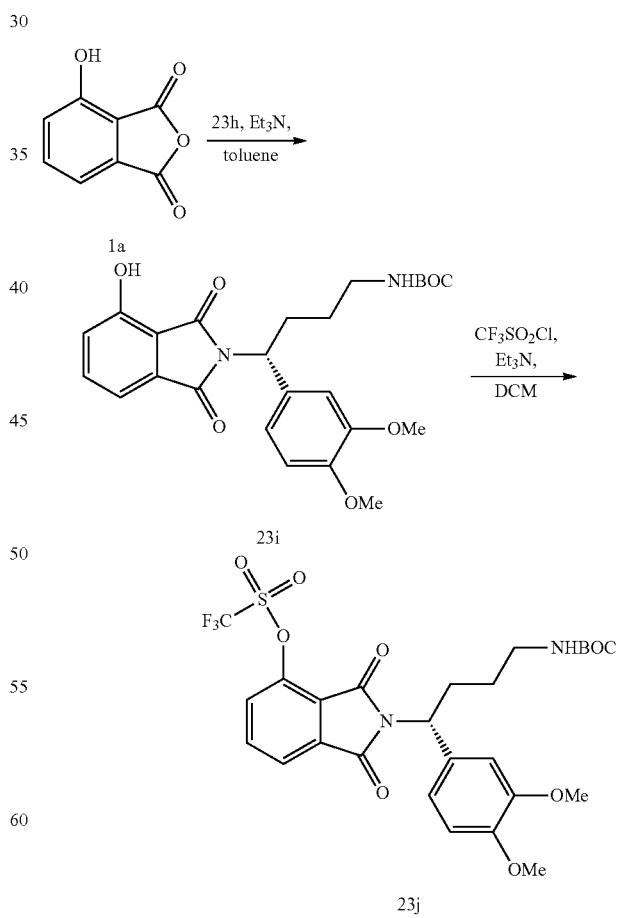

23i

23j

A 50-mL round bottom flask was charged with phthalic anhydride Compound 1a (1.1 g, 6.70 mmol) and dry toluene (30 mL). Compound 23h (2.2 g, 6.79 mmol) and triethylamine (1.2 mL, 8.61 mmol) were added to the mixture. A Dean-Stark trap was attached to the flask and the mixture was refluxed for 24 h. The mixture was cooled to room temperature, diluted with dichloromethane (200 mL), and washed with 1.0 N HCl (100 mL). The organic layer was dried using $MgSO_4$, filtered through Celite®, and concentrated in vacuo to give 3.1 g (98%) of Compound 23i as a yellow solid. $^1$H NMR (300 MHz, $CDCl_3$) δ 7.66-7.70 (m, 1 H), 7.52-7.57 (m, 1 H), 7.06-7.16 (m, 1 H), 6.79-6.88 (m, 3 H), 5.16-5.21 (m, 1 H), 3.88 (s, 3 H), 3.85 (s, 3 H), 3.06-3.19 (m, 1 H), 2.49-2.56 (m, 1 H), 2.26-2.33 (m, 1 H), 1.46-1.56 (m, 2 H), and 1.42 (s, 9 H).

A 500-mL round bottom flask was charged with Compound 23i (6.60 g, 0.014 mol), DCM (60 mL), and $Et_3N$ (2.3 mL, 0.017 mol). The mixture was cooled using an ice/water bath. A solution of trifluoromethanesulfonyl chloride (1.6 mL, 0.015 mol) in dichlormethane (10 mL) was added dropwise via an addition funnel. The mixture was stirred for 1 h in an ice/water bath. The mixture was diluted with dichloromethane (200 mL), washed with 1.0 N HCl (100 mL), and saturated aqueous sodium bicarbonate (1×100 mL). The organic layer was dried using $MgSO_4$, filtered through Celite®, and concentrated in vacuo to give 7.06 g (84%) of Compound 23j as a yellow solid. $^1$H NMR (300 MHz, $CDCl_3$) δ 7.76-7.83 (m, 2 H), 7.51 (d, J=7.8 Hz, 1 H), 7.07-7.12 (m, 2 H), 6.80 (d, J=8.0 Hz, 1 H), 5.22-5.27 (m, 1 H), 3.88 (s, 3 H), 3.85 (s, 3 H), 3.16-3.26 (m, 2 H), 2.42-2.59 (m, 1 H), 2.29-2.40 (m, 1 H), 1.55-1.66 (m, 2 H), and 1.42 (s, 9 H); MS (ES$^+$) 603 (M+1).

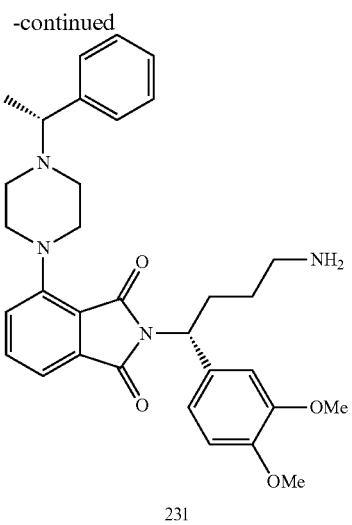

231

A 50-mL sealed tube was charged with Compound 23j (7.53 g, 0.013 mol), Compound 13h (2.50 g, 0.013 mol), toluene (13 mL), and $Et_3N$ (2.4 mL, 0.017 mol). The tube was sealed under argon and heated to 110° C. for 21 h. The mixture was cooled to room temperature and purified via flash silica gel chromatography (230-400 mesh silica gel 60, 80:20 hexanes:EtOAc) to give 4.61 g (57%) of Compound 23k as a yellow solid. $^1$H NMR (300 MHz, $CDCl_3$) δ 7.48-7.54 (m, 1 H), 7.23-7.36 (m, 7 H), 7.07-7.11 (m, 2 H), 6.78 (d, J=8.2 Hz, 1 H), 5.18-5.23 (m, 1 H), 4.08-4.16 (m, 1 H), 3.87 (s, 3 H), 3.83 (s, 3 H), 3.26-3.45 (m, 4 H), 3.14-3.22 (m, 2 H), 2.72-2.76 (m, 2 H), 2.55-2.64 (m, 2 H), 2.44-2.52 (m, 1 H), 2.23-2.30 (m, 1 H), and 1.38-1.54 (m, 14 H); MS (ES$^+$) 643 (M+1).

A 50-mL round bottom flask was charged with Compound 23k (1.90 g, 2.95 mmol) and dioxane (15.0 mL). 4.0N HCl in dioxane (10.0 mL) was added and the mixture was stirred at room temperature for 4 h. The mixture was concentrated in-vacuo. The crude solid Compound 23l (1.0 g, 1.63 mmol) was dissolved in dichloromethane (8.2 mL).

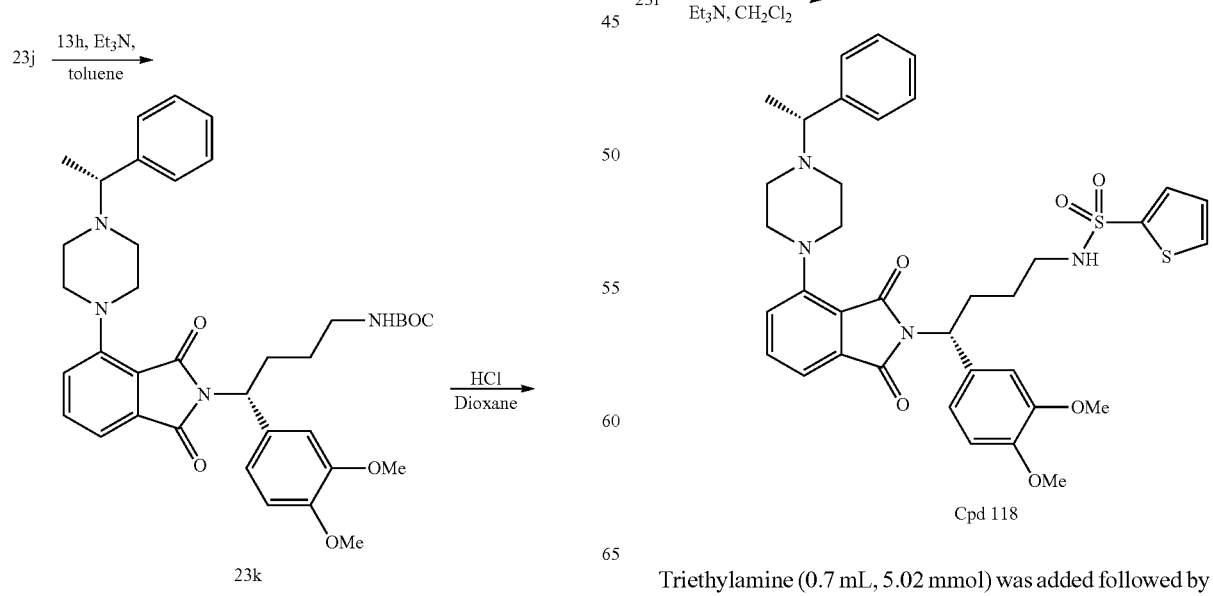

Cpd 118

Triethylamine (0.7 mL, 5.02 mmol) was added followed by 2-thiophene-sulfonyl chloride (0.37 g, 2.03 mmol). The mixture was stirred at room temperature for 24 h and concentrated in vacuo. The crude oil was purified on a Gilson HPLC with a reversed phase Kromasil column (10μ, 100 Å C18, column length 250×50 mm, gradient 80:20-0:100 H$_2$O:MeCN). The purified material was dissolved in dichlormethane (50 mL), treated with 1M HCl in diethyl ether (10 mL), and concentrated in vacuo. This procedure was repeated two more times to give 1.18 g (96%) of the title Compound 118 as a yellow solid. $^1$H NMR (300 MHz, CDCl$_3$) δ 7.68-7.71 (m, 2 H), 7.45-7.61 (m, 7 H), 7.12-7.21 (m, 1 H), 6.98-7.10 (m, 3 H), 6.94 (d, J=8.2 Hz, 1 H), 5.06-5.15 (m, 1 H), 4.76-4.80 (m, 1 H), 3.92-4.20 (m, 2 H), 3.86 (s, 3 H), 3.84 (s, 3 H), 3.61-3.77 (m, 3 H), 3.25-3.41 (m, 1 H), 3.01-3.16 (m, 4 H), 2.49-2.60 (m, 1 H), 2.19-2.27 (m, 1 H), 1.98 (d, J=6.8 Hz, 3 H), and 1.42-1.59 (m, 2 H); MS (ES$^+$) 689 (M+1); Anal. Calcd for C$_{36}$H$_{40}$N$_4$O$_6$S$_2$.1.4 HCl.0.6H$_2$O: C, 57.60; H, 5.72; N, 7.46; Cl, 6.61; H$_2$O, 1.44. Found: C, 57.91; H, 5.64; N, 7.17; Cl, 6.84; H$_2$O, 1.63; [α]$^{25}_D$=+ 40.2 (c 1.0, CHCl$_3$).

Other compounds of the present invention may be prepared by those skilled in the art by varying the starting materials, reagent(s) and conditions used. Using the procedure of Example 23, the following compounds were prepared:

| Cpd | Name |
|---|---|
| 120 | 1-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-thiophen-2-yl-urea<br>$^1$H NMR (300 MHz, CDCl$_3$) δ 7.39-7.62 (m, 7 H), 6.74-7.12 (m, 5 H), 6.61-6.67 (m, 1 H), 5.13-5.22 (m, 1 H), 4.28-4.42 (m, 1 H), 3.81-3.95 (m, 7 H), 3.61-3.76 (m, 2 H), 3.21-3.50 (m, 5 H), 2.93-3.15 (m, 2 H), 2.48-2.51 (m, 1 H), 2.12-2.29 (m, 1 H), 1.84 (d, J = 6.9 Hz, 3 H), and 1.43-1.58 (m, 2 H); MS (ES$^+$) 668.2 (M + 1). |
| 121 | 1-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-3-thiophen-2-yl-urea<br>$^1$H NMR (300 MHz, CDCl$_3$) δ 7.51-7.56 (m, 1 H), 4.71-7.49 (m, 6 H), 7.22-7.38 (m, 3 H), 6.81-6.87 (m, 3 H), 6.21-6.49 (m, 1 H), 5.17-5.23 (m, 1 H), 4.12-4.19 (m, 1 H), 3.74-3.90 (m, 7 H), 3.35-3.68 (m, 5 H), 2.98-3.28 (m, 6 H), 2.72-2.86 (m, 1 H), 2.24-2.32 (m, 1 H), and 1.85 (d, J = 6.9 Hz, 5 H); MS (ES+) 654.8 (M + 1). |
| 124 | (R)-2,4-dimethyl-thiazole-5-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.60 (ovdd, J = 7.8 Hz, 1 H), 7.44-7.51 (m, 5 H), 7.42 (d, J = 7.2 Hz, 1 H), 7.11 (d, J = 8.2 Hz, 1 H), 6.99-7.03 (m, 2 H), 6.78 (d, J = 8.1 Hz, 1 H), 5.10-5.16 (m, 1 H), 4.84-4.95 (m, 1 H), 4.37-4.42 (m, 1 H), 3.93-3.97 (m, 1 H), 3.86 (s, 3 H), 3.84 (s, 3 H), 3.69-3.77 (m, 2 H), 3.38-3.51 (m, 3 H), 2.98-3.25 (m, 4 H), 2.68 (s, 3 H), 2.46-2.60 (m, 4 H), 2.19-2.37 (m, 1 H), 1.85 (d, J = 6.9 Hz, 1 H), and 1.45-1.62 (m, 2 H); MS (ES+) 718.8 (M + 1). |
| 125 | (R)-3,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.59 (ovdd, J = 7.7 Hz, 1 H), 7.45-7.52 (m, 5 H), 7.42 (d, J = 7.2 Hz, 1 H), 7.10 (d, J = 8.2 Hz, 1 H), 6.97-7.02 (m, 2 H), 6.77 (d, J = 8.2 Hz, 1 H), 5.09-5.14 (m, 1 H), 4.37-4.42 (m, 1 H), 3.94-4.07 (m, 1 H), 3.85 (s, 3 H), 3.83 (s, 3 H), 3.67-3.77 (m, 2 H), 3.38-3.54 (m, 3 H), 2.98-3.13 (m, 4 H), 2.47-2.57 (m, 1 H), 2.44 (s, 3 H), 2.17-2.27 (m, 1 H), 1.86 (d, J = 6.9 Hz, 3 H), and 1.42-1.57 (m, 2 H); MS (ES+) 701.8 (M + 1). |
| 126 | (R)-5-methyl-thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.59 (ovdd, J = 7.6 Hz, 1 H), 7.45-7.53 (m, 5 H), 7.41 (d, J = 7.2 Hz, 1 H), 7.37 (d, J = 3.7 Hz, 1 H), 7.11 (d, J = 8.2 Hz, 1 H), 6.98-7.03 (m, 2 H), 6.79 (d, J = 8.2 Hz, 1 H), 6.69 (d, J = 3.6 Hz, 1 H), 5.10-5.16 (m, 1 H), 4.47-4.60 (m, 1 H), 4.35-4.39 (m, 1 H), 3.91-4.09 (1 H), 3.86 (s, 3 H), 3.84 (s, 3 H), 3.62-3.72 (m, 2 H), 3.34-3.52 (m, 2 H), 2.96-3.28 (m, 5 H), 2.44-2.61 (m, 4 H), 2.18-2.35 (m, 1 H), 1.86 (d, J = 6.7 Hz, 3 H), and 1.29-1.67 (m, 2 H); MS (ES+) 703.8 (M + 1). |
| 127 | (R)-2,3-dimethyl-3H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.62 (s, 1 H), 7.56 (ovdd, J = 7.7 Hz, 1 H), 7.44-7.51 (m, 5 H), 7.38 (d, J = 7.3 Hz, 1 H), 7.07 (d, J = 8.3 Hz, 1 H), 6.96-7.02 (m, 2 H), 6.76-6.91 (m, 2 H), 5.11-5.16 (m, 1 H), 4.26-4.35 (m, 1 H), 3.60-3.87 (m, 12 H), 3.43-3.58 (m, 3 H), 2.99-3.30 (m, 4 H), 2.52-2.69 (m, 4 H), 2.14-2.21 (m, 1 H), 1.83 (d, J = 6.8 Hz, 3 H), and 1.48-1.61 (m, 2 H); MS (ES+) 701.8 (M + 1). |
| 128 | (R)-1,3-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.71 (s, 1 H), 7.59 (ovdd, J = 7.6 Hz, 1 H), 7.45-7.52 (m, 5 H), 7.41 (d, J = 7.2 Hz, 1 H), 7.10 (d, J = 8.2 Hz, 1 H), 6.91-7.03 (m, 2 H), 6.78 (d, J = 8.2 Hz, 1 H), 5.10-5.15 (m, 1 H), 4.53-4.63 (m, 1 H), 4.30-4.39 (m, 1 H), 3.93-4.10 (1 H), 3.87 (s, 3 H), 3.86 (s, 3 H), 3.84 (s, 3 H), 3.60-3.72 (m, 2 H), 3.36-3.50 (m, 3 H), 2.98-3.34 (m, 4 H), 2.47-2.58 (m, 1 H), 2.37 (s, 3 H), 2.21-2.31 (m, 1 H), 1.86 (d, J = 6.8 Hz, 3 H), and 1.46-1.57 (m, 2 H); MS (ES+) 701.8 (M + 1). |

| Cpd | Name |
|---|---|
| 130 | (R)-N-[5-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butylsulfamoyl)-4-methyl-thiazol-2-yl]-acetamide<br>$^1$H NMR (300 MHz, CDCl$_3$) δ 7.58 (ovdd, J = 8.0 Hz, 1 H), 7.46-7.51 (m, 5 H), 7.40 (d, J = 7.1 Hz, 1 H), 7.09 (d, J = 8.4 Hz, 1 H), 6.91-7.01 (m, 2 H), 6.77 (d, J = 8.1 Hz, 1 H), 5.08-5.14 (m, 1 H), 4.79-4.83 (m, 1 H), 4.29-4.35 (m, 1 H), 3.97 (s, 3 H), 3.86 (s, 3 H), 3.84 (s, 3 H), 3.32-3.76 (m, 4 H), 2.68-3.16 (m, 7 H), 2.59 (s, 3 H), 2.06-2.48 (m, 4 H), 1.88 (d, J = 6.9 Hz, 1 H), and 1.49-1.60 (m, 2 H); MS (ES+) 761.7 (M + 1). |
| 131 | (R)-2,5-dimethyl-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.35-7.71 (m, 7 H), 6.91-7.14 (m, 3 H), 6.76-6.83 (m, 2 H), 5.10-5.16 (m, 1 H), 4.35-4.39 (m, 1 H), 3.86 (s, 3 H), 3.84 (s, 3 H), 3.16-3.59 (m, 5 H), 2.98-3.11 (m, 2 H), 2.41-2.85 (m, 7 H), 2.09-2.36 (m, 4 H), and 1.43-1.81 (m, 5 H); MS (ES+) 718.2 (M + 1). |
| 132 | (R)-1,5-dimethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.69 (s, 1 H), 7.36-7.61 (m, 7 H), 6.91-7.11 (m, 3 H), 6.77 (d, J = 8.2 Hz, 1 H), 5.10-5.19 (m, 1 H), 4.31-4.40 (m, 1 H), 3.86 (s, 3 H), 3.84 (s, 3 H), 3.79 (s, 3 H), 3.29-3.72 (m, 5 H), 2.96-3.10 (m, 2 H), 2.66-2.88 (m, 3 H), 2.38-2.56 (m, 4 H), 2.17-2.29 (m, 1 H), and 1.43-1.78 (m, 5 H); MS (ES+) 701.2 (M + 1). |
| 133 | (R)-1,1-dioxo-tetrahydro-1λ$^6$-thiophene-3-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.55 (ovdd, J = 7.8 Hz, 1 H), 7.35-7.40 (m, 6 H), 7.03-7.12 (m, 3 H), 6.78 (d, J = 8.0 Hz, 1 H), 5.16-5.22 (m, 1 H), 3.86 (s, 3 H), 3.84 (s, 3 H), 3.06-3.63 (m, 10 H), 2.63-2.97 (m, 3 H), 2.45-2.61 (m, 5 H), 2.13-2.33 (m, 1 H), and 1.42-1.83 (m, 8 H); MS (ES+) 725.3 (M + 1). |
| 134 | (R)-1-ethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.78 (s, 1 H), 7.74 (s, 1 H), 7.37-7.63 (m, 7 H), 7.01-7.12 (m, 3 H), 6.77 (d, J = 8.2 Hz, 1 H), 5.12-5.17 (m, 1 H), 4.30-4.40 (m, 1 H), 4.18 (q, J = 7.3 Hz, 2 H), 3.97 (s, 3 H), 3.86 (s, 3 H), 3.84 (s, 3 H), 3.20-3.78 (m, 5 H), 2.99-3.06 (m, 2 H), 2.56-2.86 (m, 3 H), 2.47-2.52 (m, 1 H), 2.17-2.30 (m, 1 H), and 1.43-1.74 (m, 8 H); MS (ES+) 701.2 (M + 1). |
| 135 | (R)-1-methyl-3-trifluoromethyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.89 (s, 1 H), 7.40-7.76 (m, 7 H), 7.11 (d, J = 8.0 Hz, 1 H), 6.91-7.04 (m, 2 H), 6.78 (d, J = 8.1 Hz, 1 H), 5.11-5.16 (m, 1 H), 4.15-4.29 (m, 1 H), 3.97 (s, 3 H), 3.86 (s, 3 H), 3.84 (s, 3 H), 3.63-3.74 (m, 2 H), 3.27-3.49 (m, 2 H), 2.98-3.02 (m, 4 H), 2.55-2.74 (m, 1 H), 2.13-2.28 (m, 1 H), 1.96-2.10 (m, 2 H), and 1.43-1.70 (m, 5 H); MS (ES+) 655.8 (M + 1). |
| 136 | (R)-1-methyl-1H-pyrazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.77 (s, 1 H), 7.73 (s, 1 H), 7.32-7.65 (m, 7 H), 6.91-7.15 (m, 3 H), 6.77 (d, J = 8.2 Hz, 1 H), 5.03-5.17 (m, 1 H), 4.48-4.60 (m, 1 H), 3.92 (s, 3 H), 3.86 (s, 3 H), 3.83 (s, 3 H), 3.27-3.69 (m, 5 H), 2.97-3.04 (m, 2 H), 2.69-2.88 (m, 3 H), 2.49-2.58 (m, 1 H), 2.20-2.32 (m, 1 H), and 1.43-1.72 (m, 5 H); MS (ES+) 687.8 (M + 1). |
| 137 | (R)-5-fluoro-3-methyl-benzo[b]thiophene-2-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.71-7.79 (m, 1 H), 7.50-7.55 (m, 1 H), 7.31-7.45 (m, 7 H), 7.20-7.26 (m, 1 H), 7.12 (d, J = 8.0 Hz, 1 H), 6.92-7.02 (m, 3 H), 6.72 (d, J = 8.1 Hz, 1 H), 5.05-5.16 (m, 1 H), 4.84-5.01 (m, 1 H), 3.78-3.85 (m, 7 H), 3.43-3.76 (m, 3 H), 3.05-3.19 (m, 4 H), 2.93-3.01 (m, 2 H), 2.61 (s, 3 H), 2.42-2.58 (m, 1 H), 2.18-2.27 (m, 1 H), 1.78-2.02 (m, 2 H), and 1.41-1.68 (m, 5 H); MS (ES$^+$) 771.7 (M + 1). |
| 138 | (R)-5-methyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.42-7.64 (m, 7 H), 7.38 (d, J = 8.2 Hz, 1 H), 7.01-7.13 (m, 3 H), 6.78 (d, J = 8.1 Hz, 1 H), 5.16-5.21 (m, 1 H), 4.21-4.30 (m, 1 H), 3.86 (s, 3 H), 3.83 (s, 3 H), 3.59-3.68 (m, 3 H), 3.34-3.48 (m, 1 H), 3.01-3.16 (m, 6 H), 2.62-2.70 (m, 1 H), 2.20-2.33 (m, 4 H), 1.94 (d, J = 6.0 Hz, 3 H), and 1.63-1.82 (m, 2 H); [α]25$_D$ = +31.4 (c 0.98, CHCl$_3$). |

| Cpd | Name |
|---|---|
| 139 | (R)-3,5-dimethyl-isoxazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 7.38-7.69 (m, 8 H), 7.11 (d, J = 8.3 Hz, 1 H), 6.97-7.06 (m, 2 H), 6.77 (d, J = 8.2 Hz, 1 H), 5.01-5.20 (m, 2 H), 3.92-4.19 (m, 2 H), 3.86 (s, 3 H), 3.84 (s, 3 H), 3.61-3.80 (m, 3 H), 3.33-3.44 (m, 1 H), 2.98-3.25 (m, 4 H), 2.61 (s, 3 H), 2.43-2.55 (m, 1 H), 2.38 (s, 1 H), 2.21-2.34 (m, 1 H), 1.98 (d, J = 6.8 Hz, 3 H), and 1.52-1.62 (m, 2 H); MS (ES+) 702.8 (M + 1); [α]25$_D$ = +43.0 (c 1.29, CHCl₃). |
| 140 | (R)-1,2-dimethyl-1H-imidazole-4-sulfonic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 7.33-7.75 (m, 8 H), 6.98-7.11 (m, 3 H), 6.77 (d, J = 8.3 Hz, 1 H), 5.11-5.17 (m, 1 H), 4.22-4.26 (m, 1 H), 3.92-4.19 (m, 14 H), 3.32-3.49 (m, 1 H), 3.18-3.29 (m, 1 H), 2.99-3.15 (m, 2 H), 2.73 (s, 3 H), 2.53-2.61 (m, 1 H), 2.17-2.35 (m, 1 H), 1.98 (d, J = 6.6 Hz, 3 H), and 1.50-1.61 (m, 2 H); MS (ES+) 701.8 (M + 1); [α]25$_D$ = +26.0 (c 1.18, CHCl₃). |
| 168 | (R)-thiophene-2-sulfonic acid {4-(3,4-dimethoxy-phenyl)-4-[4-(4-ethyl-piperazin-1-yl)-1,3-dioxo-1,3-dihydro-isoindol-2-yl]-butyl}-amide<br>¹H NMR (300 MHz, CDCl₃) δ 7.54-7.64 (m, 3 H), 7.44 (d, J = 7.1 Hz, 1 H), 7.14 (d, J = 8.1 Hz, 1 H), 7.02-7.06 (m, 3 H), 6.79 (d, J = 8.0 Hz, 1 H), 5.10-5.19 (m, 1 H), 4.64-4.76 (m, 1 H), 3.88 (s, 3 H), 3.85 (s, 3 H), 3.74-3.78 (m, 2 H), 3.50-3.66 (m, 2 H), 3.09-3.37 (m, 6 H), 2.52-2.65 (m, 1 H), 2.05-2.30 (m, 3 H), 1.50-1.61 (m, 2 H), and 1.44 (t, J = 7.3 Hz, 3 H); MS (ES⁺) 613.3 (M + 1). |
| 169 | (R)-thiophene-2-sulfonic acid {4-(3,4-dimethoxy-phenyl)-4-[4-(4-methyl-piperazin-1-yl)-1,3-dioxo-1,3-dihydro-isoindol-2-yl]-butyl}-amide<br>¹H NMR (300 MHz, CDCl₃) δ 7.54-7.64 (m, 3 H), 7.45 (d, J = 7.2 Hz, 1 H), 7.13 (d, J = 8.3 Hz, 1 H), 7.02-7.06 (m, 3 H), 6.79 (d, J = 8.1 Hz, 1 H), 5.13-5.19 (m, 1 H), 4.62-4.77 (m, 1 H), 3.88 (s, 3 H), 3.85 (s, 3 H), 3.64-3.72 (m, 4 H), 3.39-3.56 (m, 2 H), 3.05-3.26 (m, 4 H), 2.92 (s, 3 H), 2.52-2.64 (m, 1 H), 2.19-2.31 (m, 1 H), and 1.47-1.60 (m, 2 H); MS (ES⁺) 599.2 (M + 1). |
| 197 | (R)-{4-(3,4-dimethoxy-phenyl)-4-[4-(4-ethyl-piperazin-1-yl)-1,3-dioxo-1,3-dihydro-isoindol-2-yl]-butyl}-carbamic acid tert-butyl ester<br>¹H NMR (300 MHz, CDCl₃) δ 7.61 (t, J = 8 Hz, 1H), 7.45 (d, J = 7.1 Hz, 1H), 7.2-7.0 (m, 3H), 6.79 (d, J = 8.2 Hz, 1H), 5.21 (m, 1H), 4.52 (m, 1H), 3.88 (s, 3H), 3.85 (s, 3H), 3.76 (m, 4H), 3.46 (m, 2H), 3.3-3.1 (m, 4H), 2.7-2.2 (m, 6H), 1.6-1.4 (m, 3H), 1.42 (s, 9H); MS (ES+) 567.5 (M + 1). |
| 203 | (R)-1,2-dimethyl-1H-imidazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide<br>¹H NMR (300 MHz, CDCl₃) δ 7.6 (t, J = 8 Hz, 1H), 7.42 (d, J = 7.1 Hz, 1H), 7.38 (s, 1H), 7.12 (d, J = 8.1 Hz, 1H), 7.1-7.0 (m, 2H), 6.78 (d, J = 8.1 Hz, 1H), 5.97 (m, 1H), 5.16 (m, 1H), 3.88 (s, 3H), 3.85 (s, 3H), 3.67 (s, 3H), 3.8-2.2 (m, 14H), 2.45 (s, 3H), 1.54 (m, 2H), 1.43 (t, J = 7.3 Hz, 3H); MS (ES+) 625.3 (M + 1). |
| 204 | (R)-1,3,5-trimethyl-1H-pyrazole-4-sulfonic acid {4-(3,4-dimethoxy-phenyl)-4-[4-(4-ethyl-piperazin-1-yl)-1,3-dioxo-1,3-dihydro-isoindol-2-yl]-butyl}-amide<br>¹H NMR (300 MHz, CDCl₃) δ 7.62 (t, J = 8 Hz, 1H), 7.44 (d, J = 6.8 Hz, 1H), 7.13 (d, J = 8.3 Hz, 1H), 7.1-7.0 (m, 2H), 6.80 (d, J = 8.3 Hz, 1H), 5.27 (m, 1H), 4.49 (m, 1H), 3.88 (s, 3H), 3.85 (s, 3H), 3.73 (s, 3H), 3.8-2.2 (m, 14H), 2.44 (s, 3H), 2.35 (s, 3H), 1.53 (m, 2H), 1.44 (t, J = 7.3 H, 3H); MS (ES+) 639.3 (M + 1). |
| 216 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-carbamic acid benzyl ester<br>¹H NMR (300 MHz, CDCl₃) δ 7.58 (ovdd, J = 8.1 Hz, 1 H), 7.42-7.47 (m, 6 H), 7.28-7.41 (m, 5 H), 7.01-7.13 (m, 3 H), 6.78 (d, J = 8.1 Hz, 1 H), 4.94-5.31 (m, 3 H), 4.31-4.38 (m, 1 H), 3.84-3.92 (m, 7 H), 3.59-3.77 (m, 2 H), 2.93-3.46 (m, 7 H), 2.61-2.78 (m, 1 H), 2.38-2.52 (m, 1 H), and 1.84 (d, J = 6.9 Hz, 3 H); MS (ES⁺) 663.2 (M + 1). |
| 219 | (R)-1,2-dimethyl-1H-imidazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide<br>¹H NMR (300 MHz, CDCl₃) δ 7.57 (ovdd, J = 8.1 Hz, 1 H), 7.47-7.52 (m, 5 H), 7.38 (d, J = 7.2 Hz, 1 H), 7.32 (s, 1 H), 7.01-7.10 (m, 3 H), 6.78 (d, J = 8.6 Hz, 1 H), 5.35-5.45 (m, 1 H), 4.34-4.41 (m, 1 H), 3.81-3.89 (m, 7 H), 3.62-3.71 (m, 4 H), 3.37-3.58 (m, 4 H), 3.03-3.18 (m, 2 H), 2.91-2.98 (m, 2 H), 2.72-2.84 (m, 1 H), 2.34-2.52 (m, 4 H), and 1.87 (d, J = 6.8 Hz, 3 H); MS (ES⁺) 687.5 (M + 1). |

| Cpd | Name |
|---|---|
| 222 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-C-phenyl-methanesulfonamide<br>$^1$H NMR (300 MHz, CDCl$_3$) δ 7.59 (ovdd, J = 7.8 Hz, 1 H), 7.43-7.48 (m, 5 H), 7.41 (d, J = 7.1 Hz, 1 H), 7.08 (d, J = 8.3 Hz, 1 H), 6.97-7.01 (m, 2 H), 6.77 (d, J = 8.1 Hz, 1 H), 5.22-5.29 (m, 1 H), 4.46-4.57 (m, 1 H), 4.33-4.39 (m, 1 H), 3.81-3.99 (m, 8 H), 3.58-3.77 (m, 3 H), 3.42-3.52 (m, 3 H), 2.84-3.11 (m, 3 H), 2.71-2.82 (m, 1 H), 2.36 (s, 3 H), 2.17 (s, 3 H), and 1.87 (d, J = 7.0 Hz, 3 H); MS (ES$^+$) 683.4 (M + 1). |
| 223 | (R)-3,5-dimethyl-1H-pyrazole-4-sulfonic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide<br>$^1$H NMR (300 MHz, CDCl$_3$) δ 7.60 (ovdd, J = 8.0 Hz, 1 H), 7.45-7.48 (m, 5 H), 7.42 (d, J = 7.2 Hz, 1 H), 7.28-7.34 (m, 5 H), 7.10 (d, J = 8.7 Hz, 1 H), 6.98-7.04 (m, 2 H), 6.78 (d, J = 8.2 Hz, 1 H), 5.24-5.29 (m, 1 H), 4.37-4.42 (m, 1 H), 4.23-4.30 (m, 1 H), 4.20 (s, 2 H), 3.68-3.90 (m, 8 H), 3.38-3.52 (m, 3 H), 2.65-3.11 (m, 6 H), 2.31-2.60 (m, 1 H), and 1.85 (d, J = 6.9 Hz, 3 H); MS (ES$^+$) 687.5 (M + 1). |

Example 24

(R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-sulfamic acid Cpd 129

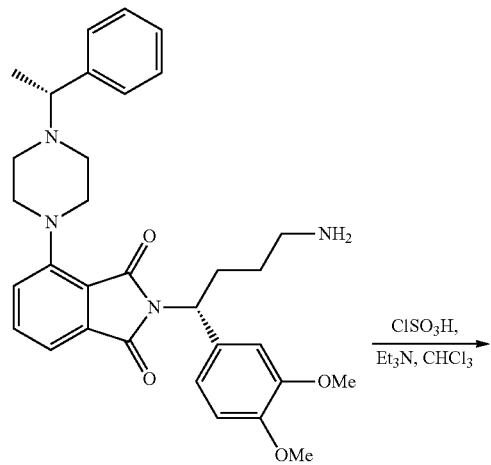

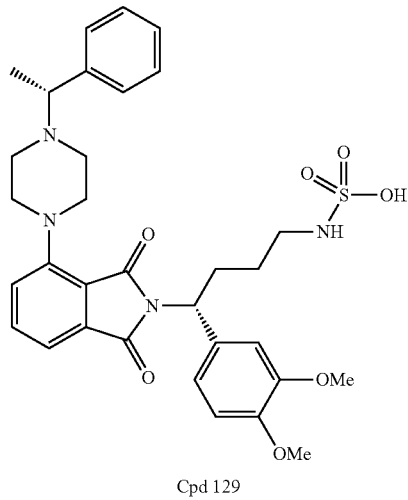

A 100-mL round bottom flask was charge with Compound 231 (2.0 g, 3.26 mmol) and chloroform (18 mL). The mixture was cooled using an ice/water bath. Triethylamine (1.6 mL, 11.5 mmol) was added to the mixture followed by chlorosulfonic acid (0.28 mL, 4.19 mmol). After 4 h the crude material was concentrated in vacuo. The crude material was purified on a Gilson HPLC with a reversed phase Kromasil column (10µ, 100 Å C18, column length 250×50 mm, gradient 90:10-0:100 H$_2$O:MeCN). The purified material was dissolved in dichlormethane (100 mL), treated with 1M HCl in diethyl ether (30 mL), and concentrated in vacuo. This procedure was repeated two more times to give 1.40 g of the title Compound 129 as a yellow solid. $^1$H NMR (300 MHz, CDCl$_3$) δ 11.02 (bs, 1 H), 7.55-7.60 (m, 2 H), 7.31-7.44 (m, 5 H), 6.91-7.20 (m, 3 H), 6.73-6.76 (m, 1 H), 5.19-5.30 (m, 1 H), 4.22-4.37 (m, 1 H), 3.83 (s, 3 H), 3.80 (s, 3 H), 3.34-3.76 (m, 8 H), 2.85-3.07 (m, 4 H), 2.08-2.28 (m, 2 H), and 1.21-1.27 (m, 3 H); MS (ES$^+$) 623 (M+1).

Other compounds of the present invention may be prepared by those skilled in the art by varying the starting materials, reagent(s) and conditions used. Using the procedure of Example 24, the following compounds were prepared:

| Cpd | Name |
|---|---|
| 220 | (R)-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-sulfamic acid<br>$^1$H NMR (300 MHz, CDCl$_3$) δ 7.33-7.58 (m, 7 H), 6.91-7.09 (m, 3 H), 6.78 (d, J = 8.6 Hz, 1 H), 5.23-5.40 (m, 1 H), 4.21-4.32 (m, 1 H), 3.78-3.92 (m, 7 H), 3.26-3.49 (m, 2 H), 2.89-3.17 (m, 4 H), 2.22-2.78 (m, 6H), and 1.84 (d, J = 6.8 Hz, 3 H); MS (ES$^+$) 609.2 (M + 1). |

Example 25

(R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-methyl-sulfamic acid Cpd 228

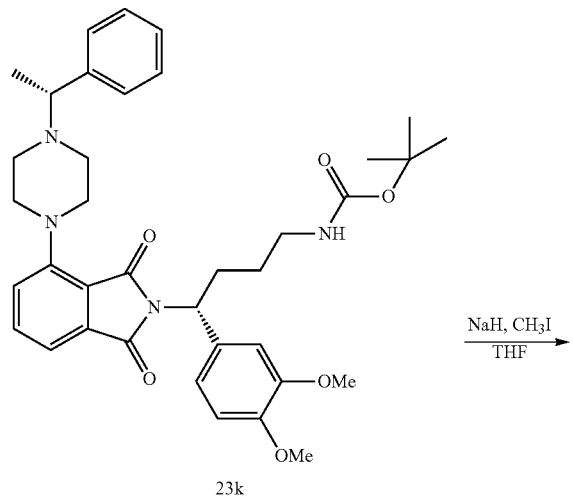

23k

NaH, CH₃I / THF

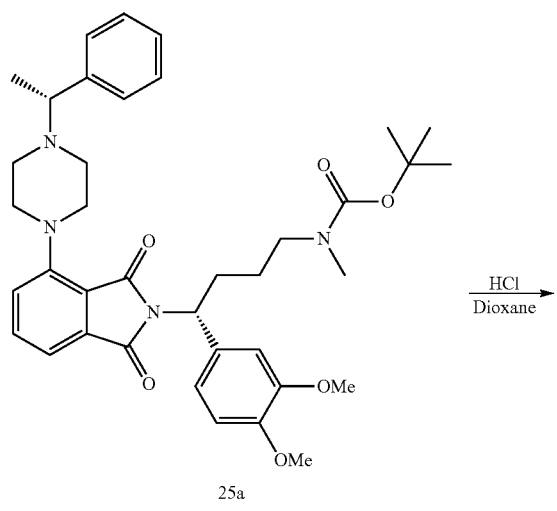

25a

HCl / Dioxane

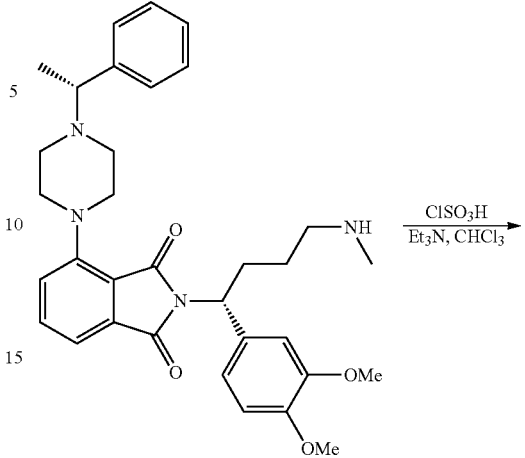

25b

ClSO₃H / Et₃N, CHCl₃

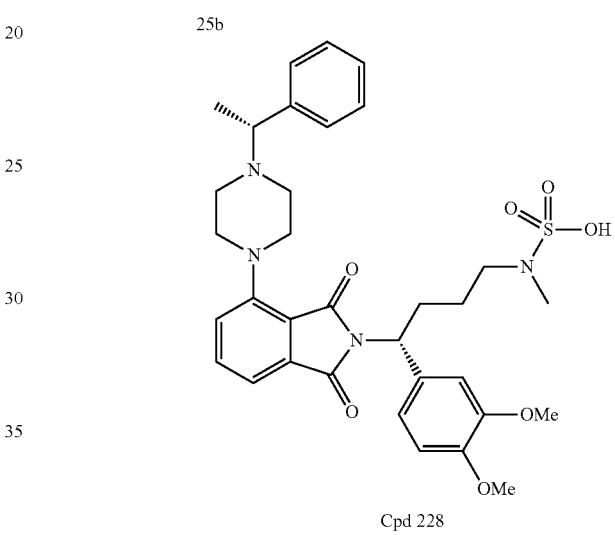

Cpd 228

A 50-mL round bottom flask was charged with Compound 23k (480 mg, 0.75 mmol) and dimethylformamide (7.5 mL). 95% Sodium hydride (28 mg, 1.17 mmol) was added and the mixture was stirred at room temperature for 20 minutes. Methyl iodide (0.05 mL, 0.80 mmol) was added and the mixture was stirred at room temperature for 24 h. The mixture was diluted with DCM (200 mL), washed with 1.0 N HCl (100 mL), and saturated aqueous sodium bicarbonate (1×100 mL). The organic layer was dried using MgSO₄, filtered through Celite®, and concentrated in vacuo to give 150 mg Compound 25a. A 50 mL round bottom flask was charged with the crude solid Compound 25a (600 mg, 0.91 mmol) and dioxane (1.8 mL). 4.0N HCl in dioxane (1.8 mL) was added and the mixture was stirred at room temperature for 4 h. The mixture was concentrated in-vacuo to give 380 mg of Compound 25b.

A 50 mL round bottom flask was charge with Compound 25b (380 mg, 0.61 mmol) and chloroform (3.0 mL). The mixture was cooled using an ice/water bath. Triethylamine (0.3 mL, 2.15 mmol) was added to the mixture followed by chlorosulfonic acid (0.05 mL, 0.75 mmol). After 4 h the crude material was concentrated in vacuo. The crude material was purified on a Gilson HPLC with a reversed phase Kromasil column (10µ, 100 Å C18, column length 250×50 mm, gradient 90:10-0:100 H₂O:MeCN). The purified material was dissolved in dichlormethane (100 mL), treated with 1M HCl in diethyl ether (30 mL), and concentrated in vacuo. This procedure was repeated two more times to give 1.40 g of the title Compound 228 as a yellow solid. $^1$H NMR (300 MHz, CDCl₃) δ 11.08 (bs, 1 H), 7.28-7.45 (m, 7 H), 6.99-7.20 (m, 3 H), 6.70 (d, J=8.5 Hz, 1 H), 5.19-5.24 (m, 1 H), 4.21-4.35 (m, 1 H), 3.80 (s, 3 H), 3.77 (s, 3 H), 3.25-3.42 (m, 6 H), 2.60-3.10 (m, 6 H), 2.50 (s, 3 H), 1.91-2.16 (m, 2 H), and 1.24-1.28 (m, 3 H); MS (ES⁺) 637 (M+1).

Other compounds of the present invention may be prepared by those skilled in the art by varying the starting materials, reagent(s) and conditions used. Using the procedure of Example 25, the following compounds were prepared:

| Cpd | Name |
|---|---|
| 236 | (R)-2-[4-(benzyl-methyl-amino)-1-(3,4-dimethoxy-phenyl)-butyl]-4-(4-ethyl-piperazin-1-yl)-isoindole-1,3-dione<br>$^1$H NMR (300 MHz, CDCl$_3$) δ 7.61 (ovdd, J = 7.8 Hz, 1 H), 7.33-7.51 (m, 6 H), 6.99-7.18 (m, 3 H), 6.80 (d, J = 8.5 Hz, 1 H), 5.15-5.24 (m, 1 H), 4.28, 4.05 (ABq, J = 13.0 Hz, 2 H), 3.87 (s, 3 H), 3.85 (s, 3 H), 3.72-3.80 (m, 4 H), 3.43-3.59 (m, 2 H), 3.18-3.29 (m, 6 H), 2.57-2.70 (m, 4 H), 2.29-2.44 (m, 1 H), 1.67-1.81 (m, 2 H), and 1.44 (t, J = 7.3 Hz, 3 H); MS (ES$^+$) 571.3 (M + 1). |

Example 26

(S)-thiophene-2-sulfonic acid 4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide Cpd 119

Compound 119 was prepared by the methods described in Example 23 for the synthesis of Compound 119, substituting (S)-tol-BINAP (0.03 mL) for (R)-tol-BINAP in Example 23, Step C. Compound 119 was isolated as a yellow solid. $^1$H NMR (300 MHz, CDCl$_3$) δ 7.68-7.72 (m, 2 H), 7.33-7.58 (m, 8 H), 6.98-7.14 (m, 3 H), 6.77 (d, J=7.6 Hz, 1 H), 5.11-5.16 (m, 1 H), 4.50-4.54 (m, 1 H), 3.86 (s, 3 H), 3.84 (s, 3 H), 3.41-3.47 (m, 1 H), 3.25-3.35 (m, 4 H), 2.62-2.74 (m, 2 H), 2.54-2.60 (m, 2 H), 2.47-2.52 (m, 1 H), 2.21-2.31 (m, 1 H), 1.46-1.54 (m, 3 H), and 1.42 (d, J=6.6 Hz, 3 H); MS (ES$^+$) 689 (M+1); [α]$^{25}_D$=−4.7 (c 1.0, CHCl$_3$).

Example 27

(R)-2-[4-benzyloxy-1-(3,4-dimethoxy-phenyl)-butyl]-4-(4-ethyl-piperazin-1-yl)-isoindole-1,3-dione Cpd 201

(R)-2-[1-(3,4-dimethoxy-phenyl)-4-hydroxy-butyl]-4-(4-ethyl-piperazin-1-yl)-isoindole-1,3-dione Cpd 206

(R)-dimethyl-sulfamic acid 4-(3,4-dimethoxy-phenyl)-4-[4-(4-ethyl-piperazin-1-yl)-1,3-dioxo-1,3-dihydro-isoindol-2-yl]-butyl ester Cpd 209

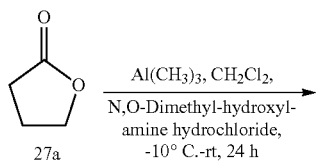

A 1-L round bottom flask was charge with N,O-dimethyl-hydroxylamine hydrochloride (20.2 g, 0.21 mol) and dichloromethane (260 mL). The mixture was cooled to −10° C. using an acetone bath with careful addition of dry ice. Trimethylaluminum (100 mL, 0.20 mol) was added dropwise via addition funnel. The mixture was stirred at room temperature for 30 minutes. The mixture was cooled using an ice/water bath. Compound 27a (5.1 mL, 0.067 mmol) was dissolved in dichloromethane (73 mL) and added slowly via addition funnel. The mixture was stirred at room temperature for 24 h. The reaction was quenched with 1M KHSO$_4$ (250 mL) and extracted with dichloromethane (2×300 mL). The organic layer was dried using MgSO$_4$, filtered through Celite®, concentrated in vacuo to give 8.83 g of Compound 27b. A 1-L round bottom flask was charged with Compound 27b (8.83 g, 0.06 mol) and tetrahydrofuran (300 mL). The mixture was cooled using an ice/water bath. 95% Sodium hydride (1.7 g, 0.07 mol) was added in two portions. The mixture was stirred in the ice/water bath for 20 minutes. Benzylbromide (7.9 mL, 0.066 mol) was added dropwise via syringe and the mixture was stirred at room temperature for 24 h. Water (200 mL) was added to the mixture, followed by extraction with dichloromethane (500 mL). The organic layer was dried using MgSO$_4$, filtered through Celite®, concentrated in vacuo. The crude material was purified on a Analogix IntelliFlash 280 with a normal phase Super Flash column (SF65—400 g, gradient 90:10-0:100 Heptane:EtOAc) to give 6.74 g of Compound 27c. $^1$H NMR (300 MHz, CDCl$_3$) δ 7.27-7.38 (m, 5 H), 4.51 (s, 2 H), 3.67 (s, 3 H), 3.54 (t, J=6.2 Hz, 2 H), 3.17 (s, 3 H), 2.55 (t, J=7.4 Hz, 2 H), and 1.91-2.01 (m, 2 H); MS (ES$^+$) 238 (M+1).

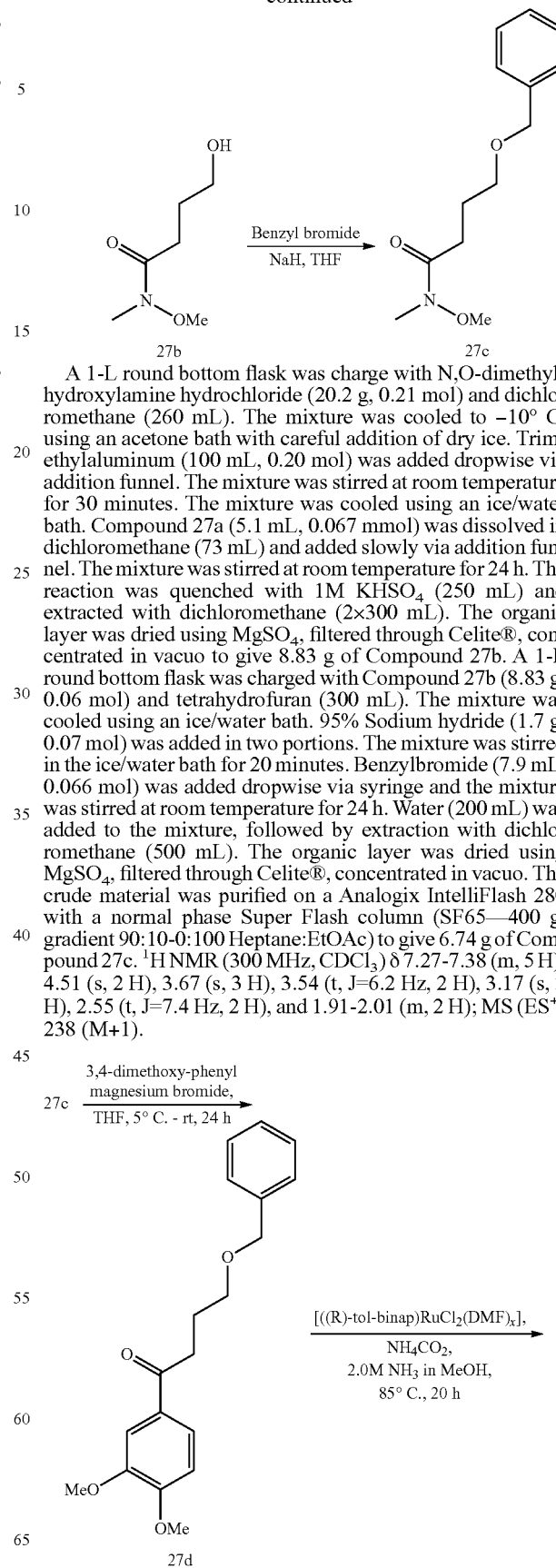

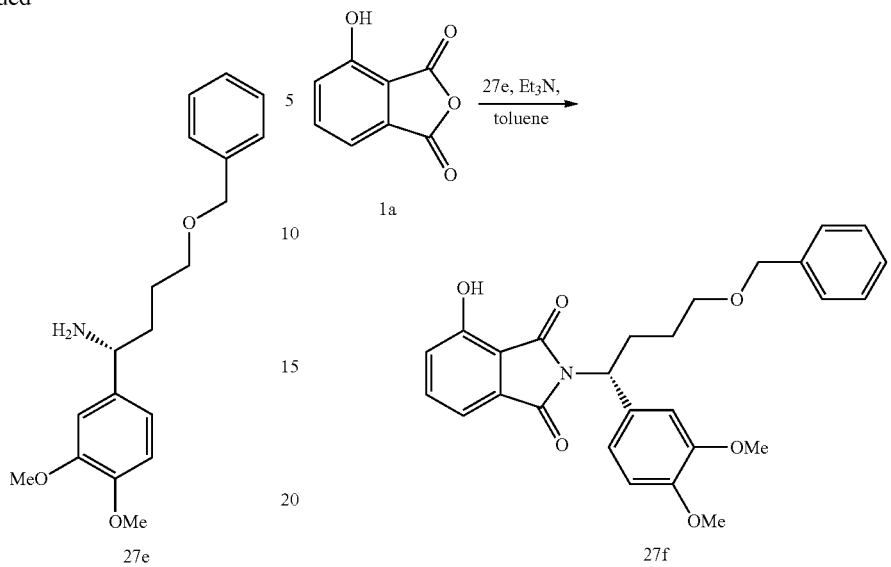

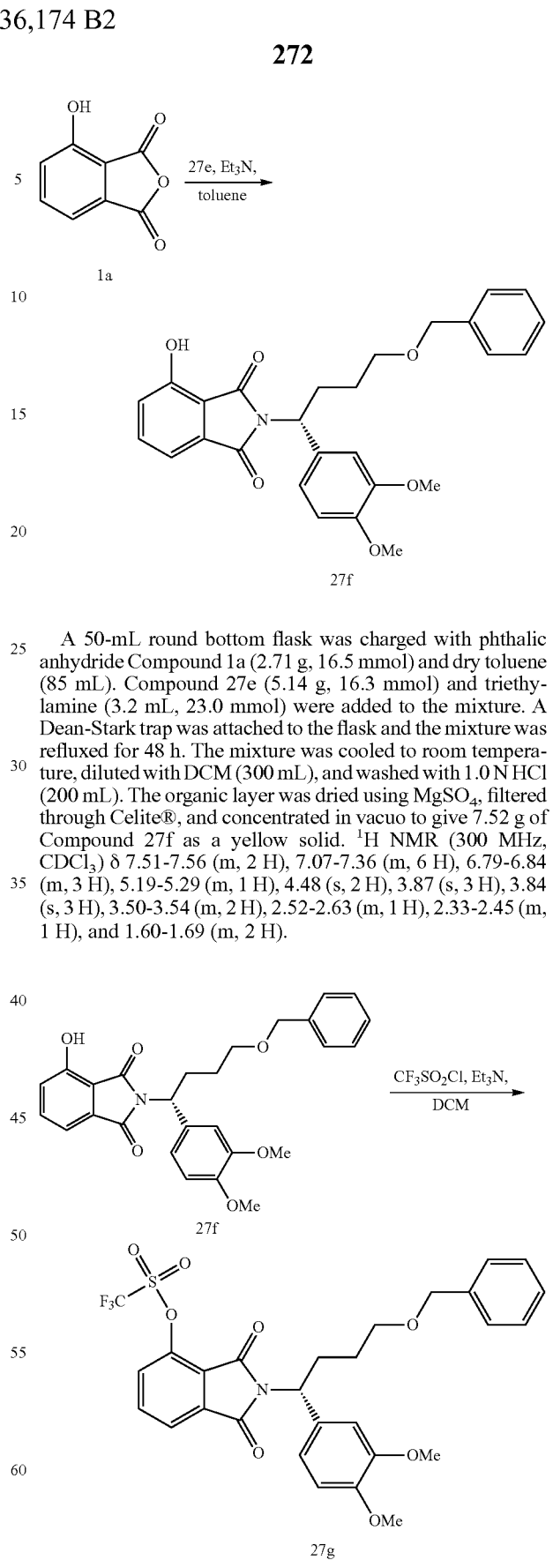

A 1-L round bottom flask was charged with Compound 27c (6.74 g, 28.4 mmol) and tetrahydrofuran (500 mL). The mixture was cooled using an ice/water bath. A solution of 3,4-Dimethoxyphenyl magnesium bromide in tetrahydrofuran (284 mL, 142 mmol) was added dropwise via addition funnel over 30 minutes. The mixture was allowed to warm to room temperature and stirred for 2 h. Water (150 mL) was added to the mixture and concentrated in vacuo. The mixture was extracted with dichloromethane (600 mL) and washed with 1N NaOH (1×200 mL), 1N HCl (1×200 mL), and water (1×200 mL). The organic layer was dried with MgSO$_4$, filtered through Celite®, concentrated in vacuo to give 8.11 g of Compound 27d as a white solid. $^1$H NMR (300 MHz, CDCl$_3$) δ 7.62 (d, J=8.4 Hz, 1 H), 7.55 (s, 1 H), 7.26-7.39 (m, 5 H), 6.89 (d, J=8.4 Hz, 1 H), 4.53 (s, 2 H), 3.97 (s, 3 H), 3.94 (s, 3 H), 3.60 (t, J=6.1 Hz, 2 H), 3.08 (t, J=7.2 Hz, 2 H), and 2.04-2.13 (m, 2 H); MS (ES$^+$) 315 (M+1).

A 200-mL sealed tube was charged with Compound 27d (8.01 g, 25.5 mmol), [((R)-tol-binap)RuCl2(DMF)x] (2.3 g, 2.7 mmol), ammonium formate (16.6 g, 263.2 mmol), and a 2.0M solution of ammonia in methanol (102 mL). The tube was flushed with argon and sealed. The mixture was heated to 85° C. for 22 h. The mixture was cooled to room temperature and the sealed tube was opened carefully due to the release of pressure from excess ammonia. The mixture was concentrated in vacuo and diluted with 1N HCl (300 mL) and ethanol (150 mL), then heated to reflux for 2 h. The reaction mixture was then cooled to room temperature, and washed with diethyl ether (1×500 mL). The aqueous layer was basified with 3N NaOH to pH>10, then extracted using dichloromethane (3×200 mL). The organic layers were dried with MgSO$_4$, filtered through Celite®, and concentrated in vacuo to give 5.14 g of Compound 27e as a white solid. $^1$H NMR (300 MHz, CDCl$_3$) δ 7.24-7.36 (m, 5 H), 6.79-6.87 (m, 3 H), 4.47 (s, 2 H), 3.80-3.92 (m, 7 H), 3.44-3.50 (m, 2 H), and 1.44-1.78 (m, 6 H); MS (ES$^+$) 316 (M+1); Daicel Chiralpak AD-H, 4.6 mm×25 cm, Hex:IPA:0.1% DEA (97:3), 1.0 ml/min, S-enantiomer 25.92 min, R-enantiomer 27.17 min (27e), 95% ee.

A 50-mL round bottom flask was charged with phthalic anhydride Compound 1a (2.71 g, 16.5 mmol) and dry toluene (85 mL). Compound 27e (5.14 g, 16.3 mmol) and triethylamine (3.2 mL, 23.0 mmol) were added to the mixture. A Dean-Stark trap was attached to the flask and the mixture was refluxed for 48 h. The mixture was cooled to room temperature, diluted with DCM (300 mL), and washed with 1.0 N HCl (200 mL). The organic layer was dried using MgSO$_4$, filtered through Celite®, and concentrated in vacuo to give 7.52 g of Compound 27f as a yellow solid. $^1$H NMR (300 MHz, CDCl$_3$) δ 7.51-7.56 (m, 2 H), 7.07-7.36 (m, 6 H), 6.79-6.84 (m, 3 H), 5.19-5.29 (m, 1 H), 4.48 (s, 2 H), 3.87 (s, 3 H), 3.84 (s, 3 H), 3.50-3.54 (m, 2 H), 2.52-2.63 (m, 1 H), 2.33-2.45 (m, 1 H), and 1.60-1.69 (m, 2 H).

A 500-mL round bottom flask was charged with Compound 27f (2.41 g, 5.23 mmol), DCM (26 mL), and Et$_3$N (0.87 mL, 6.24 mmol). The mixture was cooled using an ice/water bath. Trifluoromethanesulfonyl chloride (0.61 mL, 5.73 mmol) was added dropwise via syringe. The mixture was then stirred for 1 h in an ice/water bath. The mixture was then diluted with DCM (150 mL) and washed with 1.0 N HCl (50 mL), saturated aqueous sodium bicarbonate (1×50 mL), and saturated aqueous sodium chloride (1×50 mL). The organic layer was dried using MgSO$_4$, filtered through Celite®, and concentrated in vacuo to give 2.96 g of Compound 27g as a yellow solid. $^1$H NMR (300 MHz, CDCl$_3$) δ 7.75-7.84 (m, 2 H), 7.50 (d, J=7.6 Hz, 1 H), 7.23-7.36 (m, 5 H), 7.11 (s, 1 H), 6.80 (d, J=8.1 Hz, 1 H), 5.25-5.28 (m, 1 H), 4.48 (s, 2 H), 3.86 (s, 3 H), 3.84 (s, 3 H), 3.51 (t, J=6.4 Hz, 2 H), 2.53-2.66 (m, 1 H), 2.37-2.49 (m, 1 H), and 1.58-1.68 (m, 2 H).

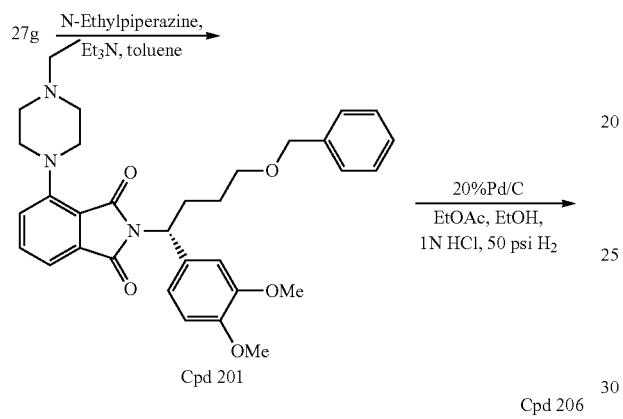

Cpd 201

Cpd 206

A 20-mL sealed tube was charged with Compound 27g (2.96 g, 4.99 mmol), N-ethylpiperazine (0.63 mL, 4.96 mmol), toluene (5.0 mL), and Et$_3$N (0.97 mL, 6.96 mmol). The tube was sealed under argon and heated to 130° C. for 19 h. The mixture was cooled to room temperature and purified Analogix IntelliFlash 280 with a normal phase Super Flash column (SF65—150 g, gradient 100:0-90:10 CH$_2$Cl$_2$:CH$_3$OH) to give 2.32 g of Compound 201 as a yellow solid. $^1$H NMR (300 MHz, CDCl$_3$) δ 7.50-7.55 (m, 2 H), 7.23-7.35 (m, 5 H), 7.08-7.13 (m, 3 H), 6.78 (d, J=8.2 Hz, 1 H), 5.22-5.28 (m, 1 H), 4.47 (s, 2 H), 3.87 (s, 3 H), 3.84 (s, 3 H), 3.49-3.53 (m, 2 H), 3.35-3.38 (m, 4 H), 2.72-2.79 (m, 4 H), 2.50-2.65 (m, 3 H), 2.31-2.43 (m, 1 H), 1.58-1.68 (m, 2 H), and 1.15 (t, J=7.2 Hz, 3 H); MS (ES$^+$) 558 (M+1).

A 500-mL hydrogenation was charged with Compound 201 (2.26 g, 4.06 mmol), ethylacetate (20 mL), ethanol (20 mL), 1N HCl (2.0 mL), and 20% Pd/C (0.23 g). The mixture was put under 50 psi hydrogen using a parr shaker for 48 h. The mixture was filtered through Celite® and concentrated in-vacuo to give 2.04 g of Compound 206 as a yellow solid. $^1$H NMR (300 MHz, CD$_3$OD) δ 7.70 (dd, J=8.2 Hz, J=7.4 Hz, 1 H), 7.45 (d, J=7.1 Hz, 1 H), 7.33 (d, J=8.2 Hz, 1 H), 7.14 (s, 1 H), 7.02 (d, J=8.4 Hz, 1 H), 6.88 (d, J=8.3 Hz, 1 H), 5.23-5.28 (m, 1 H), 3.86-3.97 (m, 2 H), 3.81 (s, 3 H), 3.79 (s, 3 H), 3.64-3.72 (m, 2 H), 3.54-3.63 (m, 2 H), 3.21-3.36 (m, 6 H), 2.49-2.62 (m, 1 H), 2.27-2.39 (m, 1 H), 1.46-1.56 (m, 2 H), and 1.41 (t, J=7.3 Hz, 3 H); MS (ES$^+$) 468 (M+1).

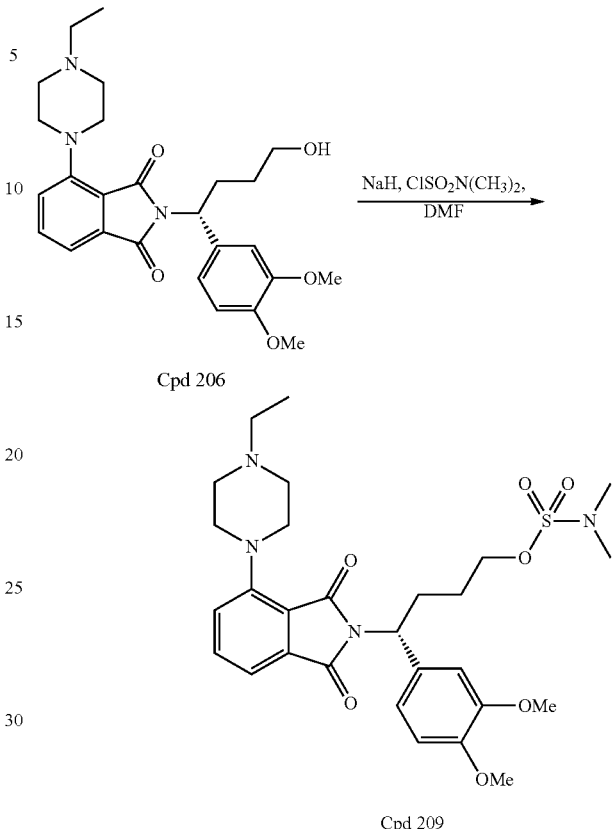

Cpd 206

Cpd 209

A 10-mL round bottom flask was charged with Compound 206 (50.0 mg, 0.10 mmol) and dimethylformamide (0.5 mL). 95% Sodium hydride (6.9 mg, 0.29 mmol) was added and the mixture was stirred at room temperature for 15 minutes. N,N-Dimethylsulfamoyl chloride (0.01 mL, 0.11 mmol) was added and the mixture was stirred at room temperature for 20 h. The mixture was purified on a Analogix IntelliFlash 280 with a normal phase Super Flash column (SF25—40 g, gradient 100:0-90:10 CH$_2$Cl$_2$:CH$_3$OH). The purified material was dissolved in dichlormethane (10 mL), treated with 1M HCl in diethyl ether (1 mL), and concentrated in vacuo. This procedure was repeated two more times to give 15.3 mg of Compound 209 as a yellow solid. $^1$H NMR (300 MHz, CDCl$_3$) δ 7.58-7.70 (m, 1 H), 7.42-7.45 (m, 1 H), 7.06-7.18 (m, 3 H), 6.61-6.79 (m, 1 H), 5.19-5.25 (m, 1 H), 4.17-4.28 (m, 2 H), 3.88 (s, 3 H), 3.85 (s, 3 H), 3.62-3.77 (m, 6 H), 3.10-3.30 (m, 4 H), 2.88 (s, 3 H), 2.86 (s, 1 H), 2.61-2.65 (m, 1 H), 2.44-2.58 (m, 1 H), 1.65-1.79 (m, 2 H), and 1.49 (t, J=7.2 Hz, 3 H); MS (ES$^+$) 575 (M+1).

Other compounds of the present invention may be prepared by those skilled in the art by varying the starting materials, reagent(s) and conditions used. Using the procedure of Example 27, the following compounds were prepared:

| Cpd | Name |
|---|---|
| 207 | (R)-2-[1-(3,4-dimethoxy-phenyl)-4-ethoxy-butyl]-4-(4-ethyl-piperazin-1-yl)-isoindole-1,3-dione<br>$^1$H NMR (300 MHz, CDCl$_3$) δ 7.53 (dd, J = 8.3 Hz, J = 7.2 Hz, 1 H), 7.33 (d, J = 7.1 Hz, 1 H), 7.09-7.15 (m, 3 H), 6.79 (d, J = 8.2 Hz, 1 H), 5.20-5.27 (m, 1 H), 3.88 (s, 3 H), 3.84 (s, 3 H), 3.30-3.57 (m, 8 H), 2.65-2.71 (m, 3 H), 2.49-2.63 (m, 4 H), 2.22-2.46 (m, 1 H), 1.54-1.63 (m, 2 H), and 1.11-1.21 (m, 6 H); MS (ES+) 496.4 (M + 1). |

-continued

| Cpd | Name |
|---|---|
| 208 | (R)-thiophene-2-sulfonic acid 4-(3,4-dimethoxy-phenyl)-4-[4-(4-ethyl-piperazin-1-yl)-1,3-dioxo-1,3-dihydro-isoindol-2-yl]-butyl ester<br>$^1$H NMR (300 MHz, CDCl$_3$) δ 8.02-8.17 (m, 1 H), 7.29-7.81 (m, 3 H), 6.92-7.21 (m, 3 H), 6.69-6.87 (m, 2 H), 5.17-5.27 (m, 1 H), 4.05-4.23 (m, 1 H), 3.88 (s, 3 H), 3.84 (s, 3 H), 3.11-3.79 (m, 6 H), 2.22-2.79 (m, 6 H), 1.60-1.84 (m, 2 H), and 1.16-1.42 (m, 5 H). |
| 210 | (R)-2-[1-(3,4-dimethoxy-phenyl)-4-isobutoxy-butyl]-4-(4-ethyl-piperazin-1-yl)-isoindole-1,3-dione<br>$^1$H NMR (300 MHz, CD$_3$OD) δ 7.71 (ovdd, J = 7.3 Hz, 1 H), 7.46 (d, J = 7.2 Hz, 1 H), 7.35 (d, J = 8.3 Hz, 1 H), 7.13 (s, 1 H), 7.01-7.05 (m, 1 H), 6.86-6.91 (m, 1 H), 5.23-5.30 (m, 1 H), 3.82 (s, 3 H), 3.79 (s, 3 H), 3.60-3.73 (m, 7 H), 3.33-3.47 (m, 3 H), 2.52-2.68 (m, 1 H), 2.28-2.49 (m, 2 H), 1.71-1.80 (m, 1 H), 1.39 (t, J = 7.1 Hz, 3 H), and 1.18 (d, J = 6.7 Hz, 6 H); MS (ES$^+$) 524.4 (M + 1). |
| 214 | (R)-2-[1-(3,4-dimethoxy-phenyl)-4-(thiophen-2-ylmethoxy)-butyl]-4-(4-ethyl-piperazin-1-yl)-isoindole-1,3-dione<br>$^1$H NMR (300 MHz, CDCl$_3$) δ 7.56-7.69 (m, 2 H), 7.48-7.49 (m, 2 H), 7.15-7.25 (m, 2 H), 7.05-7.08 (m, 2 H), 6.78-6.83 (m, 1 H), 5.19-5.24 (m, 1 H), 4.94 (s, 2 H), 3.52-3.98 (m, 18 H), 2.52-2.65 (m, 1 H), 2.26-2.46 (m, 1 H), 1.72-1.81 (m, 2 H), and 1.55 (t, J = 7.1 Hz, 3 H); MS (ES$^+$) 564.3 (M + 1). |
| 227 | (R)-2-[4-(2,6-difluoro-benzyloxy)-1-(3,4-dimethoxy-phenyl)-butyl]-4-(4-ethyl-piperazin-1-yl)-isoindole-1,3-dione<br>$^1$H NMR (300 MHz, CDCl$_3$) δ 7.60 (ovdd, J = 7.8 Hz, 1 H), 7.44 (d, J = 7.2 Hz, 1 H), 7.29-7.39 (m, 1 H), 7.03-7.24 (m, 3 H), 6.85-6.91 (m, 2 H), 6.78 (d, J = 8.3 Hz, 1 H), 5.18-5.23 (m, 1 H), 4.57 (s, 2 H), 3.87 (s, 3 H), 3.84 (s, 3 H), 3.63-3.78 (m, 4 H), 3.46-3.60 (m, 4 H), 3.14-3.23 (m, 4 H), 2.48-2.61 (m, 1 H), 2.28-2.39 (m, 1 H), 1.54-1.64 (m, 2 H), and 1.44 (t, J = 7.0 Hz, 3 H); MS (ES$^+$) 594.3 (M + 1). |

Example 28

(R)-{4-(3,4-dimethoxy-phenyl)-4-[4-(4-ethyl-piperazin-1-yl)-1,3-dioxo-1,3-dihydro-isoindol-2-yl]-butoxy}-acetic acid Cpd 218

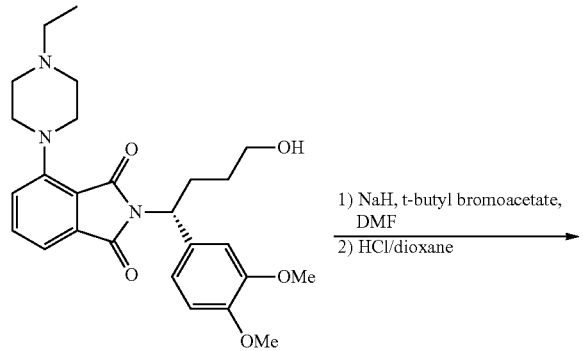

A 10-mL round bottom flask was charged with Compound 206 (61.0 mg, 0.12 mmol) and dimethylformamide (0.61 mL). 95% Sodium hydride (8.6 mg, 0.36 mmol) was added and the mixture was stirred at room temperature for 15 minutes. tert-Butyl bromoacetate (0.02 mL, 0.14 mmol) was added and the mixture was stirred at room temperature for 20 h. The mixture was purified on a Analogix IntelliFlash 280 with a normal phase Super Flash column (SF25—40g, gradient 100:0-90:10 CH$_2$Cl$_2$:CH$_3$OH). A 10 mL round bottom flask was charged with the purified solid (30 mg, 0.052 mmol) and dioxane (0.5 mL). 4.0N HCl in dioxane (0.5 mL) was added and the mixture was stirred at room temperature for 4 h. The mixture was concentrated in-vacuo to give 13.8 mg of Compound 218. $^1$H NMR (300 MHz, CDCl$_3$) δ 12.34 (bs, 1 H), 7.60 (dd, J=8.0 Hz, J=7.4 Hz, 1 H), 7.44 (d, J=7.2 Hz, 1 H), 7.05-7.13 (m, 3 H), 6.80 (d, J=8.1 Hz, 1 H), 5.24-5.29 (m, 1 H), 4.04 (s, 2 H), 3.88 (s, 3 H), 3.84 (s, 3 H), 3.40-3.79 (m, 8 H), 3.14-3.22 (m, 4 H), 2.73-2.85 (m, 1 H), 2.15-2.27 (m, 1 H), 1.64-1.71 (m, 2 H), and 1.43 (t, J=7.2 Hz, 3 H); MS (ES$^+$) 526 (M+1).

Example 29

2-[(3-benzylamino-phenyl)-(3,4-dimethoxy-phenyl)-methyl]-4-(4-ethyl-piperazin-1-yl)-isoindole-1,3-dione Cpd 230

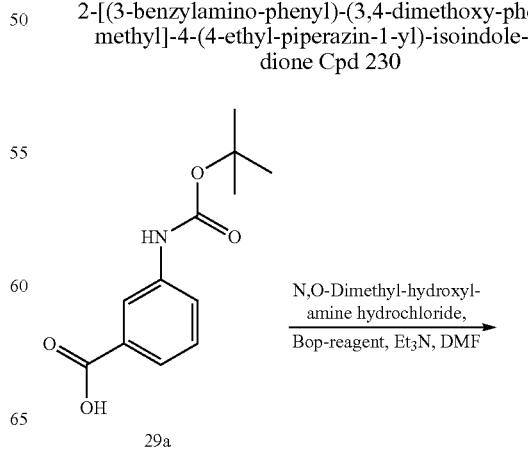

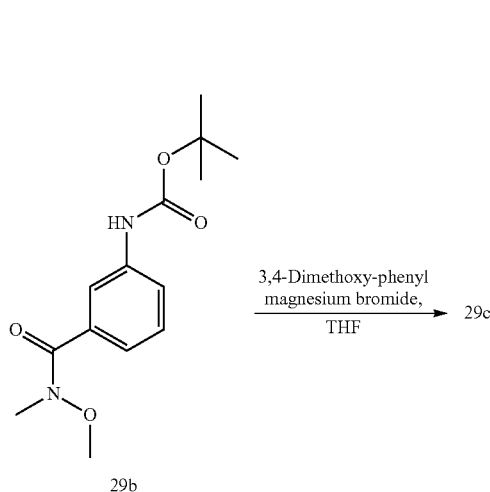

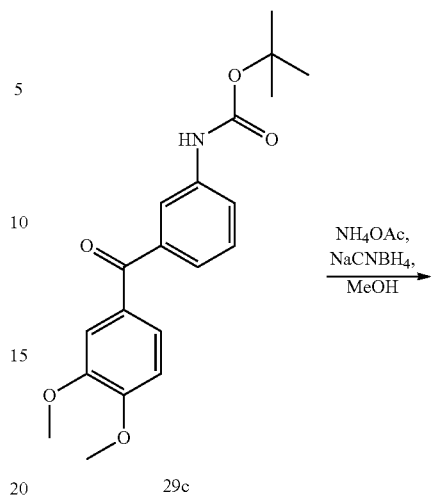

A 500-mL round bottom flask was charged with Compound 29a (5.0 g, 21.1 mmol) and dimethylformamide (70 mL). The mixture was cooled using an ice/water bath. Triethylamine (8.8 mL, 63.1 mmol) was added to the mixture followed by the benzotriazol-1-yloxy-tris(dimethylamino)phosphonium hexafluorophosphate (10.5 g, 23.7 mmol). N,O-dimethylhydroxylamine hydrochloride (3.19 g, 32.7 mmol) was added and the mixture was stirred at room temperature for 24 h. The mixture was concentrated in vacuo. The crude oil was diluted with ethyl acetate (500 mL) and transferred to a separatory funnel. The organic layer was washed with 1N HCl (100 mL), 1N NaOH (100 mL), and water (100 mL). The organic layer was dried using MgSO$_4$, filtered through Celite®, concentrated in vacuo to give 5.80 g of Compound 29b. $^1$H NMR (300 MHz, CDCl$_3$) δ 7.63-7.69 (m, 1 H), 7.53-7.59 (m, 1 H), 7.31-7.35 (m, 2 H), 6.71 (bs, 1 H), 3.58 (s, 3 H), 3.35 (s, 3 H), and 1.52 (s, 9 H); MS (ES$^+$) 281 (M+1).

A 1-L round bottom flask was charged with Compound 29b (5.90 g, 21.1 mmol) and tetrahydrofuran (400 mL). The mixture was cooled using an ice/water bath. A solution of 3,4-Dimethoxyphenyl magnesium bromide in tetrahydrofuran (230 mL, 115 mmol) was added dropwise via addition funnel over 30 minutes. The mixture was allowed to warm to room temperature and stirred for 2 h. Water (150 mL) was added to the mixture and concentrated in vacuo. The mixture was extracted with dichloromethane (500 mL) and washed with 1N NaOH (100 mL), 1N HCl (100 mL), and water (100 mL). The organic layer was dried with MgSO$_4$, filtered through Celite®, concentrated in vacuo to give 6.56 g of Compound 29c as a white solid. $^1$H NMR (300 MHz, CDCl$_3$) δ 7.66 (s, 1 H), 7.40-7.50 (m, 3 H), 6.88-6.92 (m, 2 H), 6.73 (d, J=8.6 Hz, 1 H), 3.95 (s, 3 H), 3.82 (s, 3 H), and 1.52 (s, 9 H); MS (ES$^+$) 358 (M+1).

A 300-mL round bottom flask was charged with Compound 29c (2.08 g, 5.83 mmol), ammonium acetate (4.5 g, 58.4 mmol), and methanol (19.0 mL). Sodium cyanoborohydride (0.27 g, 4.30 mmol) was added and the mixture was heated to 40° C. for 24 h. The mixture was cooled to room temperature and 1N NaOH (50 mL) was added. The mixture was transferred to a separatory funnel and extracted with dichloromethane (2×200 mL). The organic layer was dried with MgSO$_4$, filtered through Celite®, and concentrated in vacuo. The mixture was purified on a Analogix IntelliFlash 280 with a normal phase Super Flash column (SF40—150 g, gradient 100:0-90:10 CH$_2$Cl$_2$:CH$_3$OH) to give 1.01 g of Compound 29d as a white. $^1$H NMR (300 MHz, CD$_3$OD) δ 7.68 (s, 1 H), 7.32-7.42 (m, 2 H), 6.98-7.10 (m, 4 H), 5.55 (s, 1 H), 4.95 (s, 6 H), and 1.55 (s, 9 H); MS (ES$^+$) 359 (M+1).

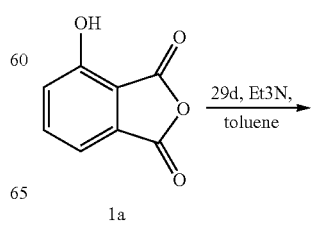

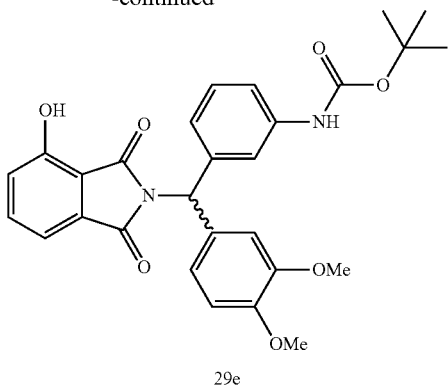

A 50-mL round bottom flask was charged with phthalic anhydride Compound 1a (232 mg, 1.41 mmol) and dry toluene (7.0 mL). Compound 29d (500 mg, 1.40 mmol) and triethylamine (0.27 mL, 1.94 mmol) were added to the mixture. A Dean-Stark trap was attached to the flask and the mixture was refluxed for 24 h. The mixture was cooled to room temperature and diluted with DCM (50 mL) and washed with 1.0 N HCl (10 mL). The organic layers were combined and dried using MgSO$_4$, filtered through Celite®, and concentrated in vacuo. The mixture was purified on a Analogix IntelliFlash 280 with a normal phase Super Flash column (SF40—80 g, gradient 90:10-60:40 heptane:EtOAc) to give 250 mg of Compound 29e as a yellow solid. $^1$H NMR (300 MHz, CDCl$_3$) δ 7.52-7.62 (m, 2 H), 7.37-7.39 (m, 2 H), 7.25-7.28 (m, 1 H), 7.10-7.19 (m, 2 H), 6.91-6.98 (m, 2 H), 6.81-6.84 (m, 1 H), 6.43 (s, 1 H), 3.87 (s, 3 H), 3.82 (s, 3 H), and 1.48 (m, 9 H).

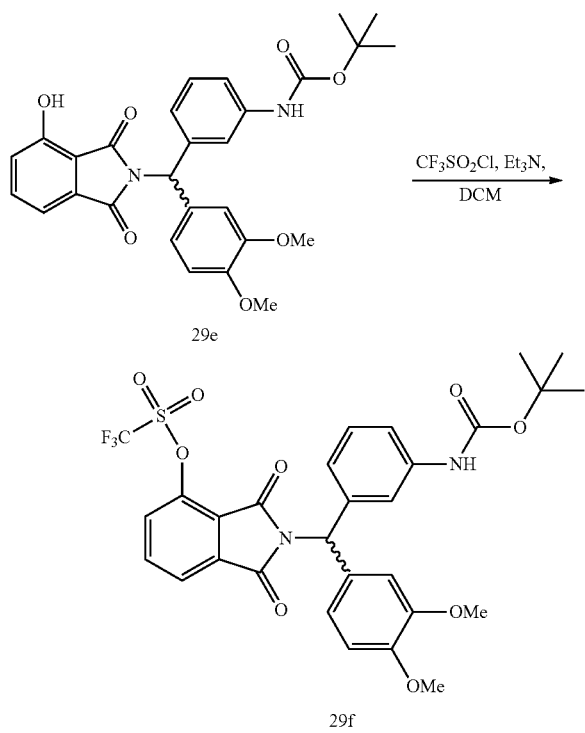

A 500-mL round bottom flask was charged with Compound 29e (200 mg, 0.40 mmol), DCM (2.0 mL), and Et$_3$N (0.07 mL, 0.50 mmol) and then cooled using an ice/water bath. Trifluoromethanesulfonyl chloride (0.05 mL, 0.47 mmol) was added dropwise via syringe and the mixture was then stirred for 45 minutes with cooling in an ice/water bath. The mixture was diluted with DCM (50 mL) and washed with 1.0 N HCl (10 mL), saturated aqueous sodium bicarbonate (10 mL), and saturated aqueous sodium chloride (10 mL). The organic layer was dried using MgSO$_4$, filtered through Celite®, and concentrated in vacuo to give 173 mg of Compound 29f as a yellow solid. $^1$H NMR (300 MHz, CDCl$_3$) δ 7.79-7.89 (m, 2 H), 7.53-7.60 (m, 2 H), 7.27 (dd, J=10.2 Hz, J=8.0 Hz, 1 H), 7.11 (s, 1 H), 6.93-6.99 (m, 3 H), 6.80-6.83 (m, 1 H), 6.60 (s, 1 H), 3.86 (s, 3 H), 3.81 (s, 3 H), and 1.47 (m, 9 H).

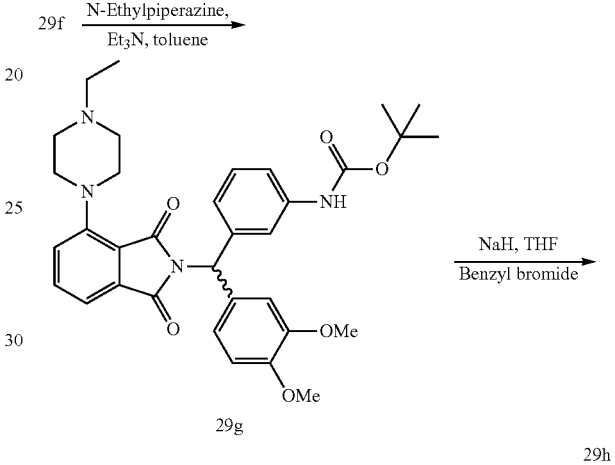

A 5-mL sealed tube was charged with Compound 29f (173 mg, 0.27 mmol), N-ethylpiperazine (0.04 mL, 0.31 mmol), toluene (0.4 mL), and Et$_3$N (0.05 mL, 0.36 mmol). The tube was sealed under argon and heated to 130° C. for 20 h. The mixture was cooled to room temperature and purified on a Analogix IntelliFlash 280 with a normal phase Super Flash column (SF25—40 g, gradient 100:0-90:10 CH$_2$Cl$_2$:CH$_3$OH) to give 126 mg of Compound 29g as a yellow solid.

$^1$H NMR (300 MHz, CDCl$_3$) δ 7.54-7.59 (m, 2 H), 7.35 (d, J=7.0 Hz, 1 H), 7.22-7.28 (m, 1 H), 7.15 (d, J=8.3 Hz, 1 H), 7.06 (s, 1 H), 6.93-7.01 (m, 3 H), 6.79-6.82 (m, 1 H), 6.58 (s, 1 H), 3.86 (s, 3 H), 3.80 (s, 3 H), 3.37-3.49 (m, 4 H), 2.65-2.72 (m, 4 H), 2.52 (q, J=7.2 Hz, 2 H), 1.47 (m, 9 H), and 1.14 (t, J=7.2 Hz, 3 H); MS (ES$^+$) 601 (M+1).

A 10-mL round bottom flask was charged with Compound 29g (43 mg, 0.07 mmol) and tetrahydrofuran (0.72 mL). 95% Sodium hydride (2.6 mg, 0.11 mol) was added and the mixture was stirred at room temperature for 10 minutes. Benzylbromide (0.01 mL, 0.08 mmol) was added and the mixture was stirred at room temperature for 2 h. The crude mixture was purified on a Analogix IntelliFlash 280 with a normal phase Super Flash column (SF25—40g, gradient 100:0-90:10 CH$_2$Cl$_2$:CH$_3$OH) to give 40 mg of Compound 29h as a yellow solid.

$^1$H NMR (300 MHz, CD$_3$OD) δ 7.54-7.60 (m, 1 H), 7.34 (d, J=7.0 Hz, 1 H), 7.05-7.23 (m, 9 H), 6.88-6.93 (m, 3 H), 6.77 (d, J=8.2 Hz, 1 H), 6.54 (s, 1 H), 4.76 (s, 2 H), 3.86 (s, 3 H), 3.77 (s, 3 H), 3.38-3.49 (m, 4 H), 2.62-2.72 (m, 4 H), 2.53 (q, J=7.2 Hz, 2 H), 1.37 (m, 9 H), and 1.14 (t, J=7.2 Hz, 3 H); MS (ES$^+$) 691 (M+1).

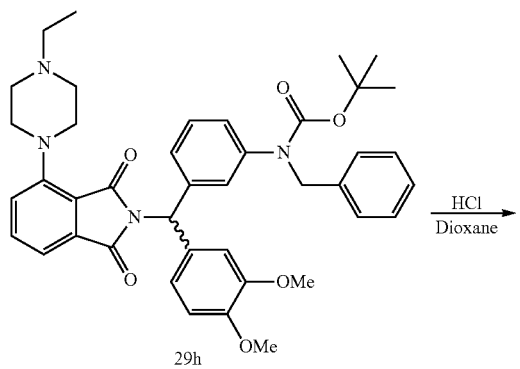

29h

→ HCl Dioxane

A 5-mL round bottom flask was charged with Compound 29h (40.0 mg, 0.06 mmol) and dioxane (0.5 mL). 4N HCl in dioxane (0.5 mL, 2.0 mmol) was added and the mixture was stirred at room temperature for 4 h. The mixture was concentrated in vacuo and triturated with heptane (1 mL). The solid was put on the hivac for 24 h to give 18.9 mg of Compound 230 as a yellow solid. $^1$H NMR (300 MHz, CDCl$_3$) δ 7.52-7.65 (m, 1 H), 7.46 (d, J=7.2 Hz, 1 H), 7.15-7.35 (m, 9 H), 6.57-7.02 (m, 4 H), 6.49 (s, 1 H), 4.30 (s, 2 H), 3.86 (s, 3 H), 3.78 (s, 3 H), 3.53-3.71 (m, 4 H), 3.26-3.30 (m, 2 H), 2.91-3.14 (m, 4 H), and 1.25-1.39 (m, 3 H); MS (ES$^+$) 591 (M+1).

Other compounds of the present invention may be prepared by those skilled in the art by varying the starting materials, reagent(s) and conditions used. Using the procedure of Example 29, the following compounds were prepared:

| Cpd | Name |
|---|---|
| 231 | (3-{(3,4-dimethoxy-phenyl)-[4-(4-ethyl-piperazin-1-yl)-1,3-dioxo-1,3-dihydro-isoindol-2-yl]-methyl}-phenyl)-sulfamic acid<br>$^1$H NMR (300 MHz, CD$_3$OD) δ 7.57-7.65 (m, 2 H), 7.19-7.48 (m, 6 H), 6.91 (s, 1 H), 6.83 (s, 3 H), 6.54 (s, 1 H), 6.49 (s, 1 H), 4.08-4.12 (m, 1 H), 3.82-3.95 (m, 2 H), 3.71 (s, 3 H), 3.62 (s, 3 H), 3.52-3.60 (m, 3 H), 3.17-3.24 (m, 4 H), and 0.82 (t, J = 8.7 Hz, 3 H); MS (ES+) 581.3 (M + 1). |
| 232 | 2-[2-(1-benzyl-piperidin-4-yl)-1-(3,4-dimethoxy-phenyl)-ethyl]-4-(4-ethyl-piperazin-1-yl)-isoindole-1,3-dione<br>$^1$H NMR (300 MHz, CDCl$_3$) δ 7.61 (dd, J = 7.5, 8.0 Hz, 1H), 7.33-7.45 (m, 6H), 7.0-7.19 (m, 3H), 6.78 (d, J = 8.2 Hz, 1H), 5.26 (dd, J = 7.8, 8.5 Hz, 1H), 4.13 (s, 2H), 3.87 (s, 3H), 3.84 (s, 3H), 3.73-3.80 (m, 4H), 3.43-3.58 (m, 4 H), 3.11-3.22 (m, 4H), 2.45-2.60 (m, 4H), 2.25-2.34 (m, 1H), 1.77-1.96 (m, 4H), 1.44 (t, J = 7.2 Hz, 3H); MS (ES+) 597 (M + 1). |
| 233 | 4-{2-(3,4-dimethoxy-phenyl)-2-[4-(4-ethyl-piperazin-1-yl)-1,3-dioxo-1,3-dihydro-isoindol-2-yl]-ethyl}-piperidine-1-sulfonic acid<br>$^1$H NMR (300 MHz, CDCl$_3$) δ 7.62 (dd, J = 7.6, 7.9 Hz, 1H), 7.43 (d, J = 7.2 Hz, 1H), 7.03-7.19 (m, 3H), 6.80 (d, J = 8.2 Hz, 1H), 5.25-5.34 (m, 1H), 3.89 (s, 3H), 3.85 (s, 3H), 3.70-3.80 (m, 4H), 3.40-3.55 (m, 2 H), 2.95-3.25 (m, 6H), 2.68-2.95 (m, 4H), 1.95-2.11 (m, 3H), 1.52-1.73 (m, 2H), 1.43 (t, J = 7.2 Hz, 3H); MS (ES+) 587 (M + 1). |
| 234 | 2-{1-(3,4-dimethoxy-phenyl)-2-[1-(thiophene-2-sulfonyl)-piperidin-4-yl]-ethyl}-4-(4-ethyl-piperazin-1-yl)-isoindole-1,3-dione<br>$^1$H NMR (300 MHz, CDCl$_3$) δ 7.57-7.65 (m, 2H), 7.48 (d, J = 2.8 Hz, 1H), 7.43 (d, J = 7.2 Hz, 1H), 7.02-7.15 (m, 4H), 6.78 (d, J = 8.2 Hz, 1H), 5.29 (dd, J = 7.6, 8.6 Hz, 1H), 3.87 (s, 3H), 3.84 (s, 3H), 3.50-3.80 (m, 10H), 3.05-3.25 (m, 4 H), 2.43-2.53 (m, 1H), 2.19-2.29 (m, 3H), 1.80-1.88 (m, 2H), 1.10-1.55 (m, 4H); MS (ES+) 653 (M + 1). |

Example 30

2-(3,4-dimethoxy-benzyl)-5-[4-(1R)-(1-phenyl-ethyl)-piperazin-1-yl]-isoindole-1,3-dione Cpd 226

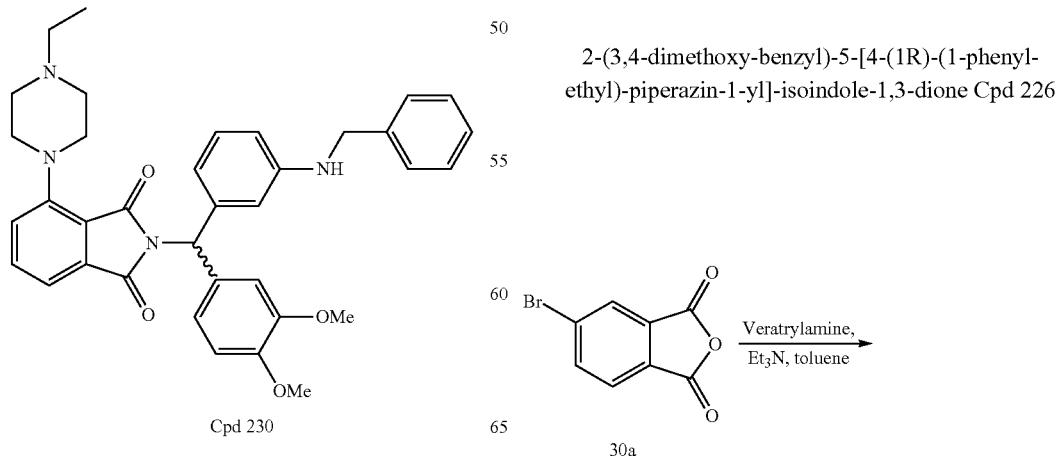

Cpd 230

30a → Veratrylamine, Et$_3$N, toluene

Example 31

(R)-2-[1-(3,4-dimethoxy-phenyl)-4-(pyrimidin-2-ylamino)-butyl]-4-[4-(1R)-(1-phenyl-ethyl)-piperazin-1-yl]-isoindole-1,3-dione Cpd 145

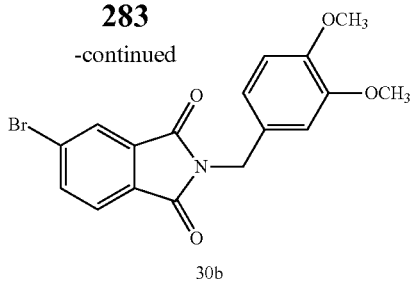

30b

A 200-mL round bottom flask was charged with 4-bromophthalic anhydride Compound 30a (2.0 g, 8.81 mmol) and dry toluene (44 mL). Veratrylamine (1.6 mL, 10.6 mmol) and triethylamine (1.8 mL, 12.9 mmol) were added to the mixture. A Dean-Stark trap was attached to the flask and the mixture was refluxed for 24 h. The mixture was cooled to room temperature and diluted with dichlormethane (200 mL) and washed with 1.0 N HCl (100 mL). The organic layers were combined and dried using MgSO$_4$, filtered through Celite®, and concentrated in vacuo to give 1.67 g of Compound 30b as a yellow solid. $^1$H NMR (300 MHz, CDCl$_3$) δ 7.97 (s, 1 H), 7.84 (d, J=7.9 Hz, 1 H), 7.69 (d, J=7.9 Hz, 1 H), 6.99-7.02 (m, 2 H), 6.80 (d, J=8.1 Hz, 1 H), 4.77 (s, 2 H), 3.87 (s, 3 H), and 3.84 (s, 3 H).

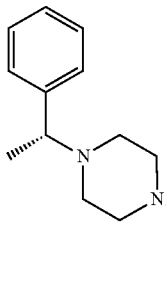

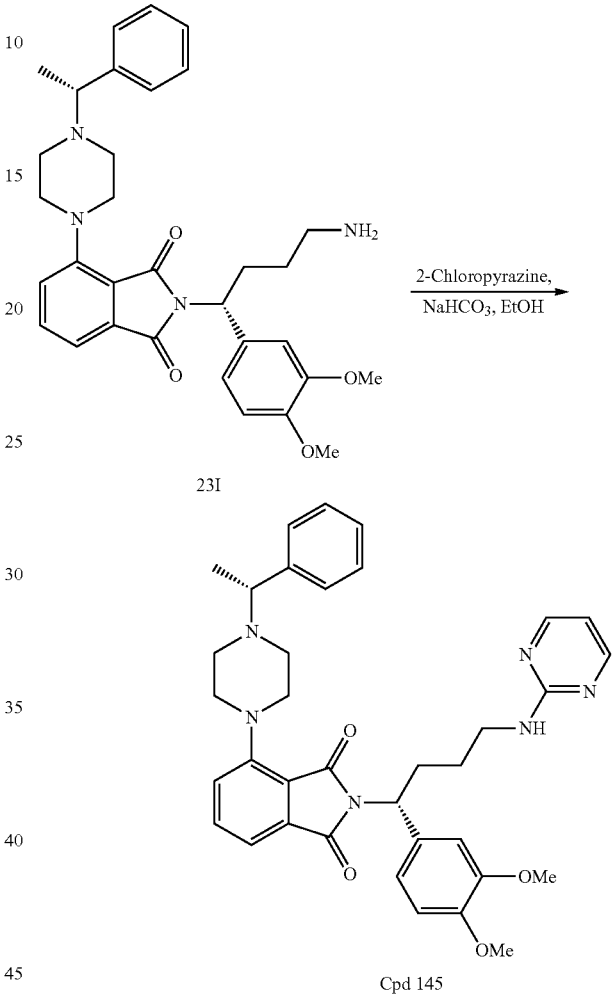

Cpd 145

A 5-mL sealed tube was charged with Compound 30b (202 mg, 0.54 mmol), cetyltrimethylammonium bromide (11.0 mg, 0.030 mmol), Bis(tri-t-butylphosphine)palladium (0) (29 mg, 0.023 mmol), Compound 13h (120 mg, 0.63 mmol), toluene (0.53 mL), and 45% aqueous KOH (0.07 mL). The tube was sealed under argon and heated to 90° C. for 5 h. The mixture was cooled to room temperature and concentrated in vacuo. The crude oil was purified on a Gilson HPLC with a reversed phase Kromasil column (10 u, 100 Å C18, column length 250×50 mm, gradient 80:20-0:100 H$_2$O:MeCN). The purified material was dissolved in dichloromethane (50 mL), treated with 1M HCl in diethyl ether (10 mL), and concentrated in vacuo. This procedure was repeated two more times to give 34.1 mg of the title Compound 226 as a yellow solid. $^1$H NMR (300 MHz, CDCl$_3$) δ 7.63 (d, J=8.4 Hz, 1 H), 7.22-7.42 (m, 7 H), 6.95-7.01 (m, 2 H), 6.77-6.81 (m, 1 H), 4.72 (s, 2 H), 4.07-4.13 (m, 1 H), 3.86 (s, 3 H), 3.83 (s, 3 H), 3.34-3.44 (m, 4 H), 2.49-2.67 (m, 4 H), and 1.40 (d, J=6.7 Hz, 3 H); MS (ES$^+$) 486 (M+1).

A 100-mL round bottom flask was charge with Compound 23l (30.0 mg, 0.05 mmol) and ethanol (0.5 mL). Sodium bicarbonate (12.8 mg, 0.15 mmol) was added to the mixture followed by 2-chloropyrimidine (8.0 mg, 0.07 mmol). The mixture was heated to 90° C. for 24 h. The crude material was purified on a Gilson HPLC with a reversed phase Kromasil column (10 u, 100 Å C18, column length 250×50 mm, gradient 80:20-0:100 H$_2$O:MeCN) to give 9.9 mg of the title Compound 145 as a yellow solid. $^1$H NMR (300 MHz, CDCl$_3$) δ 8.53-8.62 (m, 1 H), 8.01-8.10 (m, 1 H), 7.59 (dd, J=8.4 Hz, 8.0 Hz, 1 H), 7.43-7.50 (m, 5 H), 7.41 (d, J=7.1 Hz, 1 H), 6.91-7.10 (m, 3 H), 6.78 (d, J=8.3 Hz, 1 H), 6.68-6.71 (m, 1 H), 5.20-5.25 (m, 1 H), 4.32-4.41 (m, 1 H), 3.86 (s, 3 H), 3.84 (s, 3 H), 3.45-3.73 (m, 6 H), 2.82-3.07 (m, 4 H), 2.58-2.61 (m, 1 H), 2.36-2.45 (m, 1 H), 1.86 (d, J=6.9 Hz, 3 H), and 1.62-1.73 (m, 2 H); MS (ES$^+$) 621 (M+1).

Other compounds of the present invention may be prepared by those skilled in the art by varying the starting materials, reagent(s) and conditions used. Using the procedure of Example 31, the following compounds were prepared:

| Cpd | Name |
|---|---|
| 142 | (R)-2-[1-(3,4-dimethoxy-phenyl)-4-(pyridin-2-ylamino)-butyl]-4-[4-(1R)-(1-phenyl-ethyl)-piperazin-1-yl]-isoindole-1,3-dione MS (ES+) 620.3 (M + 1). |

Example 32

(R)-2-[4-(4,5-dihydro-1H-pyrrol-2-ylamino)-1-(3,4-dimethoxy-phenyl)-butyl]-4-[4-(1R)-(1-phenyl-ethyl)-piperazin-1-yl]-isoindole-1,3-dione Cpd 165

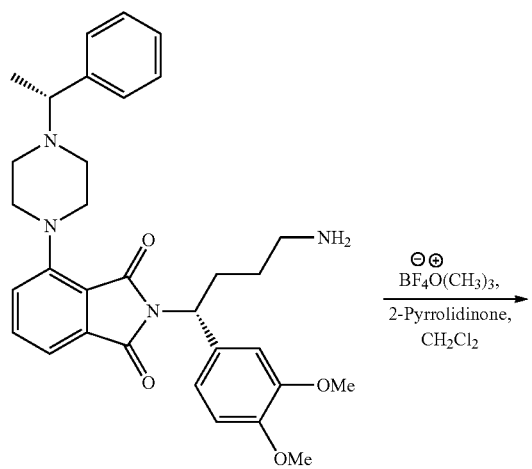

A 100-mL round bottom flask was charge with 2-pyrrolidinone (4.1 mg, 0.05 mmol) and dichloromethane (0.5 mL). Triethyloxonium tetrafluoroborate (7.4 mg, 0.05 mmol) was added and the mixture was stirred at room temperature for 24 h. Compound 23l (30.0 mg, 0.05 mmol) was dissolved in dichloromethane (0.5 mL) and added to the mixture and stirred at 40° C. for 24 h. The crude material was purified on a Gilson HPLC with a reversed phase Kromasil column (10 u, 100 Å C18, column length 250×50 mm, gradient 80:20-0:100 H$_2$O:MeCN) to give 28.5 mg of the title Compound 165 as a yellow solid. $^1$H NMR (300 MHz, CDCl$_3$) δ 7.59 (dd, J=8.0 Hz, 7.4 Hz, 1 H), 7.45-7.50 (m, 5H), 7.41 (d, J=7.1 Hz, 1 H), 6.91-7.11 (m, 3 H), 6.79 (d, J=8.2 Hz, 1 H), 5.14-5.20 (m, 1 H), 4.30-4.38 (m, 1 H), 3.86 (s, 3 H), 3.84 (s, 3 H), 3.62-3.77 (m, 4 H), 3.42-3.52 (m, 2 H), 3.24-3.31 (m, 2 H), 2.93-3.08 (m, 2 H), 2.56-2.74 (m, 2 H), 2.02-2.49 (m, 6 H), 1.86 (d, J=6.9 Hz, 3 H), and 1.60-1.66 (m, 2 H); MS (ES$^+$) 610 (M+1).

Other compounds of the present invention may be prepared by those skilled in the art by varying the starting materials, reagent(s) and conditions used. Using the procedure of Example 32, the following compounds were prepared:

| Cpd | Name |
|---|---|
| 146 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-guanidine $^1$H NMR (300 MHz, CDCl$_3$) δ 7.56 (t, J = 8 Hz, 1H), 7.51 (m, 5H), 7.39 (d, J = 7.1 Hz, 1H), 7.1-7.0 (m, 3H), 6.7 (d, J = 8.4 Hz, 1H), 5.18 (m, 1H), 4.30 (m, 1H), 3.86 (s, 3H), 3.83 (s, 3H), 3.9-2.2 (m, 13H), 1.83 (d, J = 6.8 Hz, 1H), 1.57 (m, 2H); MS (ES+) 585.2 (M + 1). |
| 166 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamidine MS (ES+) 584.2 (M + 1). |

Example 33

(R)-thiophene-2-sulfonic acid [4-(3,4-dimethoxy-phenyl)-4-(1,3-dioxo-4-piperazin-1-yl-1,3-dihydro-isoindol-2-yl)-butyl]-amide Cpd 167

(R)-thiophene-2-sulfonic acid {4-(3,4-dimethoxy-phenyl)-4-[4-(4-furan-3-ylmethyl-piperazin-1-yl)-1,3-dioxo-1,3-dihydro-isoindol-2-yl]-butyl}-amide Cpd 170

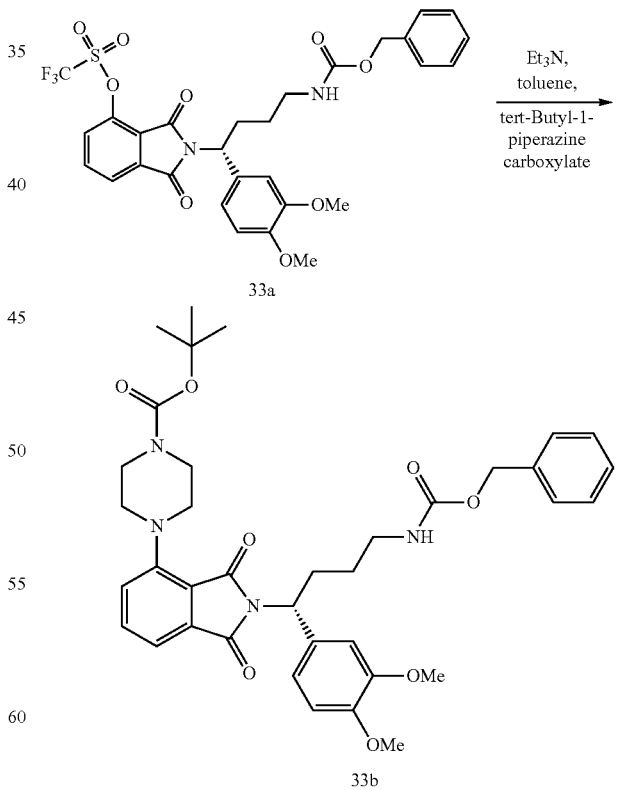

A 20-mL sealed tube was charged with Compound 33a (2.52 g, 3.96 mmol, prepared analogously to 23j), tert-butyl 1-piperazinecarboxylate (0.75 g, 4.03 mmol), toluene (4.0 mL), and triethylamine (0.8 mL, 5.74 mmol). The tube was sealed under argon and heated to 110° C. for 22 h. The mixture was cooled to room temperature and purified on a Analogix IntelliFlash 280 with a normal phase Super Flash column (SF40—150 g, gradient 80:20-40:60 Heptane: EtOAc) to give 1.1 g of Compound 33b as a yellow solid. $^1$H NMR (300 MHz, CDCl$_3$) δ 7.54 (dd, J=8.2 Hz, J=7.4 Hz, 1 H), 7.29-7.37 (m, 6 H), 7.06-7.13 (m, 3 H), 6.79 (d, J=8.3 Hz, 1 H), 5.18-5.30 (m, 1 H), 5.07 (s, 2 H), 3.87 (s, 3 H), 3.84 (s, 3 H), 3.65-3.68 (m, 4 H), 3.24-3.29 (m, 6 H), 2.49-2.59 (m, 1 H), 2.26-2.36 (m, 1 H), 1.49 (s, 9 H), and 1.24-1.28 (m, 2 H); MS (ES$^+$) 673 (M+1).

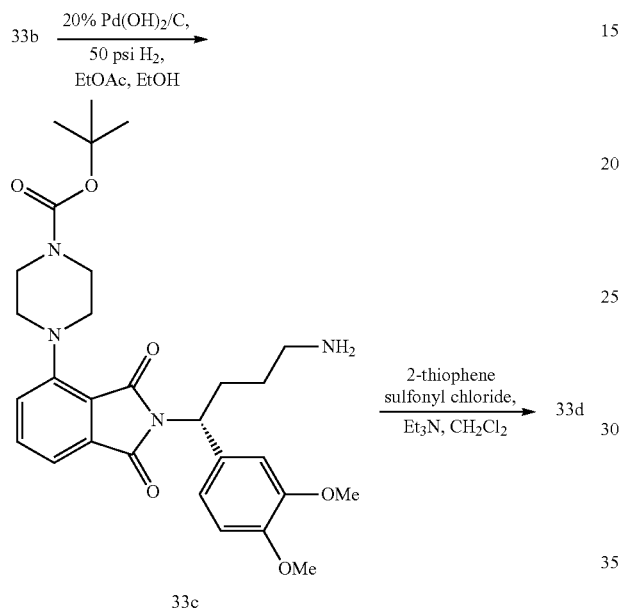

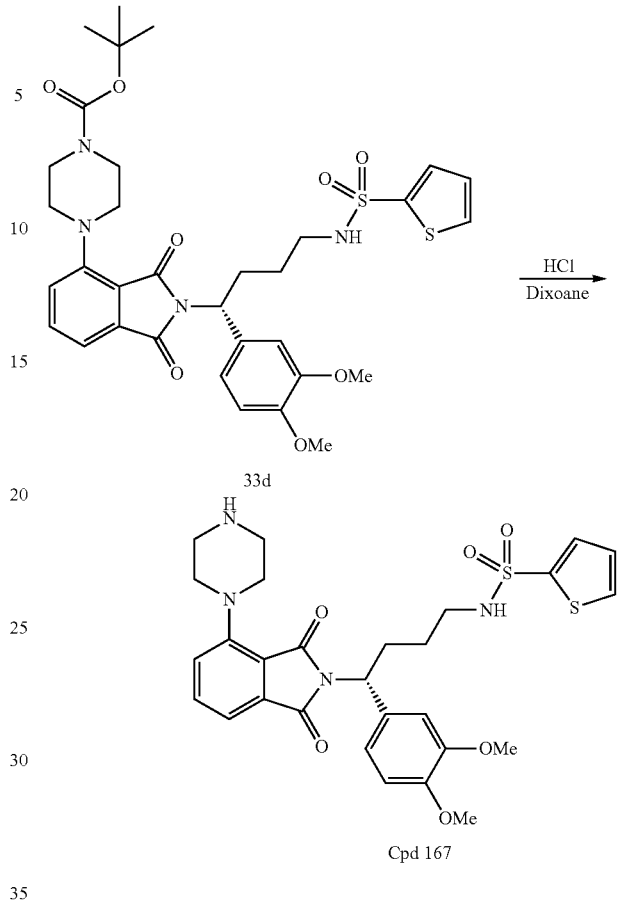

A 250-mL hydrogenation vessel was charged with Compound 33b (0.45 g, 0.68 mmol), ethyl acetate (10 mL), 20% palladium hydroxide on carbon (0.1 g), 1N aqueous HCl (1.0 mL), and ethanol (10 mL). The mixture was put under 50 psi hydrogen using a Parr shaker for 24 h. The mixture was filtered through Celite® and concentrated in-vacuo to give 0.33 g of Compound 33c as a yellow solid. $^1$H NMR (300 MHz, CDCl$_3$) δ 7.49-7.60 (m, 1 H), 7.20-7.29 (m, 1 H), 6.91-7.10 (m, 3 H), 6.76-6.79 (m, 1 H), 5.21-5.25 (m, 1 H), 3.87-3.93 (m, 1 H), 3.84 (s, 3 H), 3.82 (s, 3 H), 3.60-3.68 (m, 4 H), 3.23-3.36 (m, 4 H), 3.07-3.15 (m, 2 H), 2.54-2.80 (m, 2 H), 1.70-1.86 (m, 2 H), and 1.47 (s, 9 H); MS (ES$^+$) 539 (M+1).

A 250-mL round bottom flask was charged with Compound 33c (0.25 g, 0.43 mmol) and dichloromethane (21.5 mL). Triethylamine (0.21 mL, 1.51 mmol) was added followed by 2-thiophenesulfonyl chloride (86.4 mg, 0.47 mmol). The mixture was stirred at room temperature for 24 h and concentrated in vacuo. The mixture was cooled to room temperature and purified on a Analogix IntelliFlash 280 with a normal phase Super Flash column (SF40—150 g, gradient 99:1-80:20 CH$_2$Cl$_2$:EtOH:0.1% Et$_3$N) to give 0.28 g of Compound 33d as a yellow solid. $^1$H NMR (300 MHz, CDCl$_3$) δ 7.52-7.61 (m, 3 H), 7.35 (d, J=7.1 Hz, 1 H), 7.03-7.12 (m, 4 H), 6.78 (d, J=8.3 Hz, 1 H), 5.13-5.19 (m, 1 H), 4.43-4.47 (m, 1 H), 3.88 (s, 3 H), 3.85 (s, 3 H), 3.65-3.74 (m, 4 H), 3.23-3.35 (m, 4 H), 3.06-3.13 (m, 2 H), 2.49-2.59 (m, 1 H), 2.24-2.34 (m, 1 H), 1.49 (s, 9 H), and 1.22-1.27 (m, 2 H); MS (ES$^+$) 685 (M+1).

A 5-mL round bottom flask was charged with Compound 33d (0.28 g, 0.41 mmol) and dioxane (8.0 mL). 4N HCl in dioxane (8.0 mL) was added and the mixture was stirred at room temperature for 4 h. The mixture was concentrated in vacuo. The crude oil was purified on a Gilson HPLC with a reversed phase Kromasil column (10 u, 100 Å C18, column length 250×50 mm, gradient 90:10-0:100 H$_2$O:MeCN) to give 0.26 g of Compound 167 as a yellow solid. $^1$H NMR (300 MHz, CDCl$_3$) δ 7.52-7.63 (m, 3 H), 7.43 (d, J=7.2 Hz, 1 H), 7.03-7.18 (m, 4 H), 6.79 (d, J=8.1 Hz, 1 H), 5.14-5.26 (m, 1 H), 4.77-4.84 (m, 1 H), 3.88 (s, 3 H), 3.84 (s, 3 H), 3.49-3.63 (m, 8 H), 3.04-3.10 (m, 2 H), 2.53-2.65 (m, 1 H), 2.21-2.39 (m, 1 H), and 1.25-1.47 (m, 2 H); MS (ES$^+$) 585 (M+1).

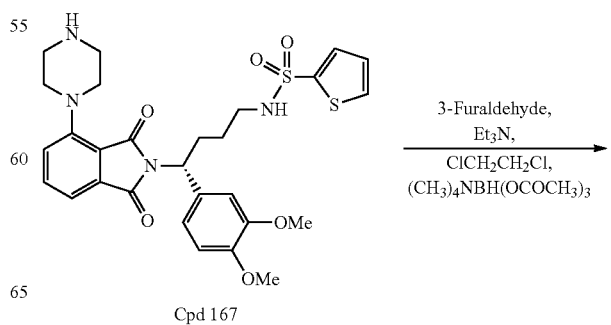

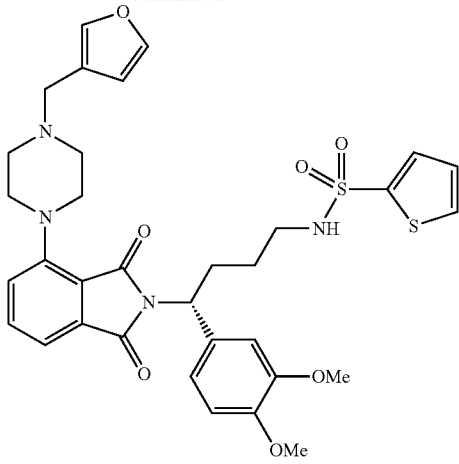

Cpd 170

A 50-mL round bottom flask was charged with Compound 167 (20.0 mg, 0.032 mmol) and dichloroethane (4.0 mL). Trietheylamine (5.0 μL) was added followed by 3-furaldehyde (6.0 mg, 0.06 mmol) and tetramethylammonium triacetoxyborohydride (11.8 mg, 0.045 mmol). The mixture was stirred at room temperature for 3 h. The mixture quenched with saturated aqueous sodium bicarbonate (10 mL) and extracted with dichloromethane (50 mL). The organic layer was dried using $Na_2SO_4$, filtered through Celite®, and concentrated in vacuo. The crude oil was purified on a on a Gilson HPLC with a reversed phase Kromasil column (10 u, 100 Å C18, column length 250×50 mm, gradient 90:10-0:100 $H_2O$: MeCN) to give 13.7 mg of Compound 170 as a yellow solid. $^1$H NMR (300 MHz, $CDCl_3$) δ 7.50-7.64 (m, 5 H), 7.43 (d, J=7.2 Hz, 1 H), 7.13 (d, J=8.2 Hz, 1 H), 7.00-7.06 (m, 3 H), 6.79 (d, J=8.0 Hz, 1 H), 6.56 (s, 1 H), 5.12-5.23 (m, 1 H), 4.61-4.74 (m, 1 H), 3.87 (s, 3 H), 3.84 (s, 3 H), 3.63-3.75 (m, 4 H), 3.41-3.51 (m, 2 H), 2.94-3.35 (m, 4 H), 2.53-2.65 (m, 1 H), 2.18-2.30 (m, 1 H), and 1.46-1.71 (m, 2 H); MS (ES$^+$) 665 (M+1).

Other compounds of the present invention may be prepared by those skilled in the art by varying the starting materials, reagent(s) and conditions used. Using the procedure of Example 33, the following compounds were prepared:

| Cpd | Name |
|---|---|
| 171 | (R)-thiophene-2-sulfonic acid {4-(3,4-dimethoxy-phenyl)-4-[1,3-dioxo-4-(4-pyridin-3-ylmethyl-piperazin-1-yl)-1,3-dihydro-isoindol-2-yl]-butyl}-amide<br>$^1$H NMR (300 MHz, $CDCl_3$) δ 9.00 (s, 1 H), 8.79 (d, J = 4.5 Hz, 1H), 8.39 (d, J = 8.1 Hz, 1H), 7.74 (m, 1H), 7.6-7.5 (m, 3H), 7.43 (d, J = 7.2 Hz, 1H), 7.1-7.0 (m, 4H), 6.79 (d, J = 8.2 Hz, 1H), 5.16 (m, 1H), 4.47 (s, 2H), 3.87 (s, 3H), 3.84 (s, 3H), 3.8-2.7 (m, 10H), 2.2-1.4 (m, 4H); MS (ES+) 676.3 (M + 1). |
| 172 | (R)-thiophene-2-sulfonic acid {4-(3,4-dimethoxy-phenyl)-4-[1,3-dioxo-4-(4-thiophen-3-ylmethyl-piperazin-1-yl)-1,3-dihydro-isoindol-2-yl]-butyl}-amide<br>$^1$H NMR (300 MHz, $CDCl_3$) δ 7.7-7.4 (m, 6H), 7.20 (d, J = 5.0 Hz, 1H), 7.11 (d, J = 8.2 Hz, 1H), 7.1-7.0 (m, 3H), 6.79 (d, J = 8.0 Hz, 1H), 5.15 (m, 1H), 4.34 (m, 1H), 4.34 (m, 2H), 3.87 (s, 3H), 3.85 (s, 3H), 4.2-2.2 (m, 10H), 1.5-1.2 (m, 4H); MS (ES+) 681.3 (M + 1). |
| 192 | (R)-thiophene-2-sulfonic acid [4-[4-(4-cyclobutyl-piperazin-1-yl)-1,3-dioxo-1,3-dihydro-isoindol-2-yl]-4-(3,4-dimethoxy-phenyl)-butyl]-amide<br>$^1$H NMR (300 MHz, $CDCl_3$) δ 7.6-7.5 (m, 3H), 7.44 (d, J = 7.1 Hz, 1H), 7.14 (d, J = 8.2 Hz, 1H), 7.1-7.0 (m, 3H), 6.79 (d, J = 8.1 Hz, 1H), 5.15 (m, 1H), 4.61 (m, 1H), 3.88 (s, 3H), 3.85 (s, 3H), 4.3-1.3 (m, 20H); MS (ES+) 639.3 (M + 1). |
| 194 | (R)-thiophene-2-sulfonic acid [4-[4-(4-allyl-piperazin-1-yl)-1,3-dioxo-1,3-dihydro-isoindol-2-yl]-4-(3,4-dimethoxy-phenyl)-butyl]-amide<br>$^1$H NMR (300 MHz, $CDCl_3$) δ 7.52-7.64 (m, 3 H), 7.44 (d, J = 7.0 Hz, 1 H), 7.13 (d, J = 8.4 Hz, 1 H), 7.00-7.06 (m, 3 H), 6.79 (d, J = 8.2 Hz, 1 H), 5.58-6.03 (m, 1 H), 5.52-5.13 (m, 2 H), 5.12-5.19 (m, 1 H), 4.54-4.61 (m, 1 H), 3.88 (s, 3 H), 3.85 (s, 3 H), 3.69-3.75 (m, 4 H), 3.41-3.56 (m, 2 H), 3.07-3.28 (m, 4 H), 2.52-2.64 (m, 1 H), 2.19-2.38 (m, 2 H), 1.97-2.09 (m, 1 H), and 1.47-1.60 (m, 2 H); MS (ES$^+$) 625.3 (M + 1). |
| 195 | (R)-thiophene-2-sulfonic acid (4-(3,4-dimethoxy-phenyl)-4-{1,3-dioxo-4-[4-(2,2,2-trifluoro-ethyl)-piperazin-1-yl]-1,3-dihydro-isoindol-2-yl}-butyl)-amide<br>$^1$H NMR (300 MHz, $CDCl_3$) δ 7.6-7.5 (m, 3H), 7.35 (d, J = 7.1 Hz, 1H), 7.2-7.0 (m, 4 H), 6.78 (d, J = 8.3 Hz, 1H), 5.15 (m, 1H), 4.45 (m, 1H), 3.88 (s, 3H), 3.84 (s, 3H), 3.4-2.9 (m, 8H), 2.6-2.0 (m, 4H), 1.6-1.3 (m, 4H); MS (ES+) 667.3 (M + 1). |
| 196 | (R)-thiophene-2-sulfonic acid [4-[4-(4-cyclohexyl-piperazin-1-yl)-1,3-dioxo-1,3-dihydro-isoindol-2-yl]-4-(3,4-dimethoxy-phenyl)-butyl]-amide<br>$^1$H NMR (300 MHz, $CDCl_3$) δ 7.6-7.5 (m, 3H), 7.45 (d, J = 7 Hz, 1H), 7.13 (d, J = 8 Hz, 1H), 7.1-7.0 (m, 3H), 6.78 (d, J = 8 Hz, 1H), 5.15 (m, 1H), 4.62 (m, 1H), 3.88 (s, 3H), 3.85 (s, 3H), 3.8-3.1 (m, 11 H), 2.6-1.3 (m, 14H); MS (ES+) 667.3 (M + 1). |
| 198 | (R)-thiophene-2-sulfonic acid {4-(3,4-dimethoxy-phenyl)-4-[4-(4-isopropyl-piperazin-1-yl)-1,3-dioxo-1,3-dihydro-isoindol-2-yl]-butyl}-amide<br>$^1$H NMR (300 MHz, $CDCl_3$) δ 7.6-7.5 (m, 3H), 7.44 (d, J = 7.2 Hz, 1H), 7.14 (d, J = 8.3 Hz, 1H), 7.1-7.0 (m, 3H), 6.79 (d, J = 8.1 Hz, 1H), 5.16 (m, 1H), 4.53 (m, 1H), 3.88 (s, 3H), 3.85 (s, 3H), 3.8-3.0 (m, 9 H), 2.7-1.4 (m, 6H), 144 (d, J = 6.7 Hz, 6H); MS (ES+) 627.3 (M + 1). |

Example 34

(R)-thiophene-2-sulfonic acid [4-[4-(4-cyclopentyl-piperazin-1-yl)-1,3-dioxo-1,3-dihydro-isoindol-2-yl]-4-(3,4-dimethoxy-phenyl)-butyl]-amide Cpd 193

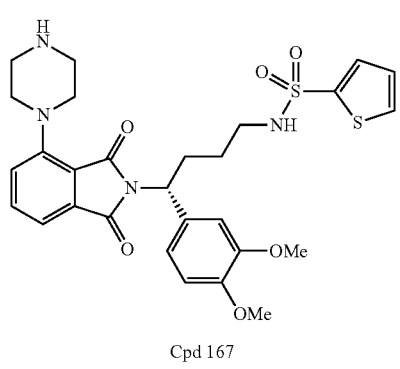

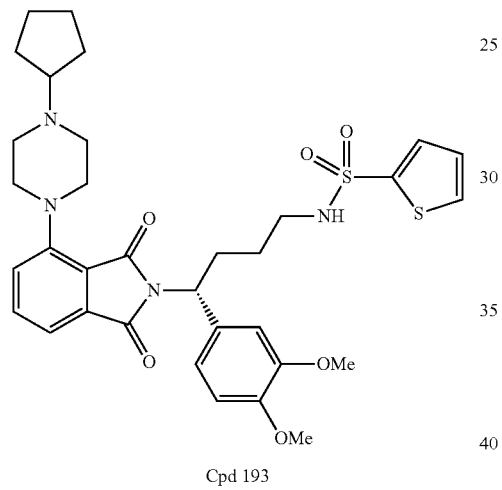

A 50-mL round bottom flask was charged with Compound 167 (10.0 mg, 0.016 mmol) and dichloroethane (2.3 mL). Triethylamine (2.5 µL, 0.018 mmol) was added followed by cyclopentanone (7.1 µL, 0.06 mmol) and sodium triacetoxyborohydride (4.7 mg, 0.022 mmol). The mixture was stirred at room temperature for 3 h. The mixture was quenched with saturated aqueous sodium bicarbonate (10 mL) and extracted with dichloromethane (50 mL). The organic layer was dried using $Na_2SO_4$, filtered through Celite®, and concentrated in vacuo. The crude oil was purified on a on a Gilson HPLC with a reversed phase Kromasil column (10 u, 100 Å C18, column length 250×50 mm, gradient 75:25-0:100 $H_2O$:MeCN) to give 5.1 mg of Compound 193 as a yellow solid. $^1H$ NMR (300 MHz, $CDCl_3$) δ 7.53-7.64 (m, 3 H), 7.44 (d, J=7.2 Hz, 1 H), 7.14 (d, J=8.2 Hz, 1 H), 6.91-7.06 (m, 2 H), 6.79 (d, J=8.0 Hz, 1 H), 6.56 (s, 1 H), 5.13-5.19 (m, 1 H), 4.51-4.64 (m, 1 H), 3.88 (s, 3 H), 3.85 (s, 3 H), 3.73-3.83 (m, 2 H), 3.42-3.64 (m, 2 H), 2.78-3.22 (m, 6 H), 2.48-2.61 (m, 1 H), 1.88-2.31 (m, 4 H), 1.47-1.69 (m, 4 H), and 1.27-1.33 (m, 4 H); MS (ES$^+$) 653 (M+1).

Example 35

(R)—N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide Cpd 141

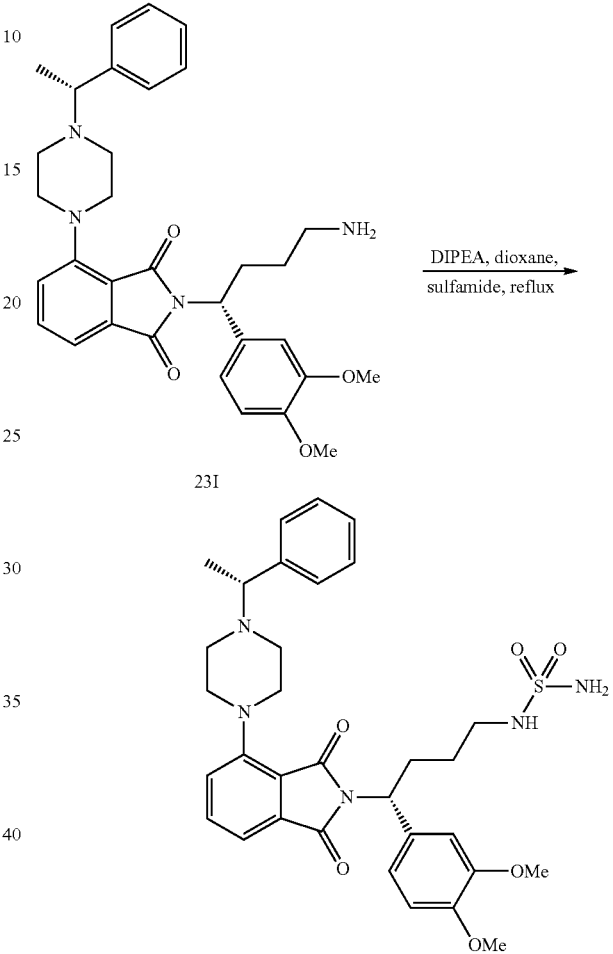

A 100-mL round bottom flask was charged with Compound 231 (120 mg, 0.195 mmol) and dioxane (10 mL). Sulfamide (56 mg, 0.585 mmol) was added followed by diisopropylethylamine (68.0 µL, 0.391 mmol) and the mixture was refluxed for 5 h. The mixture was cooled to room temperature and diluted with ethylacetate (100 mL), washed with water (30 mL), 1N sodium hydroxide (30 mL), and 2% aqueous citric acid (30 mL). The organic layers were combined and dried using $Na_2SO_4$, filtered through Celite®, and concentrated in vacuo. The crude material was purified on a Gilson HPLC with a reversed phase Kromasil column (10 u, 100 Å C18, column length 250×50 mm, gradient 80:20-0:100 $H_2O$:MeCN) to give 24.6 mg of the title Compound 141 as a yellow solid. $^1H$ NMR (300 MHz, $CDCl_3$) δ 7.41-7.71 (m, 7 H), 7.01-7.13 (m, 3 H), 6.79 (d, J=8.2 Hz, 1 H), 5.15-5.21 (m, 1 H), 4.02-4.23 (m, 2 H), 3.86 (s, 3 H), 3.84 (s, 3 H), 3.61-3.80 (m, 6 H), 3.33-3.49 (m, 5 H), 2.94-3.09 (m, 2 H), 2.50-2.63 (m, 1 H), 2.22-2.34 (m, 1 H), 1.99 (d, J=6.8 Hz, 3 H), and 1.59-1.67 (m, 5 H); MS (ES$^+$) 622 (M+1); [α]25$_D$=+ 53.6 (c 1.41, $CHCl_3$).

Other compounds of the present invention may be prepared by those skilled in the art by varying the starting materials, reagent(s) and conditions used. Using the procedure of Example 35, the following compounds were prepared:

| Cpd | Name |
|---|---|
| 122 | N'-[(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)]-sulfamide
$^1$H NMR (300 MHz, CDCl$_3$) δ 7.58 (ovdd, J = 8.0 Hz, 1 H), 7.45-7.51 (m, 5 H), 7.41 (d, J = 7.2 Hz, 1 H), 6.91-7.11 (m, 3 H), 6.78 (d, J = 8.2 Hz, 1 H), 5.17-5.23 (m, 1 H), 4.26-4.39 (m, 1 H), 3.86 (s, 3 H), 3.84 (s, 3 H), 3.62-3.73 (m, 2 H), 3.38-3.59 (m, 4 H), 2.86-3.25 (m, 4 H), 2.60-2.67 (m, 1H), 2.12-2.33 (m, 1 H), 1.84 (d, J = 6.9 Hz, 3 H), and 1.40-1.66 (m, 2 H); MS (ES$^+$) 622 (M + 1). |

Example 36

(R)-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide Cpd 190

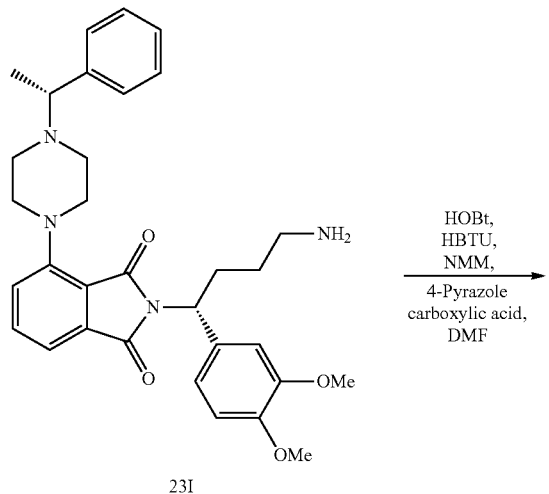

231

HOBt, HBTU, NMM, 4-Pyrazole carboxylic acid, DMF

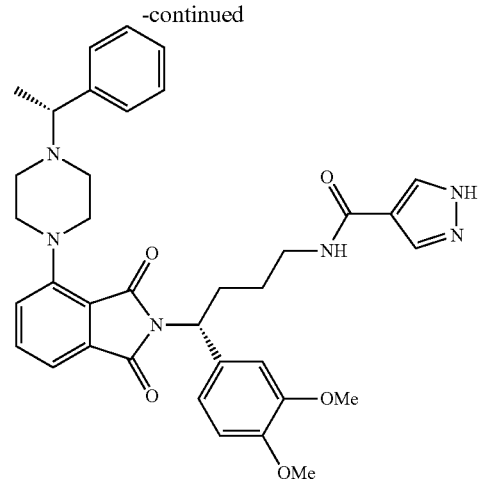

Cpd 190

A 50-mL round bottom flask was charged with Compound 231 (30 mg, 0.05 mmol) and dimethylformamide (1.0 mL). The mixture was cooled using an ice/water bath. N-Methylmorpholine (NMM) (16.0 µL, 0.147 mmol), 4-pyrazolecarboxylic acid (9.0 mg, 0.08 mmol), hydroxybenzotriazole hydrate (HOBT) (6.0 mg, 0.044 mmol), and O-benzothiazol-1-yl-N,N,N',N'-tetramethyluronium hexafluorophosphate (HBTU) (37 mg, 0.10 mmol) were added. The mixture was stirred at room temperature for 20 h. The mixture was diluted with ethylacetate (100 mL), washed with 1N sodium hydroxide (2×30 mL), and saturated aqueous sodium chloride (30 mL). The organic layer was dried using Na$_2$SO$_4$, filtered through Celite®, and concentrated in vacuo. The crude material was purified on a Gilson HPLC with a reversed phase Kromasil column (10 u, 100 Å C18, column length 250×50 mm, gradient 85:15-0:100 H$_2$O:MeCN) to give 10.0 mg of the title Compound 190 as a yellow solid. $^1$H NMR (300 MHz, CDCl$_3$) δ 8.07 (s, 1 H), 7.58 (ovdd, J=8.0 Hz, 1 H), 7.41-7.49 (m, 6 H), 6.98-7.09 (m, 3 H), 6.77-6.88 (m, 3 H), 6.40-6.51 (m, 1 H), 5.20-5.24 (m, 1 H), 4.34-4.36 (m, 1 H), 3.85 (s, 3 H), 3.83 (s, 3 H), 3.71-3.80 (m, 3 H), 3.36-3.51 (m, 5 H), 2.92-3.18 (m, 3 H), 2.62-2.74 (m, 1 H), 2.19-2.28 (m, 1 H), 1.85 (d, J=5.9 Hz, 3 H), and 1.51-1.75 (m, 2 H); MS (ES+) 637.3 (M+1).

Other compounds of the present invention may be prepared by those skilled in the art by varying the starting materials, reagent(s) and conditions used. Using the procedure of Example 36, the following compounds were prepared:

| Cpd | Name |
|---|---|
| 102 | N-(2-(3,4-dimethoxy-phenyl)-2-{1,3-dioxo-4-[4-(1R)-(1-phenyl-ethyl)-piperazin-1-yl]-1,3-dihydro-isoindol-2-yl}-ethyl)-2-pyridin-4-yl-acetamide
Compound 66 was carried forward.
$^1$H NMR (300 MHz, CDCl$_3$) δ 8.30-8.36 (m, 2 H), 7.53 (ovdd, J = 8.0 Hz, 1 H), 7.21-7.37 (m, 7 H), 7.12 (d, J = 8.2 Hz, 1 H), 6.88-7.02 (m, 3 H), 6.76 (d, J = 8.2 Hz, 1 H), 5.98-6.03 (m, 1 H), 5.41-5.49 (m, 1 H), 4.23-4.37 (m, 1 H), 3.72-3.98 (m, 8 H), 3.44 (s, 2 H), 3.26-3.33 (m, 4 H), 2.67-2.76 (m, 2 H), 2.52-2.65 (m, 2 H), and 1.42 (d, J = 6.9 Hz, 3 H); MS (ES$^+$) 635.0 (M + 1). |
| 103 | N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-2-pyridin-4-yl-acetamide
Compound 66 was carried forward.
$^1$H NMR (300 MHz, CDCl$_3$) δ 8.52-8.59 (m, 2 H), 7.49 (ovdd, J = 8.0 Hz, 1 H), 7.18-7.37 (m, 7 H), 7.09 (d, J = 8.2 Hz, 1 H), 6.98-7.05 (m, 3 H), 6.76 (d, J = 8.2 Hz, 1 H), 5.58-5.62 (m, 1 H), 5.14-5.22 (m, 1 H), 3.73-3.94 (m, 9 H), 3.49 (s, 2 H), 3.26-3.41 (m, 4 H), 3.02-3.19 (m, 1 H), 2.67-2.76 (m, 2 H), 2.54-2.65 (m, 2 H), 2.31-2.51 (m, 1 H), and 1.43 (d, J = 6.9 Hz, 3 H); MS (ES$^+$) 648.8 (M + 1). |

| Cpd | Name |
|---|---|
| 104 | thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>Compound 66 was carried forward.<br>$^1$H NMR (300 MHz, CDCl$_3$) δ 7.30-7.61 (m, 9 H), 7.03-7.11 (m, 4 H), 6.78 (d, J = 8.2 Hz, 1 H), 6.09-6.14 (m, 1 H), 5.19-5.24 (m, 1 H), 4.21-4.38 (m, 1 H), 3.86 (s, 3 H), 3.84 (s, 3 H), 3.62-3.76 (m, 2 H), 3.47-3.59 (m, 6 H), 2.91-3.10 (m, 2 H), 2.54-2.67 (m, 1 H), 2.08-2.33 (m, 1 H), 1.85 (d, J = 6.9 Hz, 3 H), and 1.54-1.74 (m, 2 H); MS (ES+) 653.8 (M + 1). |
| 143 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-dimethylamino-acetamide<br>$^1$H NMR (300 MHz, CDCl$_3$) δ 5.30-8.37 (bs, 1 H), 7.57 (ovdd, J = 8.0 Hz, 1 H), 7.45-7.49 (m, 5 H), 6.91-7.08 (m, 3 H), 6.78 (d, J = 8.0 Hz, 1 H), 5.17-5.25 (m, 1 H), 4.27-4.32 (m, 1 H), 3.91-3.96 (m, 1 H), 3.82-3.86 (m, 8 H), 3.22-3.59 (m, 6 H), 2.88 (s, 6 H), 2.33-2.75 (m, 4 H), 2.04-2.23 (m, 1 H), 1.85 (d, J = 6.9 Hz, 1 H), and 1.41-1.53 (m, 2 H); MS (ES+) 629.9 (M + 2). |
| 144 | (R)-5-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.46 (s, 1 H), 7.52 (ovdd, J = 8.2 Hz, 1 H), 7.28-7.36 (m, 6 H), 7.05-7.14 (m, 2 H), 6.78 (d, J = 8.7 Hz, 1 H), 5.93-6.01 (m, 1 H), 5.20-5.25 (m, 1 H), 3.86 (s, 3 H), 3.83 (s, 3 H), 3.26-3.56 (m, 7 H), 2.59-2.72 (m, 7 H), 2.22-2.36 (m, 1 H), 1.58-1.78 (m, 2 H), and 1.42 (d, J = 6.6 Hz, 3 H); MS (ES$^+$) 652 (M + 1). |
| 147 | (R)-1-methyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.58 (dd, J = 8.2 Hz, J = 7.3 Hz, 1 H), 7.48-7.52 (m, 5 H), 7.42 (d, J = 6.8 Hz, 1 H), 7.03-7.11 (m, 3 H), 6.77-6.79 (m, 1 H), 6.70-6.73 (m, 1 H), 6.50-6.52 (m, 1 H), 6.05-6.10 (m, 1 H), 5.85-5.92 (m, 1 H), 5.19-5.22 (m, 1 H), 4.34-4.36 (m, 1 H), 3.81-3.93 (m, 10 H), 3.72-3.75 (m, 2 H), 3.39-3.48 (m, 6 H), 3.00-3.05 (m, 2 H), 2.92-2.37 (m, 1 H), 1.85 (d, J = 6.9 Hz, 3 H), and 0.92-1.03 (m, 2 H); MS (ES+) 650.3 (M + 1). |
| 148 | (R)-1-methyl-5-sulfamoyl-1H-pyrrole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.58 (ovdd, J = 8.1 Hz, 1 H), 7.42-7.54 (m, 6 H), 7.43 (d, J = 7.1 Hz, 1 H), 7.01-7.09 (m, 3 H), 6.84-6.89 (m, 1 H), 6.78 (d, J = 8.1 Hz, 1 H), 6.07-6.13 (m, 1 H), 5.21-5.26 (m, 1 H), 4.36-4.46 (m, 1 H), 3.78-3.96 (m, 10 H), 3.34-3.62 (m, 6 H), 2.89-3.05 (m, 2 H), 2.64-2.72 (m, 1 H), 2.17-2.23 (m, 1 H), 1.84 (d, J = 6.9 Hz, 3 H), and 1.62-1.75 (m, 2 H); MS (ES+) 729.2 (M + 1). |
| 149 | (R)-1-acetyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>MS (ES+) 682.3 (M + 1). |
| 150 | (R)-pyridine-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.52 (d, J = 4.4 Hz, 1 H), 8.16 (d, J = 7.8 Hz, 1 H), 8.03-8.10 (m, 1 H), 7.84 (dd, J = 7.6 Hz, J = 6.1 Hz, 1 H), 7.58 (ovdd, J = 8.2 Hz, 1 H), 7.43-7.50 (m, 5 H), 6.77-6.82 (d, J = 7.2 Hz, 1 H), 7.04-7.10 (m, 3 H), 6.78 (d, J = 8.3 Hz, 1 H), 5.21-5.25 (m, 1 H), 4.34-4.41 (m, 1 H), 3.84-3.91 (m, 17 H), 3.69-3.75 (m, 2 H), 3.46-3.54 (m, 5 H), 3.01-3.06 (m, 2 H), 2.52-2.59 (m, 1 H), 2.35-2.41 (m, 1 H), 1.86 (d, J = 6.9 Hz, 3 H), and 1.62-1.65 (m, 2 H); MS (ES+) 648.2 (M + 1). |
| 151 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-nicotinamide<br>$^1$H NMR (300 MHz, CDCl$_3$) δ 7.59 (ovdd, J = 8.0 Hz, 1 H), 7.41-7.52 (m, 7 H), 7.01-7.15 (m, 3 H), 6.78-6.83 (m, 1 H), 6.70 (s, 1 H), 6.50-6.54 (m, 1 H), 6.04-6.09 (m, 1 H), 5.82-5.91 (m, 1 H), 5.18-5.23 (m, 1 H), 4.32-4.40 (m, 1 H), 3.81-3.97 (m, 7 H), 3.63-3.78 (m, 3 H), 3.37-3.58 (m, 4 H), 2.96-3.10 (m, 2 H), 2.51-2.63 (m, 1 H), 2.23-2.41 (m, 1 H), 1.84 (d, J = 6.9 Hz, 3 H), and 1.52-1.61 (m, 2 H); MS (ES$^+$) 648.2 (M + 1). |
| 152 | (R)-3-methyl-3H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.35 (s, 1 H), 8.15 (s, 1 H), 7.57 (ovdd, J = 8.0 Hz, 1 H), 7.45-7.49 (m, 5 H), 7.41 (d, J = 7.2 Hz, 1 H), 7.00-7.09 (m, |

| Cpd | Name |
|---|---|
| | 3 H), 6.77 (d, J = 8.2 Hz, 1 H), 5.18-5.24 (m, 1 H), 4.32-4.39 (m, 1 H), 4.08 (s, 3 H), 3.86 (s, 3 H), 3.83 (s, 3 H), 3.24-3.70 (m, 6 H), 2.87-3.09 (m, 4 H), 2.61-2.69 (m, 1 H), 2.18-2.32 (m, 1 H), 1.86 (d, J = 6.9 Hz, 3 H), and 1.52-1.64 (m, 2 H); MS (ES+) 651.8 (M + 1). |
| 153 | (R)-1-methyl-1H-imidazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.22 (s, 1 H), 7.87 (s, 1 H), 7.56 (ovdd, J = 8.0 Hz, 1 H), 7.45-7.49 (m, 5 H), 7.40 (d, J = 7.1 Hz, 1 H), 7.00-7.07 (m, 3 H), 6.78 (d, J = 8.0 Hz, 1 H), 5.18-5.26 (m, 1 H), 4.25-4.34 (m, 1 H), 3.65-3.97 (m, 12 H), 3.22-3.58 (m, 4 H), 2.92-3.15 (m, 3 H), 2.61-2.69 (m, 1 H), 2.15-2.24 (m, 1 H), 1.86 (d, J = 6.9 Hz, 3 H), and 1.52-1.66 (m, 2 H); MS (ES+) 651.3 (M + 1). |
| 154 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isonicotinamide<br>$^1$H NMR (300 MHz, CDCl$_3$) δ 7.59 (dd, J = 8.3 Hz, J = 7.3 Hz, 1 H), 7.41-7.54 (m, 7 H), 7.02-7.14 (m, 3 H), 6.78-6.82 (m, 1 H), 6.71 (s, 1 H), 6.49-6.55 (m, 1 H), 6.03-6.09 (m, 1 H), 5.88-5.92 (m, 1 H), 5.19-5.24 (m, 1 H), 4.31-4.42 (m, 1 H), 3.82-3.99 (m, 7 H), 3.63-3.77 (m, 3 H), 3.39-3.61 (m, 4 H), 2.92-3.10 (m, 2 H), 2.56-2.68 (m, 1 H), 2.22-2.38 (m, 1 H), 1.86 (d, J = 6.9 Hz, 3 H), and 1.56-1.78 (m, 2 H); MS (ES$^+$) 648.2 (M + 1). |
| 155 | (R)-tetrahydro-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.52 (ovdd, J = 7.6 Hz, 1 H), 7.38-7.46 (m, 5 H), 7.35 (d, J = 7.3 Hz, 1 H), 6.94-7.08 (m, 3 H), 6.68-6.70 (m, 2 H), 5.02-5.14 (m, 1 H), 4.23-4.39 (m, 2 H), 3.77-3.89 (m, 8 H), 3.53-3.67 (m, 3 H), 2.95-3.43 (m, 7 H), 2.38-2.51 (m, 1 H), 2.15-2.26 (m, 2 H), 1.70-1.99 (m, 6 H), and 1.38-1.48 (m, 2 H); MS (ES+) 641.3 (M + 1). |
| 156 | (R)-2-methyl-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.95 (s, 1 H), 7.58 (dd, J = 8.1 Hz, J = 7.5 Hz, 1 H), 7.41-7.48 (m, 6 H), 7.03-7.11 (m, 3 H), 6.78 (d, J = 8.2 Hz, 1 H), 5.18-5.24 (m, 1 H), 4.35-4.42 (m, 1 H), 3.84-3.94 (m, 7 H), 3.70-3.77 (m, 2 H), 3.37-3.52 (m, 5 H), 3.01-3.13 (m, 2 H), 2.69 (s, 3 H), 2.50-2.63 (m, 1 H), 2.28-2.47 (m, 1 H), 1.85 (d, J = 6.9 Hz, 3 H), and 1.57-1.66 (m, 2 H); MS (ES+) 668.2 (M + 1). |
| 157 | (R)-5-methanesulfonyl-thiophene-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.62-7.66 (m, 3 H), 7.48-7.60 (m, 6 H), 6.91-7.16 (m, 3 H), 6.79 (d, J = 8.0 Hz, 1 H), 6.16-6.23 (m, 1 H), 5.18-5.24 (m, 1 H), 4.30-4.41 (m, 1 H), 3.70-3.95 (m, 8 H), 3.39-3.62 (m, 5 H), 3.20 (s, 3 H), 2.48-3.11 (m, 6 H), 2.09-2.43 (m, 1 H), 1.85 (d, J = 7.0 Hz, 3 H), and 1.57-1.69 (m, 2 H); MS (ES+) 731.2 (M + 1). |
| 158 | (R)-3-methyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.75 (s, 1 H), 7.60 (ovdd, J = 8.1 Hz, 1 H), 7.41-7.49 (m, 6 H), 7.11 (d, J = 8.3 Hz, 1 H), 7.00-7.08 (m, 2 H), 6.78 (d, J = 8.0 Hz, 1 H), 6.01-6.16 (m, 1 H), 5.18-5.23 (m, 1 H), 4.37-4.41 (m, 1 H), 3.92-3.98 (m, 1 H), 3.86 (s, 3 H), 3.84 (s, 3 H), 3.63-3.79 (m, 2 H), 3.37-3.76 (m, 5 H), 2.97-3.15 (m, 2 H), 2.63-2.74 (m, 1 H), 2.48 (s, 3 H), 2.19-2.36 (m, 1 H), 1.86 (d, J = 6.9 Hz, 3 H), and 1.54-1.70 (m, 2 H); MS (ES+) 652.2 (M + 1). |
| 159 | (R)-5-methyl-isoxazole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.59 (ovdd, J = 8.0 Hz, 1 H), 7.41-7.48 (m, 6 H), 7.02-7.14 (m, 3 H), 6.77-6.82 (m, 2 H), 6.41 (s, 1 H), 5.18-5.23 (m, 1 H), 4.36-4.50 (m, 1 H), 3.23-3.94 (m, 14 H), 3.03-3.13 (m, 2 H), 2.51-2.61 (m, 1 H), 2.47 (s, 3 H), 2.18-2.37 (m, 1 H), 1.86 (d, J = 7.0 Hz, 3 H), and 1.50-1.65 (m, 2 H); MS (ES+) 652.2 (M + 1). |
| 160 | (R)-pyridazine-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 9.61 (s, 1 H), 9.32-9.43 (m, 1 H), 7.96 (d, J = 3.7 Hz, 1 H), 7.33-7.62 (m, 6 H), 6.95-7.13 (m, 4 H), 6.76-6.81 (m, 1 H), 5.21-5.26 (m, 1 H), 4.44-4.47 (m, 1 H), 3.94-3.98 (m, 1 H), 3.85 (s, 3 H), 3.83 (s, 3 H), 3.38-3.68 (m, 4 H), 3.01-3.22 (m, 3 H), 2.84-2.95 (m, 2 H), 2.62-2.78 (m, 1 H), 2.18-2.54 (m, 1 H), 1.86 (d, J = 6.8 Hz, 3 H), and 1.44-1.73 (m, 2 H); MS (ES+) 648.9 (M + 1). |
| 161 | (R)-1-methyl-1H-imidazole-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 9.17 (bs, 1 H), 7.57 (ovdd, J = 8.0 Hz, 1 |

| Cpd | Name |
|---|---|
| | H), 7.44-7.51 (m, 5 H), 7.39 (d, J = 7.1 Hz, 1 H), 7.03-7.11 (m, 3 H), 6.77 (d, J = 8.2 Hz, 1 H), 5.19-5.24 (m, 1 H), 4.31-4.37 (m, 1 H), 4.11 (s, 3 H), 3.86 (s, 3 H), 3.83 (s, 3 H), 3.59-3.71 (m, 2 H), 3.24-3.52 (m, 5 H), 2.92-3.18 (m, 3 H), 2.57-2.67 (m, 1 H), 2.21-2.31 (m, 1 H), 1.86 (d, J = 6.9 Hz, 3 H), and 1.57-1.65 (m, 2 H); MS (ES+) 651.9 (M + 1). |
| 162 | (R)-4,5-dimethyl-furan-2-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.58 (ovdd, J = 8.0 Hz, 1 H), 7.46-7.52 (m, 5 H), 7.41 (d, J = 7.2 Hz, 1 H), 7.03-7.11 (m, 3 H), 6.86 (s, 1 H), 6.78 (d, J = 8.2 Hz, 1 H), 6.23-6.30 (m, 1 H), 5.18-5.23 (m, 1 H), 4.33-4.37 (m, 1 H), 3.84-3.93 (m, 7 H), 3.65-3.80 (m, 2 H), 3.25-3.60 (m, 5 H), 2.83-3.11 (m, 2 H), 2.48-2.61 (m, 1 H), 2.26-2.43 (m, 1 H), 2.22 (s, 3 H), 1.95 (s, 3 H), 1.86 (d, J = 6.9 Hz, 3 H), and 1.53-1.63 (m, 2 H); MS (ES+) 665.8 (M + 1). |
| 163 | (R)-thiazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.73 (s, 1 H), 8.17 (s, 1 H), 7.58 (ovdd, J = 8.0 Hz, 1 H), 7.41-7.48 (m, 6 H), 7.03-7.14 (m, 3 H), 6.78 (d, J = 8.2 Hz, 1 H), 5.19-5.25 (m, 1 H), 4.33-4.40 (m, 1 H), 3.97-4.10 (m, 1 H), 3.83-3.93 (m, 7 H), 3.70-3.77 (m, 1 H), 3.47-3.54 (m, 5 H), 2.99-3.12 (m, 2 H), 2.52-2.64 (m, 1 H), 2.24-2.40 (m, 1 H), 1.86 (d, J = 6.9 Hz, 3 H), and 1.57-1.67 (m, 2 H); MS (ES+) 654.9 (M + 1). |
| 164 | (R)-3,5-dimethyl-isoxazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.57 (ovdd, J = 8.0 Hz, 1 H), 7.45-7.49 (m, 5 H), 7.41 (d, J = 7.2 Hz, 1 H), 7.01-7.12 (m, 3 H), 6.78 (d, J = 8.2 Hz, 1 H), 5.61-5.70 (m, 1 H), 5.17-5.23 (m, 1 H), 4.37-4.43 (m, 1 H), 3.90-3.99 (m, 1 H), 3.86 (s, 3 H), 3.84 (s, 3 H), 3.61-3.76 (m, 2 H), 3.38-3.58 (m, 5 H), 2.83-3.24 (m, 2 H), 2.57-2.67 (m, 4 H), 2.40 (s, 3 H), 2.18-2.34 (m, 1 H), 1.86 (d, J = 6.9 Hz, 3 H), and 1.55-1.69 (m, 2 H); MS (ES+) 666.9 (M + 1). |
| 173 | (R)-tetrahydro-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.29-7.61 (m, 7 H), 6.97-7.20 (m, 3 H), 6.71 (d, J = 8.1 Hz, 1 H), 5.61-5.68 (m, 1 H), 5.09-5.14 (m, 1 H), 3.64-3.93 (m, 10 H), 3.30-3.58 (m, 5 H), 3.10-3.25 (m, 2 H), 2.60-2.99 (m, 4 H), 2.42-2.55 (m, 1 H), 2.00-2.29 (m, 3 H), and 1.32-1.87 (m, 15 H); MS (ES+) 641.3 (M + 1). |
| 174 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-isobutyramide<br>$^1$H NMR (300 MHz, CDCl$_3$) δ 7.53 (ovdd, J = 7.8 Hz, 1 H), 7.31-7.46 (m, 6 H), 7.06-7.11 (m, 3 H), 6.78 (d, J = 7.9 Hz, 1 H), 5.39-5.47 (m, 1 H), 5.18-5.23 (m, 1 H), 3.87 (s, 3 H), 3.84 (s, 3 H), 3.21-3.59 (m, 6 H), 2.43-2.78 (m, 5 H), 2.07-2.36 (m, 2 H), 1.38-1.68 (m, 5 H), and 1.12 (d, J = 6.9 Hz, 6 H); MS (ES+) 613.3 (M + 1). |
| 175 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-methoxy-acetamide<br>$^1$H NMR (300 MHz, CDCl$_3$) δ 7.36-7.69 (m, 7 H), 7.06-7.18 (m, 3 H), 6.78 (d, J = 8.1 Hz, 1 H), 6.49-6.53 (m, 1 H), 5.17-5.30 (m, 1 H), 3.87 (s, 3 H), 3.85 (s, 2 H), 3.84 (s, 3 H), 3.30-3.72 (m, 10 H), 2.63-2.92 (m, 3 H), 2.46-2.59 (m, 1 H), 2.14-2.35 (m, 1 H), and 1.47-1.83 (m, 5 H); MS (ES+) 615.5 (M + 1). |
| 176 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-butyramide<br>$^1$H NMR (300 MHz, CDCl$_3$) δ 7.33-7.68 (m, 7 H), 6.91-7.11 (m, 3 H), 6.78 (d, J = 8.1 Hz, 1 H), 5.30-5.41 (m, 1 H), 5.16-5.22 (m, 1 H), 3.87 (s, 3 H), 3.84 (s, 3 H), 3.61-3.77 (m, 2 H), 3.26-3.41 (m, 5 H), 2.55-2.86 (m, 3 H), 2.17-2.28 (m, 1 H), 2.11 (t, J = 7.3 Hz, 2 H), 1.83-1.99 (m, 1 H), 1.47-1.69 (m, 7 H), and 0.92 (t, J = 7.0 Hz, 3 H); MS (ES+) 613.4 (M + 1). |
| 177 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methoxy-propionamide<br>$^1$H NMR (300 MHz, CDCl$_3$) δ 7.52 (ovdd, J = 8.1 Hz, 1 H), 7.28-7.35 (m, 6 H), 7.07-7.10 (m, 3 H), 6.78 (d, J = 7.8 Hz, 1 H), 6.16-6.21 (m, 1 H), 5.18-5.23 (m, 1 H), 3.87 (s, 3 H), 3.84 (s, 3 H), 3.60 (t, J = 5.7 Hz, 2 H), 3.27-3.43 (m, 8 H), 2.56-2.84 (m, 3 H), 2.39-2.51 (m, 3 H), 2.19-2.31 (m, 1 H), and 1.38-1.62 (m, 5 H); MS (ES+) 629.4 (M + 1). |
| 178 | (R)-cyclobutanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.33-7.67 (m, 7 H), 7.05-7.11 (m, 3 H), 6.78 (d, J = 8.1 Hz, 1 H), 5.30-5.39 (m, 1 H), 5.16-5.22 (m, 1 H), |

| Cpd | Name |
|---|---|
| | 3.86 (s, 3 H), 3.84 (s, 3 H), 3.19-3.59 (m, 5 H), 2.88-3.03 (m, 3 H), 2.47-2.68 (m, 3 H), 2.07-2.30 (m, 5 H), 1.77-1.97 (m, 3 H), and 1.44-1.70 (m, 5 H); MS (ES+) 625.3 (M + 1). |
| 179 | (R)-cyclopentanecarboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.28-7.72 (m, 7 H), 7.03-7.13 (m, 3 H), 6.78 (d, J = 8.2 Hz, 1 H), 5.48-5.76 (m, 1 H), 5.16-5.22 (m, 1 H), 3.97-4.10 (m, 1 H), 3.86 (s, 3 H), 3.84 (s, 3 H), 3.48-3.77 (m, 3 H), 3.25-3.34 (m, 4 H), 2.40-2.62 (m, 3 H), 2.17-2.32 (m, 1 H), and 1.41-2.07 (m, 15 H); MS (ES+) 639.5 (M + 1). |
| 180 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-propionamide<br>$^1$H NMR (300 MHz, CDCl$_3$) δ 7.33-7.70 (m, 7 H), 7.04-7.13 (m, 3 H), 6.78 (d, J = 8.2 Hz, 1 H), 5.40-5.49 (m, 1 H), 5.16-5.22 (m, 1 H), 3.87 (s, 3 H), 3.84 (s, 3 H), 3.40-3.78 (m, 5 H), 3.22-3.32 (m, 2 H), 2.69-3.13 (m, 3 H), 2.47-2.60 (m, 1 H), 2.13-2.31 (m, 3 H), 1.47-1.94 (m, 5 H), and 1.12 (t, J = 7.6 Hz, 6 H); MS (ES+) 599.4 (M + 1). |
| 181 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-methyl-butyramide<br>$^1$H NMR (300 MHz, CDCl$_3$) δ 7.34-7.68 (m, 7 H), 7.02-7.13 (m, 3 H), 6.78 (d, J = 8.2 Hz, 1 H), 5.45-5.59 (m, 1 H), 5.16-5.28 (m, 1 H), 3.86 (s, 3 H), 3.84 (s, 3 H), 3.55-3.72 (m, 5 H), 3.20-3.48 (m, 2 H), 2.71-3.02 (m, 3 H), 2.46-2.59 (m, 1 H), 2.22-2.32 (m, 1 H), 1.81-2.17 (m, 6 H), 1.41-1.69 (m, 2 H), and 0.92 (d, J = 6.4 Hz, 6 H); MS (ES+) 627.5 (M + 1). |
| 182 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2-ethoxy-acetamide<br>$^1$H NMR (300 MHz, CDCl$_3$) δ 7.34-7.72 (m, 7 H), 7.02-7.13 (m, 3 H), 6.77-6.81 (m, 1 H), 6.51-6.58 (m, 1 H), 5.14-5.23 (m, 1 H), 3.92-4.12 (m, 1 H), 3.84-3.89 (m, 8 H), 3.51-3.66 (m, 6 H), 3.21-3.45 (m, 2 H), 2.81-3.05 (m, 3 H), 2.51-2.64 (m, 1 H), 2.22-2.45 (m, 1 H), 1.43-1.67 (m, 5 H), and 1.22 (t, J = 7.0 Hz, 3 H); MS (ES+) 686.4 (M + 1). |
| 183 | (R)-5-chloro-1-methyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-amide<br>$^1$H NMR (300 MHz, CDCl$_3$) δ 7.90 (s, 1 H), 7.33-7.60 (m, 7 H), 7.05-7.11 (m, 3 H), 6.78 (d, J = 8.1 Hz, 1 H), 6.11-6.14 (m, 3 H), 5.19-5.24 (m, 1 H), 3.86 (s, 3 H), 3.83 (s, 3 H), 3.42-3.74 (m, 7 H), 2.78-3.01 (m, 3 H), 2.54-2.69 (m, 3 H), 2.24-2.36 (m, 1 H), and 1.44-1.88 (m, 5 H); MS (ES+) 686.4 (M + 1). |
| 184 | (R)-1,3,5-trimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-amide<br>$^1$H NMR (300 MHz, CDCl$_3$) δ 7.33-7.75 (m, 7 H), 7.04-7.11 (m, 3 H), 6.78 (d, J = 8.2 Hz, 1 H), 5.56-5.59 (m, 1 H), 5.19-5.24 (m, 1 H), 3.86 (s, 3 H), 3.84 (s, 3 H), 3.61-3.79 (m, 8 H), 3.40-3.51 (m, 2 H), 2.81-3.25 (m, 3 H), 2.49-2.60 (m, 1 H), 2.44 (s, 3 H), 2.38 (s, 3 H), 2.22-2.36 (m, 1 H), and 1.54-1.94 (m, 5 H); MS (ES+) 679.5 (M + 1). |
| 185 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2-dimethyl-propionamide<br>$^1$H NMR (300 MHz, CDCl$_3$) δ 7.50-7.60 (m, 1 H), 7.33-7.49 (m, 6 H), 7.10-7.21 (m, 3 H), 6.78 (d, J = 8.1 Hz, 1 H), 5.61-5.66 (m, 1 H), 5.17-5.30 (m, 1 H), 3.87 (s, 3 H), 3.84 (s, 3 H), 3.11-3.62 (m, 7 H), 2.53-2.88 (m, 4 H), 2.07-2.29 (m, 1 H), 1.38-1.52 (m, 5 H), and 1.18 (s, 9 H); MS (ES+) 627.5 (M + 1). |
| 186 | (R)-furan-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 7.93 (s, 1 H), 7.36-7.70 (m, 8 H), 7.05-7.13 (m, 3 H), 6.74-6.84 (m, 1 H), 6.62 (s, 1 H), 5.83-5.92 (m, 1 H), 5.19-5.30 (m, 1 H), 3.86 (s, 3 H), 3.83 (s, 3 H), 3.20-3.61 (m, 7 H), 2.58-2.96 (m, 4 H), 2.21-2.33 (m, 1 H), and 1.43-1.67 (m, 5 H); MS (ES+) 637.3 (M + 1). |
| 187 | (R)-isoxazole-5-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>$^1$H NMR (300 MHz, CDCl$_3$) δ 8.30 (s, 1 H), 7.52 (ovdd, J = 8.3 Hz, 1 H), 7.31-7.49 (m, 7 H), 7.03-7.11 (m, 3 H), 6.77-6.88 (m, 2 H), 6.53-6.61 (m, 1 H), 5.20-5.26 (m, 1 H), 3.87 (s, 3 H), 3.84 (s, 3 H), 3.20-3.70 (m, 6 H), 2.61-2.96 (m, 5 H), 2.30-2.40 (m, 1 H), and 1.42-1.65 (m, 5 H); MS (ES+) 638.4 (M + 1). |
| 188 | (R)-2,5-dimethyl-1H-pyrrole-3-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide |

| Cpd | Name |
|---|---|
| | ¹H NMR (300 MHz, CDCl₃) δ 7.33-7.85 (m, 7 H), 7.00-7.16 (m, 3 H), 6.77 (d, J = 8.5 Hz, 1 H), 5.70-5.88 (m, 1 H), 5.18-5.30 (m, 1 H), 3.94-4.13 (m, 1 H), 3.85 (s, 3 H), 3.83 (s, 3 H), 3.64-3.77 (m, 3 H), 3.33-3.46 (m, 6 H), 2.46-2.67 (m, 4 H), 2.19-2.35 (m, 4 H), 1.76-2.07 (m, 3 H), and 1.54-1.63 (m, 2 H); MS (ES+) 664.5 (M + 1). |
| 189 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-ethoxy-propionamide<br>¹H NMR (300 MHz, CDCl₃) δ 7.33-7.72 (m, 7 H), 7.05-7.19 (m, 3 H), 6.77-6.80 (m, 1 H), 6.24-6.32 (m, 1 H), 5.17-5.22 (m, 1 H), 3.83 (s, 3 H), 3.83 (s, 3 H), 3.63 (t, J = 5.8 Hz, 2 H), 3.45-3.59 (m, 2 H), 3.25-3.32 (m, 2 H), 2.64-2.93 (m, 3 H), 2.45-2.62 (m, 1 H), 2.42 (t, J = 5.8 Hz, 2 H), 2.19-2.31 (m, 1 H), 1.43-1.81 (m, 5 H), and 1.14 (t, J = 6.9 Hz, 3 H); MS (ES+) 643.5 (M + 1). |
| 191 | (S)-1-methyl-pyrrolidine-2-carboxylic acid (R)-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 7.58 (ovdd, J = 7.5 Hz, 1 H), 7.39-7.48 (m, 6 H), 7.04-7.12 (m, 3 H), 6.78 (d, J = 8.9 Hz, 1 H), 5.19-5.32 (m, 1 H), 4.15-4.49 (m, 4 H), 3.62-3.99 (m, 8 H), 2.92-3.48 (m, 8 H), 2.85 (s, 3 H), 1.95-2.76 (m, 6 H), 1.84-1.87 (m, 3 H), and 1.48-1.61 (m, 2 H); MS (ES+) 654.5 (M + 1). |
| 202 | (R)-cyclobutanecarboxylic acid {4-(3,4-dimethoxy-phenyl)-4-[4-(4-ethyl-piperazin-1-yl)-1,3-dioxo-1,3-dihydro-isoindol-2-yl]-butyl}-amide<br>Using the procedure of Example 23 and substituting N-ethylpiperazine, the product was carried forward.<br>¹H NMR (300 MHz, CDCl₃) δ 7.61 (t, J = 8 Hz, 1H), 7.45 (d, J = 7.1 Hz, 1H), 7.13 (d, J = 7.9 Hz, 1H), 7.1-7.0 (m, 2H), 6.80 (d, J = 8.1 Hz, 1H), 5.41 (m, 1H), 5.20 (m, 1H), 3.88 (s, 3H), 3.80 (s, 3H), 3.8-2.9 (m, 10H), 2.6-1.5 (m, 13H), 1.44 (t, J = 7.3 Hz, 3H); MS (ES+) 549.3 (M + 1). |
| 211 | (R)-2-methyl-thiazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide<br>¹H NMR (300 MHz, CDCl₃) δ 7.81 (s, 1 H), 7.56 (ovdd, J = 8.1 Hz, 1 H), 7.42-7.50 (m, 5 H), 7.39 (d, J = 7.1 Hz, 1 H), 7.04-7.09 (m, 3 H), 6.78 (d, J = 8.3 Hz, 1 H), 5.29-5.33 (m, 1 H), 4.32-4.38 (m, 1 H), 3.68-3.90 (m, 9 H), 3.43-3.52 (m, 5 H), 2.89-3.23 (m, 3 H), 2.66 (s, 3 H), 2.48-2.58 (m, 1 H), and 1.85 (d, J = 7.0 Hz, 3 H); MS (ES⁺) 654.2 (M + 1). |
| 212 | (R)-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-2,2,2-trifluoro-acetamide<br>¹H NMR (300 MHz, CDCl₃) δ 7.60 (ovdd, J = 8.1 Hz, 1 H), 7.42-7.49 (m, 6 H), 7.11 (d, J = 8.2 Hz, 1 H), 7.01-7.05 (m, 2 H), 6.79 (d, J = 8.1 Hz, 1 H), 6.36-6.45 (m, 1 H), 5.16-5.21 (m, 1 H), 4.34-4.39 (m, 1 H), 3.62-4.10 (m, 8 H), 3.38-3.52 (m, 6 H), 2.96-3.19 (m, 2 H), 2.51-2.64 (m, 1 H), 2.18-2.31 (m, 1 H), 1.86 (d, J = 6.9 Hz, 3 H), and 1.44-1.63 (m, 2 H); MS (ES⁺) 639.2 (M + 1). |
| 213 | (R)-2-tert-butoxy-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-acetamide<br>¹H NMR (300 MHz, CDCl₃) δ 7.60 (ovdd, J = 8.1 Hz, 1 H), 7.42-7.53 (m, 6 H), 7.02-7.13 (m, 3 H), 6.78 (d, J = 8.3 Hz, 1 H), 6.15-6.41 (bs, 1 H), 5.18-5.23 (m, 1 H), 4.36-4.42 (m, 1 H), 3.83-3.96 (m, 9 H), 3.68-3.79 (m, 2 H), 3.32-3.56 (m, 5 H), 2.97-3.14 (m, 2 H), 2.44-2.58 (m, 1 H), 2.22-2.32 (m, 1 H), 1.86 (d, J = 6.9 Hz, 3 H), 1.48-1.59 (m, 2 H), and 1.21 (s, 9 H); MS (ES⁺) 657.5 (M + 1). |
| 215 | (R)-3,5-dimethyl-1H-pyrazole-4-carboxylic acid (4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-amide<br>¹H NMR (300 MHz, CDCl₃) δ 7.34-7.62 (m, 7 H), 7.01-7.12 (m, 3 H), 6.78 (d, J = 8.1 Hz, 1 H), 6.22-6.41 (bs, 1 H), 5.14-5.24 (m, 1 H), 4.33-4.41 (m, 1 H), 3.80-3.88 (m, 7 H), 3.34-3.72 (m, 6 H), 2.86-3.21 (m, 6 H), 2.54-2.73 (m, 1 H), 2.48 (s, 3 H), 2.19-2.37 (m, 1 H), 1.85 (d, J = 6.9 Hz, 3 H), and 1.52-1.69 (m, 2 H). |
| 217 | (R)-5-methyl-isoxazole-4-carboxylic acid (3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-amide<br>¹H NMR (300 MHz, CDCl₃) δ 8.31 (s, 1 H), 7.60 (ovdd, J = 7.8 Hz, 1 H), 7.46-7.50 (m, 5 H), 7.42 (d, J = 7.2 Hz, 1 H), 7.10 (d, J = 8.3 Hz, 1 H), 7.01-7.04 (m, 2 H), 6.79 (d, J = 8.6 Hz, 1 H), 5.98-6.03 (m, 1 H), 5.26-5.35 (m, 1 H), 4.36-4.41 (m, 1 H), 3.81-3.90 (m, 7 H), 3.60-3.78 (m, 3 H), 3.38-3.58 (m, 3 H), 3.17-3.28 (m, 1 H), 2.73-3.08 (m, 3 H), 2.64 (s, 3 H), 2.41-2.56 (m, 1 H), and 1.86 (d, J = 6.8 Hz, 3 H); MS (ES⁺) 638.2 (M + 1). |
| 221 | (R)-N-(3-(3,4-dimethoxy-phenyl)-3-{1,3-dioxo-4-[4-(1R)-(1-phenyl-ethyl)-piperazin-1-yl]-1,3-dihydro-isoindol-2-yl}-propyl)-isonicotinamide<br>¹H NMR (300 MHz, CDCl₃) δ 8.76-8.83 (m, 2 H), 7.81-7.89 (m, 2 H), 7.60 (ovdd, J = 8.0 Hz, 1 H), 7.42-7.52 (m, 6 H), 7.11 (d, J = 8.3 Hz, 1 H), 7.02-7.06 (m, 2 H), 6.79 (d, J = 8.1 Hz, 1 H), 5.32-5.36 (m, 1 H), |

| Cpd | Name |
|---|---|
| | -continued |
| | 4.31-4.38 (m, 1 H), 3.83-3.96 (m, 7 H), 3.65-3.78 (m, 3 H), 3.34-3.56 (m, 3 H), 2.93-3.19 (m, 3 H), 2.79-2.84 (m, 1 H), 2.53-2.63 (m, 1 H), and 1.85 (d, J = 6.9 Hz, 3 H); MS (ES⁺) 634.3 (M + 1). |

Example 37

(R)-2-cyano-N-(4-(3,4-dimethoxy-phenyl)-4-{1,3-dioxo-4-[4-(1R)-(1-phenyl-ethyl)-piperazin-1-yl]-1,3-dihydro-isoindol-2-yl}-butyl)-3-oxo-butyramide Cpd 199

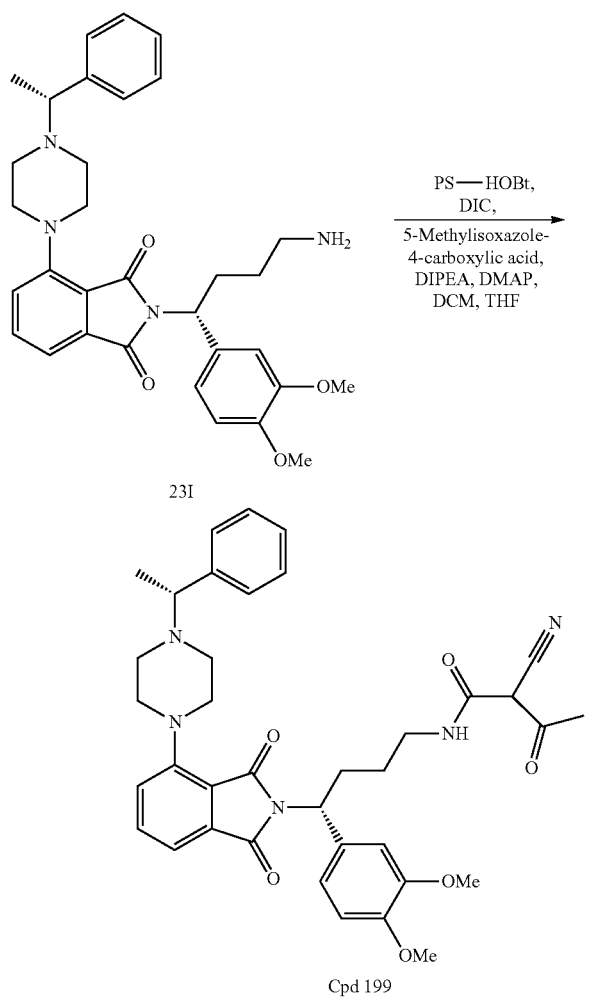

A 50-mL round bottom flask was charge with polystyrene-Hydroxybenzotriazole hydrate resin (250 mg, 0.9 mmol). A solution of 5-methylisoxazole-4-carboxylic acid (83 mg, 0.65 mmol) and 4-(dimethylamino)-pyridine (83 mg, 0.68 mmol) in dichloromethane (1.0 mL) and tetrahydrofuran (2.0 mL) was added followed by dimethylaminoisopropyl chloride hydrochloride (363 µL, 2.50 mmol). The mixture stirred at room temperature for 30 minutes. The resin was washed with dichlormethane (3×3 mL) and dried under a stream of nitrogen for 30 minutes. A solution of Compound 23I (30 mg, 0.05 mmol) in dichlormethane (2.0 mL) was added followed by diisopropylethylamine (32 µL, 0.18 mmol) and tetrahydrofuran (1 mL). The mixture was stirred at room temperature for 3 h. The solution was filtered and the resin was washed with dichloromethane (3×3 mL). The filtrate was concentrated in vacuo and purified on a Gilson HPLC with a reversed phase Kromasil column (10 u, 100 Å C18, column length 250×50 mm, gradient 85:15-0:100 H₂O:MeCN) to give 17.0 mg of the title Compound 199 as a yellow solid. ¹H NMR (300 MHz, CDCl₃) δ 7.60 (ovdd, J=8.1 Hz, 1 H), 7.43-7.50 (m, 6 H), 7.11 (d, J=8.2 Hz, 1 H), 7.03-7.06 (m, 2 H), 6.79 (d, J=8.1 Hz, 1 H), 5.90-5.99 (m, 1 H), 5.18-5.22 (m, 1 H), 4.38-4.42 (m, 1 H), 3.88-3.95 (m, 1 H), 3.86 (s, 3 H), 3.84 (s, 3 H), 3.65-3.78 (m, 2 H), 3.35-3.49 (m, 5 H), 3.01-3.18 (m, 2 H), 2.45-2.62 (m, 1 H), 2.23-2.32 (m, 4 H), 1.86 (d, J=6.9 Hz, 3 H), and 1.56-1.62 (m, 2 H); MS (ES⁺) 652 (M+1).

Example 38

(R)-thiophene-2-sulfonic acid {4-(3,4-dimethoxy-phenyl)-4-[4-(3-dimethylamino-propoxy)-1,3-dioxo-1,3-dihydro-isoindol-2-yl]-butyl}-amide Cpd 224

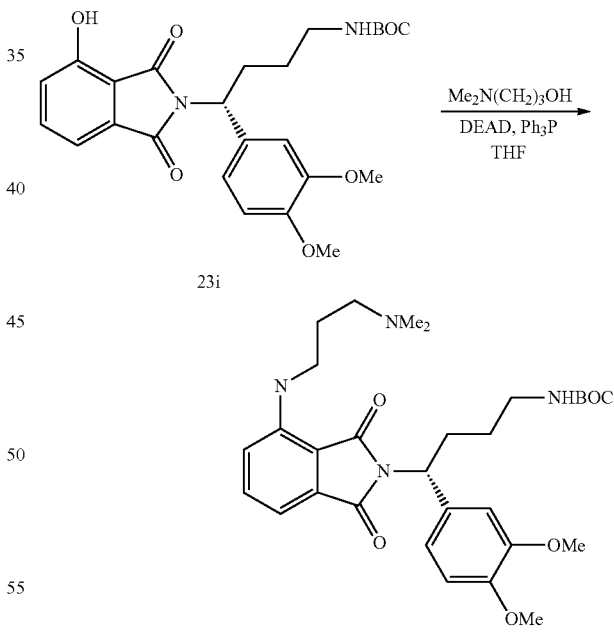

Compound 23i (141 mg, 0.30 mmol), 3-dimethylamino-propanol (34 mg, 0.33 mmol) and triphenylphosphine (118 mg, 0.45 mmol) were combined in THF (3 mL) and cooled to 0° C. with an ice bath. Diethyl azodicarboxylate (78 mg, 0.45 mmol) in tetrahydrofuran (0.50 mL) was added over 1 minute, and the reaction was stirred at room temperature for 16 h. The reaction was evaporated in vacuo and the crude product was purified via flash column (DCM:M:NH₄OH 80:4:1) to afford Compound 38a as an oil (120 mg, 74%). $^1$H NMR (300 MHz, CDCl$_3$) δ 7.56-7.61 (m, 1H), 7.33-7.40 (m, 1H), 7.18 (d, J=8.4 Hz, 1H), 7.08-7.11 (m, 2H), 6.77-6.87 (m, 2H), 5.20-5.28 (m, 1H), 4.22 (t, J=6.6 Hz, 2H), 3.88 (s, 3H), 3.84 (s, 3H), 3.25-3.10 (m, 2H), 2.50-2.60 (m, 2H), 2.26 (s, 6H), 2.20-2.3 (m, 2H), 2.05-2.15 (m, 2H), 1.50-1.60 (m, 2H), 1.42 (s, 9H); MS (ES$^+$) 556 (M+1).

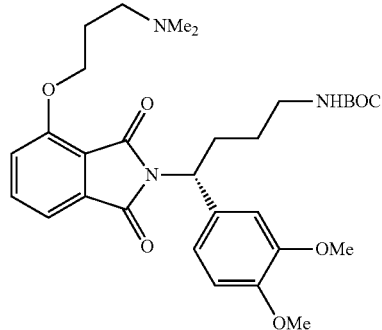

38a

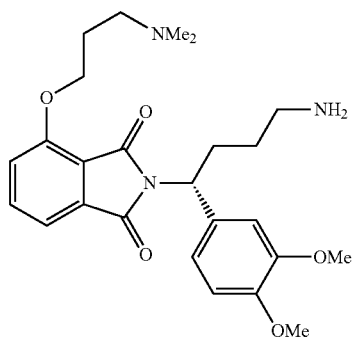

38b

Compound 38a (90 mg, 0.16 mmol) was dissolved in dioxane (2.0 mL) and cooled with an ice bath as 4.0 M HCl in dioxane (2.0 mL, 8 mmol) was added. The reaction was stirred at room temperature for 2 h and the solvent evaporated in vacuo to give white solid Compound 38b as the HCl salt: MS (ES$^+$) 456 (M+1).

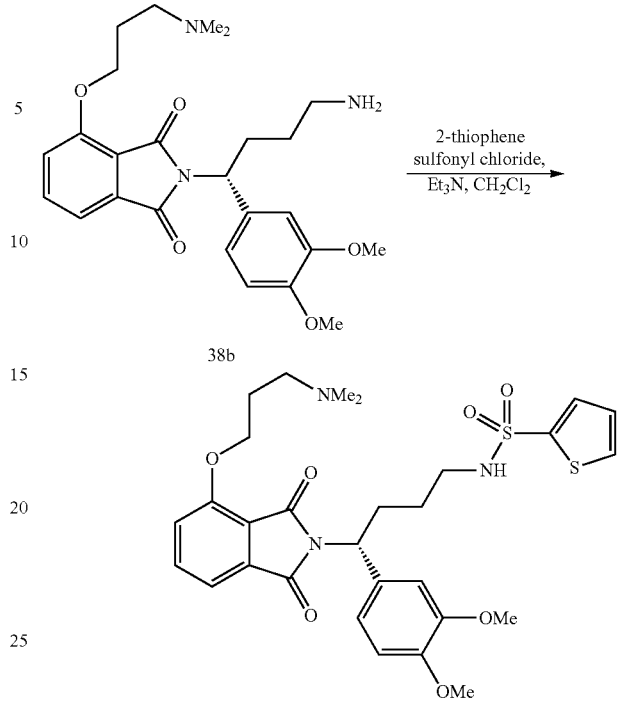

Cpd 224

A portion of Compound 38b (64 mg, 0.11 mmol) was combined with triethylamine (34 mg, 0.33 mmol) in dichloromethane (4 mL) and 2-thiophene sulfonyl chloride (21.3 mg, 0.117 mmol) was added and stirred at room temperature for 4 h. The reaction was diluted with dichloromethane and washed 1× with saturated sodium bicarbonate, 1× with brine, then dried (Na$_2$SO$_4$) and evaporated in vacuo to give a crude oil. The crude oil was purified by reverse phase HPLC on a Gilson HPLC with a reversed phase Kromasil column (10 u, 100 Å C18, gradient 90:10-0:100 H$_2$O:MeCN) and the aqueous/TFA solution was frozen and lyophilized to afford white solid Compound 224 as its trifluoroacetate salt (40 mg): $^1$H NMR (300 MHz, CDCl$_3$) δ 7.57-7.66 (M, 1 H), 7.49 (m, 2 H), 7.42 (d, J=7.3 Hz, 1 H), 7.01-7.12 (m, 4 H), 6.80 (d, J=8.3 Hz, 1 H), 6.62 (bs, 1 H), 5.29 (dd, J=3.9, 12.3 Hz, 1 H), 4.30-4.44 (m, 2 H), 3.88 (s, 3 H), 3.85 (s, 3 H), 3.30-3.63 (m, 4 H), 3.16 (d, J=3.7 Hz, 3 H), 3.05 (d, J=3.6 Hz, 3 H), 2.9-3.1 (m, 1 H), 2.20-2.50 (m, 2 H), 1.90-2.10 (m, 2 H), 1.50-1.65 (m, 2 H); MS (ES$^+$) 602 (M+1).

Other compounds of the present invention may be prepared by those skilled in the art by varying the starting materials, reagent(s) and conditions used. Using the procedure of Example 38, the following compounds were prepared:

| Cpd | Name |
|---|---|
| 200 | (R)-N-{4-(3,4-dimethoxy-phenyl)-4-[4-(1-methyl-pyrrolidin-3-yloxy)-1,3-dioxo-1,3-dihydro-isoindol-2-yl]-butyl}-isobutyramide<br>$^1$H NMR (300 MHz, CDCl$_3$) δ 7.68 (dd, J = 7.7, 8.0 Hz, 1 H), 7.49 (d, J = 7.3 Hz, 1 H), 7.16 (d, J = 8.3 Hz, 1 H), 7.06-7.09 (m, 2 H), 6.80 (d, J = 8.3 Hz, 1 H), 5.5-5.62 (m, 1 H), 5.30 (bs, 1 H), 5.20 (dd, J = 6.7, 9.4 Hz, 1 H), 4.3-4.6 (m, 2 H), 3.9-4.0 (m, 1 H), 3.88 (s, 3 H), 3.85 (s, 3 H), 3.25-3.33 (m, 4 H), 3.13 (bs, 3 H), 2.30-2.60 (m, 5 H), 1.45-1.60 (m, 2 H), and 1.13 (d, J = 6.9 Hz, 6 H); MS (ES$^+$) 524 (M + 1). |
| 205 | (R)-N-{4-(3,4-dimethoxy-phenyl)-4-[4-(1-methyl-piperidin-4-yloxy)-1,3-dioxo-1,3-dihydro-isoindol-2-yl]-butyl}-isobutyramide<br>$^1$H NMR (300 MHz, CDCl$_3$) δ 7.66 (dd, J = 7.4, 8.2 Hz, 1 H), 7.45 (d, J = 7.2 Hz, 1 H), 7.18 (d, J = 8.4 Hz, 1 H), 7.06-7.11 (m, 2 H), 6.80 (d, J = 8.2 Hz, 1 H), 5.45-5.52 (m, 1 H), 5.21 (dd, J = 6.8, 9.2 Hz, 1 H), 4.92 (bs, 1 H), 3.88 (s, 3 H), 3.85 (s, 3 H), 3.30-3.50 (m, 6 H), 2.87 (d, J = 4.4 Hz, 3 H), 2.10-2.55 (m, 8 H), 1.50-1.60 (m, 2 H), and 1.13 (d, J = 6.9 Hz, 6 H); MS (ES$^+$) 538 (M + 1). |

| Cpd | Name |
|---|---|
| 229 | (R)-thiophene-2-sulfonic acid {4-(3,4-dimethoxy-phenyl)-4-[4-(2-dimethylamino-ethoxy)-1,3-dioxo-1,3-dihydro-isoindol-2-yl]-butyl}-amide <br> $^1$H NMR (300 MHz, CDCl$_3$) δ 7.64 (dd, J = 7.7, 8.0 Hz, 1 H), 7.45-7.53 (m, 3 H), 7.14 (d, J = 8.3 Hz, 1 H), 7.02-7.07 (m, 3 H), 6.79 (d, J = 8.8 Hz, 1 H), 5.61 (bs, 1 H), 5.18 (dd, J = 5.3, 10.9 Hz, 1 H), 4.65-4.75 (m, 2 H), 3.88 (s, 3 H), 3.85 (s, 3 H), 3.58-3.61 (m, 2 H), 3.21 (s, 3 H), 3.08 (s, 3 H), 2.80-3.01 (m, 2 H), 2.05-2.20 (m, 2 H), and 1.40-1.65 (m, 2 H); MS (ES$^+$) 588 (M + 1). |

Example 39

(R)-2-[1-(3,4-dimethoxy-phenyl)-4-imidazol-1-yl-butyl]-4-(4-ethyl-piperazin-1-yl)-isoindole-1,3-dione Cpd 235

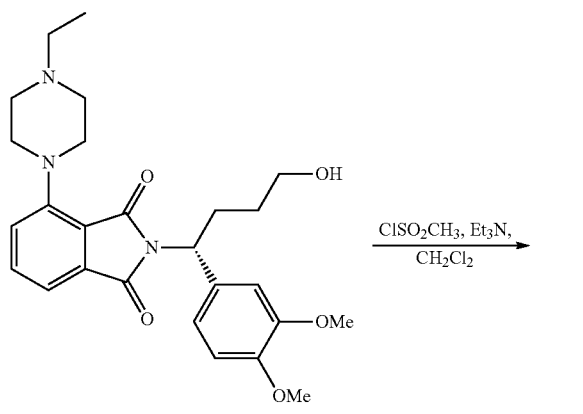

Cpd 206

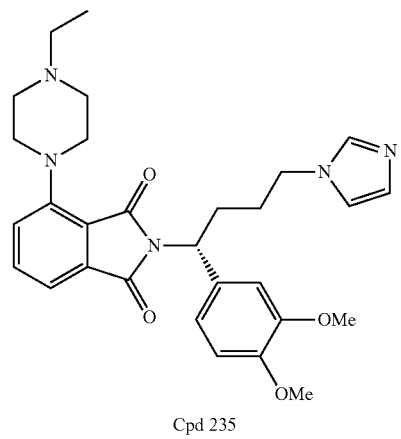

Cpd 235

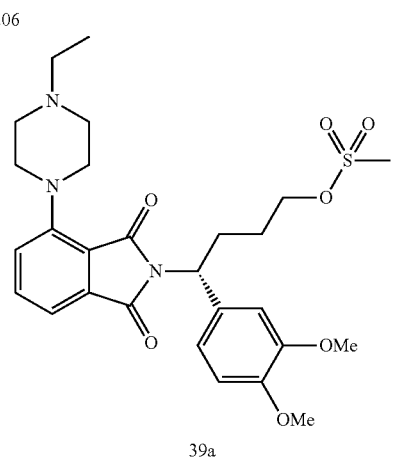

39a

A 50-mL round bottom flask was charged with (R)-2-[1-(3,4-dimethoxy-phenyl)-4-hydroxy-butyl]-4-(4-ethyl-piperazin-1-yl)-isoindole-1,3-dione Compound 206 (787 mg, 1.56 mmol) and dichloromethane (7.0 mL). Triethylamine (0.87 mL, 6.24 mmol) was added followed by methanesulfonyl chloride (0.12 mL, 1.56 mmol) and the mixture was stirred at room temperature for 1 h. The reaction was diluted with dichloromethane and washed 2× with water. The organic layer was diluted with ethyl acetate, dried (Na$_2$SO$_4$) and evaporated in vacuo to give a crude oil Compound 39a (0.84 g, 1.54 mmol).

A 100-mL round bottom flask was charged with imidazole (192 mg, 2.88 mmol) and tetrahydrofuran (5.0 mL). The mixture was cooled using an ice/water bath. 95% Sodium hydride (72 mg, 3.00 mmol) was added and the mixture was stirred in the ice/water bath for 1 h followed by stirring at room temperature for 1 h. A 100-mL sealed tube was charged with 39a (131 mg, 0.24 mmol), tetrahydrofuran (3.0 mL), and dimethylformamide (0.5 mL). The imidazole solution was transferred via syringe, the tube was flushed with argon and sealed. The mixture was heated to 55° C. for 5 h. The mixture was cooled to room temperature, filtered, and the filtrate was concentrated in vacuo. The crude oil was purified by reverse phase HPLC on a Gilson HPLC with a reversed phase Kromasil column (10 u, 100 Å C18, gradient 90:10-0:100 H$_2$O:MeCN). The purified material was dissolved in dichloromethane (10 mL), treated with 1M HCl in diethyl ether (1 mL), and concentrated in vacuo. This procedure was repeated two more times to give Compound 235 (26.73 mg) as a yellow solid. $^1$H NMR (300 MHz, d-DMSO) δ 7.61-7.69 (m, 2 H), 7.28-7.30 (m, 2 H), 7.09-7.12 (m, 1 H), 6.98-7.02 (m, 1 H), 6.88-6.93 (m, 3 H), 5.14-5.18 (m, 1 H), 3.95-4.02 (m, 2 H), 3.56-3.86 (m, 10 H), 3.19-3.45 (m, 5 H), 2.40-2.57 (m, 3 H), 2.10-2.19 (m, 1 H), 1.63-1.76 (m, 2 H), and 1.05 (t, J=7.1 Hz, 3 H); MS (ES$^+$) 518.4 (M+1).

Other compounds of the present invention may be prepared by those skilled in the art by varying the starting materials, reagent(s) and conditions used. Using the procedure of Example 39, the following compounds were prepared:

| Cpd | Name |
|---|---|
| 237 | (R)-2-[4-benzoimidazol-1-yl-1-(3,4-dimethoxy-phenyl)-butyl]-4-(4-ethyl-piperazin-1-yl)-isoindole-1,3-dione<br>$^1$H NMR (300 MHz, d-DMSO) δ 7.62-7.91 (m, 4 H), 7.24-7.52 (m, 4 H), 6.82-7.03 (m, 3 H), 5.13-5.24 (m, 1 H), 4.29-4.56 (m, 2 H), 2.98-3.81 (m, 13 H), 2.43-2.58 (m, 1 H), 2.18-2.37 (m, 1 H), 1.81-1.99 (m, 3 H), and 1.19-138 (m, 5 H); MS (ES$^+$) 568.8 (M + 1). |

BIOLOGICAL EXAMPLES

Example 1

Rat UII Calcium Mobilization FLIPR Assay

A calcium mobilization assay based on a Fluorescence Imaging Plate Reader (FLIPR, Molecular Devices, Sunnyvale, Calif.) was used to determine antagonist activity, after a 5 min incubation, in response to the agonist cyclic peptide (Ac)—CFWK(2-NaI)C—NH$_2$ (FLIPR EC$_{50}$=0.54±0.2 nM, rU-II Ki=0.12±0.05 nM) at 1 nM (W. A. Kinney, H. R. Almond, Jr., J. Qi, C. E. Smith, R. J. Santulli, L. de Garavilla, P. Andrade-Gordon, D. S. Cho, A. M. Everson, M. A. Feinstein, P. A. Leung, B. E. Maryanoff, *Angew. Chem., Intl. Ed.* 2002, 41, 2940-2944), in CHO cells transfected with rat GPR14 (U-II receptor) (M. Tal, D. A. Ammar, M. Karpuj, V. Krizhanovsky, M. Naim, D. A. Thompson, *Biochem. Biophys. Res. Commun.* 1995, 209, 752-759. A. Marchese, M. Heiber, T. Nguyen, H. H. Heng, V. R. Saldivia, R. Cheng, P. M. Murphy, L. C. Tsui, X. Shi, P. Gregor, *Genomics* 1995, 29, 335-344.).

To derive these cells, the complete coding sequence of rat U-II (Genbank Accession No. U32673) was amplified by nested PCR from rat heart marathon-Ready cDNA. PCR was carried out by using the DNA polymerase PFU (Stratagene) following conditions suggested by the manufacturer. The PCR products were cloned into pcDNA3 (Invitrogen) digested with EcoR I and Xba I. Clones containing rat U-II receptor were verified by complete sequencing of the U-II receptor insert to ensure a lack of PCR-introduced errors. The constructed vector was transfected into CHO cells by using lipofectamine (GIBCO BRL). CHO cells with high expression of rat U-II receptor were selected and established as stable cell lines by using G418. CHO cells were seeded at 25,000 cells per well into 96-well, black-wall, clear-bottom microtiter plates 24 h before assay. Cells in culture media (DMEM/F12 containing 15 mM HEPES, L-glutamine, pyridoxine hydrochloride; 10% fetal bovine serum; 1 mg/mL G418 sulfate; antibiotic-antimycotic; pH 7.4) were loaded with proprietary dye, from the FLIPR Calcium Assay Kit (Molecular Devices), prepared in assay buffer (Hanks Balanced Salts Solution, 20 mM HEPES, 0.1% BSA, 2.5 mM probenecid, pH 7.4), and incubated for 1 h at 37° C. Calcium mobilization determinations were performed at room temperature (23° C.). The use of rat GPR14 was considered acceptable, because human U-II has similar affinity for human or rat GPR14 in the transfected cells (S. A. Douglas, E. H. Ohlstein, *Trends Cardiovasc. Med.* 2000, 10, 229-237).

Results for Calcium Mobilization using the Rat UII FLIPR Assay are shown in Table 1 and Table 2. Table 2 contains IC$_{50}$ values which represent an average value for the compound tested.

TABLE 1

Inhibition of Acetyl-cyclic[Cys-Phe-Trp-Lys-(2-NaI)-Cys]-NH$_2$*
induced Ca2+ mobilization (FLIPR) in CHO cells transfected with rat UII receptor

| Cpd | IC$_{50}$ (μM) | (±) SE | N | % I @ 10 (μM) | (±) SE | N | % I @ 50 (μM) | (±) SE | N |
|---|---|---|---|---|---|---|---|---|---|
| 1 | 0.046, 0.084 | 0.005, 0.014 | 2 | 99 | 1 | 2 | 99 | | |
| 2 | 0.07 | 0.01 | 3 | 101 | 0 | 2 | 103 | | 1 |
| 3 | 0.13 | 0.02 | 2 | 100 | 1 | 3 | 101 | | 1 |
| 4 | 0.15 | 0.01 | 3 | 100 | 1 | 3 | 100 | | 1 |
| 5 | 0.151 | 0.011 | 2 | 99 | 1 | 2 | 99 | | 1 |
| 6 | 0.16 | 0.078 | 3 | 103 | 2 | 2 | 102 | | 1 |
| 7 | 0.22, 0.18 | 0.05, 0.01 | 3, 2 | 89, 74 | 11, 26 | 3 | 80, 25 | | 1 |
| 8 | 0.18 | 0.03 | 3 | 100 | 1 | 3 | 100 | | 1 |
| 9 | 0.19 | 0.03 | 2 | 91 | 10 | 3 | 81 | | 1 |
| 10 | 0.21 | | 1 | 100 | 1 | 2 | 106 | | 1 |
| 11 | 0.34 | 0.08 | 2 | 100 | 0 | 3 | 101 | | 1 |
| 12 | 2.8 (orig batch), 0.37 | 0.07 | 1, 2 | 77, 101 | 10, 0 | 2 | | | |
| 13 | 0.41 | 0.06 | 2 | 95 | 5 | 3 | 99 | | 1 |
| 14 | 0.49 | 0.13 | 2 | 98 | 6 | 3 | 101 | | 1 |
| 15 | 0.82 | 0.06 | 2 | 100 | 1 | 3 | 100 | | 1 |
| 16 | 0.86, 1.1 | 0.02 | 2, 1 | 91, 99 | 7 | 3, 1 | 97 | | 1 |
| 17 | 1.1 | 0.1 | 2 | 99 | 2 | 3 | 101 | | 1 |
| 18 | 1.4 | 0.35 | 4 | 98 | 2 | 4 | 101 | | 1 |
| 19 | 1.5 | 0.5 | 2 | 94 | 5 | 2 | 100 | | 1 |
| 20 | 1.5 | 0.12 | 3 | 78 | 23 | 4 | 15 | | 1 |
| 21 | 1.7 | 0.48 | 4 | 90 | 3 | 4 | 98 | | 1 |
| 22 | 1.9 | 0.1 | 2 | 100 | 1 | 2 | 100 | | 1 |
| 23 | 1.9 | 0.1 | 2 | 62 | 34 | 2 | 101 | 6 | 2 |
| 24 | 2.1 | 0.42 | 2 | 96 | 3 | 3 | 100 | | 1 |
| 25 | 2.8 | 1.09 | 4 | 90 | 9 | 4 | 100 | | 1 |

TABLE 1-continued

Inhibition of Acetyl-cyclic[Cys-Phe-Trp-Lys-(2-Nal)-Cys]-NH$_2$*
induced Ca2+ mobilization (FLIPR) in CHO cells transfected with rat UII receptor

| Cpd | IC$_{50}$ (µM) | (±) SE | N | % I @ 10 (µM) | (±) SE | N | % I@ 50 (µM) | (±) SE | N |
|---|---|---|---|---|---|---|---|---|---|
| 26 | 3.4 | 1.78 | 3 | 81 | 12 | 3 | 94 | | 1 |
| 27 | 3.8 | 0.81 | 3 | 78 | 6 | 3 | 100 | | 1 |
| 28 | 4.2 | 1.53 | 4 | 75 | 7 | 4 | 101 | | 1 |
| 29 | 4.4 | 0.45 | 3 | 77 | 3 | 3 | 95 | | 1 |
| 30 | 4.4 | 1.56 | 3 | 80 | 11 | 3 | 99 | | 1 |
| 31 | 4.5 | 0.5 | 2 | 65 | 3 | 2 | 89 | 10 | 2 |
| 32 | 4.9 | 1.75 | 3 | 73 | 11 | 3 | 93 | | 1 |
| 33 | 5 | | 1 | 60 | | 1 | 97 | | 1 |
| 34 | 5.9 | 1.27 | 3 | 64 | 15 | 3 | 94 | 1 | 2 |
| 35 | 6.3 | 1.92 | 4 | 55 | 11 | 5 | 65 | 19 | 2 |
| 36 | 6.5 | 1.5 | 2 | 63 | 3 | 2 | 82 | 9 | 2 |
| 37 | 6.9 | 3.15 | 2 | 62 | 10 | 2 | 71 | | 1 |
| 38 | 7.6 | 2.6 | 2 | 56 | 1 | 2 | 94 | | 1 |
| 39 | 8.9 | 1.85 | 2 | 47 | 5 | 3 | 101 | | 1 |
| 40 | 9 | | 1 | 47 | | 1 | 87 | | 1 |
| 41 | 9.8 | 1.63 | 4 | 57 | 4 | 4 | 69 | 1 | 2 |
| 42 | 10 | 2.56 | 7 | 55 | 8 | 7 | 78 | 9 | 2 |
| 43 | 10 | 2.73 | 3 | 50 | 8 | 4 | 97 | 2 | 2 |
| 44 | 12 | | 1 | 42 | | 1 | 79 | | 1 |
| 45 | 13 | 7.27 | 6 | 55 | 6 | 8 | 40 | | 1 |
| 46 | 14 | | 1 | 48 | | 1 | 54 | | 1 |
| 47 | 15 | | 1 | 25 | 0 | 2 | 78 | | 1 |
| 48 | 16 | | 1 | 41 | 10 | 2 | 78 | | 1 |
| 49 | 16 | 7.21 | 4 | 58 | 12 | 4 | 61 | | 1 |
| 50 | 17 | | 1 | 42 | 17 | 2 | 77 | | 1 |
| 51 | 18 | 4.91 | 3 | 43 | 8 | 3 | 65 | | 1 |
| 52 | 18 | | 1 | 17 | | 1 | 71 | | 1 |
| 53 | 21 | | 1 | 22 | 7 | 2 | 78 | | 1 |
| 54 | 21 | | 1 | 15 | 10 | 2 | 81 | | 1 |
| 55 | 24 | | 1 | 12 | | 1 | 75 | | 1 |
| 56 | 25 | | 1 | 21 | 6 | 2 | 68 | | 1 |
| 57 | 30 | | 1 | 19 | | 1 | 58 | | 1 |
| 58 | 32 | | 1 | 25 | 14 | 2 | 60 | | 1 |
| 59 | 34 | | 1 | 11 | 1 | 2 | 56 | | 1 |
| 60 | 42 | | 1 | 8 | | 1 | 52 | | 1 |
| 61 | 48 | | 1 | 31 | 16 | 2 | 49 | | 1 |
| 62 | 0.72 | | 1 | 99 | 2 | 2 | 102 | | 1 |
| 63 | 0.4 | 0.1 | 2 | 102 | 2 | 3 | 102 | | 1 |
| 64 | 0.3 | 0 | 2 | 101 | 2 | 3 | 98 | | 1 |
| 65 | 0.2 | 0 | 3 | 103 | 1 | 3 | 102 | | 1 |
| 66 | 0.2 | 0 | 3 | 101 | 1 | 3 | 97 | | 1 |
| 67 | 0.1, 0.11 | 0.01 | 3 | 101 | 0 | 3 | 99 | | 1 |
| 68 | 0.1, 0.080 | 0.01 | 3 | 98 | 3 | 3 | 99 | | 1 |
| 69 | 65 | 0 | 1 | 11 | | 2 | 52 | | 1 |
| 70 | 0.3, 0.27 | 0 | 2 | 102 | 1 | 3 | 101 | | 1 |
| 71 | 1.7 | 0.3 | 2 | 58 | | 3 | 37 | | 1 |
| 76 | 0.96 | 0.02 | 2 | 98 | 1 | 3 | 99 | | 1 |

*Referenced in: "Structure-Function Analysis of Urotensin II and Its Use in the Construction of a Ligand-Receptor Working Model" W. A. Kinney, H. R. Almond, Jr., J. Qi, C. E. Smith, R. J. Santulli, L. de Garavilla, P. Andrade-Gordon, D. S. Cho, A. M. Everson, M. A. Feinstein, P. A. Leung, B. E. Maryanoff, *Angewandte Chemie, Int.* Ed. 2002, 41, 2940-2944.

TABLE 2

Rat UII FLIPR Average IC$_{50}$ (uM)

| Cpd | IC$_{50}$ |
|---|---|
| 77 | 0.85 |
| 78 | 0.27 |
| 79 | 1.2 |
| 80 | 1.3 |
| 81 | 1.4 |
| 82 | 4.7 |
| 83 | 0.23 |
| 84 | 2.8 |
| 85 | 2.2 |
| 86 | 0.29 |
| 87 | 0.48 |
| 88 | 0.32 |
| 89 | 0.54 |
| 90 | 0.13 |
| 91 | 0.015 |
| 92 | 0.92 |
| 93 | 0.18 |
| 94 | 0.065 |
| 95 | 0.089 |
| 96 | 0.097 |
| 97 | 0.063 |
| 98 | 0.018 |
| 99 | 0.17 |
| 100 | 0.57 |
| 101 | 0.030 |
| 102 | 0.049 |
| 103 | 0.035 |
| 104 | 0.053 |

TABLE 2-continued

Rat UII FLIPR Average IC$_{50}$ (uM)

| Cpd | IC$_{50}$ |
|---|---|
| 105 | 0.068 |
| 106 | 0.016 |
| 107 | 0.025 |
| 108 | 0.014 |
| 109 | 0.027 |
| 110 | 0.019 |
| 111 | 0.15 |
| 112 | 0.069 |
| 113 | 2.6 |
| 114 | 0.017 |
| 115 | 0.028 |
| 116 | 1.4 |
| 117 | 0.058 |
| 118 | 0.029 |
| 119 | 0.069 |
| 120 | 0.31 |
| 121 | 0.27 |
| 122 | 0.012 |
| 123 | 0.25 |
| 124 | 0.028 |
| 125 | 0.011 |
| 126 | 0.081 |
| 127 | 0.0064 |
| 128 | 0.0089 |
| 129 | 0.0094 |
| 130 | 0.054 |
| 131 | 0.12 |
| 132 | 0.0098 |
| 133 | 0.014 |
| 134 | 0.019 |
| 135 | 0.056 |
| 136 | 0.0062 |
| 137 | 2.2 |
| 138 | 0.020 |
| 139 | 0.029 |
| 140 | 0.014 |
| 142 | 0.097 |
| 143 | 0.028 |
| 144 | 0.011 |
| 145 | 0.016 |
| 146 | 0.029 |
| 147 | 0.032 |
| 148 | 0.018 |
| 149 | 0.015 |
| 150 | 0.038 |
| 151 | 0.014 |
| 152 | 0.017 |
| 153 | 0.013 |
| 154 | 0.013 |
| 155 | 0.0094 |
| 156 | 0.035 |
| 157 | 0.032 |
| 158 | 0.016 |
| 159 | 0.034 |
| 160 | 0.012 |
| 161 | 0.019 |
| 162 | 0.035 |
| 163 | 0.015 |
| 164 | 0.013 |
| 165 | 0.018 |
| 166 | 0.026 |
| 167 | 0.04 |
| 168 | 0.0048 |
| 169 | 0.016 |
| 170 | 0.0084 |
| 171 | 0.011 |
| 172 | 0.011 |
| 173 | 0.011 |
| 174 | 0.011 |
| 175 | 0.0061 |
| 176 | 0.013 |
| 177 | 0.0071 |
| 178 | 0.013 |
| 179 | 0.024 |
| 180 | 0.0088 |
| 181 | 0.012 |
| 182 | 0.0096 |
| 183 | 0.019 |
| 184 | 0.015 |
| 185 | 0.0098 |
| 186 | 0.013 |
| 187 | 0.011 |
| 188 | 0.02 |
| 189 | 0.0086 |
| 190 | 0.0061 |
| 191 | 0.031 |
| 192 | 0.0070 |
| 193 | 0.0079 |
| 194 | 0.010 |
| 195 | 2.1 |
| 196 | 0.022 |
| 197 | 0.082 |
| 198 | 0.0035 |
| 199 | 0.0093 |
| 200 | 4.0 |
| 201 | 0.049 |
| 202 | 0.12 |
| 203 | 0.14 |
| 204 | 0.0075 |
| 205 | 3.7 |
| 206 | 0.69 |
| 207 | 0.20 |
| 208 | 0.32 |
| 209 | 0.10 |
| 210 | 6.2 |
| 211 | 0.019 |
| 212 | 0.019 |
| 213 | 0.017 |
| 214 | 9.5 |
| 215 | 0.011 |
| 216 | 0.064 |
| 217 | 0.014 |
| 218 | 0.24 |
| 219 | 0.022 |
| 220 | 0.023 |
| 221 | 0.015 |
| 222 | 0.025 |
| 223 | 0.012 |
| 224 | 0.34 |
| 225 | 1.5 |
| 226 | 10 |
| 227 | 0.16 |
| 228 | 0.049 |
| 229 | >0.1 |
| 230 | 0.29 |
| 231 | 0.68 |
| 232 | 0.41 |
| 233 | 0.66 |
| 234 | 0.051 |

Example 2

Human Radioligand Binding Assay

Human Skeletal Muscle Myoblasts (HSMM) were obtained from Cambrex, and were cultured according to manufacturer's instruction. Cell viability was examined by trypan blue exclusion. Cells at less than 4 passages were used in all studies. For the ($^{125}$I)-U-II binding experiments (Described in: "Characterization of Functional Urotensin II Receptors in Human Skeletal Muscle Myoblasts: Comparison with Angiotensin II Receptors" J. Qi, L. K. Minor, C. Smith, B, Hu, J. Yang, P. Adrade-Gordon, B. Damiano, *Peptides* 2005, 26, 683-690.), HSMM were plated in 12-well Costar plates in complete medium for 48 h to reach 70% confluence. The binding medium used was Dulbecco's modified Eagle's medium (DMEM) containing 2 mg/ml BSA and 25 mM HEPES (pH 7.4). The cells were washed at room temperature 2× with the binding medium, and were incubated with 0.2 ml per well of prepared binding medium containing 0.150 nM ($^{125}$I)-U-II and compounds for 3 h. The cells were washed 4× with the binding medium and solubilized in 1% SDS and 0.5 N NaOH. Radioactivity was quantified by gamma counting.

Radiolabeled ($^{125}$I)-U-II bound specifically and saturably to intact adherent HSMM (FIG. 1A). The binding assays were performed at 25° C. to lower nonspecific uptake of ($^{125}$I)-U-II by the cells that was seen at 37° C. Using this method, the nonspecific binding was below 10% of total binding. Analysis of the saturation data using the non-linear curve-fitting technique of GraphPad Prism Version 3.0 revealed that the best fit observed was for a one-site model. The derived Kd value was 0.309±0.022 nM (N=3 experiments) with the Hill slope close to unity. Based on the number of cells in a well and Bmax value, the number of UT receptors in HSMM was 2311±236 per cell (N=3 experiments). A time course experiment demonstrated that ($^{125}$I)-U-II binding to HSMM reached steady state at 3 h, and remained constant up to 5 hr, the longest time point measured. Human U-II, when add at time 0, efficiently displaced specific binding of ($^{125}$I)-U-II with a Ki of 0.425±0.096 nM (N=3 experiments). The resulting data is shown in Table 3 and Table 4. Table 4 contains $IC_{50}$ values which represent an average value for the compound tested.

TABLE 3

Inhibition of human UII binding to human skeletal muscle myoblasts containing endogenous human UII receptor

| Cpd | KI (µM) | SE (±) | N | est. KI (µM) |
|---|---|---|---|---|
| 1 | 0.57 | 0.19 | 2 | |
| 2 | 0.31 | | 1 | |
| 3 | 0.16 | 0.012 | 3 | |
| 4 | 0.23 | | 1 | |
| 5 | 1.5 | | 1 | |
| 6 | 1.2 | | 1 | |
| 7 | 0.2 | 0.034 | 2 | |
| 8 | 0.31 | | 1 | |
| 9 | 0.66 | 0.325 | 2 | |
| 12 | 4.5 | | 1 | |
| 13 | 4 | 0.2 | 2 | |
| 15 | 5.2 | 1.3 | 2 | |
| 16 | | | | 39% @4 uM |
| 17 | 3.5 | | 1 | |
| 18 | 2.9 | | 1 | |
| 19 | 5.2 | | 1 | |
| 28 | 5.5 | | 1 | |
| 63 | 2.8 | | 1 | |
| 64 | 0.7 | | 1 | |
| 65 | 0.20 | 0.06 | 2 | |
| 66 | 3.2 | | 1 | |
| 67 | 1.4 | | 1 | |
| 68 | 0.076 | | 1 | |
| 69 | >10 | | 1 | |
| 70 | 5.4 | | 1 | |
| 76 | 1.5 | | 1 | |

TABLE 4

Human UII Average Binding Ki (uM)

| Cpd | Binding Ki |
|---|---|
| 77 | 7.2 |
| 78 | 2.6 |
| 79 | >10 |
| 80 | >10 |
| 81 | >10 |
| 82 | 10 |
| 83 | 1.6 |
| 84 | 10 |
| 85 | 3.6 |
| 86 | 1.3 |
| 88 | 0.35 |
| 89 | 0.89 |
| 90 | 0.32 |
| 91 | 0.15 |
| 93 | 0.46 |
| 94 | 0.042 |
| 95 | 0.11 |
| 96 | 0.097 |
| 97 | 0.18 |
| 98 | 0.042 |
| 99 | 0.62 |
| 101 | 0.12 |
| 102 | 0.099 |
| 103 | 0.20 |
| 104 | 0.12 |
| 105 | 0.065 |
| 106 | 0.080 |
| 107 | 0.01 |
| 108 | 0.031 |
| 109 | 0.019 |
| 110 | 0.025 |
| 112 | 0.026 |
| 114 | 0.011 |
| 115 | 0.039 |
| 117 | 0.032 |
| 118 | 0.049 |
| 119 | 0.12 |
| 122 | 0.12 |
| 123 | 0.57 |
| 124 | 0.32 |
| 125 | 0.013 |
| 126 | 0.34 |
| 128 | 0.11 |
| 129 | 0.009 |
| 130 | >0.3 |
| 131 | >0.3 |
| 132 | 0.072 |
| 133 | 0.059 |
| 134 | 0.068 |
| 135 | 0.19 |
| 136 | 0.061 |
| 138 | 0.032 |
| 139 | 0.046 |
| 140 | 0.016 |
| 141 | 0.017 |
| 142 | 0.30 |
| 144 | 0.13 |
| 145 | 0.12 |
| 146 | 0.64 |
| 147 | 0.16 |
| 148 | >0.2 |
| 149 | 0.071 |
| 150 | 0.074 |
| 151 | 0.074 |
| 152 | 0.069 |
| 153 | 0.088 |
| 154 | 0.084 |
| 155 | 0.045 |
| 156 | 0.084 |
| 157 | 0.26 |
| 158 | 0.099 |
| 159 | 0.15 |
| 160 | 0.14 |
| 161 | 0.12 |
| 162 | 0.17 |
| 163 | 0.095 |
| 164 | 0.1 |
| 165 | 0.35 |
| 166 | 0.51 |
| 167 | 0.15 |
| 168 | 0.035 |
| 169 | 0.059 |
| 170 | 0.031 |

TABLE 4-continued

Human UII Average Binding Ki (uM)

| Cpd | Binding Ki |
|---|---|
| 171 | 0.37 |
| 172 | 0.026 |
| 173 | 0.066 |
| 174 | 0.019 |
| 175 | 0.026 |
| 176 | 0.024 |
| 177 | 0.093 |
| 178 | 0.022 |
| 179 | 0.043 |
| 180 | 0.023 |
| 181 | 0.041 |
| 182 | 0.04 |
| 183 | 0.055 |
| 184 | 0.056 |
| 185 | 0.023 |
| 186 | 0.037 |
| 187 | 0.05 |
| 188 | 0.12 |
| 189 | 0.057 |
| 190 | 0.02 |
| 191 | 0.069 |
| 192 | 0.03 |
| 193 | 0.086 |
| 194 | 0.17 |
| 196 | 0.38 |
| 197 | 0.22 |
| 198 | 0.045 |
| 199 | 0.027 |
| 201 | 0.21 |
| 202 | 0.15 |
| 203 | 0.097 |
| 206 | 0.066 |
| 207 | >0.3 |
| 208 | 0.20 |
| 209 | 0.29 |
| 210 | >0.3 |
| 211 | 0.089 |
| 212 | 0.026 |
| 213 | 0.054 |
| 214 | >0.3 |
| 215 | 0.087 |
| 216 | 0.13 |
| 217 | 0.032 |
| 218 | >0.3 |
| 219 | 0.044 |
| 220 | 0.011 |
| 221 | 0.072 |
| 222 | 0.14 |
| 223 | 0.12 |
| 224 | >0.3 |
| 225 | >0.3 |
| 226 | >0.3 |
| 227 | >0.3 |
| 228 | 0.025 |
| 229 | 0.32 |
| 230 | >0.3 |
| 231 | 0.511 |
| 232 | >0.3 |
| 233 | 0.057 |
| 234 | 0.28 |

Example 3

Human UII Calcium Mobilization Assay

6D9 human rhabdomyosarcoma cells were seeded into tissue culture treated 384-well black-walled clear bottom plates (3712, Corning Incorporated, Corning, N.Y.) at 8,000 cells/well in 25 µL of culture medium, and maintained in an incubator (5% $CO_2$ at 37° C.) for 22 hrs prior to the calcium mobilization assay. 25 µL of dye solution was added to the wells such that the final liquid volume before agonist/antagonist treatment was 50 µL for all assays. The cell plates were incubated at 37° C. for 45 minutes and the fluorescence intensity was measured on a Fluorometric Imaging Plate Reader (FLIPR$^{TETRA}$, Molecular Devices, Sunnyvale, Calif.).

Antagonist and agonist U-II were added at room temperature on the FLIPR$^{TETRA}$, and the fluorescence intensity before and after addition was measured over a period of 4 minutes. The dye incubation time and temperature as well as instrument setting was adjusted so the fluorescence intensity could be compared between plates on the same day. $EC_{50}$ and $IC_{50}$ were analyzed using GraphPad Prism 4 software (GraphPad Software Inc., San Diego, Calif.).

Materials and reagent Preparation: Human Rhabdomyosarcoma cells (6D9: isolated by dilution subcloning of RMS13 cells, ATCC® Number: CRL-2061, American Type Culture Collection ATCC, Manassas, Va.) was maintained in RPMI-1640 medium (30-2001, ATCC, Manassas, Va.) supplemented with 10% (v/v) Fetal Bovine Serum (SH30071.03, Hyclone, Logan, Utah).

Dye preparation: BD™ Calcium Assay Kit (80500-301, BD Biosciences, Rockville, Md.) was prepared according to the manufacture's instruction in 1× Hanks' balanced salt solution (HBSS, 21-023-CV, Mediatech, Inc. Herndon, Va.) containing 20 mM HEPES buffer (25-060-CI, Mediatech, Inc. Herndon, Va.). Final dye loading conditions included 1.25 mM probenecid (P36400, Invitrogen, Carlsbad, Calif.) and 0.01% FBS.

Agonist and antagonist preparation: Human U-II stock (U-7257, Sigma, St. Louis, Mo.) was prepared in acidified water (pH 4.95) at 5 mM. Urantide (PUT-3639-PI, Peptide International, Louisville, Ky.) was prepared in water at 5 mM. For assays, U-II agonist, U-II antagonist and urantide were diluted with HBSS/HEPES containing 0.01% FBS.

Test compounds were dissolved in DMSO at 10 mM concentration. The serial dilutions were carried out in HBSS/HEPES. The highest final DMSO concentration was at 0.1%.

TABLE 5

Human UII Ca$^+$ Mobilization Average IC$_{50}$ (uM)

| Cpd | IC$_{50}$ |
|---|---|
| 87 | 1.5 |
| 88 | >3 |
| 89 | >10 |
| 90 | 0.56 |
| 91 | 0.31 |
| 93 | >3 |
| 94 | 0.43 |
| 95 | 0.20 |
| 96 | 0.76 |
| 97 | 0.70 |
| 98 | 0.35 |
| 99 | 2.7 |
| 101 | 0.30 |
| 102 | 0.52 |
| 103 | 0.59 |
| 104 | 0.17 |
| 105 | 0.11 |
| 106 | 0.23 |
| 107 | 0.44 |
| 108 | 0.046 |
| 109 | 0.30 |
| 110 | 0.25 |
| 112 | 1.4 |
| 114 | 0.47 |
| 115 | 0.46 |
| 117 | 0.70 |
| 118 | 0.24 |
| 119 | 0.26 |
| 122 | 0.50 |
| 123 | 3.1 |
| 124 | 0.30 |
| 125 | 0.047 |

TABLE 5-continued

Human UII Ca+ Mobilization Average IC$_{50}$ (uM)

| Cpd | IC$_{50}$ |
|---|---|
| 127 | 0.35 |
| 128 | 0.28 |
| 129 | 0.16 |
| 132 | 0.34 |
| 136 | 0.36 |
| 138 | 0.13 |
| 139 | 0.29 |
| 140 | 0.22 |
| 142 | 1.1 |
| 143 | 0.69 |
| 144 | 0.76 |
| 145 | 0.75 |
| 146 | 2.7 |
| 147 | 2.1 |
| 148 | 1.1 |
| 149 | 0.76 |
| 150 | 0.86 |
| 151 | 1.0 |
| 152 | 0.66 |
| 153 | 1.2 |
| 154 | 1.2 |
| 155 | 0.40 |
| 156 | 0.49 |
| 157 | 0.68 |
| 158 | 0.33 |
| 159 | 0.75 |
| 160 | 0.40 |
| 161 | 0.63 |
| 162 | 0.43 |
| 163 | 0.50 |
| 164 | 0.30 |
| 165 | 1.1 |
| 166 | 2.6 |
| 167 | 0.50 |
| 168 | 0.15 |
| 169 | 0.22 |
| 170 | 0.41 |
| 171 | 1.0 |
| 172 | 0.22 |
| 173 | 0.80 |
| 174 | 0.62 |
| 175 | 0.41 |
| 176 | 0.85 |
| 177 | 1.1 |
| 178 | 0.56 |
| 179 | 1.1 |
| 180 | 0.57 |
| 181 | 0.97 |
| 182 | 0.58 |
| 183 | 1.3 |
| 184 | 1.1 |
| 185 | 1.0 |
| 186 | 0.82 |
| 187 | 0.91 |
| 188 | 1.3 |
| 189 | 1.1 |
| 190 | 0.29 |
| 191 | 1.5 |
| 192 | 0.64 |
| 193 | 0.52 |
| 194 | 0.99 |
| 195 | >10 |
| 196 | 1.2 |
| 197 | 0.54 |
| 198 | 0.15 |
| 199 | 0.16 |
| 200 | >10 |
| 201 | >3 |
| 202 | 0.96 |
| 203 | 0.81 |
| 204 | 0.20 |
| 205 | >3 |
| 206 | 0.68 |
| 207 | 1.4 |
| 208 | 4.5 |
| 209 | 3.8 |
| 210 | >10 |
| 211 | 1.2 |
| 212 | 0.79 |
| 213 | 0.73 |
| 214 | >10 |
| 215 | 0.037 |
| 217 | 1.0 |
| 218 | 2.4 |
| 219 | 1.0 |
| 220 | 0.17 |
| 221 | 0.91 |
| 222 | 1.5 |
| 223 | 0.24 |
| 224 | 2.0 |
| 225 | >10 |
| 226 | >10 |
| 227 | 2.9 |
| 228 | 0.78 |
| 229 | 1.7 |
| 230 | 1.9 |
| 231 | 3.4 |
| 232 | 4.1 |
| 233 | 0.77 |
| 234 | 1.7 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

What is claimed is:

1. A compound of Formula (I):

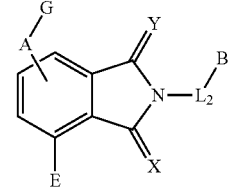

Formula (I)

wherein:

A is present, G is selected from hydrogen, $C_{1-8}$alkyl, $C_{2-8}$alkenyl, $C_{3-14}$cycloalkyl or a —C[(R$_1$)(R$_{11}$)]-L-D moiety:

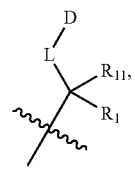

wherein $C_{1-8}$alkyl is optionally substituted with one, two or three fluoro substituents, and wherein $C_{3-14}$cycloalkyl is optionally substituted with one, two or three $C_{1-3}$alkyl substituents; or, R$_1$ is selected from the group consisting of hydrogen, $C_{1-8}$alkyl, $C_{2-8}$alkenyl, and $C_{2-8}$alkynyl;

R₁₁ is selected from the group consisting of hydrogen, C₁₋₈alkyl and cyclopropyl;

L is absent or C₁₋₄alkylene;

D is aryl (other than naphthalen-2-yl), C₃₋₁₄cycloalkyl, C₅₋₁₄cycloalkenyl, heterocyclyl, or heteroaryl,
wherein aryl and heteroaryl are optionally substituted with one, two, three or four substitutents independently selected from the group consisting of C₁₋₃alkyl, C₁₋₃alkoxy, C₂₋₈alkenyl, C₂₋₃alkenyloxy, hydroxy, C₁₋₃alkylthio, fluoro, chloro, cyano, C₁₋₃alkylcarbonyl, (C₁₋₃alkylcarbonyl)amino, (C₁₋₃alkyl)amino, di(C₁₋₃alkyl)amino and C₃₋₁₄cycloalkyl, wherein C₃₋₁₄cycloalkyl is optionally substituted with one, two, three or four C₁₋₃alkyl substituents,
provided that D is other than 2-hydroxy-5-chloro-phenyl, 3-methoxy-phenyl, 4-ethyl-phenyl, 6,6-dimethyl-bicyclo[3.1.1]hept-2-en-2-yl-methyl, cyclohex-3-enyl, 2,6-dichloro-phenyl and 2-chloro-4-fluoro-phenyl;

A is a-4
wherein, the lower portion of A is attached, relative to the nitrogen atom of Formula (I), to the 4 or 5 position on the benzene ring portion of Formula (I);

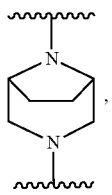

a-4 wherein a-4 is optionally substituted with one to two C₁₋₄alkyl substituents;

L₂ is —CH(R₂)—;
provided that L₂ is other than —CH(R-carboxymethyl)-;

R₂ is selected from the group consisting of a heteroaryl that is not fused to another ring, phenyl, and C₁₋₆alkyl,
wherein phenyl is optionally substituted with (R₂₀₀—C₁₋₆alkyl)amino, or [(hydroxysulfonyl)(Rₐ)]amino, and
wherein C₁₋₆alkyl is optionally substituted with carboxy, hydroxy, R₂₀₀, NRₐR_b, C₁₋₆ alkoxy, R₂₀₀—C₁₋₆alkoxy, R₂₀₀-oxy, aminocarbonyl, carboxy-C₁₋₆alkoxy, aminocarbonyl-C₁₋₆alkoxy, (C₁₋₆alkyl)aminocarbonyl, di(C₁₋₆ alkyl)aminocarbonyl, [(R₂₀₀-C₁₋₆alkyl)(Rₐ)]amino, (Ci₋₆alkylcarbonyl)amino, (trihalo-C₁₋₄alkylcarbonyl)amino, (R₂₀₀—C₁₋₆alkylcarbonyl)amino, (C₁₋₆alkoxycarbonyl)amino, (R₂₀₀—C₁₋₆alkoxycarbonyl)amino, (C₁₋₆alkoxy-C₁₋₆alkylcarbonyl)amino, (R₂₀₀-carbonyl)amino, (amino-C₁₋₆alkylcarbonyl)amino, [(C 1_6alkyl)amino-C₁₋₆alkylcarbonyl]amino, [di(C₁₋₆alkyl)amino-C₁₋₆alkylcarbonyl] amino, (C₁₋₆alkylcarbonyl-acetonitrile-carbonyl)amino, ureido, thioureido, acetamidino, guanidino, {[(R₂₀₀)(Rₐ)]aminocarbonyl-(R_c)}amino, [(R₂₀₀-oxycarbonyl)(Rₐ)] amino, [(R₂₀₀)(Rₐ)]aminocarbonyloxy, aminosulfonyl, C₁₋₆alkylsulfonyl, (C₁₋₆alkylsulfonyl)amino, (R₂₀₀—C₁₋₆alkylsulfonyl)amino, (R₂₀₀—C₂₋₆alkenylsulfonyl)amino, (C₁₋₆alkylsulfonyl-C₁₋₆alkylsulfonyl)amino, R₂₀₀-sulfonyloxy, aminosulfonyloxy, (C₁₋₆alkyl)aminosulfonylamino, di(C₁₋₆alkyl)aminosulfonyloxy, aminosulfonylamino, (C₁₋₆alkyl)aminosulfonylamino, [di(C₁₋₆alkyl)aminosulfonyl]amino, [(hydroxysulfonyl)(Rₐ)]amino, [(R₂₀₀-oxysulfonyl)(Rₐ)]amino, [(R₂₀₀-sulfonyl)(Rₐ)]amino, [(R₂₀₀)(Rₐ)]aminosulfonyloxy, or ({[(R₂₀₀)(Rₐ)]aminosulfonyl}(R_c))amino;

Rₐ and R, are independently selected from the group consisting of hydrogen and C₁₋₆alkyl; and R_b is hydrogen, C₁₋₆alkyl, C₆₋₁₀aryl, heteroaryl, C₃₋₈cycloalkyl, or heterocyclyl;

R₂₀₀ is C₆₋₁₀aryl, heteroaryl, C₃₋₈cycloalkyl, or heterocyclyl, each optionally substituted with one, two or three substituents independently selected from the group consisting of C₁₋₄alkyl, trihalo-C₁₋₄alkyl, C₁₋₄alkoxy, trihalo-C₁₋₄alkoxy, C₁₋₆alkylcarbonyl, C₁₋₆alkoxycarbonyl, (C₁₋₆alkylcarbonyl)amino, C₁₋₆alkylsulfonyl, hydroxysulfonyl, aminosulfonyl, chloro, fluoro, bromo, aryl, heteroaryl, aryl-C₁₋₆alkyl, aryl-sulfonyl and heteroaryl-sulfonyl,
wherein heterocyclyl is optionally substituted with one, two or three oxo substituents;

B is C₆₋₁₀aryl, tetralinyl, indanyl, or a heteroaryl selected from the group consisting of pyridin-2-yl, pyridin-4-yl, pyrazol-4-yl, pyrimidin-4-yl, pyrimidin-5-yl, pyrazin-2-yl, imidazol-l-yl, thien-2-yl, isoquinolinyl, indolyl, quinolinyl, and thiazol-5-yl,
wherein when B is other than C₆₋₁₀aryl, tetralinyl, indanyl, thien-2-yl, and indolyl, B is optionally substituted with one, two or three substituents independently selected from the group consisting of C₁₋₄alkyl, C₁₋₄alkoxy, fluorinated (C₁₋₄alkoxy, halogen, cyano, hydroxy, aminocarbonyl, (C₁₋₄alkylaminocarbonyl, di(C₁₋₄alkylaminocarbonyl, aminosulfonyl, (C₁₋₄alkylaminosulfonyl, di(C₁₋₄)alkylaminosulfonyl, hydroxysulfonyl, aminosulfonylamino, (C₁₋₄alkylaminosulfonylamino, di(C₁₋₄ alkylaminosulfonylamino, aminosulfonyloxy, (C₁₋₄ alkylaminosulfonyloxy, and di(C₁₋₄alkylaminosulfonyloxy,
wherein when B is selected from the group consisting of C₆₋₁₀aryl, tetralinyl, indanyl, thien-2-yl, and indolyl, then B is independently substituted with two to three substitutents selected from the group consisting of C₁₋₃alkoxy and hydroxy,
provided that, when B is phenyl substituted at the 3,4-, 3,5- or 4,5- positions with an unbranched C₁₋₃alkoxy substituent at each position, then phenyl may be further optionally substituted at a remaining open 3-, 4-, or 5-position with an additional C₁₋₃alkoxy or hydroxy substituent, and
provided that B is other than 3-hydroxy-4-methoxy-phenyl and 3-(n-propyloxy)-4-methoxy-phenyl;

E is hydrogen, halogen, C₁₋₃alkoxy, C₂₋₅alkyl-R_E, or —CH═CH—C₀₋₃alkyl-R_E;
wherein R_E is selected from the group consisting of carboxy, amino, (C₁₋₆alkyl)amino, di(C₁₋₆alkyl)amino, aminocarbonyl, (C₁₋₆alkyl)aminocarbonyl, di(C₁₋₆alkyl)aminocarbonyl, (C₁₋₆alkyl)carbonylamino, C₁₋₆alkoxycarbonylamino, aminocarbonyl(C₁₋₆)alkoxy, ureido, thioureido, aminosulfonyl, C₁₋₆alkylsulfonyl, C₁₋₆alkylsulfonylamino, aminosulfonyloxy, (C₁₋₆alkyl)aminosulfonyloxy, di(C₁₋₆alkyl)aminosulfonyloxy, aminosulfonylamino, (C₁₋₆alkyl)aminosulfonylamino, di(C₁₋₆alkyl)aminosulfonylamino, (R₂₀₀)(Rₐ) aminocarbonyl-(R_c)amino, R₂₀₀carbonylamino, R₂₀₀oxycarbonyl-(Rₐ)amino, (R₂₀₀)(Rₐ)aminocarbonyloxy, R₂₀₀oxysulfonyl-(Rₐ)amino, R₂₀₀sulfonyl-(Rₐ) amino, (R₂₀₀)(Rₐ)aminosulfonyloxy, and (R₂₀₀)(Rₐ) aminosulfonyl-(R_c)amino;

X and Y are independently O or S;
and enantiomers, diastereomers, tautomers, and pharmaceutically acceptable salts thereof.

2. The compound of claim 1, wherein
A is present, G is selected from hydrogen, $C_{1-8}$alkyl, $C_{2-8}$alkenyl, $C_{3-14}$cycloalkyl or a —C[($R_1$)($R_{11}$)]-L-D moiety:

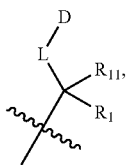

wherein $C_{1-8}$alkyl is optionally substituted with one, two or three fluoro substituents; $R_1$ is selected from the group consisting of hydrogen, $C_{1-8}$alkyl and $C_{2-8}$alkynyl;
$R_{11}$ is selected from the group consisting of hydrogen, $C_{1-8}$alkyl and cyclopropyl;
L is absent or $C_{1-4}$alkylene;
D is aryl (other than naphthalen-2-yl), $C_{3-14}$cycloalkyl or heteroaryl,
wherein aryl and heteroaryl are optionally substituted with one or two substitutents independently selected from the group consisting of $C_{1-3}$alkyl, $C_{1-3}$alkoxy, hydroxy, fluoro, chloro and cyano,
provided that D is other than 2-hydroxy-5-chloro-phenyl, 3-methoxy-phenyl, 4-ethyl-phenyl, 2,6-dichloro-phenyl and 2-chloro-4-fluoro-phenyl;
A is a-4
wherein, the lower portion of A is attached, relative to the nitrogen atom of Formula (I), to the 4 or 5 position on the benzene ring portion of Formula (I);

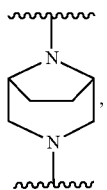

a-4 wherein a-4 is optionally substituted with two $C_{1-4}$alkyl substituents;
$L_2$ is —CH($R_2$);
provided that $L_2$ is other than —CH(R-carboxymethyl)-;
$R_2$ is selected from the group consisting of phenyl, and $C_{1-6}$alkyl, wherein phenyl is optionally substituted with ($R_{200}$-$C_{1-6}$alkyl)amino, or [hydroxysulfonyl)($R_a$)]amino, and
wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, carboxy-$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkyl carbonyl]amino, ($C_{1-6}$alkylcarbonyl-acetonitrile-carbonyl)amino, acetamidino, guanidino, {[($R_{200}$)($R_a$)]aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [hydroxysulfonyl)($R_a$)]amino or [($R_{200}$-sulfonyl)($R_a$)]amino;
$R_a$ and $R_c$ are independently selected from the group consisting of hydrogen and $C_{1-6}$alkyl; and $R_b$ is hydrogen, $C_{1-6}$alkyl, heteroaryl or heterocyclyl;
$R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, heteroaryl, aryl-$C_{1-6}$alkyl, aryl-sulfonyl and heteroaryl-sulfonyl,
wherein heterocyclyl is optionally substituted with two oxo substituents;
B is $C_{6-10}$aryl, indanyl, or a heteroaryl selected from the group consisting of pyridin-2-yl, pyridin-4-yl, pyrazol-4-yl and imidazol-l-yl,
wherein when B is heteroaryl, B is optionally substituted with one, two or three substituents independently selected from the group consisting of $C_{1-4}$alkyl, $C_{1-4}$alkoxy, halogen, and hydroxy,
wherein when B is selected from the group consisting of $C_{6-10}$aryl and indanyl, then B is independently substituted with two substituents selected from the group consisting of $C_{1-3}$alkoxy and hydroxy, and provided that B is other than 3-hydroxy-4-methoxy-phenyl and 3-(n-propyloxy)-4-methoxy-phenyl;
E is hydrogen, halogen or —CH=CH-sulfonyl-$C_{1-6}$alkyl;
X and Y are O;
and enantiomers, diastereomers, tautomers, and pharmaceutically acceptable salts thereof.

3. The compound of claim 1, wherein
A is present, G is selected from hydrogen, $C_{1-8}$alkyl, $C_{2-8}$alkenyl, indanyl, adamantanyl, cyclobutyl, cyclopentyl, cyclohexyl or a —C[($R_1$)($R_{11}$)]-L-D moiety:

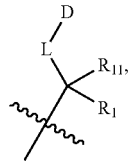

wherein $C_{1-8}$alkyl is optionally substituted with three fluoro substituents;
$R_1$ is selected from the group consisting of hydrogen, $C_{1-8}$alkyl and $C_{2-8}$alkynyl;
$R_{11}$ is selected from the group consisting of hydrogen, $C_{1-8}$alkyl and cyclopropyl;
L is absent or $C_{1-4}$alkylene;
D is selected from phenyl, cyclopentyl, furanyl, thienyl, or pyridinyl,
wherein phenyl and furanyl are optionally substituted with one or two substitutents independently selected from the group consisting of $C_{1-3}$alkyl, $C_{1-3}$alkoxy, hydroxy, fluoro, chloro and cyano,
provided that D is other than 2-hydroxy-5-chloro-phenyl, 3-methoxy-phenyl, 4-ethyl-phenyl, 2,6-dichloro-phenyl and 2-chloro-4-fluoro-phenyl;
A is a-4
wherein, the lower portion of A is attached, relative to the nitrogen atom of Formula (I), to the 4 or 5 position on the benzene ring portion of Formula (I);

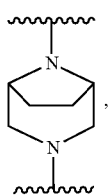

a-4

$L_2$ is —CH($R_2$)—;
provided that $L_2$ is other than —CH(R-carboxymethyl)-;
$R_2$ is selected from the group consisting of phenyl, and $C_{1-6}$alkyl,
wherein phenyl is optionally substituted with ($R_{200}$-$C_{1-6}$ alkyl)amino, or [(hydroxysulfonyl)($R_a$)]amino, and
wherein $C_{1-6}$alkyl is optionally substituted with carboxy, hydroxy, $R_{200}$, $NR_aR_b$, $C_{1-6}$alkoxy, $R_{200}$-$C_{1-6}$alkoxy, carboxy-$C_{1-6}$alkoxy, [($R_{200}$—$C_{1-6}$ alkyl)($R_{a)]amino, (C1-6}$ alkylcarbonyl]amino, (trihalo-$C_{1-4}$alkylcarbonyl) amino, ($R_{200}$—$C_{1-6}$alkylcarbonyl)amino, ($C_1$-$_{1-6}$ alkoxycarbonyl)amino, ($R_{200}$—$C_{1-6}$alkoxycarbonyl) amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino , ($C_{1-6}$alkylcarbonyl-acetonitrile-carbonyl) amino, acetamidino, guanidino, {[($R_{200}$)($R_a$)] aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($C_{1-6}$alkylsulfonyl-$C_{1-6}$alkylsulfonyl) amino, $R_{200}$-sulfonyloxy, di($C_{1-6}$alkyl)aminosulfonyloxy, aminosulfonylamino, [di($C_{1-6}$alkyl) aminosulfonyl]amino, [(hydroxysulfonyl)($R_a$)]amino or [($R_{200}$-sulfonyl)($R_a$)]amino;
$R_a$ and $R_c$ are independently selected from the group consisting of hydrogen and $C_{1-6}$alkyl; and $R_b$ is hydrogen, $C_{1-6}$alkyl, pyridinyl, pyrimidinyl, piperidinyl or 4,5-dihydro-1H-pyrrolyl;
$R_{200}$ is phenyl, furanyl, thienyl, pyrrolyl, imidazolyl, pyrazolyl, isoxazolyl, thiazolyl, pyridinyl, pyridazinyl, quinolinyl, benzothienyl, benzoimidazolyl, imidazo[2,1-b]thiazolyl, cyclobutyl, cyclopentyl, tetrahydro-furanyl, tetrahydro- thienyl, pyrrolidinyl, or piperidinyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, isoxazolyl, phenyl-$C_{1-6}$alkyl, phenyl-sulfonyl and thienyl-sulfonyl,
wherein tetrahydro-thienyl is optionally substituted with two oxo substituents;
B is phenyl, indanyl, or a heteroaryl selected from the group consisting of pyridin-2-yl, pyridin-4-yl, pyrazol-4-yl and imidazol-l-yl,
wherein when B is heteroaryl, B is optionally substituted with two or three substituents independently selected from the group consisting of $C_{1-4}$alkyl, $C_{1-4}$alkoxy, halogen and hydroxy,
wherein when B is selected from the group consisting of phenyl, and indanyl, then B is independently substituted with two substituents selected from the group consisting of $C_{1-3}$alkoxy and hydroxy, and
provided that B is other than 3-hydroxy-4-methoxy-phenyl and 3-(n-propyloxy)-4-methoxy-phenyl;
E is hydrogen, halogen or —CH═CH-sulfonyl-$C_{1-6}$alkyl;
X and Y are O;

and enantiomers, diastereomers, tautomers, and pharmaceutically acceptable salts thereof.

4. The compound of claim 1, wherein
A is present, G is selected from hydrogen, $C_{1-8}$alkyl, $C_{2-8}$alkenyl, indanyl, adamantanyl, cyclobutyl, cyclopentyl, cyclohexyl or a —C[($R_1$)($R_{1i}$)]-L-D moiety:

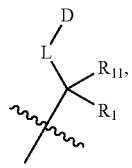

wherein $C_{1-8}$alkyl is optionally substituted with one, two or three fluoro substituents,
wherein indanyl, adamantanyl, cyclobutyl, cyclopentyl and cyclohexyl are optionally substituted with one, two or three $C_{1-3}$alkyl substituents.

5. The compound of claim 1, wherein
A is present, G is selected from hydrogen, $C_{1-8}$alkyl, $C_{2-8}$alkenyl, adamantanyl, cyclobutyl, cyclohexyl or a —C[($R_1$)($R_{11}$)]-L-D moiety:

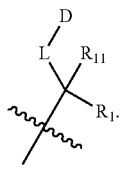

6. The compound of claim 1, wherein
D is aryl (other than naphthalen-2-yl), $C_{3-14}$cycloalkyl or heteroaryl,
wherein aryl and heteroaryl are optionally substituted with one or two substituents independently selected from the group consisting of $C_{1-3}$alkyl, $C_{1-3}$alkoxy, hydroxy, fluoro, chloro and cyano,
provided that D is other than 2-hydroxy-5-chloro-phenyl, 3-methoxy-phenyl, 4-ethyl-phenyl, 2,6-dichloro-phenyl and 2-chloro-4-fluoro-phenyl.

7. The compound of claim 1, wherein
D is aryl (other than naphthalen-2-yl), $C_{3-14}$cycloalkyl or heteroaryl,
wherein aryl and heteroaryl are optionally substituted with one or two substituents independently selected from the group consisting of $C_{1-3}$alkyl or fluoro,
provided that D is other than 4-ethyl-phenyl.

8. The compound of claim 1, wherein
D is selected from phenyl, cyclopentyl, $C_{5-14}$cycloalkenyl, heterocyclyl, furanyl, thienyl or pyridinyl,
wherein phenyl and furanyl are optionally substituted with one, two, three or four substitutents independently selected from the group consisting of $C_{1-3}$alkyl, $C_{1-3}$ alkoxy, $C_{2-8}$ alkenyl, $C_{2-3}$ alkenyloxy, hydroxy, $C_{1-3}$ alkylthio, fluoro, chloro, cyano, $C_{1-3}$alkylcarbonyl, ($C_{1-3}$alkylcarbonyl)amino, ($C_{1-3}$alkyl)amino, di($C_{1-3}$ alkyl)amino and $C_{3-14}$cycloalkyl, wherein $C_{3-14}$cycloalkyl is optionally substituted with one, two, three or four $C_{1-3}$alkyl substituents,
provided that D is other than 2-hydroxy-5-chloro-phenyl, 3-methoxy-phenyl, 4-ethyl-phenyl, 6,6-dimethyl-bicyclo[3.1.1]hept-2-en-2-yl-methyl, cyclohex-3-enyl, 2,6-dichloro-phenyl and 2-chloro-4-fluoro-phenyl.

9. The compound of claim 1, wherein
D is selected from phenyl, cyclopentyl, furanyl, thienyl, or pyridinyl,
wherein phenyl and furanyl are optionally substituted with one or two substituents independently selected from the group consisting of $C_{1-3}$alkyl, $C_{1-3}$alkoxy, hydroxy, fluoro, chloro and cyano,
provided that D is other than 2-hydroxy-5-chloro-phenyl, 3-methoxy-phenyl, 4-ethyl-phenyl, 2,6-dichloro-phenyl and 2-chloro-4-fluoro-phenyl.

10. The compound of claim 1, wherein
D is selected from phenyl, cyclopentyl, furanyl, thienyl, or pyridinyl,
wherein phenyl and furanyl are optionally substituted with one or two substituents independently selected from the group consisting of $C_{1-3}$alkyl and fluoro,
provided that D is other than 4-ethyl-phenyl.

11. The compound of claim 1, wherein A is a-4
wherein, the lower portion of A is attached, relative to the nitrogen atom of Formula (I), to the 4 or 5 position on the benzene ring portion of Formula (I);

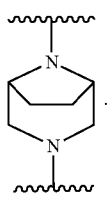

a-4

12. The compound of claim 1, wherein
A is a-4
wherein, the lower portion of A is attached, relative to the nitrogen atom of Formula (I), to the 4 position on the benzene ring portion of Formula (I);

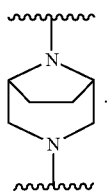

a-4

13. The compound of claim 1, wherein
$R_2$ is selected from the group consisting of phenyl, and $C_{1-6}$alkyl,
wherein phenyl is optionally substituted with ($R_{200}$-$C_{1-6}$alkyl)amino, or [(hydroxysulfonyl)($R_a$)]amino, and
wherein $C_{1-6}$alkyl is optionally substituted with carboxy, hydroxy, $R_{200}$, $NR_aR_b$, $C_{1-6}$alkoxy, $R_{200}$—$C_{1-6}$alkoxy, carboxy-$C_{1-6}$alkoxy, [($R_{200}$—$C_{1-6}$alkyl)($R_a$)]amino, ($C_{1-6}$alkylcarbonyl)amino, (trihalo-$C_{1-4}$alkylcarbonyl)amino, ($R_{200}$—$C_{1-6}$alkylcarbonyl)amino, ($C_{1-6}$alkoxycarbonyl)amino, ($R_{200}$—$C_{1-6}$alkoxycarbonyl)amino, ($C_{1-6}$alkoxy-$C_{1-6}$alkylcarbonyl)amino, ($R_{200}$-carbonyl)amino, [di($C_{1-6}$alkyl)amino-$C_{1-6}$alkylcarbonyl]amino, ($C_{1-6}$alkylcarbonyl-acetonitrile-carbonyl)amino, acetamidino, guanidino, {[($R_{200}$)($R_a$)]aminocarbonyl-($R_c$)}amino, ($C_{1-6}$alkylsulfonyl)amino, ($R_{200}$—$C_{1-6}$alkylsulfonyl)amino, ($R_{200}$—$C_{2-6}$alkenylsulfonyl)amino, ($Cl_{1-6}$alkylsulfonyl-$C_{1-6}$alkylsulfonyl)amino, $R_{200}$-sulfonyloxy, di($C_{1-6}$alkyl)aminosulfonyloxy, aminosulfonylamino, [di($C_{1-6}$alkyl)aminosulfonyl]amino, [(hydroxysulfonyl)($R_a$)]amino or [($R_{200}$-sulfonyl)($R_a$)]amino.

14. The compound of claim 1, wherein $R_a$ and $R_c$ are independently selected from the group consisting of hydrogen and $C_{1-6}$alkyl; and $R_b$ is hydrogen, $C_{1-6}$alkyl, heteroaryl or heterocyclyl.

15. The compound of claim 1, wherein $R_a$ and $R_c$ are independently selected from the group consisting of hydrogen and $C_{1-6}$alkyl; and $R_b$ is hydrogen, $C_{1-6}$alkyl, $C_{6-10}$aryl, pyridinyl, pyrimidinyl, $C_{3-8}$cycloalkyl, piperidinyl or 4,5-dihydro-1H-pyrrolyl.

16. The compound of claim 1, wherein $R_{200}$ is $C_{6-10}$aryl, heteroaryl, $C_{3-8}$cycloalkyl, or heterocyclyl, each optionally substituted with one, two or three substituents independently selected from the group consisting of $C_{1-4}$alkyl, trihalo-$C_{1-4}$alkyl, $C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, heteroaryl, aryl-$C_{1-6}$alkyl, aryl-sulfonyl and heteroaryl-sulfonyl,
wherein heterocyclyl is optionally substituted with two oxo substituents.

17. The compound of claim 1, wherein
$R_{200}$ is phenyl, furanyl, thienyl, pyrrolyl, imidazolyl, pyrazolyl, isoxazolyl, thiazolyl, pyridinyl, pyridazinyl, quinolinyl, benzothienyl, benzoimidazolyl, imidazo[2,1-b]thiazolyl, cyclobutyl, cyclopentyl, tetrahydro-furanyl, tetrahydro-thienyl, pyrrolidinyl, or piperidinyl, each optionally substituted with one, two or three substituents independently selected from the group consisting of $C_{1-4}$alkyl, trihalo-$C_{1-4}$alkyl, $C_{1-4}$alkoxy, trihalo-$C_{1-4}$alkoxy, $C_{1-6}$alkylcarbonyl, $C_{1-6}$alkoxycarbonyl, ($C_{1-6}$alkylcarbonyl)amino, $C_{1-6}$alkylsulfonyl, hydroxysulfonyl, aminosulfonyl, chloro, fluoro, bromo, aryl, isoxazolyl, phenyl-$C_{1-6}$alkyl, phenyl-sulfonyl and thienyl-sulfonyl,
wherein tetrahydro-thienyl is optionally substituted with one, two or three oxo substituents.

18. The compound of claim 1, wherein
B is $C_{6-10}$aryl, indanyl, or a heteroaryl selected from the group consisting of pyridin-2-yl, pyridin-4-yl, pyrazol-4-yl and imidazol-1-yl,
wherein when B is heteroaryl, B is optionally substituted with one, two or three substituents independently selected from the group consisting of $C_{1-4}$alkyl, $C_{1-4}$alkoxy, halogen, and hydroxy,
wherein when B is selected from the group consisting of $C_{6-10}$aryl and indanyl, then B is optionally and independently substituted with two substitutents selected from the group consisting of $C_{1-3}$alkoxy and hydroxy, and
provided that B is other than 3-hydroxy-4-methoxy-phenyl and 3-(n-propyloxy)-4-methoxy-phenyl.

19. The compound of claim 1, wherein B is $C_{6-10}$aryl or indanyl each substituted with two substituents independently selected from the group consisting of $C_{1-4}$alkoxy and hydroxy, provided that B is other than 3-hydroxy-4-methoxy-phenyl and 3-(n-propyloxy)-4-methoxy-phenyl .

20. The compound of claim 1, wherein E is hydrogen, halogen or —CH=CH-sulfonyl-$C_{1-6}$alkyl.

21. A compound selected from the group consisting of:
4-(8-benzyl-3,8-diaza-bicyclo[3.2.1]oct-3-yl)-2-(3,4-dimethoxy-benzyl)-isoindole-1,3-dione,
4-(8-benzyl-3,8-diaza-bicyclo[3.2.1]oct-3-yl)-2-[2-(3,4-dimethoxy-phenyl)-ethyl ]-isoindole-1,3-dione,
2-(3,4-dimethoxy-benzyl)-4-[8-(1-phenyl-ethyl)-3,8-diaza-bicyclo[3.2.1]oct-3-y 1]-isoindole-1,3-dione, 4-(8-benzyl-3,8-diaza-bicyclo[3.2.1]oct-3-yl)-2-pyridin-4-ylmethyl-isoindole-1,3-dione, 4-(8-benzyl-3,8-diaza-bicyclo[3.2.1]oct-3-yl)-2-(3,5-dimethoxy-benzyl)-isoindole-1,3-dione, 4-(8-benzyl-3,8-diaza-bicyclo[3.2.1]oct-3-yl)-2-pyridin-2-ylmethyl-isoindole-1,3-dione, and 4-(8-benzyl-3,8-diaza-bicyclo[3.2.1]oct-3-yl)-2-(3,4-dimethoxy-phenyl)-isoindole-1,3-dione.

22. A pharmaceutical composition comprising a compound according to claim 1 and a pharmaceutically acceptable carrier, excipient or diluent.

23. A veterinary composition comprising a compound according to claim 1 and a veterinarily acceptable carrier, excipient or diluent.

\* \* \* \* \*